US012781277B2

(12) United States Patent
Sakofsky et al.

(10) Patent No.: US 12,781,277 B2
(45) **Date of Patent: *Nov. 3, 2026**

(54) USE OF DEXTRAMER IN SINGLE CELL ANALYSIS

(71) Applicants: Becton, Dickinson and Company, Franklin Lakes, NJ (US); Immudex Aps, Virum (DK)

(72) Inventors: Cynthia Sakofsky, San Jose, CA (US); Katherine Lazaruk, San Jose, CA (US); Margaret Nakamoto, San Jose, CA (US); Devon Joseph Jensen, San Jose, CA (US); Kivin Dahl Jacobsen, Denmark (DK)

(73) Assignees: Agusta SpinCo Corporation, Franklin Lakes, NJ (US); Immudex APS, Virum (DE)

( * ) Notice: Subject to any disclaimer, the term of this patent is extended or adjusted under 35 U.S.C. 154(b) by 342 days.

This patent is subject to a terminal disclaimer.

(21) Appl. No.: 17/531,555

(22) Filed: Nov. 19, 2021

(65) Prior Publication Data

US 2022/0162695 A1 May 26, 2022

Related U.S. Application Data

(60) Provisional application No. 63/241,486, filed on Sep. 7, 2021, provisional application No. 63/116,571, filed on Nov. 20, 2020.

(51) Int. Cl.
*C12Q 1/6874* (2018.01)
*C12Q 1/6804* (2018.01)

(52) U.S. Cl.
CPC ......... *C12Q 1/6874* (2013.01); *C12Q 1/6804* (2013.01)

(58) Field of Classification Search
CPC .. C12Q 1/6874; C12Q 1/6804; C12Q 1/6806; C12Q 2537/143; C12Q 2563/149; C12Q 2563/179; C12Q 2565/537; G01N 2458/10
See application file for complete search history.

(56) References Cited

U.S. PATENT DOCUMENTS 4,499,183 A 2/1985 Sujansky
4,510,244 A 4/1985 Parks et al.
4,725,536 A 2/1988 Fritsch et al.
4,803,155 A 2/1989 Petersen et al.
4,939,082 A 7/1990 Naujoks
5,124,246 A 6/1992 Urdea et al.
5,137,809 A 8/1992 Loken et al.
5,149,625 A 9/1992 Church et al.
5,200,314 A 4/1993 Urdea
5,308,990 A 5/1994 Takahashi et al.
5,424,186 A 6/1995 Fodor et al.
5,424,413 A 6/1995 Hogan et al.
5,445,934 A 8/1995 Fodor et al.
5,470,570 A 11/1995 Taylor et al.
5,604,097 A 2/1997 Brenner
5,635,352 A 6/1997 Urdea et al.
5,635,400 A 6/1997 Brenner
5,648,245 A 7/1997 Fire et al.
5,654,413 A 8/1997 Brenner
5,656,731 A 8/1997 Urdea
5,658,737 A 8/1997 Nelson et al.
5,714,330 A 2/1998 Brenner et al.
5,744,305 A 4/1998 Fodor et al.
5,759,778 A 6/1998 Li et al.
5,763,175 A 6/1998 Brenner
5,800,992 A 9/1998 Fodor et al.
5,807,674 A 9/1998 Tyagi
5,830,712 A 11/1998 Rampersad et al.
5,846,719 A 12/1998 Brenner et al.
5,854,033 A 12/1998 Lizardi
5,866,366 A 2/1999 Kallender
5,871,928 A 2/1999 Fodor et al.
5,925,525 A 7/1999 Fodor et al.
5,935,793 A 8/1999 Wong
5,945,293 A 8/1999 Siiman
5,962,271 A 10/1999 Chenchik et al.
5,962,272 A 10/1999 Chenchik et al.
5,968,740 A 10/1999 Fodor et al.
5,981,176 A 11/1999 Wallace
5,981,179 A 11/1999 Lorinez et al.
6,013,445 A 1/2000 Albrecht et al.
6,040,138 A 3/2000 Lockhart et al.
6,046,005 A 4/2000 Ju et al.
(Continued)

FOREIGN PATENT DOCUMENTS

CA 2474509 A1 2/2003
CA 2961210 A1 3/2016
(Continued)

OTHER PUBLICATIONS

Laforte, Véronique, et al. “Antibody colocalization microarray for cross-reactivity-free multiplexed protein analysis.” Serum/Plasma Proteomics: Methods and Protocols. New York, NY: Springer New York, 2017. 239-261. (Year: 2017).*
10X Genomics, Inc., 2019, User Guide: Visium Spatial Gene Expression Reagent Kits, 10xGenomics.com, 76 pp.
2018 Top 10 Innovations, The Scientist Magazine® (2018). Available at: https://thescientist.com/features/2018-top-10-innovations-65140, 16 pp.
Achim et al., “High-throughput spatial mapping of single-cell RNA-seq data to tissue of origin,” Nature Biotechnology 2015, 33(5), 503-511.
(Continued)

*Primary Examiner* — Sahana S Kaup
(74) *Attorney, Agent, or Firm* — Dickinson Wright PLLC

(57) ABSTRACT

Disclosed herein include systems, methods, compositions, and kits suitable for the use of dextramers in single cell analysis. In some embodiments, one or more primers allowing generation of separate libraries for proteins (e.g., antibodies) and for dextramers are used.

14 Claims, 27 Drawing Sheets

Specification includes a Sequence Listing.

(56) References Cited

U.S. PATENT DOCUMENTS

| | | | |
|---|---|---|---|
| 6,060,596 | A | 5/2000 | Lerner et al. |
| 6,064,755 | A | 5/2000 | Some |
| 6,090,592 | A | 7/2000 | Adams et al. |
| 6,114,149 | A | 9/2000 | Fry et al. |
| 6,117,631 | A | 9/2000 | Nilsen |
| 6,117,635 | A | 9/2000 | Nazarendo |
| 6,117,986 | A | 9/2000 | Nardone |
| 6,124,092 | A | 9/2000 | O'neill et al. |
| 6,138,077 | A | 10/2000 | Brenner |
| 6,140,489 | A | 10/2000 | Brenner |
| 6,172,214 | B1 | 1/2001 | Brenner |
| 6,197,506 | B1 | 3/2001 | Fodor et al. |
| 6,197,554 | B1 | 3/2001 | Lin et al. |
| 6,214,558 | B1 | 4/2001 | Shuber et al. |
| 6,235,433 | B1 | 5/2001 | Wolber et al. |
| 6,235,475 | B1 | 5/2001 | Brenner et al. |
| 6,235,483 | B1 | 5/2001 | Wolber et al. |
| 6,265,163 | B1 | 7/2001 | Albrecht et al. |
| 6,268,152 | B1 | 7/2001 | Fodor et al. |
| 6,284,460 | B1 | 9/2001 | Fodor et al. |
| 6,284,485 | B1 | 9/2001 | Boyle et al. |
| 6,296,855 | B1 | 10/2001 | Hemmen |
| 6,300,093 | B1 | 10/2001 | Kindsvogel et al. |
| 6,309,822 | B1 | 10/2001 | Fodor et al. |
| 6,309,823 | B1 | 10/2001 | Cronin et al. |
| 6,326,148 | B1 | 12/2001 | Pauletti et al. |
| 6,355,431 | B1 | 3/2002 | Chee et al. |
| 6,355,432 | B1 | 3/2002 | Fodor et al. |
| 6,358,508 | B1 | 3/2002 | Ni |
| 6,372,813 | B1 | 4/2002 | Johnson et al. |
| 6,395,491 | B1 | 5/2002 | Fodor et al. |
| 6,406,848 | B1 | 6/2002 | Bridgham et al. |
| 6,436,675 | B1 | 8/2002 | Welch et al. |
| 6,440,667 | B1 | 8/2002 | Fodor et al. |
| 6,440,706 | B1 | 8/2002 | Vogelstein et al. |
| 6,444,661 | B1 | 9/2002 | Barton |
| 6,451,536 | B1 | 9/2002 | Fodor et al. |
| 6,458,530 | B1 | 10/2002 | Morris et al. |
| 6,468,744 | B1 | 10/2002 | Cronin et al. |
| 6,480,791 | B1 | 11/2002 | Strathmann |
| 6,489,114 | B2 | 12/2002 | Laayoun et al. |
| 6,489,116 | B2 | 12/2002 | Wagner |
| 6,492,121 | B2 | 12/2002 | Kurane et al. |
| 6,500,620 | B2 | 12/2002 | Yu et al. |
| 6,512,105 | B1 | 1/2003 | Hogan et al. |
| 6,514,699 | B1 | 2/2003 | O'Neill et al. |
| 6,531,283 | B1 | 3/2003 | Kingsmore et al. |
| 6,544,739 | B1 | 4/2003 | Fodor et al. |
| 6,551,784 | B2 | 4/2003 | Fodor et al. |
| 6,576,424 | B2 | 6/2003 | Fodor et al. |
| 6,600,996 | B2 | 7/2003 | Webster et al. |
| 6,629,040 | B1 | 9/2003 | Goodlett et al. |
| 6,653,077 | B1 | 11/2003 | Brenner |
| 6,753,147 | B2 | 6/2004 | Vogelstein et al. |
| 6,787,308 | B2 | 9/2004 | Balasubramanian et al. |
| 6,808,906 | B2 | 10/2004 | Shen et al. |
| 6,849,404 | B2 | 2/2005 | Park et al. |
| 6,852,488 | B2 | 2/2005 | Fodor et al. |
| 6,858,412 | B2 | 2/2005 | Willis et al. |
| 6,881,448 | B1 | 4/2005 | Hattori |
| 6,890,741 | B2 | 5/2005 | Fan et al. |
| 6,946,251 | B2 | 9/2005 | Kurn |
| 6,955,901 | B2 | 10/2005 | Schouten |
| 6,974,669 | B2 | 12/2005 | Mirkin et al. |
| 7,022,479 | B2 | 4/2006 | Wagner |
| 7,034,145 | B2 | 4/2006 | Shen et al. |
| 7,155,050 | B1 | 12/2006 | Sloge |
| 7,294,466 | B2 | 11/2007 | McMillan |
| 7,323,309 | B2 | 1/2008 | Mirkin et al. |
| 7,387,887 | B2 | 6/2008 | Wittwer et al. |
| 7,393,665 | B2 | 7/2008 | Brenner |
| 7,407,757 | B2 | 8/2008 | Brenner |
| 7,424,368 | B2 | 9/2008 | Huang et al. |
| 7,432,055 | B2 | 10/2008 | Pemov et al. |
| 7,470,515 | B2 | 12/2008 | Rashtchian et al. |
| 7,473,767 | B2 | 1/2009 | Dimitrov |
| 7,476,786 | B2 | 1/2009 | Chan et al. |
| 7,537,897 | B2 | 5/2009 | Brenner et al. |
| 7,544,473 | B2 | 6/2009 | Brenner |
| 7,635,566 | B2 | 12/2009 | Brenner |
| 7,638,612 | B2 | 12/2009 | Rashtchian et al. |
| 7,718,403 | B2 | 5/2010 | Kamberov et al. |
| 7,771,946 | B2 | 8/2010 | Kurn |
| 7,822,555 | B2 | 10/2010 | Huang et al. |
| 7,824,856 | B2 | 11/2010 | Monforte |
| 7,824,889 | B2 | 11/2010 | Vogelstein et al. |
| 7,915,015 | B2 | 3/2011 | Vogelstein et al. |
| 7,985,546 | B2 | 7/2011 | Church et al. |
| 8,071,311 | B2 | 12/2011 | Kurn |
| 8,110,351 | B2 | 2/2012 | Bosnes |
| 8,114,681 | B2 | 2/2012 | Martin et al. |
| 8,148,068 | B2 | 4/2012 | Brenner |
| 8,168,385 | B2 | 5/2012 | Brenner |
| 8,206,913 | B1 | 6/2012 | Kamberov et al. |
| 8,241,850 | B2 | 8/2012 | Brenner |
| 8,298,767 | B2 | 10/2012 | Brenner et al. |
| 8,309,306 | B2 | 11/2012 | Nolan et al. |
| 8,318,433 | B2 | 11/2012 | Brenner |
| 8,367,051 | B2 | 2/2013 | Matyjaszewski et al. |
| 8,420,324 | B2 | 4/2013 | Rashtchian et al. |
| 8,445,205 | B2 | 5/2013 | Brenner |
| 8,470,996 | B2 | 6/2013 | Brenner |
| 8,476,018 | B2 | 7/2013 | Brenner |
| 8,481,292 | B2 | 7/2013 | Casbon et al. |
| 8,535,889 | B2 | 9/2013 | Larson et al. |
| 8,563,274 | B2 | 10/2013 | Brenner et al. |
| 8,603,749 | B2 | 12/2013 | Gillevet et al. |
| 8,679,756 | B1 | 3/2014 | Brenner et al. |
| 8,685,678 | B2 | 4/2014 | Casbon et al. |
| 8,685,753 | B2 | 4/2014 | Martin et al. |
| 8,691,509 | B2 | 4/2014 | May |
| 8,715,967 | B2 | 5/2014 | Casbon et al. |
| 8,722,368 | B2 | 5/2014 | Casbon et al. |
| 8,728,766 | B2 | 5/2014 | Casbon et al. |
| 8,741,606 | B2 | 6/2014 | Casbon et al. |
| 8,835,110 | B2 | 9/2014 | Wang et al. |
| 8,835,358 | B2 | 9/2014 | Fodor et al. |
| 8,841,071 | B2 | 9/2014 | Link |
| 8,856,410 | B2 | 10/2014 | Park |
| 8,865,470 | B2 | 10/2014 | Yan et al. |
| 9,005,935 | B2 | 4/2015 | Belyaev |
| 9,040,256 | B2 | 5/2015 | Grunenwald et al. |
| 9,080,211 | B2 | 7/2015 | Grunenwald et al. |
| 9,085,801 | B2 | 7/2015 | Grunenwald et al. |
| 9,115,396 | B2 | 8/2015 | Grunenwald et al. |
| 9,150,852 | B2 | 10/2015 | Samuels et al. |
| 9,181,582 | B2 | 11/2015 | Kurn |
| 9,181,591 | B2 | 11/2015 | Robins et al. |
| 9,188,586 | B2 | 11/2015 | Fan et al. |
| 9,228,229 | B2 | 1/2016 | Olson et al. |
| 9,262,376 | B2 | 2/2016 | Tsuto |
| 9,290,808 | B2 | 3/2016 | Fodor et al. |
| 9,290,809 | B2 | 3/2016 | Fodor et al. |
| 9,297,047 | B2 | 3/2016 | Furchak et al. |
| 9,315,857 | B2 | 4/2016 | Fu et al. |
| 9,371,598 | B2 | 6/2016 | Chee |
| 9,567,645 | B2 | 2/2017 | Fan et al. |
| 9,567,646 | B2 | 2/2017 | Fan et al. |
| 9,582,877 | B2 | 2/2017 | Fu et al. |
| 9,593,365 | B2 | 3/2017 | Frisen et al. |
| 9,598,736 | B2 | 3/2017 | Fan et al. |
| 9,637,799 | B2 | 5/2017 | Fan et al. |
| 9,644,204 | B2 | 5/2017 | Hindson et al. |
| 9,677,131 | B2 | 6/2017 | Fredriksson et al. |
| 9,689,024 | B2 | 6/2017 | Hindson et al. |
| 9,695,468 | B2 | 7/2017 | Hindson et al. |
| 9,708,659 | B2 | 7/2017 | Fodor et al. |
| 9,727,810 | B2 | 8/2017 | Fodor et al. |
| 9,787,810 | B1 | 10/2017 | Chiang |
| 9,816,137 | B2 | 11/2017 | Fodor et al. |
| 9,845,502 | B2 | 12/2017 | Fodor et al. |
| 9,850,515 | B2 | 12/2017 | McCoy et al. |
| 9,856,530 | B2 | 1/2018 | Hindson et al. |
| 9,868,979 | B2 | 1/2018 | Chee et al. |

(56) References Cited

U.S. PATENT DOCUMENTS 9,879,313 B2 1/2018 Chee et al.
9,905,005 B2 2/2018 Fu et al.
9,938,523 B2 4/2018 LaBaer
9,938,524 B2 4/2018 Fernandez et al.
9,939,443 B2 4/2018 Spetzler et al.
9,951,386 B2 4/2018 Hindson et al.
9,957,549 B2 5/2018 Armour et al.
9,988,660 B2 6/2018 Rashtchian et al.
10,002,316 B2 6/2018 Fodor et al.
10,011,872 B1 7/2018 Belgrader et al.
10,017,761 B2 7/2018 Weissman et al.
10,023,910 B2 7/2018 Drmanac et al.
10,030,267 B2 7/2018 Hindson et al.
10,041,116 B2 8/2018 Hindson et al.
10,047,394 B2 8/2018 Fodor
10,059,989 B2 8/2018 Giresi et al.
10,059,991 B2 8/2018 Fodor
10,131,958 B1 11/2018 Fan et al.
10,138,518 B2 11/2018 Chun
10,150,995 B1 12/2018 Giresi et al.
10,151,003 B2 12/2018 Fan et al.
10,155,942 B2 12/2018 Kurihara
10,184,122 B2 1/2019 Grunenwald et al.
10,202,641 B2 2/2019 Shum
10,202,646 B2 2/2019 Fodor
10,208,343 B2 2/2019 Hindson et al.
10,208,356 B1 2/2019 Fan et al.
10,227,648 B2 3/2019 Hindson et al.
10,240,196 B2 3/2019 Arezi et al.
10,246,703 B2 4/2019 Church et al.
10,253,364 B2 4/2019 Hindson et al.
10,253,375 B1 4/2019 Fan et al.
10,266,874 B2 4/2019 Weissleder et al.
10,273,541 B2 4/2019 Hindson et al.
10,288,608 B2 5/2019 Kozlov et al.
10,294,511 B2 5/2019 Sanches-Kuiper et al.
10,301,677 B2 5/2019 Shum et al.
10,308,982 B2 6/2019 Chee
10,323,278 B2 6/2019 Belgrader et al.
10,337,061 B2 7/2019 Hindson et al.
10,337,062 B2 7/2019 Giresi et al.
10,338,066 B2 7/2019 Fan et al.
10,344,329 B2 7/2019 Hindson et al.
10,392,661 B2 8/2019 Fodor
10,400,235 B2 9/2019 Belhocine et al.
10,450,607 B2 10/2019 Hindson et al.
10,550,429 B2 2/2020 Harada et al.
10,619,186 B2 4/2020 Fodor et al.
10,619,203 B2 4/2020 Foder
10,619,207 B2 4/2020 Giresi et al.
RE47,983 E 5/2020 Gao et al.
10,669,570 B2 6/2020 Chang et al.
10,676,779 B2 6/2020 Chang et al.
10,689,643 B2 6/2020 Jelinek et al.
10,725,027 B2 7/2020 Bell et al.
10,738,357 B2 8/2020 Giresi et al.
10,844,372 B2 11/2020 Belhocine et al.
10,889,859 B2 1/2021 Giresi et al.
10,894,980 B2 1/2021 Chen et al.
10,907,205 B2 2/2021 Lebofsky et al.
10,914,729 B2 2/2021 Check et al.
10,927,370 B2 2/2021 Belhocine et al.
10,927,419 B2 2/2021 Fan et al.
10,934,636 B2 3/2021 Bock et al.
10,941,396 B2 3/2021 Fu et al.
10,954,570 B2 3/2021 Fan et al.
10,975,371 B2 4/2021 Salathia
11,074,991 B2 7/2021 Zheng
11,092,607 B2 8/2021 Gaublomme et al.
11,118,175 B2 9/2021 Grunenwald et al.
11,155,810 B2 10/2021 Belhocine et al.
11,198,866 B2 12/2021 Belhocine et al.
11,306,307 B2 4/2022 Jelinek et al.
11,319,583 B2 5/2022 Shum et al.
11,365,409 B2 6/2022 Shum et al.
11,390,914 B2 7/2022 Fu et al.
11,460,468 B2 10/2022 Fan et al.
11,467,157 B2 10/2022 Fan et al.
11,525,157 B2 12/2022 Shum
11,535,882 B2 12/2022 Fu et al.
11,618,929 B2 4/2023 Fan et al.
11,634,708 B2 4/2023 Fu et al.
11,661,625 B2 5/2023 Jensen et al.
11,702,706 B2 7/2023 Fan et al.
11,773,436 B2 10/2023 Chang et al.
11,773,441 B2 10/2023 Fan et al.
11,782,059 B2 10/2023 Fan et al.
11,932,849 B2 3/2024 Shum
11,932,901 B2 3/2024 Song et al.
11,939,622 B2 3/2024 Song
11,970,737 B2 4/2024 Fodor
11,993,814 B2 5/2024 Fodor
12,060,607 B2 8/2024 Fodor
12,071,617 B2 8/2024 Shum
12,084,712 B2 9/2024 Chang
2001/0024784 A1 9/2001 Wagner
2001/0036632 A1 11/2001 Yu et al.
2002/0019005 A1 2/2002 Kamb
2002/0051986 A1 5/2002 Baez et al.
2002/0065609 A1 5/2002 Ashby
2002/0072058 A1 6/2002 Voelker et al.
2002/0094116 A1 7/2002 Forst et al.
2002/0102584 A1 8/2002 Hester
2002/0106666 A1 8/2002 Hayashizaki
2002/0132241 A1 9/2002 Fan et al.
2002/0168665 A1 11/2002 Okawa
2002/0172953 A1 11/2002 Mirkin et al.
2002/0187480 A1 12/2002 Brandon
2002/0192687 A1 12/2002 Mirkin et al.
2003/0003490 A1 1/2003 Fan et al.
2003/0013091 A1 1/2003 Dimitrov
2003/0032049 A1 2/2003 Wagner
2003/0049616 A1 3/2003 Brenner et al.
2003/0077611 A1 4/2003 Slepnev
2003/0082818 A1 5/2003 Bahnson et al.
2003/0087242 A1 5/2003 Mirkin et al.
2003/0092624 A1 5/2003 Wang
2003/0104436 A1 6/2003 Morris et al.
2003/0124568 A1 7/2003 Spielvogel
2003/0143740 A1 7/2003 Wooddell
2003/0165935 A1 9/2003 Vann et al.
2003/0175908 A1 9/2003 Linnarsson
2003/0186251 A1 10/2003 Dunn et al.
2003/0207296 A1 11/2003 Park et al.
2003/0207300 A1 11/2003 Matray et al.
2004/0047769 A1 3/2004 Tanaami
2004/0091864 A1 5/2004 French et al.
2004/0096368 A1 5/2004 Davis et al.
2004/0096892 A1 5/2004 Wang et al.
2004/0121342 A1 6/2004 McKeown
2004/0142344 A1 7/2004 Bazan et al.
2004/0146901 A1 7/2004 Morris et al.
2004/0147435 A1 7/2004 Hawiger et al.
2004/0157243 A1 8/2004 Huang et al.
2004/0180361 A1 9/2004 Dahl et al.
2004/0209298 A1 10/2004 Kamberov et al.
2004/0224325 A1 11/2004 Knapp et al.
2004/0259118 A1 12/2004 Macevicz
2005/0019776 A1 1/2005 Callow et al.
2005/0032110 A1 2/2005 Shen et al.
2005/0037397 A1 2/2005 Mirkin
2005/0048500 A1 3/2005 Lawton
2005/0053952 A1 3/2005 Hong et al.
2005/0105077 A1 5/2005 Padmanabhan et al.
2005/0170373 A1 8/2005 Monforte
2005/0175993 A1 8/2005 Wei
2005/0196760 A1 9/2005 Pemov et al.
2005/0214825 A1 9/2005 Stuelpnagel
2005/0250146 A1 11/2005 McMillan
2005/0250147 A1 11/2005 Macevicz
2005/0266417 A1 12/2005 Barany
2006/0002824 A1 1/2006 Chang et al.
2006/0035258 A1 2/2006 Tadakamalla et al.
2006/0040297 A1 2/2006 Leamon et al.

(56) References Cited

U.S. PATENT DOCUMENTS

| | | | |
|---|---|---|---|
| 2006/0041385 | A1 | 2/2006 | Bauer |
| 2006/0057634 | A1 | 3/2006 | Rye |
| 2006/0073506 | A1 | 4/2006 | Christians et al. |
| 2006/0211030 | A1 | 9/2006 | Brenner |
| 2006/0257902 | A1 | 11/2006 | Mendoza et al. |
| 2006/0263709 | A1 | 11/2006 | Matsumura et al. |
| 2006/0263789 | A1 | 11/2006 | Kincaid |
| 2006/0280352 | A1 | 12/2006 | Muschler et al. |
| 2006/0281092 | A1 | 12/2006 | Wille et al. |
| 2006/0286570 | A1 | 12/2006 | Rowlen et al. |
| 2006/0294606 | A1 | 12/2006 | Moisyadi |
| 2007/0020640 | A1 | 1/2007 | Mccloskey et al. |
| 2007/0031829 | A1 | 2/2007 | Yasuno et al. |
| 2007/0042400 | A1 | 2/2007 | Choi et al. |
| 2007/0042419 | A1 | 2/2007 | Barany et al. |
| 2007/0065823 | A1 | 3/2007 | Dressman et al. |
| 2007/0065844 | A1 | 3/2007 | Golub et al. |
| 2007/0105090 | A1 | 5/2007 | Cassidy et al. |
| 2007/0117121 | A1 | 5/2007 | Hutchison et al. |
| 2007/0117134 | A1 | 5/2007 | Kou |
| 2007/0117177 | A1 | 5/2007 | Luo et al. |
| 2007/0133856 | A1 | 6/2007 | Dutta-Choudhury |
| 2007/0166741 | A1 | 7/2007 | Heil et al. |
| 2007/0172873 | A1 | 7/2007 | Brenner et al. |
| 2007/0178478 | A1 | 8/2007 | Dhallan et al. |
| 2007/0202523 | A1 | 8/2007 | Becker et al. |
| 2007/0281317 | A1 | 12/2007 | Becker et al. |
| 2008/0038727 | A1 | 2/2008 | Spier |
| 2008/0038735 | A1 | 2/2008 | Sepp |
| 2008/0064042 | A1 | 3/2008 | Bazan et al. |
| 2008/0070303 | A1 | 3/2008 | West et al. |
| 2008/0119736 | A1 | 5/2008 | Dentinger |
| 2008/0194414 | A1 | 8/2008 | Albert et al. |
| 2008/0261204 | A1 | 10/2008 | Lexow |
| 2008/0268508 | A1 | 10/2008 | Sowlay |
| 2008/0269068 | A1 | 10/2008 | Church et al. |
| 2008/0274458 | A1 | 11/2008 | Latham et al. |
| 2008/0293164 | A1 | 11/2008 | Gaylord et al. |
| 2008/0299609 | A1 | 12/2008 | Kwon et al. |
| 2008/0318802 | A1 | 12/2008 | Brenner |
| 2009/0011943 | A1 | 1/2009 | Drmanac |
| 2009/0053669 | A1 | 2/2009 | Liu et al. |
| 2009/0053698 | A1 | 2/2009 | Hayashida |
| 2009/0061513 | A1 | 3/2009 | Andersson Svahn et al. |
| 2009/0105959 | A1 | 4/2009 | Braverman et al. |
| 2009/0131269 | A1 | 5/2009 | Martin et al. |
| 2009/0137407 | A1 | 5/2009 | Church et al. |
| 2009/0163366 | A1 | 6/2009 | Nickerson |
| 2009/0208936 | A1 | 8/2009 | Tan et al. |
| 2009/0220385 | A1 | 9/2009 | Brown et al. |
| 2009/0226891 | A2 | 9/2009 | Nova et al. |
| 2009/0252414 | A1 | 10/2009 | Suzuki |
| 2009/0253586 | A1 | 10/2009 | Nelson et al. |
| 2009/0283676 | A1 | 11/2009 | Skoglund |
| 2009/0290151 | A1 | 11/2009 | Agrawal et al. |
| 2009/0298709 | A1 | 12/2009 | Ma |
| 2009/0311694 | A1 | 12/2009 | Gallagher et al. |
| 2010/0069250 | A1 | 3/2010 | White, III |
| 2010/0075436 | A1 | 3/2010 | Urdea |
| 2010/0105049 | A1 | 4/2010 | Ehrich et al. |
| 2010/0105112 | A1 | 4/2010 | Holtze et al. |
| 2010/0105886 | A1 | 4/2010 | Woudenberg et al. |
| 2010/0120098 | A1 | 5/2010 | Grunenwald et al. |
| 2010/0120630 | A1 | 5/2010 | Huang et al. |
| 2010/0136544 | A1 | 6/2010 | Agresti et al. |
| 2010/0136702 | A1 | 6/2010 | Bazan et al. |
| 2010/0151471 | A1 | 6/2010 | Faham et al. |
| 2010/0159533 | A1 | 6/2010 | Lipson et al. |
| 2010/0167354 | A1 | 7/2010 | Kurn |
| 2010/0184076 | A1 | 7/2010 | Lawton |
| 2010/0255471 | A1 | 10/2010 | Clarke |
| 2010/0267028 | A1 | 10/2010 | Pasche |
| 2010/0291666 | A1 | 11/2010 | Collier et al. |
| 2010/0297644 | A1 | 11/2010 | Kokoris |
| 2010/0298152 | A1 | 11/2010 | Brown |
| 2010/0300895 | A1 | 12/2010 | Nobile et al. |
| 2010/0304445 | A1 | 12/2010 | Szybalski |
| 2010/0323348 | A1 | 12/2010 | Hamady et al. |
| 2010/0330574 | A1 | 12/2010 | Whitman |
| 2011/0038507 | A1 | 2/2011 | Hager |
| 2011/0059436 | A1 | 3/2011 | Hardin et al. |
| 2011/0059556 | A1 | 3/2011 | Strey |
| 2011/0070584 | A1 | 3/2011 | Wohlgemuth et al. |
| 2011/0072889 | A1 | 3/2011 | Albitar et al. |
| 2011/0160078 | A1 | 6/2011 | Fodor et al. |
| 2011/0171749 | A1 | 7/2011 | Alocilja |
| 2011/0201507 | A1 | 8/2011 | Rava et al. |
| 2011/0230358 | A1 | 9/2011 | Rava |
| 2011/0244455 | A1 | 10/2011 | Larson et al. |
| 2011/0245111 | A1 | 10/2011 | Chee |
| 2011/0256549 | A1 | 10/2011 | Gaylord et al. |
| 2011/0257031 | A1 | 10/2011 | Bodeau |
| 2011/0263457 | A1 | 10/2011 | Krutzik et al. |
| 2011/0294689 | A1 | 12/2011 | Namsaraev |
| 2011/0312511 | A1 | 12/2011 | Winquist et al. |
| 2011/0319289 | A1 | 12/2011 | Libutti |
| 2012/0004132 | A1 | 1/2012 | Zhang et al. |
| 2012/0010091 | A1 | 1/2012 | Linnarson |
| 2012/0014977 | A1 | 1/2012 | Furihata et al. |
| 2012/0028828 | A1 | 2/2012 | Gaylord et al. |
| 2012/0034221 | A1 | 2/2012 | Bonvini |
| 2012/0034607 | A1 | 2/2012 | Rothberg et al. |
| 2012/0040843 | A1 | 2/2012 | Ducree et al. |
| 2012/0045844 | A1 | 2/2012 | Rothberg et al. |
| 2012/0058520 | A1 | 3/2012 | Hayashida |
| 2012/0058902 | A1 | 3/2012 | Livingston et al. |
| 2012/0065081 | A1 | 3/2012 | Chee |
| 2012/0071331 | A1 | 3/2012 | Casbon |
| 2012/0087862 | A1 | 4/2012 | Hood et al. |
| 2012/0142018 | A1 | 6/2012 | Jiang |
| 2012/0149603 | A1 | 6/2012 | Cooney et al. |
| 2012/0156675 | A1 | 6/2012 | Lueerssen et al. |
| 2012/0163681 | A1 | 6/2012 | Lohse |
| 2012/0165219 | A1 | 6/2012 | Van Der Zaag et al. |
| 2012/0173159 | A1 | 7/2012 | Davey et al. |
| 2012/0190020 | A1 | 7/2012 | Oliphant et al. |
| 2012/0202293 | A1 | 8/2012 | Martin et al. |
| 2012/0220022 | A1 | 8/2012 | Ehrlich et al. |
| 2012/0220494 | A1 | 8/2012 | Samuels et al. |
| 2012/0231972 | A1 | 9/2012 | Golyshin et al. |
| 2012/0252012 | A1 | 10/2012 | Armougom et al. |
| 2012/0252986 | A1 | 10/2012 | Liu et al. |
| 2012/0253689 | A1 | 10/2012 | Rogan |
| 2012/0316074 | A1 | 12/2012 | Saxonov |
| 2012/0322681 | A1 | 12/2012 | Kung et al. |
| 2013/0005585 | A1 | 1/2013 | Anderson et al. |
| 2013/0022977 | A1 | 1/2013 | Lapidus et al. |
| 2013/0045994 | A1 | 2/2013 | Shinozuka et al. |
| 2013/0116130 | A1 | 5/2013 | Fu et al. |
| 2013/0137094 | A1 | 5/2013 | Espina et al. |
| 2013/0190193 | A1 | 7/2013 | Bazan et al. |
| 2013/0190206 | A1 | 7/2013 | Leonard |
| 2013/0203047 | A1 | 8/2013 | Casbon et al. |
| 2013/0210643 | A1 | 8/2013 | Casbon et al. |
| 2013/0210659 | A1 | 8/2013 | Watson et al. |
| 2013/0224743 | A1 | 8/2013 | Casbon et al. |
| 2013/0225418 | A1 | 8/2013 | Watson |
| 2013/0225623 | A1 | 8/2013 | Buxbaum et al. |
| 2013/0237458 | A1 | 9/2013 | Casbon et al. |
| 2013/0267424 | A1 | 10/2013 | Casbon et al. |
| 2013/0274117 | A1 | 10/2013 | Church |
| 2013/0303461 | A1 | 11/2013 | Iafrate et al. |
| 2013/0323732 | A1 | 12/2013 | Anderson et al. |
| 2013/0338038 | A1 | 12/2013 | DuBridge |
| 2014/0004569 | A1 | 1/2014 | Lambowitz et al. |
| 2014/0057799 | A1 | 2/2014 | Johnson et al. |
| 2014/0066318 | A1 | 3/2014 | Frisen et al. |
| 2014/0093916 | A1 | 4/2014 | Belyaev |
| 2014/0100122 | A1 | 4/2014 | Rearick |
| 2014/0147860 | A1 | 5/2014 | Kaduchak et al. |
| 2014/0155274 | A1 | 6/2014 | Xie et al. |
| 2014/0155295 | A1 | 6/2014 | Hindson et al. |
| 2014/0178438 | A1 | 6/2014 | Sahin et al. |
| 2014/0194324 | A1 | 7/2014 | Gormley et al. |

(56) References Cited

U.S. PATENT DOCUMENTS

2014/0206079 A1 7/2014 Malinoski et al.
2014/0206547 A1 7/2014 Wang
2014/0216128 A1 8/2014 Trotter et al.
2014/0227684 A1 8/2014 Hindson et al.
2014/0227705 A1 8/2014 Vogelstein et al.
2014/0228239 A1 8/2014 McCoy et al.
2014/0228255 A1 8/2014 Hindson et al.
2014/0235506 A1 8/2014 Hindson et al.
2014/0243242 A1 8/2014 Nicol et al.
2014/0244742 A1 8/2014 Yu et al.
2014/0256568 A1 9/2014 Link
2014/0256918 A1 9/2014 Chu
2014/0272952 A1 9/2014 May et al.
2014/0274811 A1 9/2014 Arnold
2014/0287963 A1 9/2014 Hindson et al.
2014/0303005 A1 10/2014 Samuels et al.
2014/0309945 A1 10/2014 Park et al.
2014/0315211 A1 10/2014 Sugino et al.
2014/0322716 A1 10/2014 Robins
2014/0357500 A1 12/2014 Vigneault et al.
2014/0378322 A1 12/2014 Hindson et al.
2014/0378345 A1 12/2014 Hindson et al.
2014/0378349 A1 12/2014 Hindson et al.
2014/0378350 A1 12/2014 Hindson et al.
2015/0005185 A1 1/2015 Fodor
2015/0005199 A1 1/2015 Hindson et al.
2015/0005200 A1 1/2015 Hindson et al.
2015/0011396 A1 1/2015 Schroeder et al.
2015/0017654 A1 1/2015 Gorfinkel et al.
2015/0066385 A1 3/2015 Schnall-levin et al.
2015/0072867 A1 3/2015 Soldatov et al.
2015/0072873 A1 3/2015 Heinz et al.
2015/0080266 A1 3/2015 Volkmuth et al.
2015/0087535 A1 3/2015 Patel
2015/0099661 A1 4/2015 Fodor et al.
2015/0099673 A1 4/2015 Fodor et al.
2015/0111256 A1 4/2015 Church et al.
2015/0118680 A1 4/2015 Fodor et al.
2015/0119255 A1 4/2015 Fodor et al.
2015/0119256 A1 4/2015 Fodor et al.
2015/0119257 A1 4/2015 Fodor et al.
2015/0119258 A1 4/2015 Fodor et al.
2015/0119290 A1 4/2015 Fodor et al.
2015/0133319 A1 5/2015 Fu et al.
2015/0141292 A1 5/2015 Fodor et al.
2015/0148685 A1 5/2015 Baym
2015/0152409 A1 6/2015 Seitz et al.
2015/0203897 A1 7/2015 Robons et al.
2015/0204862 A1 7/2015 Fan et al.
2015/0211050 A1 7/2015 Iafrate et al.
2015/0218620 A1 8/2015 Behlke et al.
2015/0225777 A1 8/2015 Hindson et al.
2015/0225778 A1 8/2015 Hindson et al.
2015/0247182 A1 9/2015 Faham et al.
2015/0253237 A1 9/2015 Castellarnau et al.
2015/0259734 A1 9/2015 Asbury et al.
2015/0275295 A1 10/2015 Wang et al.
2015/0298091 A1 10/2015 Weitz
2015/0299784 A1 10/2015 Fan et al.
2015/0307874 A1 10/2015 Jaitin
2015/0329852 A1 11/2015 Nolan
2015/0337369 A1 11/2015 Davis et al.
2015/0360193 A1 12/2015 Fan et al.
2015/0376609 A1 12/2015 Hindson et al.
2016/0010151 A1 1/2016 Fan et al.
2016/0017320 A1 1/2016 Wang et al.
2016/0025735 A1 1/2016 Gaylord et al.
2016/0026758 A1 1/2016 Jabara et al.
2016/0053253 A1 2/2016 Salathia et al.
2016/0055632 A1 2/2016 Fu et al.
2016/0060621 A1 3/2016 Agresti et al.
2016/0060682 A1 3/2016 Pregibon et al.
2016/0068889 A1 3/2016 Gole et al.
2016/0122751 A1 5/2016 LaBaer
2016/0122753 A1 5/2016 Mikkelsen et al.
2016/0138086 A1 5/2016 Seelig
2016/0138091 A1 5/2016 Chee et al.
2016/0145677 A1 5/2016 Chee et al.
2016/0145683 A1 5/2016 Fan et al.
2016/0153973 A1 6/2016 Smith
2016/0201125 A1 7/2016 Samuels et al.
2016/0208322 A1 7/2016 Anderson et al.
2016/0222378 A1 8/2016 Fodor et al.
2016/0232291 A1 8/2016 Kyriazopoulou-Panagiotopoulou et al.
2016/0244742 A1 8/2016 Linnarsson et al.
2016/0244825 A1 8/2016 Vigneault et al.
2016/0244828 A1 8/2016 Mason
2016/0253584 A1 9/2016 Fodor et al.
2016/0257993 A1 9/2016 Fu et al.
2016/0258012 A2 9/2016 Sanches-Kuiper et al.
2016/0265027 A1 9/2016 Sanches-Kuiper et al.
2016/0265069 A1 9/2016 Fan et al.
2016/0266094 A1 9/2016 Ankrum et al.
2016/0289669 A1 10/2016 Fan et al.
2016/0289670 A1 10/2016 Samuels et al.
2016/0289740 A1 10/2016 Fu et al.
2016/0298180 A1 10/2016 Chee
2016/0312276 A1 10/2016 Fu et al.
2016/0320720 A1 11/2016 Murata et al.
2016/0326584 A1 11/2016 Fodor et al.
2016/0340720 A1 11/2016 Fan et al.
2016/0355879 A1 12/2016 Kamberov et al.
2016/0362730 A1 12/2016 Alexander et al.
2016/0369329 A1 12/2016 Cai
2016/0376583 A1 12/2016 Fodor et al.
2016/0376648 A1 12/2016 Fodor et al.
2017/0044525 A1 2/2017 Kaper et al.
2017/0073730 A1 3/2017 Betts et al.
2017/0089892 A1 3/2017 Aghvanyan et al.
2017/0136458 A1 5/2017 Dunne et al.
2017/0138942 A1 5/2017 Fan et al.
2017/0154421 A1 6/2017 Fu et al.
2017/0192013 A1 7/2017 Agresti et al.
2017/0260584 A1 9/2017 Zheng et al.
2017/0268981 A1 9/2017 Diebold
2017/0275669 A1 9/2017 Weissleder et al.
2017/0314067 A1 11/2017 Shum et al.
2017/0321251 A1 11/2017 Nolan
2017/0337459 A1 11/2017 Fodor et al.
2017/0342405 A1 11/2017 Fu et al.
2017/0342465 A1 11/2017 Shum et al.
2017/0342484 A1 11/2017 Shum et al.
2017/0344866 A1 11/2017 Fan et al.
2018/0002738 A1 1/2018 Wang et al.
2018/0002764 A1 1/2018 Fan et al.
2018/0016632 A1 1/2018 Penkler
2018/0016634 A1 1/2018 Hindson et al.
2018/0024139 A1 1/2018 Peikon et al.
2018/0030504 A1 2/2018 Nolan et al.
2018/0030522 A1 2/2018 Kamberov et al.
2018/0037942 A1 2/2018 Fu et al.
2018/0057873 A1 3/2018 Zhou et al.
2018/0088112 A1* 3/2018 Fan ..................... G01N 33/505
2018/0094312 A1 4/2018 Hindson et al.
2018/0094314 A1 4/2018 Hindson et al.
2018/0094315 A1 4/2018 Hindson et al.
2018/0105808 A1 4/2018 Mikkelsen et al.
2018/0112266 A1 4/2018 Hindson et al.
2018/0119143 A1 5/2018 Pirozhkova
2018/0127743 A1 5/2018 Vigneault et al.
2018/0142292 A1 5/2018 Hindson et al.
2018/0163201 A1 6/2018 Larson
2018/0179590 A1 6/2018 Belgrader et al.
2018/0179591 A1 6/2018 Belgrader et al.
2018/0201923 A1 7/2018 LaBaer
2018/0201980 A1 7/2018 Chee et al.
2018/0208975 A1 7/2018 Peterson et al.
2018/0216162 A1 8/2018 Belhocine et al.
2018/0216163 A1 8/2018 Willey
2018/0216174 A1 8/2018 Shum et al.
2018/0230527 A1 8/2018 Fang et al.
2018/0245069 A1 8/2018 Desantis et al.
2018/0251825 A1 9/2018 Stoeckius et al.

(56) References Cited

U.S. PATENT DOCUMENTS

2018/0258482 A1 9/2018 Hindson et al.
2018/0258500 A1 9/2018 Fan et al.
2018/0267036 A1 9/2018 Fan et al.
2018/0276332 A1 9/2018 Fan et al.
2018/0282803 A1 10/2018 Belgrader et al.
2018/0291470 A1 10/2018 Fan et al.
2018/0320224 A1 11/2018 Gaublomme et al.
2018/0320241 A1 11/2018 Nolan et al.
2018/0327835 A1 11/2018 Fodor et al.
2018/0327836 A1 11/2018 Fodor et al.
2018/0327838 A1 11/2018 Giresi et al.
2018/0327866 A1 11/2018 Fan et al.
2018/0327867 A1 11/2018 Fan et al.
2018/0340169 A1 11/2018 Bethocine et al.
2018/0340170 A1 11/2018 Belhocine et al.
2018/0340172 A1 11/2018 Belhocine et al.
2018/0346969 A1 12/2018 Chang et al.
2018/0346970 A1 12/2018 Chang et al.
2018/0346979 A1 12/2018 Hindson et al.
2018/0371536 A1 12/2018 Fu et al.
2019/0002971 A1 1/2019 Koslover
2019/0010552 A1 1/2019 Xu et al.
2019/0025304 A1 1/2019 Vigneault et al.
2019/0032129 A1 1/2019 Hindson et al.
2019/0040464 A1 2/2019 Giresi et al.
2019/0040474 A1 2/2019 Fan et al.
2019/0071656 A1 3/2019 Chang et al.
2019/0085324 A1 3/2019 Revev et al.
2019/0085412 A1 3/2019 Fan et al.
2019/0093146 A1 3/2019 Nolan
2019/0095578 A1 3/2019 Shum et al.
2019/0100798 A1 4/2019 Fodor et al.
2019/0119726 A1 4/2019 Shum et al.
2019/0136316 A1 5/2019 Hindson et al.
2019/0136317 A1 5/2019 Hindson et al.
2019/0136319 A1 5/2019 Hindson et al.
2019/0145982 A1 5/2019 Chee et al.
2019/0161743 A1 5/2019 Church et al.
2019/0177788 A1 6/2019 Hindson et al.
2019/0177800 A1 6/2019 Boutet et al.
2019/0185936 A1 6/2019 Babiarz
2019/0203270 A1 7/2019 Amit et al.
2019/0203291 A1 7/2019 Hindson et al.
2019/0211395 A1 7/2019 Tsao et al.
2019/0218276 A1 7/2019 Regev et al.
2019/0218607 A1 7/2019 Love et al.
2019/0221287 A1 7/2019 Tsujimoto
2019/0221292 A1 7/2019 Tsujimoto
2019/0256888 A1 8/2019 Weissleder et al.
2019/0256907 A1 8/2019 Ryan et al.
2019/0270983 A1 9/2019 Belhocine et al.
2019/0292592 A1 9/2019 Shum et al.
2019/0338278 A1 11/2019 Shum et al.
2019/0338353 A1 11/2019 Belgrader et al.
2019/0338357 A1 11/2019 Fan et al.
2019/0361017 A1 11/2019 Mallick
2019/0376058 A1 12/2019 Belhocine et al.
2019/0376118 A1 12/2019 Belhocine et al.
2019/0390253 A1 12/2019 Kennedy et al.
2020/0042007 A1 2/2020 Zhang et al.
2020/0102598 A1 4/2020 Xie et al.
2020/0109437 A1 4/2020 Chang et al.
2020/0115753 A1 4/2020 Shalek et al.
2020/0124601 A1 4/2020 Fan et al.
2020/0149037 A1 5/2020 Shum
2020/0157600 A1 5/2020 Fu et al.
2020/0190564 A1 6/2020 Shum
2020/0216877 A1 7/2020 Betts et al.
2020/0232032 A1 7/2020 Shum et al.
2020/0291454 A1 9/2020 Belhocine et al.
2020/0299764 A1 9/2020 Miller et al.
2020/0332359 A1 10/2020 Giresi et al.
2020/0385782 A1 12/2020 McDermott
2020/0407781 A1 12/2020 Schnall-Levin et al.
2021/0010070 A1 1/2021 Schnall-Levin et al.
2021/0039582 A1 2/2021 Patton et al.
2021/0047635 A1 2/2021 Gloeckner
2021/0047677 A1 2/2021 Jhutty et al.
2021/0054436 A1 2/2021 Lam et al.
2021/0102936 A1 4/2021 Belhocine et al.
2021/0123044 A1 4/2021 Zhang et al.
2021/0132078 A1 5/2021 Peikon et al.
2021/0139970 A1 5/2021 Chang et al.
2021/0164036 A1 6/2021 Lebofsky et al.
2021/0190770 A1 6/2021 Delaney
2021/0198754 A1 7/2021 Fan et al.
2021/0213413 A1 7/2021 Saligrama et al.
2021/0214770 A1 7/2021 Prosen et al.
2021/0214784 A1 7/2021 Prosen et al.
2021/0222163 A1 7/2021 Wu et al.
2021/0222244 A1 7/2021 Martin et al.
2021/0230582 A1 7/2021 Fu et al.
2021/0230583 A1 7/2021 Lam et al.
2021/0230666 A1 7/2021 Wu et al.
2021/0246492 A1 8/2021 Song et al.
2021/0263019 A1 8/2021 Martin et al.
2021/0269849 A1 9/2021 Giresi
2021/0270818 A1 9/2021 Bell et al.
2021/0285045 A1 9/2021 Giresi et al.
2021/0332354 A1 10/2021 Shah et al.
2021/0355484 A1 11/2021 Jensen et al.
2021/0364502 A1 11/2021 Belhocine et al.
2021/0371909 A1 12/2021 Lazaruk
2021/0371914 A1 12/2021 Stoeckius et al.
2022/0010361 A1 1/2022 Song et al.
2022/0010362 A1 1/2022 Campbell
2022/0033810 A1 2/2022 Song et al.
2022/0154288 A1 5/2022 Mortimer
2022/0162695 A1 5/2022 Sakofsky et al.
2022/0162773 A1 5/2022 Sakofsky et al.
2022/0178909 A1 6/2022 Huang et al.
2022/0214356 A1 7/2022 Henikoff et al.
2022/0219170 A1 7/2022 Khurana et al.
2022/0220549 A1 7/2022 Shum et al.
2022/0228203 A1 7/2022 Henikoff et al.
2022/0259586 A1 8/2022 Belhocine et al.
2022/0267759 A1 8/2022 Sanjana et al.
2022/0333185 A1 10/2022 Fu et al.
2022/0348904 A1 11/2022 Shum et al.
2022/0372554 A1 11/2022 Yang et al.
2023/0083422 A1 3/2023 Fu et al.
2023/0109336 A1 4/2023 Shum et al.
2023/0125113 A1 4/2023 Fan et al.
2023/0193372 A1 6/2023 Shum et al.

FOREIGN PATENT DOCUMENTS

CN 103443338 A 12/2013
CN 104364392 2/2015
CN 104812915 7/2015
CN 105705659 A 6/2016
CN 105886500 A 8/2016
CN 105886620 A 8/2016
CN 106460033 A 2/2017
CN 107208158 A 9/2017
CN 107250379 A 10/2017
CN 107580632 A 1/2018
CN 109526228 A 3/2019
CN 109791157 A 5/2019
CN 110382708 10/2019
CN 110498858 A 11/2019
CN 110719959 A 1/2020
CN 110741092 A 1/2020
DE 102008025656 12/2009
EP 0799897 A1 10/1997
EP 1250463 10/2002
EP 1473080 A2 11/2004
EP 1647600 A2 4/2006
EP 1845160 A1 10/2007
EP 2036989 A1 3/2009
EP 1379693 B1 5/2009
EP 2204456 A1 7/2010
EP 2431465 A1 3/2012
EP 2203749 B1 8/2012

(56) References Cited

FOREIGN PATENT DOCUMENTS

| | | | |
|---|---|---|---|
| EP | 2511708 | A1 | 10/2012 |
| EP | 2538220 | A1 | 12/2012 |
| EP | 2623613 | A1 | 8/2013 |
| EP | 2675819 | | 12/2013 |
| EP | 2697391 | | 2/2014 |
| EP | 2702146 | | 3/2014 |
| EP | 1745155 | B1 | 10/2014 |
| EP | 2805769 | A1 | 11/2014 |
| EP | 2820158 | | 1/2015 |
| EP | 2852682 | | 4/2015 |
| EP | 2861760 | | 4/2015 |
| EP | 2556171 | B1 | 9/2015 |
| EP | 2954065 | | 12/2015 |
| EP | 2989215 | | 3/2016 |
| EP | 3013983 | | 5/2016 |
| EP | 3013984 | | 5/2016 |
| EP | 3089822 | | 11/2016 |
| EP | 3137601 | | 3/2017 |
| EP | 3161160 | | 5/2017 |
| EP | 3234602 | | 10/2017 |
| EP | 2970958 | B1 | 12/2017 |
| EP | 3262192 | | 1/2018 |
| EP | 3263715 | A1 | 1/2018 |
| EP | 3286326 | | 2/2018 |
| EP | 2670863 | B1 | 6/2018 |
| EP | 3341494 | | 7/2018 |
| EP | 3347465 | | 7/2018 |
| EP | 3136103 | B1 | 8/2018 |
| EP | 3353326 | | 8/2018 |
| EP | 2954102 | B1 | 12/2018 |
| EP | 3428290 | A1 | 1/2019 |
| EP | 3436581 | | 2/2019 |
| EP | 2970957 | B1 | 4/2019 |
| EP | 3465502 | | 4/2019 |
| EP | 3058092 | B1 | 5/2019 |
| EP | 3256606 | B1 | 5/2019 |
| EP | 3480321 | | 5/2019 |
| EP | 3516400 | | 7/2019 |
| EP | 3327123 | B1 | 8/2019 |
| EP | 3529357 | | 8/2019 |
| EP | 3587589 | A1 | 1/2020 |
| GB | 2293238 | A | 3/1996 |
| JP | H04108385 | | 4/1992 |
| JP | 2001078768 | A | 3/2001 |
| JP | 2001517460 | | 10/2001 |
| JP | 2002253237 | | 9/2002 |
| JP | 2005233974 | A | 9/2005 |
| JP | 2007504831 | A | 3/2007 |
| JP | 2008256428 | A | 10/2008 |
| JP | 2012506704 | | 3/2012 |
| JP | 2013039275 | A | 2/2013 |
| JP | 2015511819 | A | 4/2015 |
| JP | 2015533296 | | 11/2015 |
| JP | 2016533187 | A | 10/2016 |
| JP | 2018501776 | | 1/2018 |
| JP | 2018509896 | A | 4/2018 |
| JP | 2018535652 | A | 12/2018 |
| JP | 2019522268 | | 8/2019 |
| JP | 7413351 | | 1/2024 |
| WO | WO1989001050 | | 2/1989 |
| WO | WO1996024061 | | 8/1996 |
| WO | WO1997010365 | | 3/1997 |
| WO | WO1999015702 | | 4/1999 |
| WO | WO1999028505 | | 6/1999 |
| WO | WO2000058516 | | 10/2000 |
| WO | WO2001020035 | | 3/2001 |
| WO | WO2001048242 | | 7/2001 |
| WO | WO2001053539 | | 7/2001 |
| WO | WO2002018643 | | 3/2002 |
| WO | WO2002046472 | | 6/2002 |
| WO | WO2002056014 | | 7/2002 |
| WO | WO2002059355 | | 8/2002 |
| WO | WO2002070684 | | 9/2002 |
| WO | WO2002072772 | | 9/2002 |
| WO | WO2002079490 | | 10/2002 |
| WO | WO2002083922 | | 10/2002 |
| WO | WO2002101358 | | 12/2002 |
| WO | WO2003031591 | | 4/2003 |
| WO | WO2003035829 | | 5/2003 |
| WO | WO2004017374 | | 2/2004 |
| WO | WO2004021986 | | 3/2004 |
| WO | WO2004033669 | | 4/2004 |
| WO | WO2004066185 | | 8/2004 |
| WO | WO2004081225 | | 9/2004 |
| WO | WO2005010209 | | 2/2005 |
| WO | WO2005017206 | | 2/2005 |
| WO | WO2005021731 | | 3/2005 |
| WO | WO2005026329 | | 3/2005 |
| WO | WO2005042759 | | 5/2005 |
| WO | WO2005071110 | | 8/2005 |
| WO | WO2005080604 | | 9/2005 |
| WO | WO2005111242 | | 11/2005 |
| WO | WO2005111243 | | 11/2005 |
| WO | WO2006026828 | | 3/2006 |
| WO | WO2006071776 | | 7/2006 |
| WO | WO2006102264 | | 9/2006 |
| WO | WO2006137932 | | 12/2006 |
| WO | WO2007087310 | | 8/2007 |
| WO | WO2007087312 | | 8/2007 |
| WO | WO2007147079 | | 12/2007 |
| WO | WO2008047428 | | 4/2008 |
| WO | WO2008051928 | | 5/2008 |
| WO | WO2008057163 | | 5/2008 |
| WO | WO2008096318 | | 8/2008 |
| WO | WO2008104380 | | 9/2008 |
| WO | WO2008147428 | | 12/2008 |
| WO | WO2008150432 | | 12/2008 |
| WO | WO2009048530 | | 4/2009 |
| WO | WO2009148560 | | 12/2009 |
| WO | WO2009152928 | | 12/2009 |
| WO | WO2010048605 | | 4/2010 |
| WO | WO2010059820 | | 5/2010 |
| WO | WO2010117620 | | 10/2010 |
| WO | WO2010128091 | | 11/2010 |
| WO | WO2010131645 | | 11/2010 |
| WO | WO2011091393 | | 7/2011 |
| WO | WO2011106738 | | 9/2011 |
| WO | WO2011123246 | | 10/2011 |
| WO | WO2011127099 | | 10/2011 |
| WO | WO2011142836 | | 11/2011 |
| WO | WO2011143659 | | 11/2011 |
| WO | WO2011155833 | | 12/2011 |
| WO | WO2011156529 | | 12/2011 |
| WO | WO2012038839 | | 3/2012 |
| WO | WO2012041802 | | 4/2012 |
| WO | WO2012042374 | | 4/2012 |
| WO | WO2012047297 | | 4/2012 |
| WO | WO2012048341 | | 4/2012 |
| WO | WO2012083225 | | 6/2012 |
| WO | WO2012099896 | | 7/2012 |
| WO | WO2012103154 | | 8/2012 |
| WO | WO2012106385 | | 8/2012 |
| WO | WO2012106546 | | 8/2012 |
| WO | WO2012108864 | | 8/2012 |
| WO | WO2012112804 | | 8/2012 |
| WO | WO2012129363 | | 9/2012 |
| WO | WO2012140224 | | 10/2012 |
| WO | WO2012142213 | | 10/2012 |
| WO | WO2012148477 | | 11/2012 |
| WO | WO2012148497 | | 11/2012 |
| WO | WO2012149042 | | 11/2012 |
| WO | WO2012156744 | | 11/2012 |
| WO | WO2012162267 | | 11/2012 |
| WO | WO2012177639 | | 12/2012 |
| WO | WO2013019075 | | 2/2013 |
| WO | WO2013070990 | | 5/2013 |
| WO | WO2013096802 | | 6/2013 |
| WO | WO2013117595 | | 8/2013 |
| WO | WO2013130674 | | 9/2013 |
| WO | WO2013137737 | | 9/2013 |
| WO | WO2013148525 | | 10/2013 |
| WO | WO2013173394 | | 11/2013 |
| WO | WO2013176767 | | 11/2013 |
| WO | WO2013177206 | | 11/2013 |

(56) References Cited

FOREIGN PATENT DOCUMENTS

| | | | |
|---|---|---|---|
| WO | WO2013188831 | 12/2013 | |
| WO | WO2013188872 | 12/2013 | |
| WO | WO2013191775 | 12/2013 | |
| WO | WO2014015084 | 1/2014 | |
| WO | WO2014015098 | 1/2014 | |
| WO | WO2014018093 | 1/2014 | |
| WO | WO2014018460 | 1/2014 | |
| WO | WO2014028537 | 2/2014 | |
| WO | WO2014031997 | 2/2014 | |
| WO | WO2014062717 | 4/2014 | |
| WO | WO2014065756 | 5/2014 | |
| WO | WO2014093676 | 6/2014 | |
| WO | WO2014108850 | 7/2014 | |
| WO | WO2014124046 | 8/2014 | |
| WO | WO2014124336 | 8/2014 | |
| WO | WO2014124338 | 8/2014 | |
| WO | WO2014126937 | 8/2014 | |
| WO | WO2014144495 | 9/2014 | |
| WO | WO2014145458 | 9/2014 | |
| WO | WO2014176575 | 10/2014 | |
| WO | WO2014189957 | 11/2014 | |
| WO | WO2014200767 | 12/2014 | |
| WO | WO2014201273 | 12/2014 | |
| WO | WO2014204939 | 12/2014 | |
| WO | WO2014210223 | 12/2014 | |
| WO | WO2014210225 | 12/2014 | |
| WO | WO2014210353 | 12/2014 | |
| WO | WO2015002908 | 1/2015 | |
| WO | WO2018015365 | 1/2015 | |
| WO | WO2015017586 | 2/2015 | |
| WO | WO2015031691 | 3/2015 | |
| WO | WO2015035087 | 3/2015 | |
| WO | WO2015044428 | 4/2015 | |
| WO | WO2015047186 | 4/2015 | |
| WO | WO2015057985 | 4/2015 | |
| WO | WO2014071361 | 5/2015 | |
| WO | WO2015061844 | 5/2015 | |
| WO | WO2015103339 | 7/2015 | |
| WO | WO2015104302 | 7/2015 | |
| WO | WO2015117163 | 8/2015 | |
| WO | WO2015134787 | 9/2015 | |
| WO | WO2015160439 | 10/2015 | |
| WO | WO2015168161 | 11/2015 | |
| WO | WO2015179339 | 11/2015 | |
| WO | WO2015188839 | 12/2015 | |
| WO | WO-2015188839 A2 * | 12/2015 | ........... G01N 33/532 |
| WO | WO2015200869 | 12/2015 | |
| WO | WO2015200893 | 12/2015 | |
| WO | WO2016044227 | 3/2016 | |
| WO | WO2016049418 | 3/2016 | |
| WO | WO2016061517 | 4/2016 | |
| WO | WO2016073690 | 5/2016 | |
| WO | WO2016100976 | 6/2016 | |
| WO | WO2016118915 | 7/2016 | |
| WO | WO2016126871 | 8/2016 | |
| WO | WO2016130578 | 8/2016 | |
| WO | WO2016160965 | 8/2016 | |
| WO | WO2016138490 | 9/2016 | |
| WO | WO2016138496 | 9/2016 | |
| WO | WO2016138500 | 9/2016 | |
| WO | WO2016145409 | 9/2016 | |
| WO | WO2016149418 | 9/2016 | |
| WO | WO2016160844 | 10/2016 | |
| WO | WO2016168825 | 10/2016 | |
| WO | WO2016172373 | 10/2016 | |
| WO | WO2016176091 | 11/2016 | |
| WO | WO2016190795 | 12/2016 | |
| WO | WO2016191272 | 12/2016 | |
| WO | WO2017025594 | 2/2017 | |
| WO | WO2017032808 | 3/2017 | |
| WO | WO2017040306 | 3/2017 | |
| WO | WO2017044574 | 3/2017 | |
| WO | WO2017048993 | 3/2017 | |
| WO | WO2017053905 | 3/2017 | |
| WO | WO2017075265 | 5/2017 | |
| WO | WO2017079593 | 5/2017 | |
| WO | WO2017087873 | 5/2017 | |
| WO | WO2017096239 | 6/2017 | |
| WO | WO2017097939 | 6/2017 | |
| WO | WO2017117358 | 7/2017 | |
| WO | WO2017125508 | 7/2017 | |
| WO | WO2017139690 | 8/2017 | |
| WO | WO2017156336 | 9/2017 | |
| WO | WO2017164936 | 9/2017 | |
| WO | WO2017171985 | 10/2017 | |
| WO | WO2017173328 | 10/2017 | |
| WO | WO2017204940 | 11/2017 | |
| WO | WO2017205691 | 11/2017 | |
| WO | WO2018013724 | 1/2018 | |
| WO | WO2018017949 | 1/2018 | |
| WO | WO2018018008 | 1/2018 | |
| WO | WO2018020489 | 2/2018 | |
| WO | WO2018031631 | 2/2018 | |
| WO | WO2018058073 | 3/2018 | |
| WO | WO2018064640 | 4/2018 | |
| WO | WO2018075693 | 4/2018 | |
| WO | WO2018111872 | 6/2018 | |
| WO | WO2018115852 | 6/2018 | |
| WO | WO2018119447 | 6/2018 | |
| WO | WO2018119452 | 6/2018 | |
| WO | WO2018132635 | 7/2018 | |
| WO | WO2018140966 | 8/2018 | |
| WO | WO2018144240 | 8/2018 | |
| WO | WO2018144813 | 8/2018 | |
| WO | WO2018152129 | 8/2018 | |
| WO | WO2018165366 | 9/2018 | |
| WO | WO2018174827 | 9/2018 | |
| WO | WO2018217862 | 11/2018 | |
| WO | WO2018217912 | 11/2018 | |
| WO | WO2018218222 | 11/2018 | |
| WO | WO2018218226 | 11/2018 | |
| WO | WO2018222548 | 12/2018 | |
| WO | WO2018226293 | 12/2018 | |
| WO | WO2019055852 | 3/2019 | |
| WO | WO2019076768 | 4/2019 | |
| WO | WO2019084043 | 5/2019 | |
| WO | WO2019084046 | 5/2019 | |
| WO | WO2019089959 | 5/2019 | |
| WO | WO2019099906 | 5/2019 | |
| WO | WO2019113457 | 6/2019 | |
| WO | WO2019113499 | 6/2019 | |
| WO | WO2019113506 | 6/2019 | |
| WO | WO2019113533 | 6/2019 | |
| WO | WO2019118355 | 6/2019 | |
| WO | WO2019126789 | 6/2019 | |
| WO | WO2019157529 | 8/2019 | |
| WO | WO2019178164 | 9/2019 | |
| WO | WO2019210049 | 10/2019 | |
| WO | WO2019213237 | 11/2019 | |
| WO | WO2019213294 | 11/2019 | |
| WO | WO2019218101 | 11/2019 | |
| WO | WO2020009665 | 1/2020 | |
| WO | WO2020028266 | 2/2020 | |
| WO | WO2020033164 | 2/2020 | |
| WO | WO2020037065 | 2/2020 | |
| WO | WO2020041148 | 2/2020 | |
| WO | WO2020046833 | 3/2020 | |
| WO | WO2020047005 | 3/2020 | |
| WO | WO2020072380 | 4/2020 | |
| WO | WO2020097315 | 5/2020 | |
| WO | WO2020123384 | 6/2020 | |
| WO | WO2020131626 | 6/2020 | |
| WO | WO2020131699 | 6/2020 | |
| WO | WO2020154247 | 7/2020 | |
| WO | WO2020159757 | 8/2020 | |
| WO | WO2020167830 | 8/2020 | |
| WO | WO2020167920 | 8/2020 | |
| WO | WO2020168013 | 8/2020 | |
| WO | WO2020247685 | 8/2020 | |
| WO | WO2020176788 | 9/2020 | |
| WO | WO2020214642 | 10/2020 | |
| WO | WO2020219721 | 10/2020 | |
| WO | WO2020242377 | 12/2020 | |
| WO | WO2020243160 | 12/2020 | |

(56) References Cited

FOREIGN PATENT DOCUMENTS

| | | |
|---|---|---|
| WO | WO2021011433 | 1/2021 |
| WO | WO2021046232 | 3/2021 |
| WO | WO2021092386 | 5/2021 |
| WO | WO2021102039 | 5/2021 |
| WO | WO2021113353 | 6/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021163611 | 8/2021 |
| WO | WO2021168015 | 8/2021 |
| WO | WO2021168261 | 8/2021 |
| WO | WO2021178199 | 9/2021 |
| WO | WO2021231779 | 11/2021 |
| WO | WO2021247593 | 12/2021 |
| WO | WO2021257795 | 12/2021 |
| WO | WO2021262671 | 12/2021 |
| WO | WO2021262805 | 12/2021 |
| WO | WO2022015667 | 1/2022 |
| WO | WO2022026243 | 2/2022 |
| WO | WO2022026909 | 2/2022 |
| WO | WO2022040453 | 2/2022 |
| WO | WO2022115608 A1 | 2/2022 |
| WO | WO2022115608 A9 | 2/2022 |
| WO | WO2022056309 | 3/2022 |
| WO | WO2022076912 | 4/2022 |
| WO | WO2022094474 | 5/2022 |
| WO | WO2022109339 | 5/2022 |
| WO | WO2022109343 | 5/2022 |
| WO | WO2022132206 | 6/2022 |
| WO | WO2022143221 | 7/2022 |
| WO | WO2022256324 | 12/2022 |
| WO | WO2023034739 | 3/2023 |
| WO | WO2023034789 | 3/2023 |
| WO | WO2023034790 | 3/2023 |
| WO | WO2023034794 | 3/2023 |
| WO | WO2023034872 | 3/2023 |
| WO | WO2023039433 | 3/2023 |
| WO | WO2024097718 | 5/2024 |
| WO | WO2024097719 | 5/2024 |
| WO | WO2024243298 | 11/2024 |

OTHER PUBLICATIONS

Adey et al., "Rapid, low-input, low-bias construction of shotgun fragment libraries by high-density in vitro transposition," Genome Biology 2010, 11(R19), in 17 pages.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.
Ahern, "Biochemical, Reagent Kits Offer Scientists Good Return on Investment," The Scientist 1995, 9(15), in 5 pages.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, Aug. 21, 2010, "Useful fundamental Nos. in molecular biology," 2001-2004. http://bionumbers.hms.harvard.edu/KeyNumbers/aspx, 1-4.
Biosciences Product Catalogue, Dynal® Catalog 1999, Oslo, Norway, 49-51.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.

(56) References Cited

OTHER PUBLICATIONS

Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis, " Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research 2002, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "SMART™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Complaint filed in *Becton, Dickinson and Company and Cellular Research Inc.* v. *10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila,*" Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.

(56) References Cited

OTHER PUBLICATIONS

Delley et al., "Combined aptamer and transcriptome sequencing of single cells," bioRxiv 2017, 1-10.
Dengl et al., "Engineered hapten-binding antibody derivatives for modulation of pharmacokinetic properties of small molecules and targeted payload delivery," Immunol Rev. 2016, 270, 165-177.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Extended European Search Report dated May 6, 2021 in European Patent Application No. 20207621.2.
Extended European Search Report dated May 28, 2021 in European Patent Application No. 20209777.0.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," SCIENCE 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.

(56) References Cited

OTHER PUBLICATIONS

Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Fitzgerald and Grivel, "A Universal Nanoparticle Cell Secretion Capture Assay," Cytometry Part A 2012, 83A(2), 205-211.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
GenBank Accession No. NM_000518.5 for Homo sapiens hemoglobin subunit beta (HBB), mRNA. Mar. 22, 2021 [online], [retrieved on Apr. 27, 2021], retrieved from the Internet: <URL: www.ncbi.nlm.nih.gov/nuccore/NM_000518.5?report=Genbank (Year: 2021).
Gerry et al., "Universal DNA Microarray Method for Multiplex Detection of Low Abundance Point Mutations," Journal of Molecular Biology 1999, 292, 251-262.
Gertz et al., "Transposase mediated construction of RNA-seq libraries," Genome Research 2012, 22, 134-141.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Grant et al., "SNP genotyping on a genome-wide amplified DOP-PCR template," Nucleic Acids Res 2002, 30(22), e25, 1-6.
Gratton et al., "Cell-permeable peptides improve cellular uptake and therapeutic gene delivery of replication-deficient viruses in cells and in vivo," Nature Medicine 2003, 9(3), 357-362.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.

(56) References Cited

OTHER PUBLICATIONS

Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Nov. 12, 2021, in PCT Application No. PCT/US2021/044036.
International Search Report and Written Opinion dated Nov. 6, 2021, in PCT Application No. PCT/US2021/044036.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 25, 2021 in PCT Application No. PCT/US2021/01598.
Invitation to Pay Additional Search Fees dated May 7, 2020 in PCT Application No. PCT/US2020/017890.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from aretroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Janeway et al., "Structural variation in immunoglobulin constant regions," Immunology: The Immune System in Health and Disease 1999, 101-103.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.

(56) References Cited

OTHER PUBLICATIONS

Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting DrugResistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture toAchieve High Sensitivity, Fast Response, and Robust Behavior," Journal of Polymer Science: Part B: Polymer Physics 2011, 49, 173-178.
Kivioja et al., "Counting absolute Nos. of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.
Kotake et al., "A simple nested RT-PCR method for quantitation of the relative amounts of multiple cytokine mRNAs in small tissue samples," Journal of Immunological Methods 1996, 199, 193-203.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Lan et al., "Droplet barcoding for massively parallel single-molecule deep sequencing," Nature Communications 2016, 7(11784), in 10 pages.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Livingstone, "rRNA depletion, poly(A) enrichment, or exonuclease treatment?" Tebu-Bio Blog 2015, in 1 page.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," ThermoFisher Scientific, Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Lutz et al., "Isolation and analysis of high quality nuclear DNA with reduced organellar DNA for plant genome sequencing and resequencing," BMC Biotechnology 2011, 11(54), in 9 pages.
Maamar et al., "Noise in Gene Expression Determines Cell Fate in Bacillus subtilis," Science 2007, 317, 526-529.
Macaulay et al., "Single Cell Genomics: Advances and Future Perspectives," PLoS Genetics 2014, 10(1), 1-9.
Macaulay et al., "G&T-seq: parallel sequencing of single-cell genomes and transcriptomes," Nature Methods 2015, 1-7.

(56) References Cited

OTHER PUBLICATIONS

Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Mair et al., "A Targeted Multi-omic Analysis Approach Measures Protein Expression and Low-Abundance Transcripts on the Single-Cell Level", Cell Reports 2020, 31(1), 107499, in 20 pages.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
Mccloskey et al., "Encoding PCR products with batch-stamps and barcodes," Biochem Genet. 2007, 45(11-12), 761-767.
Medvedev et al., "Detecting copy No. variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Monneron, "One-step Isolation and Characterization of Nuclear Membranes, 1974 ElectronMicroscopy and Composition of Biological Membranes and Envelops," The Royal Publishing Society 1974, 268, 101-108.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
New COVID-19 Variants, Centers for Disease Control and Prevention 2021, accessed Jan. 21, 2021, 3 pp.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.

(56) References Cited

OTHER PUBLICATIONS

Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice of Allowance dated Sep. 23, 2020 in Korean Patent Application No. 10-2016-7008144.
Notice of Allowance dated Oct. 29, 2020 in U.S. Appl. No. 15/987,851.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice of Allowance dated Jun. 10, 2021 in Chinese Patent Application No. 2018800377201.
Notice of Allowance dated Aug. 16, 2021 in Japanese Patent Application No. 2018-512152.
Notice of Allowance dated Sep. 10, 2021 in U.S. Appl. No. 16/535,080.
Notice of Allowance dated Nov. 16, 2021 in U.S. Appl. No. 16/836,750.
Notice of Allowance dated Jan. 24, 2022 in Korean Patent Application No. 16/836,750.
Notice of Allowance dated Feb. 9, 2022 in U.S. Appl. No. 16/781,814.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.

(56) References Cited

OTHER PUBLICATIONS

Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novus Biologicals, "Fixation and Permeability in ICC IF," Novus Biologicals 2021, 1-3.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991 .
Office Action dated Aug. 27, 2021 in Chinese Patent Application No. 2016800076525.
Office Action dated Aug. 30, 2021 in Japanese Patent Application No. 2019-540515 .
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Dec. 23, 2021, in Japanese Patent Application No. 2019-566787.
Office Action dated Dec. 17, 2021 in Korean Patent Application No. 10-2018-7008560.
Office Action dated Feb. 9, 2022 in Japanese Patent Application No. 2019-540515.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Ozkumur et al., "Inertial Focusing for Tumor Antigen-Dependent and - Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes andsample integrity: BestKeeper—Excel-based tool using pair-wise correlations," Biotechnology Letters 2004, 26(6), 505-515.

(56) References Cited

OTHER PUBLICATIONS

Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible bymicrofluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tagsfrom a Maize cDNA Library Constructed Using Multiple mRNA Sources," Plant Physiol. 2003, 133, 475-481.
Quail et al., "SASI-Seq: sample assurance Spike-Ins, and highly differentiating 384 barcoding for Illumina sequencing," BMC Genomics 2014, 15(110), in 13 pages.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated May 5, 2021 in U.S. Appl. No. 16/400,886.
Restriction Requirement dated May 28, 2021 in U.S. Appl. No. 16/781,814.
Restriction Requirement dated Jun. 19, 2019 in U.S. Appl. No. 15/596,364.
Restriction Requirement dated Jun. 4, 2021 in U.S. Appl. No. 16/551,620.
Restriction Requirement dated Sep. 20, 2019 in U.S. Appl. No. 15/875,816.
Restriction Requirement dated Sep. 20, 2021 in U.S. Appl. No. 16/525,054.
Restriction Requirement dated Oct. 1, 2021 in U.S. Appl. No. 16/525,054.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Schouten et al., "Relative quantification of 40 nucleic acid sequences by multiplex ligation-dependent probe amplification," Nucleic Acids Research 2002, 30(12), e57.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shapiro et al., "Single-cell sequencing-based technologies will revolutionize whole-organism science," Nature Reviews Genetics 2013, 14, 618-629.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.Ko, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.

(56) References Cited

OTHER PUBLICATIONS

Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stoeckius et al., "Cell Hashing with barcoded antibodies enables multiplexing and doublet detection for single cell genomics," Genome Biology 2018, 19(224), 1-12.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Summons to Attend Oral Proceedings dated Nov. 16, 2020 in European Patent Application No. 17202409.3.
Sun et al., "Ultra-deep profiling of alternatively spliced *Drosophila* Dscam isoforms by circularization-assisted multi-segment sequencing," Embo J. 2013, 32(14), 2029-2038.
Takahashi et al., "Novel technique of quantitative nested real-time PCR assay for *Mycobacterium tuberculosis* DNA," Journal of Clinical Microbiology 2006, 44, 1029-1039.
Takara Bio, "SMARTer Human BCR IgG IgM H/K/L Profiling Kit User Manual," Takara Bio USA Inc. 2019, 1-22.
Tan et al., "Genome-wide comparison of DNA hydroxymethylation in mouse embryonic stem cells andneural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy No. estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
TotalSeq™-A0251 anti-human Hashtag 1 Antibody, BioLegend®, Jul. 2018, 1-10.
Treutlein et al., Reconstructing lineage hierarchies of the distal lung epithelium using single-cell RNA-seq, Nature 2014, 509, 371-375.
Trzupek et al., "Discovery of CD8O and CD86 as recent activation markers on regulatory T cells by protein-RNA single-cell analysis", Genome Medicine 2020, 12(1), in 22 pages.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vestheim et al., "Application of Blocking Oligonucleotides to Improve Signal-to-Noise Ratio in a PCR," Methods in Molecular Biology 2011, 687, 265-274.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Wang et al., "Tagmentation-based whole-genome bisulfite sequencing," Nature Protocols 2013, 8(10), 2022-2032.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae,*" Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quan-

(56) References Cited

OTHER PUBLICATIONS tities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Yang & Zhao, "Quantitative Analysis of Nonoxynol-9 in Blood," Contraception 1991, 43(2), 161-166.
Ye et al., "Fluorescent microsphere-based readout technology for multiplexed human single nucleotide polymorphism analysis and bacterial identification," Human Mutation 2001, 17(4), 305-316.
Yoon et al., "Sensitive and accurate detection of copy number variants using read depth of coverage," Genome Res. 2009, 19, 1586-1592.
Zeberg et al., "The major genetic risk factor for severe COVID-19 is inherited from Neanderthals," Nature 2020, 587(7835), 1-13.
Zagordi et al., "Error correction of next-generation sequencing data and reliable estimation of HIV quasispecies," Nucleic Acids Research 2010, 38(21), 7400-7409.
Zhang et al., "Immunoaffinity Purification of Plasma Membrane with Secondary Antibody Superparamagnetic Beads," Journal of Proteome 2006, 6, 34-43.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung CarcinomasRevealed by Single Nucleotide Polymorphism Array Analysis," Cancer Research 2005, 65(13), 5561-5570.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
10X Genomics, Inc., 2022, "Chromium Fixed RNA Profiling Reagent Kits." 10xGenomics.com. User Guide, in 95 pages.
10x_LIT099_Product-Sheet_Chromium-Single-Cell-Multiome-ATAC-Gene-Expression_Letter_digital.
Advisory Action dated May 31, 2023 in U.S. Appl. No. 16/789,311.
Arguel et al., "A cost effective 5' selective single cell transcriptome profiling approach with improved UMI design." Nucleic Acids Research 2017, 45(7), e48, in 11 pages.
Armbrecht, et al. "Single-cell protein profiling in microchambers with barcoded beads", Microsystems & Nanoengineering, 2019, 5:55.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Buenrostro et al., "Transposition of native chromatin for multimodal regulatory analysis and personal epigenomics," Nat Methods 2013, 10(12), 1213-1218.
Buenrostro et al., "ATAC-seq: A Method for Assaying Chromatin Accessibility Genome-Wide," Curr Protoc Mol Biol 2016, 109, 1-21.
CG000209_Chromium_NextGEM_SingleCell_ATAC_ReagentKits_v1.1_UserGuide_RevG.
CG000496_Chromium_NextGEM_SingleCell_ATAC_ReagentKits_v2_UserGuide_RevB.
CG000505_Chromium_Nuclei_Isolation_Kit_UG_RevA.
Chang et al., "Single-cell protein and gene expression profiling of stem memory T cells by BD Ab-seq," Annual Joint Meeting of the American Society for Cell Biology and the European Molecular Biology Organization 2017, 28(26), p. 1896.
Chen et al., "High-throughput sequencing of the transcriptome and chromatin accessibility in the same cell," Nature Biotechnology 2019, 37, 1452-1457.
De Simone et al., "Single Cell T Cell Receptor Sequencing: Techniques and Future Challenges," Frontiers in Immunology 2018, 9(1638), 1-7.
Decision of Grant dated Aug. 21, 2023 in Japanese Patent Application 2020-561800.
Delebecque et al. "Designing and using RNA scaffolds to assemble proteins in vivo". Nature protocols, 2012, 7(10), 1797-1807.
Dickey and Giangrande. "Oligonucleotide Aptamers: A Next-Generation Technology for the Capture and Detection of Circulating Tumor Cells." Methods, 2016 97:94-103.
Dovgan et al., "Antibody-Oligonucleotide Conjugates as Therapeutic, Imaging, and Detection Agents," Bioconjugate Chem. 2019, 30, 2483-2501.
Dua, et al. "Patents on SELEX and therapeutic aptamers. Recent patents on DNA & gene sequences," 2008, 2( 3), 172-186.
Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Eulberg, et al. "Development of an automated in vitro selection protocol to obtain RNA-based aptamers: identification of a biostable substance P antagonist," Nucleic acids research, 2005, 33(4) e45. https://doi.org/ 10.1093/nar/gni044.
Examination Report dated Apr. 7, 2022 in Singapore Patent Application No. 10201806890V.
Examination Report dated Apr. 8, 2022 in Australian Patent Application No. 2018281745.
Examination Report dated Oct. 31, 2023 in European Patent Application 20753616.0.
Examination Report dated Nov. 9, 2023 in Eurpean Patent Application 20711394.5.
Extended European Search Report Dated Oct. 4, 2023 in European Patent Application No. 23166582.9.
Fathi,, P. Design and Characterization of SSDNA Aptamer Candidates to Bind Bacteroides Fragilis Toxin Subtypes BFT-1 and BFT-2 (Doctoral dissertation, Johns Hopkins University).2017.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
Final Office Action dated Apr. 25, 2023 in U.S. Appl. No. 16/525,054.
Final Office Action dated May 15, 2023 in U.S. Appl. No. 16/551,638 .
Final Office Action dated May 19, 2023 in U.S. Appl. No. 17/163,177.
Final Office Action dated May 31, 2023 in U.S. Appl. No. 16/934,530.
Final Office Action dated Jun. 8, 2023 in U.S. Appl. No. 17/147,283.
Final Office Action dated Oct. 5, 2023 in U.S. Appl. No. 17/151,050.
Final Office Action dated Oct. 13, 2023 in U.S. Appl. No. 15/055,407.
Final Office Action dated Oct. 23, 2023 in U.S. Appl. No. 16/540,971.
Hoinka and Przytycka. "AptaPLEX—A Dedicated, Multithreaded Demultiplexer for HT-SE LEX Data." Methods, 2016, 106:82-85.
International Search Report and Written Opinion dated Mar. 10, 2022, in PCT Application No. PCT/US2021/060206.

(56) References Cited

OTHER PUBLICATIONS

International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
International Search Report and Written Opinion dated Jun. 5, 2023, in PCT Application No. PCT/US2023/061980.
International Search Report and Written Opinion dated Jun. 23, 2023 in PCT Application No. PCT/US2023/062070.
Invitrogen, "The attraction is simply magnetisk, Dynabeads Strptavidin products and applications" Invitrogen, 2010, 1-8.
Jacobsen et al., "33rd Annual Meeting & Pre-Conference Programs of the Society for Immunotherapy of Cancer," Journal for Immunotherapy of Cancer 2018, 6(S1), 7-11.
Ku, et al. "Nucleic Acid Aptamers: An Emerging Tool for Biotechnology and Biomedical Sensing." Sensors, 2015, 15, 16281-16313.
Lake et al., "Integrative single-cell analysis of transcriptional and epigenetic states in the human adult brain," Nature Biotechnology 2018, 36(1), 70-80.
KO. "An 'equalized cDNA library' by the reassociation of short double-stranded cDNAs," Nucleic Acids Res. 1990, 18(19), 5705-5711.
Livingstone, "rRNA depletion, poly(A) enrichment, or exonuclease treatment?" Tebu-Bio Blog 2015,. 5 pgs.
Mairal et al. "Aptamers: Molecular Tools for Analytical Applications." Analytical and bioanalytical chemistry 2008.390: 989-1007.
Mayer et al., "Obtaining deeper insights into microbiome diversity using a simple method to block host and nontargets in amplicon sequencing." Molecular Ecology Resources 2021, 21(6), 1952-1965.
Minnoye et al., "Chromatin accessibility profiling methods," Nature Reviews Method Primers 2021, 1-24.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Non-Final Office Action dated Apr. 26, 2023 in U.S. Appl. No. 16/540,971.
Non-Final Office Action dated Apr. 26, 2023 in U.S. Appl. No. 16/374,626.
Non-Final Office Action dated Jun. 14, 2023 In U.S. Appl. No. 17/174,249.
Non-Final Office Action dated Jun. 30, 2023 In U.S. Appl. No. 17/684,289.
Non-Final Office Action dated Jul. 27, 2023 in U.S. Appl. No. 17/373,519.
Non-Final Office Action dated Sep. 21, 2023 in Canadian Patent Application No. 3,034,924.
Non-Final Office Action dated Sep. 28, 2023 in U.S. Appl. No. 16/789,311.
Non-Final Office Action Dated Sep. 28, 2023 in U.S. Appl. No. 17/184,405.
Non-Final Office Action Dated Oct. 5, 2023 in U.S. Appl. No. 16/848,241.
Non-Final Office Action Dated Nov. 7, 2023 in U.S. Appl. No. 17/528,104.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 26, 2022 in Chinese Patent Application No. 201780058799.1.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.

(56) References Cited

OTHER PUBLICATIONS

Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Notice of Allowance dated Jun. 8, 2023 in U.S. Appl. No. 16/459,444.
Notice of Allowance dated Aug. 23, 2023 in Canadian Patent Application No. 2,865,575.
Notice of Allowance dated Aug. 25, 2023 in European Patent Application No. 22 200 785.8.
Notice of Allowance dated Aug. 28, 2023 in U.S. Appl. No. 16/374,626.
Notice of Allowance dated Sep. 14, 2023 in Canada Application No. 2982467.
Notice of Allowance dated Sep. 29, 2023 in European Application No. 22165594.7.
Notice of Allowance dated Oct. 2, 2023 in European Application 21735067.8.
Notice of Allowance dated Oct. 25, 2023 in European Application 20816802.1.
Nowak et al., "Does the KIR2DS5 gene protect from some human diseases?," PLoS One 2010, 5(8), in 6 pages.
Office Action dated Aug. 31, 2021 in Chinese Patent Application No. 2016800157452.
Office Action dated Nov. 2, 2021, in Japanese Patent Application No. 2017-549390.
Office Action dated Jan. 13, 2022 in Chinese Patent Application No. 2017800587991.
Office Action dated Feb. 23, 2022 in Chinese Patent Application No. 2016800523302.
Office Action dated March 7. 2022 in Korean Patent Application No. 10-2022-7004715.
Office Action dated May 2, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.
Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Nov. 24, 2022 in Chinese Patent Application No. 2018800147939.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Office Action dated Apr. 24, 2023 in European Patent Application No. 21714995.4.
Office Action dated Apr. 26, 2023 in European Patent Application No. 18703156.2.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated May 30, 2023 in Chinese Patent Application No. 2019800653102.
Office Action dated Jun. 1, 2023 in Japanese Patent Application No. 2020-561807.
Office Action dated Jun. 16, 2023 in Chinese Patent Application No. 2019800708938.
Office Action dated Jun. 22, 2023 in Japanese Patent Application No. 2022-071002.
Office Action dated Jun. 28, 2023 in European Patent Application 19836239.4.
Office Action dated Jul. 12, 2023 in Chinese Patent Application No. 2020800212600.
Office Action Dated Jul. 13, 2023 in Chinese Patent Application No. 202080077712.7.
Office Action dated Jul. 28, 2023 in Chinese Patent Application No. 201880014793.9.
Office Action dated Jul. 29, 2023 in Chinese Patent Application No. 201980073850.5.
Office Action dated Jul. 31, 2023 in Chinese Patent Application No. 201980068704.3.
Office Action dated Jul. 31, 2023 in Chinese Patent Application No. 201980037175.0.
Office Action dated Aug. 11, 2023 in European Patent Application 19752792.2.
Office Action dated Aug. 21, 2023 in Japanese Patent Application No. 2021-507836.
Office Action dated Aug. 30, 2023 in Chinese Patent Application 2019111653930.
Office Action dated Aug. 31, 2023 in Chinese Patent Application 2020800483617.
Office Action dated Sep. 21, 2023 in Japanese Patent Application 2022-030956.
Office Action dated Sep. 21, 2023 in Israel Patent Application 265478.
Office Action dated Oct. 10, 2023 in European Patent Application 16719706.0.
Office Action dated Oct. 13, 2023 in Chinese Patent Application 202080014409.2.

(56) References Cited

OTHER PUBLICATIONS

Office Action dated Oct. 19, 2023 in Japanese Patent Application 2019-566787.
Office Action dated Oct. 23, 2023 in Japanese Patent Application 2021-517856.
Office Action dated Oct. 26, 2023 In Japanese Patent Application 2022-525692.
Office Action Dated Oct. 30, 2023 in Japanese Patent Application 2021-523956.
Office Action Dated Nov. 9, 2023 in Japanese Patent Application 2017-549390 .
Ogawa, T. et al., "The Efficacy and further functional advantages of random-base molecular barcodes for absolute and digital quantification of nucleic acid molecules", Sci Rep 7, 2017 12576.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 3, 2023 in U.S. Appl. No. 17/161,558.
Restriction Requirement dated Jun. 28, 2023 in U.S. Appl. No. 17/336,055.
Restriction Requirement dated Oct. 5, 2023 in U.S. Appl. No. 17/373,653.
Restriction Requirement dated Oct. 11, 2023 in U.S. Appl. No. 17/531,555.
Summons to Attend Oral Proceedings Dated Aug. 8, 2023 in European Patent Application No. 14749671.5.
Uellendahl-Werth et al., "A benchmark of hemoglobin blocking during library preparation for mRNA Sequencing of human blood samples," Scientific Reports 2020, 10(1), 5630.
Wang et al., "Development of Multicolor Flow Cytometry Calibration Standards: Assignment of Equivalent Reference Fluorophores (ERF) Unit" J. Res. Natl. Inst. Stand, Technol. 2011 116, 671-683.
Wangsanuwat et al., "Efficient and cost-effective bacterial mRNA sequencing from low input samples through ribosomal RNA depletion." BMC Genomics 2020, 21(1), 1-12.
Wu & Lambowitz, "Facile single-stranded DNA sequencing of human plasma DNA via thermostable group II intron reverse transcriptase template switching," Scientific Reports 2017, 7(8421), 1-14.
Zheng, et al. "Aptamer-Functionalized Barcode Particles for the Capture and Detection of Multiple Types of Circulating Tumor Cells." Advanced materials (Weinheim), 2014, 26, 7333-7338.
Zhou and Rossi. "Aptamers as Targeted Therapeutics: Current Potential and Challenges." Nature reviews, Drug discovery, 2017, 16:181-202.
Zhulidov et al., "Simple cDNA normalization using kamchatka crab duplex-specific nuclease," Nucleic Acids Research. 2004, 32(3)e37.
AAT Bioquest, Calcein-Based Cell Viability Assays, AssayWise Letters, 2016, 5(1), 1-16.
Attar, Moustafa, et al. "A practical solution for preserving single cells for RNA sequencing." Scientific Reports 8.1 (2018): 2151.
Biotium, Fura-2, AM Ester, Biotium, 2023, 1-3. Obtained online at: https://biotium.com/product/fura-2-am-ester/ on Feb. 14, 2023.
Blumenthal, "RNA Replication: Function and Structure of Qb-Replicase" Ann. Rev. Biochem. 1979 48:525-48.
Burger et al., "Maximizing mutagenesis with solubilized CRISPR-Cas9 ribonucleoprotein complexes," Development 2016, vol. 143, No. 11, 2025-2037.
Cahill et al., "Polymerase Chain Reaction and Qb Replicase Amplification" Clin._Chem. 1991, 37(9), 1482-1485.
Cao et al., "Supplementary Materials, Comprehensive Single-Cell Transcriptional Profiling of a Multicellular Organism," Science (2017), 337, 1-70.
Carninci et al., "Normalization and Subtraction of Cap-Trapper-Selected cDNAs to Prepare Full-Length cDNA Libraries for Rapid Discovery of New Genes," Genome Research 2000, 10:1617-1630.
Chen et al., "Single-Cell Protein Secretion Detection and Profiling", Annual Reviews, Anal. Chem, 2019, 12, 431-449.
Choi et al., "Programmable in situ amplification for multiplexed imaging of mRNA expression," Nature Biotechnology (2010), 28(11), 1208-1212.
Delley et al., "Combined aptamer and transcriptome sequencing of single cells," Scientific Reports (2018), 8(2919), 1-8.
Dey et al., "Integrated genome and transcriptome sequencing of the same cell", Nature Biotechnology, 33(3) 2015, 285.
Dunker et al., "Single-cell transcriptomics enters the age of mass production," Molecular Cell. 58:563-564, May 21, 2015.
Elghanian, Robert, et al. "Selective colorimetric detection of polynucleotides based on the distance- dependent optical properties of gold nanoparticles." Science 277.5329 (1997): 1078-1081.
Fisher Scientific, Invitrogen "Calcein AM, Cell-Permanent Green and Blue Dyes", Invitrogen, 2024, 1-4.
Gao et al., "The Comparison of Two Single-cell Sequencing Platforms: BD Rhapsody and 10x Genomics Chromium," Current Genomics 2020, 21(8), 602-609.
Gerlach, et al., "Combined quantification of intracellular (phospho-) proteins and transcriptomics from fixed single cells", Scientific Reports, 2019 vol. 9:1469, pp. 1-10.
Granja, Jeffrey M., et al. "Single-cell multiomic analysis identifies regulatory programs in mixed-phenotype acute leukemia." *Nature biotechnology* 37.12 (2019): 1458-1465.
Haddock, "DAPI Permeability," Flow Post-Itsm, Dec. 2020, obtained on httpswi.mit.edusitesdefaultfiles2021-05202012DAPI_Permeability.pdf.
Henry, et al., "Cell type specific genomics of *Drosophila* neuron" Nucleic Acids Research, vol. 40, No. 19, 2012.
Illumina, "Data Processing of Nextera Mate Pair Reads on Illumina Sequencing Platforms", Data Processing Technical Note from 2012.
Illumina, "Estimating Sequencing Coverage" Technical Note: Sequencing from 2014.
Illumina, "Optimizing Cluster Density on Illumina Sequencing Systems", Publication No. 770-2014-031, 2016.
Jara-Acevedo et al., "Exosome beads array for multiplexed phenotyping in cancer," Journal of Proteomics 2019, 198(30), 87-97.
Jiang et al., "Whole transcriptome analysis with sequencing: methods, challenges and potential solutions," Cellular and Molecular Life Sciences 2015; 72: 3425-3439.
Jovelet et al., "Circulating Cell-Free Tumor DNA Analysis of 50 Genes by Next-Generation Sequencing in the Prospective MOSCATO Trial," Clinical Cancer Research (2016), 22(12), 2960-2968.
Kalamasz et al., "Optimization of Human T-Cell Expansion Ex Vivo Using Magnetic Beads Conjugated with Anti-CD3 and Anti-CD28 Antibodies," Journal of Immunother 2004, 27(5), 405-418.
Kurschat et al., "Optimizing splinted ligation of highly structured small RNAs", RNA, Cold Spring Harbor Laboratory Press, US, vol. 11, No. 12. Dec. 2005, 1909-1914.
Lao et al., "mRNA-Sequencing Whole Transcriptome Analysis of a Single Cell on the SOLiD tm System," Journal of Biomolecular Techniques 20:266-271.
Lebl et al. "A High-Complexity, Multiplexed Solution-Phase Assay for Profiling Protease Activity in Microarrays", Combinatorial Chemistry and High Throughput Screening, 2008, 11(1), 24-35.

(56) References Cited

OTHER PUBLICATIONS

Lee et al., "Comparison of Surface Markers between Human and Rabbit Mesenchymal Stem Cells," PLoS ONE 2014, 9(11), in 10 pages.
Lee et al., "Mutant Enrichment with 3'-Modified Oligonucleotides: A Practical PCR Method for Detecting Trace Mutant DNAs," The Journal of Molecular Diagnostics 2011; 13: 657-668.
Levay, et al. "Identifying High-Affinity Aptamer Ligands with Defined Cross-Reactivity Using High-Throughput Guided Systematic Evolution of Ligands by Exponential Enrichment." Nucleic acids research Dec. 2015, 43.
Liu et al., "Identification of lung adenocarcinoma-specific exosome RNAs in peripheral blood by RNA-Seq analysis," European Review for Medical and Pharmacological Sciences 2020, 24(4), 1877-1886.
Lustig et al., Long poly(A) tracts in the human genome are associated with the Alu family of repeated elements J of Molecular Biology 180 :753-759 1984.
Ma, "Affinity-based isolation of tagged nuclei from *Drosophila* tissues for gene expression analysis," Journal of Visualized Experiments (2014), 85, 1-9.
Matula et al., "Single-Cell Analysis Using Droplet Microfluidics," Adv Biosyst. Jan. 2020; 4(1), 28 pages.
Medepalli, Krishnakiran, et al. "A new technique for reversible permeabilization of live cells for intracellular delivery of quantum dots." Nanotechnology 24.20 (2013): 205101.
Monoclonal Antibody Production, Icosagen.com, accessed Apr. 17, 2014, 3 pages.
Nair, et al., "Enzymatic cleavage of uracil-containing single-stranded DNA linkers for the efficient release of affinity-selected circulating tumor cells" Chem Commun (Camb). Feb. 21, 2015 ;51 (15):3266-9.
Nitsch et al., "Determination of In Vitro Membrane Permeability by Analysis of Intracellular and Extracellular Fluorescein Signals in Renal Cells," In Vivo (2019), 33, 1767-1771.
Novak et al., "Single-Cell Multiplex Gene Detection and Sequencing with Microfluidically Generated Agarose Emulsions," Angew. Chem. Int. Ed. 2011, 50, 390-395.
Picelli et al., "Full-length RNA-seq from single cells using Smart-seq2," Nat Protoc 2014, 9, 171-181.
Rhie et al., "The Complete Sequence of a Human Y Chromosome," Nature 2023, vol. 621, 344-354.
Rittie et al., "Enzymes used in molecular biology: a useful guide," J. Cell Commun. Signal. 2008, 2:25-45.
Rohland et al., "Cost-Effective, High-Throughput DNA Sequencing Libraries for Multiplexed Target Capture," Genome Research 2012, 22:939-946.
Schroder, "The Protein Puzzle", Biology & Medicine-Cell Research, 2017.
Scotto-Lavino et al., "3' End cDNA amplification using classic RACE," Nature Protocols 2006, vol. 1, 2742-2745.
Sefi et al., "Amplication of GC-rich Putative Mouse PeP Promoter using Betaine and DMSO in Ammonium Sulfate Polymerase Chain Reaction Buffer," Avicenna J. Med. Biotechnol. Oct. 2012; 4(4):206-9.
Sharma et al., "Immunoaffinity-based isolation of melanoma cell-derived exosomes from plasma of patients with melanoma," Journal of Extracellular Vesicles 2018, 7(1), 1435138.
Singh, R., "Target Enrichment Approaches for Next-Generation Sequencing Applications in Oncology", Diagnostics, vol. 12, No. 7, Jun. 2022 p. 1539.
Spanova et al., "Magnetic hydrophilic methacrylate-based polymer microspheres designed for polymerase chain reaction applications", Journal of Chromatography vol. 800, 2004, 27-32.
Stratagene 1988 Catalog, Gene Characterization Kits, 39.
Tsompana et al., "Chromatin Accessibility: a window into the genome" Epigenetics & Chromatin 2014 7:33.
Van Nieuwerburgh, et al., "Quantitative Bias in Illumina TruSeq and a Novel Post Amplification Barcoding Strategy for Multiplexed DNA and Small RNA Deep Sequencing", PLOS ONE, vol. 6, No. 10, 2011.
Winter, E, Varshavsky A. "A DNA binding protein that recognizes oligo(dA). oligo(dT) tracts." EMBO J. Jun. 1989;8(6):1867-77.
Wu, et al., "Time-resolved assessment of single-cell protein secretion by sequencing", bioRxiv, Dec. 21, 2021.
Wulf et al., "Non-templated addition and template switching by Moloney murine leukemia virus (MMLV)-based reverse transcriptases co-occur and compete with each other", J. Biol. Chem. 2019, 294(48) 18220-18231.
Xiang, Charlie C., et al. "Using DSP, a reversible cross-linker, to fix tissue sections for immunostaining, microdissection and expression profiling." *Nucleic acids research* 32.22 (2004).
Yang et al., HHS Public Access, Author Manuscript, Getting Across the Cell Membrane: An Overview for Small Molecules, Peptides, and Proteins, 2015, 1-25.
Advisory Action dated Jul. 9, 2019 in U.S. Appl. No. 15/260,106.
Advisory Action dated Jul. 27, 2023 in U.S. Appl. No. 17/163,177.
Advisory Action dated Nov. 15, 2024 in U.S. Appl. No. 16/789,311.
Corrected Notice of Allowability dated Aug. 25, 2023 in U.S. Appl. No. 16/459,444.
Corrected Notice of Allowability dated Mar. 27, 2024 in U.S. Appl. No. 17/370,923.
Final Office Action dated Apr. 22, 2019 in U.S. Appl. No. 16/219,553.
Final Office Action dated Apr. 9, 2024 in U.S. Appl. No. 17/147,283.
Final Office Action dated Aug. 21, 2025 in U.S. Appl. No. 17/684,289.
Final Office Action dated Dec. 27, 2023 in U.S. Appl. No. 17/174,249.
Final Office Action dated Dec. 21, 2022 in U.S. Appl. No. 16/747,737.
Final Office Action dated Dec. 9, 2024 in U.S. Appl. No. 17/373,653.
Final Office Action dated Feb. 19, 2025 in U.S. Appl. No. 17/174,249.
Final Office Action dated Feb. 21, 2025 in U.S. Appl. No. 16/525,054.
Final Office Action dated Feb. 21, 2025 in U.S. Appl. No. 17/592,271.
Final Office Action dated Feb. 27, 2025 in U.S. Appl. No. 17/157,872.
Final Office Action dated Feb. 9, 2024 in U.S. Appl. No. 17/151,058.
Final Office Action dated Jan. 24, 2025 in U.S. Appl. No. 17/531,555.
Final Office Action dated Jan. 7, 2025 in U.S. Appl. No. 17/147,283.
Final Office Action dated Jul. 18, 2025 in U.S. Appl. No. 17/151,058.
Final Office Action dated Jul. 24, 2024 in U.S. Appl. No. 17/684,289.
Final Office Action dated Jul. 24, 2024 in U.S. Appl. No. 18/053,603.
Final Office Action dated Jul. 9, 2025 in U.S. Appl. No. 16/551,620.
Final Office Action dated Jun. 18, 2024 in U.S. Appl. No. 16/551,620.
Final Office Action dated Jun. 5, 2025 in U.S. Appl. No. 18/194,590.
Final Office Action dated Mar. 10, 2025 in U.S. Appl. No. 17/151,050.
Final Office Action dated Mar. 17, 2025 in U.S. Appl. No. 17/151,058.
Final Office Action dated Mar. 21, 2024 in U.S. Appl. No. 16/788,743.
Final Office Action dated Mar. 28, 2019 in U.S. Appl. No. 15/260,106.
Final Office Action dated May 13, 2024 in U.S. Appl. No. 17/157,872.
Final Office Action dated May 30, 2024 in U.S. Appl. No. 17/528,104.
Final Office Action dated May 8, 2024 in U.S. Appl. No. 17/373,653.
Final Office Action dated Nov. 20, 2024 in U.S. Appl. No. 16/540,971.
Final Office Action dated Oct. 10, 2024 in U.S. Appl. No. 17/592,271.
Final Office Action dated Oct. 18, 2024 in U.S. Appl. No. 18/186,940.
Final Office Action dated Oct. 9, 2024 in U.S. Appl. No. 17/163,177.
Final Office Action dated Sep. 15, 2025 in U.S. Appl. No. 18/194,590.
Final Office Action dated Sep. 19, 2024 in U.S. Appl. No. 18/324,880.
Final Office Action dated Sep. 19, 2024 in U.S. Appl. No. 18/324,890.
Final Office Action dated Sep. 6, 2024 in U.S. Appl. No. 16/789,311.
Non-Final Office Action dated Apr. 17, 2024 in U.S. Appl. No. 16/789,311.
Non-Final Office Action dated Aug. 14, 2025 in U.S. Appl. No. 17/147,283.
Non-Final Office Action dated Aug. 19, 2025 in U.S. Appl. No. 17/174,249.
Non-Final Office Action dated Aug. 21, 2025 in U.S. Appl. No. 18/186,936.
Non-Final Office Action dated Aug. 26, 2025 in U.S. Appl. No. 17/163,177.
Non-Final Office Action dated Dec. 28, 2023 in U.S. Appl. No. 17/157,872.
Non-Final Office Action dated Feb. 19, 2019 in U.S. Appl. No. 14/381,526.
Non-Final Office Action dated Feb. 3, 2025 in U.S. Appl. No. 17/528,104.
Non-Final Office Action dated Feb. 9, 2024 in U.S. Appl. No. 16/846,133.

(56) References Cited

OTHER PUBLICATIONS

Non-Final Office Action dated Jan. 19, 2024 in U.S. Appl. No. 17/336,055.
Non-Final Office Action dated Jan. 2, 2024 in U.S. Appl. No. 17/373,653.
Non-Final Office Action dated Jan. 6, 2025 in U.S. Appl. No. 16/551,620.
Non-Final Office Action dated Jan. 6, 2025 in U.S. Appl. No. 18/190,465.
Non-Final Office Action dated Jul. 1, 2025 in U.S. Appl. No. 16/525,054.
Non-Final Office Action dated Jul. 15, 2025 in U.S. Appl. No. 17/957,386.
Non-Final Office Action dated Jun. 14, 2024 in U.S. Appl. No. 16/525,054.
Non-Final Office Action dated Jun. 18, 2025 in U.S. Appl. No. 17/707,409.
Non-Final Office Action dated Jun. 5, 2025 in U.S. Appl. No. 17/157,872.
Non-Final Office Action dated Jun. 29, 2023 in U.S. Appl. No. 17/151,058.
Non-Final Office Action dated Mar. 20, 2024 in U.S. Appl. No. 17/163,177.
Non-Final Office Action dated Mar. 26, 2024 in U.S. Appl. No. 18/053,603.
Non-Final Office Action dated Mar. 28, 2024 in U.S. Appl. No. 17/531,555.
Non-Final Office Action dated Mar. 28, 2025 in U.S. Appl. No. 17/545,845.
Non-Final Office Action dated May 20, 2024 in U.S. Appl. No. 18/324,880.
Non-Final Office Action dated May 20, 2024 in U.S. Appl. No. 18/324,890.
Non-Final Office Action dated May 7, 2024 in U.S. Appl. No. 17/390,640.
Non-Final Office Action dated May 7, 2025 in U.S. Appl. No. 18/643,870.
Non-Final Office Action dated Nov. 13, 2024 in U.S. Appl. No. 18/194,590.
Non-Final Office Action dated Nov. 19, 2024 in U.S. Appl. No. 17/684,289.
Non-Final Office Action dated Nov. 8, 2024 in U.S. Appl. No. 18/053,603.
Non-Final Office Action dated Sep. 4, 2025 in U.S. Appl. No. 17/373,653.
Non-Final Office Action dated Sep. 3, 2024 in U.S. Appl. No. 17/174,249.
Non-Final Office Action dated Sep. 5, 2024 in U.S. Appl. No. 17/147,283.
Non-Final Office Action dated Sep. 10, 2025 in U.S. Appl. No. 19/022,242.
Notice of Allowability dated Mar. 7, 2023 for U.S. Appl. No. 17/147,272.
Notice of Allowance dated Apr. 24, 2024 in U.S. Appl. No. 16/788,743.
Notice of Allowance dated Apr. 25, 2024 in U.S. Appl. No. 16/848,241.
Notice of Allowance dated Apr. 29, 2020 in U.S. Appl. No. 15/937,713.
Notice of Allowance dated Apr. 8, 2024 in U.S. Appl. No. 16/846,133.
Notice of Allowance dated Dec. 28, 2023 in U.S. Appl. No. 16/551,638.
Notice of Allowance dated Dec. 5, 2023 in U.S. Appl. No. 17/373,519.
Notice of Allowance dated Dec. 6, 2023 in U.S. Appl. No. 16/934,530.
Notice of Allowance dated Feb. 24, 2023 in U.S. Appl. No. 17/183,840.
Notice of Allowance dated Feb. 23, 2023 in U.S. Appl. No. 17/320,052.
Notice of Allowance dated Mar. 20, 2024 in U.S. Appl. No. 18/190,884.
Notice of Allowance dated May 28, 2025 in U.S. Appl. No. 18/324,880.
Notice of Allowance dated May 27, 2025 in U.S. Appl. No. 18/324,890.
Notice of Allowance dated Nov. 16, 2023 in U.S. Appl. No. 16/677,012.
Notice of Allowance dated Nov. 17, 2021 in U.S. Appl. No. 16/836,750.
Notice of Allowance dated Sep. 19, 2024 in U.S. Appl. No. 17/161,558.
Notice of Allowance dated Sep. 24, 2018 in U.S. Appl. No. 16/038,887.
Notice of Allowance dated Sep. 24, 2018 in U.S. Appl. No. 16/038,979.
Notice of Panel Decision from Pre-Appeal Brief Review in U.S. Appl. No. 17/151,058, dated Sep. 4, 2024.
Restriction Requirement dated Aug. 26, 2024 in U.S. Appl. No. 18/194,590.
Restriction Requirement dated Dec. 27, 2021 in U.S. Appl. No. 16/747,737.
Restriction Requirement dated Mar. 26, 2025 in U.S. Appl. No. 17/707,409.
Restriction Requirement dated May 22, 2018 in U.S. Appl. No. 15/260,106.
Supplemental Notice of Allowability dated Apr. 2, 2024 in U.S. Appl. No. 18/190,884.
International Preliminary Report on Patentability dated Aug. 6, 2019 in PCT Application No. PCT/US2018/014385.
International Preliminary Report on Patentability dated Feb. 23, 2021 in PCT Application No. PCT/US2019/046549.
International Preliminary Report on Patentability dated Feb. 9, 2021 in PCT Application No. PCT/US2019/043949.
International Preliminary Report on Patentability dated Jun. 24, 2021 in PCT Application No. PCT/US2019/065237.
International Preliminary Report on Patentability dated Mar. 2, 2021 in PCT Application No. PCT/US2019/048179.
International Preliminary Report on Patentability dated Mar. 26, 2019 in PCT Application No. PCT/US2017/053331.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Search Report and Written Opinion dated Dec. 6, 2021, in PCT Application No. PCT/US2021/046750.
International Search Report and Written Opinion dated Feb. 27, 2024 in PCT Application No. PCT/US2023/036545.
International Search Report and Written Opinion dated Jan. 12, 2024 in PCT Application No. PCT/US2023/078302.
International Search Report and Written Opinion dated Jun. 11, 2024 in PCT Application No. PCT/US2023/084669.
International Search Report and Written Opinion dated Nov. 18, 2024 in PCT Application No. PCT/US2024/031765.
International Search Report and Written Opinion dated Sep. 12, 2024 in PCT Application No. PCT/US2024/030552.
Invitation to Pay Fees dated Mar. 16, 2016 in PCT Application No. PCT/US2016/019971.
Decision to Grant dated Oct. 18, 2018 in European Patent Application No. 1461937.3.
Decision to Grant dated Oct. 14, 2021 in European Patent Application No. 17202409.3.
Decision to Grant dated Jul. 20, 2023 in European Patent Application No. 17781265.8.
Decision to Grant dated Jul. 24, 2025 in Japanese Patent Application No. 2023-165263.
Decision to Grant dated Feb. 29, 2024 in European Patent Application No. 21735076.8.
Decision of Grant dated Aug. 28, 2025 in Japanese Patent Application No. 2024000242.
Decision of Grant dated Dec. 4, 2023 in Japanese Patent Application No. 2022-096387.
Decision of Grant dated Nov. 27, 2023 In Japanese Patent Application No. 2021-505735.

(56) References Cited

OTHER PUBLICATIONS

Decision of Grant dated Oct. 17, 2024 in Japanese Patent Application No. 2021-507836.
Decision of Grant dated Sep. 9, 2024 in Japanese Patent Application No. 2022-077421.
Decision to Grant dated Jul. 25, 2024 in Japanese Patent Application No. 2022-071002.
Decision to Grant dated Jul. 18, 2024 in European Patent Application No. 21707112.5.
Decision to Grant dated Jul. 8, 2024 in Japanese Patent Application No. 2019-566787.
Examination Report dated Apr. 16, 2025 in European Patent Application No. 23166582.9.
Examination Report dated Apr. 17, 2025 in European Patent Application No. 24166876.3.
Examination Report dated Apr. 18, 2024 in Australian Patent Application No. 2022211826.
Examination Report dated Apr. 19, 2024 in European Patent Application No. 23166391.5.
Examination Report dated Aug. 28, 2024 in European Patent Application No. 21730393.2.
Examination Report dated Dec. 12, 2024 in European Patent Application No. 20711394.5.
Examination Report dated Dec. 19, 2024 in European Patent Application No. 18703156.2.
Examination Report dated Dec. 2, 2024 in European Patent Application No. 22777544.2.
Examination Report dated Feb. 13, 2025 in Australian Patent Application No. 2023203512.
Examination Report dated Feb. 14, 2025 in European Patent Application No. 21851636.7.
Examination Report dated Feb. 26, 2025 in European Patent Application No. 23191518.2.
Examination Report dated Feb. 6, 2025 in European Patent Application No. 21827480.1.
Examination Report dated Jan. 24, 2025 in Australian Patent Application No. 2022291534.
Examination Report dated Jan. 7, 2025 in European Patent Application No. 21704096.3.
Examination Report dated Jul. 10, 2025 in European Patent Application No. 21708803.8.
Examination Report dated Mar. 21, 2025 in European Patent Application No. 21714720.6.
Examination Report dated Mar. 31, 2025 in European Patent Application No. 24166038.0.
Examination Report dated Mar. 6, 2024 in European Patent Application No. 19836239.4.
Examination Report dated May 17, 2022 in Australian Patent Application No. 2019204928.
Examination Report dated Nov. 18, 2024 in Canadian Patent Application No. 3,059,559.
Examination Report dated Nov. 24, 2023 in European Patent Application No. 20209777.0.
Examination Report dated Nov. 27, 2024 in European Patent Application No. 19836239.4.
Examination Report dated Oct. 25, 2021 in European Patent Application No. 17781265.8.
Examination Report dated Oct. 25, 2024 in European Patent Application No. 23166391.5.
Examination Report dated Sep. 21, 2023 in Canadian Patent Application No. 3,034,924.
Examination Report dated Sep. 3, 2024 in Australian Patent Application No. 2019262048.
Extended European Search Report dated Aug. 13, 2024 in European Patent Application No. 24166038.0.
Extended European Search Report dated Aug. 28, 2024 in European Patent Application No. 24166876.3.
Extended European Search Report dated Feb. 23, 2024 in European Patent Application No. 23191518.2.
Extended European Search Report dated Feb. 7, 2025 in European Patent Application No. 24194064.2.
Extended European Search Report dated Jan. 24, 2025 in European Patent Application No. 24194281.2.
Extended European Search Report dated Jun. 3, 2024 in European Patent Application No. 23216012.7.
Extended European Search Report dated Jun. 5, 2025 in European Patent Application No. 24221567.1.
Extended European Search Report dated Nov. 20, 2024 in European Patent Application No. 24194082.4.
Extended European Search Report dated Sep. 5, 2025 in European Patent Application No. 25152849.3.
Grounds for Opposition dated Jul. 21, 2016 and filed in European Patent 2414548B1.
Notice of Allowance dated Apr. 1, 2019 in Singapore Patent Application No. 11201405274W.
Notice of Allowance dated Dec. 6, 2023 in Korean Patent Application No. 10-2023-7012325.
Notice of Allowance dated Dec. 7, 2021 in Chinese Patent Application No. 201680007652.
Notice of Allowance dated Feb. 20, 2025 in Korean Patent Application No. 10-2022-7029623.
Notice of Allowance dated Jan. 20, 2024 in Chinese Patent Application No. 201911165393.0.
Notice of Allowance dated Jan. 24, 2024 in Israeli Patent Application No. 265478.
Notice of Allowance dated Jan. 24, 2022 in Korean Patent Application No. 10-2019-7011635.
Notice of Allowance dated Jun. 14, 2018 in Singapore Patent Application No. 11201601188T.
Notice of Allowance dated Jun. 17, 2020 in European Patent Application No. 18195513.9.
Notice of Allowance dated Jun. 18, 2021 in European Patent Application No. 17202409.3.
Notice of Allowance dated Jul. 7, 2017 in European Patent Application No. 13755319.4.
Notice of Allowance dated Jul. 12, 2018 in Japanese Patent Application No. 2014-558975.
Notice of Allowance dated Jul. 24, 2025 in Japanese Patent Application No. 2023-220540.
Notice of Allowance dated Mar. 18, 2025 in Japanese Patent Application No. 2021-517856.
Notice of Allowance dated May 23, 2024 in Chinese Patent Application No. 201980037342.1.
Notice of Allowance dated Nov. 21, 2024 in Korean Patent Application No. 10-2023-7017312.
Notice of Allowance dated Oct. 8, 2020 in Singapore Patent Application No. 11201901733P.
Notice of Preliminary Rejection dated Feb. 23, 2024 for Korean Patent Application No. 10-2023-7017312.
Office Action dated Apr. 17, 2025 in Chinese Patent Application No. 202180014118.8.
Office Action dated Apr. 26, 2025 in Chinese Patent Application No. 202180060954.X.
Office Action dated Apr. 27, 2024 in Chinese Patent Application No. 202080048361.7.
Office Action dated Apr. 27, 2024 in Chinese Patent Application No. 2021980065685.9.
Office Action dated Apr. 27, 2025 in Chinese Patent Application No. 202180065616.5.
Office Action dated Apr. 9, 2025 in Canadian Patent Application No. 3218231.
Office Action dated Aug. 10, 2024 in Chinese Patent Application No. 201980037175.0.
Office Action dated Aug. 4, 2025 in Japanese Patent Application No. 2024-088926.
Office Action dated Dec. 15, 2023 in Chinese Patent Application No. 201980082680.7.
Office Action dated Dec. 17, 2024 in Japanese Patent Application No. 2023-165263.
Office Action dated Dec. 26, 2024 in Chinese Patent Application No. 202180025606.9.

(56) References Cited

OTHER PUBLICATIONS

Office Action dated Feb. 1, 2024 in Japanese Patent Application No. 2021-507836.
Office Action dated Feb. 1, 2024 in Japanese Patent Application No. 2022-071002.
Office Action dated Feb. 13, 2024 in Japanese Patent Application No. 2022-525692.
Office Action dated Feb. 25, 2020 in Japanese Patent Application No. 2019-014564.
Office Action dated Feb. 28, 2024 in Chinese Patent Application No. 202080014409.2.
Office Action dated Jan. 31, 2024 in Chinese Patent Application No. 201980037342.1.
Office Action dated Jan. 6, 2025 in Japanese Patent Application No. 2023-220540.
Office Action dated Jul. 10, 2023 in Japanese Patent Application No. 2022-096387.
Office Action dated Jul. 10, 2024 in Chinese Patent Application No. 202080014409.2.
Office Action dated Jul. 12, 2023 in Canadian Patent Application No. 3,059,559.
Office Action dated Jul. 24, 2024 in Chinese Patent Application No. 201980068704.3.
Office Action dated Jul. 28, 2025 in Japanese Patent Application No. 2024-111567.
Office Action dated Jul. 6, 2024 in Chinese Patent Application No. 202080048361.7.
Office Action dated Jul. 7, 2025 in Chinese Patent Application No. 202180026337.8.
Office Action dated Jun. 10, 2024 in Japanese Patent Application No. 2021-517856.
Office Action dated Jun. 18, 2024 In Japanese Patent Application No. 2021-523956.
Office Action dated Jun. 24, 2025 in Chinese Patent Application No. 202180020701.X.
Office Action dated Mar. 10, 2022 in Canadian Patent Application No. 2,865,575.
Office Action dated Mar. 24, 2025 in Japanese Patent Application No. 2024-000242.
Office Action dated Mar. 25, 2025 in Chinese Patent Application No. 202180020686.9.
Office Action dated Mar. 25, 2025 in Chinese Patent Application No. 202180022155.3.
Office Action dated Mar. 31, 2025 in Japanese Patent Application No. 2023-213088.
Office Action dated Mar. 3, 2025 in Chinese Patent Application No. 202210713090.3.
Office Action dated May 1, 2024 in Chinese Patent Application No. 201980070893.8.
Office Action dated May 30, 2023 in Korean Patent Application No. 10-2023-7012325.
Office Action dated May 30, 2024 in Korean Patent Application No. 10-2022-7029623.
Office Action dated May 31, 2024 in Chinese Patent Application No. 201980037175.0.
Office Action dated Nov. 2, 2024 in Chinese Patent Application No. 201980073850.5.
|Office Action dated Oct. 10, 2017 in European Patent Application No. 14761937.3.
Office Action dated Oct. 17, 2024 in Chinese Patent Application No. 202180014118.8.
Office Action dated Oct. 19, 2024 in Chinese Patent Application No. 202080077712.7.
Office Action dated Sep. 15, 2015 in Chinese Patent Application No. 201380022187.9.
Defendant 10X Genomics, Inc.'s Motion to Dismiss and Opening Brief in Support of the Motion to Dismiss filed in *Becton, Dickinson and Company and Cellular Research Inc.* v. *10X Genomics, Inc.* (C.A. No. 18-1800-RGA) on Jan. 18, 2019 in 72 pages.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 101 pp.
Petition for Inter Partes Review of U.S. Pat. No. 10,155,981, *Parse Biosciences, Inc.* v. *10X Genomics, Inc.* filed Apr. 20, 2023, Case No. IPR2023-00876, 93 pp.
IPR2023-00876, *Parse Biosciences Inc.* v. *10X Genomics Inc.,* filed Apr. 20, 2023.
IPR2023-00958, *Parse Biosciences Inc.* v. *10X Genomics Inc.,* filed May 25, 2023.
Ex Parte David H. Gelfand, Ivo Glynne Gut, Keith A. Bauer, and Florence Mauger, Appeal No. 2017-001917 (PTAB Aug. 6, 2018).
Ex Parte Olga Oranatsky, Appeal No. 2018-001623 (PTAB Jul. 29, 2019).
Ex Parte Brian Jon Peter, Appeal No. 2017-008386 (PTAB May 29, 2018).
Abcam, ab109202 DRAQ7 1ml (0.3mM) Protocol, Abcam, 2014, 1-20.
AccuPrimeTM Pfx DNA polymerase brochure, Invitrogen pp. 1-4 (Year 2010).
BD FACSMelody Cell Sorter, Technical Specifications, BD Biosciences 2016, 1-4.
BD Rhapsody Single-Cell Analysis System User Guide, Becton, Dickinson and Company 2019, 1-230.
Brilliant Stain Buffer Technical Data Sheet, BD Horizon, 2014, 1-3.
Chaintoutis et at., "A Novel Real-Time RT-PCR-Based Methodology for the Preliminary Typing of SARS-CoV-2 Variants, Employing Non-Extendable LNA Oligonucleotides and Three Signature Mutations at the Spike Protein Receptor-Binding Domain," LIFE 2021, vol. 11, No. 10, 1015, 15 pages.
Dower et al., "Detection and Characterization of high affinity plasma membrane receptors for human interleukin," The Rockefeller University Press 1985, 162:501-515.
Fixation and Permeabilization Solution, pp. 1-2, 2007, BD Biosciences.
Fluoro Trends, Celle Fixation, Permeabilization, and Intracellular Staining, pp. 1-8, May 2019, vol. 1, Issue 2.
Gehring, "Expanding Single-Cell RNA-Sequencing in Scale and Dimension," US Berkeley 2018, ProQuest ID: Gehring_berkeley_0028E_18003.
Guan et al., "Methods and Application of Plant Gene Cloning," Science and Technology Press of China 2009, 21-24.
Hobro et al., "An evaluation of fixation methods: Spatial and Compositional Cellular Changes Observed by Raman Imaging," Elsevier 2016, 31-45.
Jamur et al., "Permeabilization of Cell Membranes," Humana Press 2010, 63-66.
Ji et al., "Protein- and Sequencing-based Massively Parallel Single-cell Approaches to Gene Expression Profiling," BioProtocol, 2019, 3161, 1-24.
Johnson, "Detergents: Triton X-100, Tween-20, and More," pp. 1-12, Original Version Jan. 18, 2013 Labome, Mater Methods 3:163.
Lausted et al., "POSaM: a fast, flexible, open-source, inkjet oligonucleotide synthesizer and microarrayer," Genome Biol 2004, 5(8), R58.1-R58.17.
Stoeckius, "CITE-Seq Protocol", NYGS Innovation Lab 2017, 1-8.
US Forest Service Caring for the Land and Serving People, USDA Accessed from Internet on Jan. 21, 2022, pp. 1-7.
Weber et al., "Database entry EH937753," Plant Physiol., 2007, 32-42.
Final Office Action dated Dec. 1, 2025 in U.S. Appl. No. 18/186,940.
Final Office Action dated Feb. 20, 2026 in U.S. Appl. No. 16/525,054.
Final Office Action dated Jan. 9, 2026 in U.S. Appl. No. 18/058,216.
Final Office Action dated Oct. 9, 2025 in U.S. Appl. No. 17/157,872.
Final Office Action dated Oct. 24, 2025 in U.S. Appl. No. 17/545,845.
Non-Final Office Action dated Jan. 28, 2026 in U.S. Appl. No. 17/684,289.
Non-Final Office Action dated Jan. 28, 2026 in U.S. Appl. No. 18/186,449.
Non-Final Office Action dated Nov. 6, 2025 in U.S. Appl. No. 16/540,971.

(56) References Cited

OTHER PUBLICATIONS

Non-Final Office Action dated Nov. 18, 2025 in U.S. Appl. No. 16/551,620.
Non-Final Office Action dated Oct. 31, 2025 in U.S. Appl. No. 17/531,555.
Notice of Allowance dated Dec. 17, 2025 in U.S. Appl. No. 17/147,283.
Notice of Allowance dated Nov. 10, 2025 in U.S. Appl. No. 18/643,870.
Restriction Requirement dated Feb. 19, 2026 in U.S. Appl. No. 17/745,806.
Decision to Grant dated Feb. 24, 2026 in Japanese Patent Application No. 2024-088926.
Decision of Grant dated Jan. 5, 2026 In Japanese Patent Application No. 2023213088.
Rejection Decision dated Feb. 25, 2026 in Chinese Patent Application No. 2021800206869.
Decision of Rejection dated Jan. 6, 2026 in Chinese Patent Application No. 202180060954X.
Examination Report dated Dec. 15, 2025 in European Patent Application No. 241940642.
Examination Report dated Feb. 5, 2026 in European Patent Application No. 238176168.
Examination Report dated Jan. 23, 2026 in European Patent Application No. 222037848.
Examination Report dated Nov. 6, 2025 in European Patent Application No. 217303932.
Examination Report dated Nov. 7, 2025 in European Patent Application No. 217116607.
Examination Report dated Oct. 8, 2024 in European Patent Application No. 222037848.
Examination Report dated Oct. 17, 2025 in European Patent Application No. 24194082.4.
Extended European Search Report dated Feb. 6, 2026 in European Patent Application No. 252116439.
Extended European Search Report dated Sep. 24, 2025 in European Patent Application No. 25173019.8.
Notice of Acceptance dated Jan. 23, 2026 in Australian Patent Application No. 2022291534.
Notice of Acceptance dated Feb. 6, 2026 in Australian Patent Application No. 2023203512.
Notice of Reasons for Rejection dated Nov. 19, 2025 in Japanese Patent Application No. 2024-165113.
Notice of Reexamination dated Dec. 5, 2025 in Chinese Patent Application No. 2016800157452.
Office Action dated Feb. 12, 2026 in Chinese Patent Application No. 2022107130903.
Office Action dated Feb. 17, 2026 in Japanese Patent Application No. 2022-030956.
Office Action dated Jan. 24, 2026 in Chinese Patent Application No. 2021800656165.
Office Action dated Jan. 22, 2026 in Chinese Patent Application No. 2021800256069.
Office Action dated Nov. 25, 2025 in Chinese Patent Application No. 2021800206869.
Office Action dated Nov. 26, 2025 in Chinese Patent Application No. 2021800221553.
Office Action dated Oct. 31, 2025 in Canadian Patent Application No. 3097976.
Office Action dated Sep. 24, 2025 in Chinese Patent Application No. 202210713090.3.
Office Action dated Sep. 29, 2025 in Chinese Patent Application No. 202180014118.8.
Examination Report dated Jul. 21, 2025 in European Patent Application No. 218303634.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PCR1 primer

<400> SEQUENCE: 1

ggagggaggt tagcgaaggt                                                20


<210> SEQ ID NO 2
<211> LENGTH: 42
<212> TYPE: DNA
<213> ORGANISM: Artificial Sequence
<220> FEATURE:
<223> OTHER INFORMATION: PCR2 Primer

<400> SEQUENCE: 2

cagacgtgtg ctcttccgat ctggagggag gttagcgaag gt                       42


<210> SEQ ID NO 3
<211> LENGTH: 93
<212> TYPE: DNA
<213> ORGANISM: Artificial Sequence
<220> FEATURE:
<223> OTHER INFORMATION: dCODE Dextramer oligonucleotide
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(28)
<223> OTHER INFORMATION: n is a, c, g, or t
```

-continued

```
<220> FEATURE:
<221> NAME/KEY: misc_feature
<222> LOCATION: (30)..(31)
<223> OTHER INFORMATION: n is a, c, g, or t

<400> SEQUENCE: 3

ggagggaggt tagcgaaggt vnnvnnnnvn nvgtgttggg ttggcctatg ttaattacgg     60

agtgggtgaa aaaaaaaaaa aaaaaaaaaa aaa                                  93


<210> SEQ ID NO 4
<211> LENGTH: 13
<212> TYPE: PRT
<213> ORGANISM: Artificial Sequence
<220> FEATURE:
<223> OTHER INFORMATION: antigen peptide (EBV)

<400> SEQUENCE: 4

Thr Ser Leu Tyr Asn Leu Arg Arg Gly Thr Ala Leu Ala
1               5                   10


<210> SEQ ID NO 5
<211> LENGTH: 13
<212> TYPE: PRT
<213> ORGANISM: Artificial Sequence
<220> FEATURE:
<223> OTHER INFORMATION: antigen peptide (Tetanus toxoid)

<400> SEQUENCE: 5

Lys Ile Tyr Ser Tyr Phe Pro Ser Val Ile Ser Lys Val
1               5                   10


<210> SEQ ID NO 6
<211> LENGTH: 15
<212> TYPE: PRT
<213> ORGANISM: Artificial Sequence
<220> FEATURE:
<223> OTHER INFORMATION: antigen peptide (Negative Control Clip)

<400> SEQUENCE: 6

Pro Val Ser Lys Met Arg Met Ala Thr Pro Leu Leu Met Gln Ala
1               5                   10                  15
```

USE OF DEXTRAMER IN SINGLE CELL ANALYSIS

RELATED APPLICATIONS

The present application claims priority under 35 U.S.C. § 119(e) to U.S. Provisional Application No. 63/116,571, filed Nov. 20, 2020; and U.S. Provisional Application No. 63/241,486, filed Sep. 7, 2021. The contents of these applications are hereby expressly incorporated by reference in their entireties.

PARTIES TO A JOINT RESEARCH AGREEMENT

The claimed invention was made by, on behalf of, and/or in connection with one or more of the following parties to a joint research agreement: BECTON, DICKINSON AND COMPANY and IMMUDEX APS. The joint research agreement was in effect on or before the date the claimed invention was made, and the claimed invention was made as a result of activities undertaken within the scope of the joint research agreement.

REFERENCE TO SEQUENCE LISTING

The present application is being filed along with a Sequence Listing in electronic format. The Sequence Listing is provided as a file entitled 68EB_317310_US, created Nov. 3, 2021, which is 4.0 kilobytes in size. The information in the electronic format of the Sequence Listing is incorporated herein by reference in its entirety.

BACKGROUND

Field

The present disclosure relates generally to the field of molecular biology, for example determining gene expression and immune profiling using molecular barcoding.

Description of the Related Art

The adaptive immune system is directed through specific interactions between immune cells and antigen-presenting cells (e.g. dendritic cells, B-cells, monocytes and macrophages) or target cells (e.g. virus infected cells, bacteria infected cells or cancer cells). In important field in immunology relates to the understanding of the molecular interaction between an immune cell and the target cell.

Specifically for T-lymphocytes (T-cells), this interaction is mediated through binding between a clonotypic T-cell receptor (TCR) and the Major Histocompatibility Complex (MHC) class I or class II, called human leukocyte antigens (HLA) in man. The MHC molecules carries a peptide cargo—antigenic peptide epitope, and this peptide is decisive for T-cell recognition. Depending on the type of pathogen, being intracellular or extracellular, the antigenic peptides are bound to MHC class I or MHC class II, respectively. The two classes of MHC complexes are recognized by different subsets of T cells; Cytotoxic CD8+ T cells recognizing MHC class I and CD4+ helper cells recognizing MHC class II. In general, TCR recognition of MHC-peptide complexes result in T cell activation, clonal expansion and differentiation of the T cells into effector, memory and regulatory T cells.

MHC complexes function as antigenic peptide receptors, collecting peptides inside the cell and transporting them to the cell surface, where the MHC-peptide complex can be recognized by T-lymphocytes. Two classes of classical MHC complexes exist, MHC class I and II. The most important difference between these two molecules lies in the protein source from which they obtain their associated peptides. MHC class I molecules present peptides derived from endogenous antigens degraded in the cytosol and are thus able to display fragments of viral proteins and unique proteins derived from cancerous cells. Almost all nucleated cells express MHC class I on their surface even though the expression level varies among different cell types. MHC class II molecules bind peptides derived from exogenous antigens. Exogenous proteins enter the cells by endocytosis or phagocytosis, and these proteins are degraded by proteases in acidified intracellular vesicles before presentation by MHC class II molecules. MHC class II molecules are only expressed on professional antigen presenting cells like B cells and macrophages.

The three-dimensional structure of MHC class I and II molecules are very similar but important differences exist. MHC class I molecules consist of two polypeptide chains, a heavy chain, a, spanning the membrane and a light chain, p2-microglobulin (p2m). The heavy chain is encoded in the gene complex termed the major histocompatibility complex (MHC), and its extracellular portion comprises three domains, a1, a2 and a3. The p2m chain is not encoded in the MHC gene and consists of a single domain, which together with the a3 domain of the heavy chain make up a folded structure that closely resembles that of the immunoglobulin. The a1 and a2 domains pair to form the peptide binding cleft, consisting of two segmented a helices lying on a sheet of eight p-strands. In humans as well as in mice three different types of MHC class I molecule exist. HLA-A, B, C are found in humans while MHC class I molecules in mice are designated H-2K, H-2D and H-2L.

A remarkable feature of MHC genes is their polymorphism accomplished by multiple alleles at each gene. The polygenic and polymorphic nature of MHC genes is reflected in the peptide-binding cleft so that different MHC complexes bind different sets of peptides. The variable amino acids in the peptide binding cleft form pockets where the amino acid side chains of the bound peptide can be buried. This permits a specific variant of MHC to bind some peptides better than others.

Due to the short half-life of the peptide-MHC-T cell receptor ternary complex (typically between 10 and 25 seconds) it is difficult to label specific T cells with labelled MHC-peptide complexes. In order to circumvent this problem, MHC multimers have been developed. These are complexes that include multiple copies of MHC-peptide complexes, providing these complexes with an increased affinity and half-life of interaction, compared to that of the monomer MHC-peptide complex. The multiple copies of MHC-peptide complexes are attached, covalently or non-covalently, to a multimerization domain. Known examples of such MHC multimers include MHC-dimers with an IgG-multimerization domain, MHC-tetramers in complex with a streptavidin tetramer protein (U.S. Pat. No. 5,635,363), MHC pentamers with a self-assembling coiled-coil domain (US20040209295), MHC streptamers having 8-12 MHC molecules attached to streptactin, and MHC dextramers having a larger number of MHC-peptide complexes, typically more than ten, attached to a dextran polymer.

The understanding of T-cell recognition experienced a dramatic technological breakthrough with the discovery in 1996 that multimerization of single peptide-MHC molecules into tetramers would allow sufficient binding-strength (avidity) between the peptide-MHC molecules and the TCR to determine this interaction through a fluorescence label attached to the MHC-multimer. Fluorescent-labelled MHC multimers (of both class I and class II molecules) are now widely used for detecting T-cells and determining T-cell specificity. The MHC multimer associated fluorescence can be determined by e.g. flow cytometry or microscopy, or T-cells can be selected based on this fluorescence label through e.g. flow cytometry or bead-based sorting. The MHC multimer techniques have since been developed e.g. to enable the detection of low-affinity T-cells by the provision of MHC multimers with a flexible backbone, namely the MHC dextramer technology (e.g., WO2002/072631), and to better match the enormous diversity in T-cell recognition with the aim to enable detection of multiple different T-cell specificities in a single sample. Multiplex detection of antigen specific T-cells may be achieved with combinatorial encoded MHC multimers using a combinatorial fluorescence labelling approach that allows for the detection of numerous different T-cell populations in a single sample, and more recently with the use of nucleotide-labelling of MHC multimers. Current technology allows gene expression profiling and protein profiling of single cells in a massively parallel manner (e.g., >10000 cells) by attaching cell specific oligonucleotide barcodes to poly(A) mRNA molecules and AbSeq Ab-Oligos from individual cells as each of the cells is co-localized with a barcoded reagent bead in a compartment. There is a need for methods, compositions, systems, and kits for the generation of dCODE Dextramer libraries, cellular component binding reagent specific oligonucleotide (e.g., AbSeq, protein profiling) libraries and/or mRNA single cell libraries for sequencing.

SUMMARY

Disclosed herein include methods. In some embodiments, the method comprises: contacting a plurality of receptor detection constructs with a plurality of cells to form a first plurality of cells associated with the receptor detection constructs, wherein the plurality of cells comprise a plurality of cellular component targets and copies of a nucleic acid target, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: barcoding copies of the nucleic acid target of the plurality of cells with the plurality of oligonucleotide barcodes to generate a plurality of barcoded nucleic acid molecules each comprising a sequence complementary to at least a portion of the nucleic acid target. The method can comprise: generating a sequencing library comprising a plurality of nucleic acid target library members, a plurality of cellular component target library members, and a plurality of receptor library members, wherein generating the sequencing library comprises: attaching sequencing adaptors to the plurality of barcoded nucleic acid molecules, or products thereof, to generate the plurality of nucleic acid target library members; and attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of nucleic acid target library members, a plurality of sequencing reads of cellular component target library members, and a plurality of sequencing reads of receptor library members.

Disclosed herein include methods. In some embodiments, the method comprises: contacting a plurality of receptor detection constructs with a plurality of cells to form a first plurality of cells associated with the receptor detection constructs, wherein the plurality of cells comprise a plurality of cellular component targets, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: generating a sequencing library comprising a plurality of cellular component target library members and a plurality of receptor library members, wherein generating the sequencing library comprises: attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of cellular component target library members and a plurality of sequencing reads of receptor library members.

In some embodiments, barcoding copies of the nucleic acid target of the plurality of cells with the plurality of oligonucleotide barcodes comprises: contacting copies of the nucleic acid target of the plurality of cells with the plurality of oligonucleotide barcodes, wherein each oligonucleotide barcode of the plurality of oligonucleotide barcodes comprises a first universal sequence, a first molecular label, and a target-binding region capable of hybridizing to the nucleic acid target; and extending the plurality of oligonucleotide barcodes hybridized to the copies of the nucleic acid target to generate a plurality of barcoded nucleic acid molecules each comprising a sequence complementary to the at least a portion of the nucleic acid target. In some embodiments, barcoding the cellular component-binding reagent specific oligonucleotides with the plurality of oligonucleotide barcodes comprises: contacting the cellular component-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the cellular component-binding reagent specific oligonucleotides; and extending the plurality of oligonucleotide barcodes hybridized to the cellular component-binding reagent specific oligonucleotides to generate a plurality of barcoded cellular component-binding reagent specific oligonucleotides each comprising a sequence complementary to at least a portion of the unique identifier sequence. In some embodiments, barcoding the receptor-binding reagent specific oligonucleotides with the plurality of oligonucleotide barcodes comprises: contacting receptor-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the receptor-binding reagent specific oligonucleotide; and extending the plurality of oligonucleotide barcodes hybridized to the receptor-binding reagent specific oligonucleotides to generate a plurality of barcoded receptor-binding reagent specific oligonucleotides each comprising a sequence complementary to at least a portion of the unique receptor identifier sequence.

In some embodiments, the target-binding region comprises a capture sequence. In some embodiments, (i) the cellular component-binding reagent specific oligonucleotides comprise a sequence complementary to the capture sequence configured to capture the cellular component-binding reagent specific oligonucleotide and/or (ii) the receptor-binding reagent specific oligonucleotides comprise a sequence complementary to the capture sequence configured to capture the receptor-binding reagent specific oligonucleotides. In some embodiments, the target-binding region comprises a poly(dT) region, a random sequence, a target-specific sequence, or a combination thereof.

In some embodiments, (i) each barcoded nucleic acid molecule of the plurality of barcoded nucleic acid molecules comprise a first universal sequence and a first molecular label; (ii) each barcoded cellular component-binding reagent specific oligonucleotide of the plurality of barcoded cellular component-binding reagent specific oligonucleotides comprise a first universal sequence and a first molecular label; and/or (iii) each barcoded receptor-binding reagent specific oligonucleotide of the plurality of barcoded receptor-binding reagent specific oligonucleotides comprise a first universal sequence and a first molecular label.

In some embodiments, the second plurality of cells comprises one or more single cells. The method can comprise: prior to (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes: partitioning the second plurality of cells to a plurality of partitions, wherein a partition of the plurality of partitions comprises a single cell from the second plurality of cells; and in the partition comprising the single cell, (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes. In some embodiments, the partition is a well or a droplet. In some embodiments, the plurality of oligonucleotide barcodes are associated with a solid support, the method comprising associating the solid support with the single cell in the partition, and wherein a partition of the plurality of partitions comprises a single solid support. The method can comprise: lysing the single cell after the partitioning step and before the contacting step. In some embodiments, lysing the single cell comprises heating, contacting with a detergent, changing the pH, or any combination thereof. In some embodiments, the plurality of cells comprises T cells, B cells, tumor cells, myeloid cells, blood cells, normal cells, fetal cells, maternal cells, or a mixture thereof.

In some embodiments, at least 10 of the plurality of oligonucleotide barcodes comprise different first molecular label sequences. In some embodiments, the plurality of oligonucleotide barcodes each comprise a cell label. In some embodiments, each cell label of the plurality of oligonucleotide barcodes comprises at least 6 nucleotides. In some embodiments, oligonucleotide barcodes of the plurality of oligonucleotide barcodes associated with the same solid support comprise the same cell label. In some embodiments, oligonucleotide barcodes of the plurality of oligonucleotide barcodes associated with different solid supports comprise different cell labels. In some embodiments, the solid support comprises a synthetic particle, a planar surface, or a combination thereof. In some embodiments, at least one oligonucleotide barcode of the plurality of oligonucleotide barcodes is immobilized or partially immobilized on the synthetic particle, or at least one oligonucleotide barcode of the plurality of oligonucleotide barcodes is enclosed or partially enclosed in the synthetic particle. In some embodiments, the synthetic particle is disruptable (e.g., a disruptable hydrogel particle). In some embodiments, the synthetic particle comprises a bead (e.g., the bead is a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, each oligonucleotide barcode of the plurality of oligonucleotide barcodes comprises a linker functional group. In some embodiments, the synthetic particle comprises a solid support functional group. In some embodiments, the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

In some embodiments, generating the sequencing library comprises: contacting random primers with the plurality of barcoded nucleic acid molecules, wherein each of the random primers comprises a fourth universal sequence, or a complement thereof; and extending the random primers hybridized to the plurality of barcoded nucleic acid molecules to generate a first plurality of extension products. The method can comprise: amplifying the first plurality of extension products using primers capable of hybridizing to the first universal sequence or complements thereof, and primers capable of hybridizing the fourth universal sequence or complements thereof, thereby generating a first plurality of barcoded amplicons, wherein the plurality of nucleic acid target library members comprise the first plurality of barcoded amplicons, or products thereof. In some embodiments, amplifying the first plurality of extension products comprises adding sequences of binding sites of sequencing primers and/or sequencing adaptors, complementary sequences thereof, and/or portions thereof, to the first plurality of extension products. The method can comprise: determining the copy number of the nucleic acid target in each of the one or more single cells based on the number of first molecular labels with distinct sequences associated with the first plurality of barcoded amplicons, or products thereof.

In some embodiments, generating the sequencing library comprises: amplifying the first plurality of barcoded amplicons using primers capable of hybridizing to the first universal sequence or complements thereof, and primers capable of hybridizing the fourth universal sequence or complements thereof, thereby generating a second plurality of barcoded amplicons; wherein the plurality of nucleic acid target library members comprise the second plurality of barcoded amplicons, or products thereof. In some embodiments, amplifying the first plurality of barcoded amplicons comprises adding sequences of binding sites of sequencing primers and/or sequencing adaptors, complementary sequences thereof, and/or portions thereof, to the first plurality of barcoded amplicons. The method can comprise: determining the copy number of the nucleic acid target in each of the one or more single cells based on the number of first molecular labels with distinct sequences associated with the second plurality of barcoded amplicons, or products thereof. In some embodiments, the first plurality of barcoded amplicons and/or the second plurality of barcoded amplicons comprise whole transcriptome amplification (WTA) products.

In some embodiments, generating the sequencing library comprises: synthesizing a third plurality of barcoded amplicons using the plurality of barcoded nucleic acid molecules as templates to generate a third plurality of barcoded amplicons, wherein the plurality of nucleic acid target library members comprise the third plurality of barcoded amplicons, or products thereof. In some embodiments, synthesizing the third plurality of barcoded amplicons comprises PCR amplification using primers capable of hybridizing to the first universal sequence, or a complement thereof, and a target-specific primer. In some embodiments, synthesizing the third plurality of barcoded amplicons comprises adding sequences of binding sites of sequencing primers and/or sequencing adaptors, complementary sequences thereof, and/or portions thereof, to barcoded nucleic acid molecules. The method can comprise: determining the copy number of the nucleic acid target in each of the one or more single cells based on the number of first molecular labels with distinct sequences associated with the third plurality of barcoded amplicons, or products thereof. In some embodiments, the target-specific primer specifically hybridizes to an immune receptor. In some embodiments, the target-specific primer specifically hybridizes to a constant region of an immune receptor, a variable region of an immune receptor, a diversity region of an immune receptor, the junction of a variable region and diversity region of an immune receptor, or a combination thereof. In some embodiments, the immune receptor is a T cell receptor (TCR) and/or a B cell receptor (BCR) receptor. In some embodiments, the TCR comprises TCR alpha chain, TCR beta chain, TCR gamma chain, TCR delta chain, or any combination thereof. In some embodiments, the BCR receptor comprises BCR heavy chain and/or BCR light chain.

In some embodiments, each of the plurality of sequencing reads of the plurality of barcoded nucleic acid molecules, or products thereof, comprise (1) a molecular label sequence, and/or (2) a subsequence of the nucleic acid target. The method can comprise: determining the copy number of the nucleic acid target in each of the one or more single cells based on the plurality of sequencing reads of nucleic acid target library members. In some embodiments, determining the copy number of the nucleic acid target in each of the one or more single cells comprises determining the copy number of the nucleic acid target in each of the one or more single cells based on the number of first molecular labels with distinct sequences, complements thereof, or a combination thereof, associated with the one or more nucleic acid target library members, or products thereof. In some embodiments, the plurality of barcoded nucleic acid molecules comprises barcoded deoxyribonucleic acid (DNA) molecules, barcoded ribonucleic acid (RNA) molecules, or a combination thereof. In some embodiments, the nucleic acid target comprises a nucleic acid molecule (e.g., ribonucleic acid (RNA), messenger RNA (mRNA), microRNA, small interfering RNA (siRNA), RNA degradation product, RNA comprising a poly(A) tail, or any combination thereof). In some embodiments, the mRNA encodes an immune receptor.

In some embodiments, the cellular component-binding reagent specific oligonucleotide comprises a third universal sequence. In some embodiments, generating the sequencing library comprises: amplifying the plurality of barcoded cellular component-binding reagent specific oligonucleotides, or products thereof, using a primer capable of hybridizing to the first universal sequence, or a complement thereof, and a primer capable of hybridizing to the third universal sequence, or a complement thereof, to generate a plurality of amplified barcoded cellular component-binding reagent specific oligonucleotides, wherein the plurality of cellular component target library members comprise the plurality of amplified barcoded cellular component-binding reagent specific oligonucleotides, or products thereof. In some embodiments, amplifying the plurality of barcoded cellular component-binding reagent specific oligonucleotides comprises adding sequences of binding sites of sequencing primers and/or sequencing adaptors, complementary sequences thereof, and/or portions thereof, to the plurality of barcoded cellular component-binding reagent specific oligonucleotides. The method can comprise: determining the number of copies of at least one cellular component target of the plurality of cellular component targets in the one or more single cells based on the plurality of sequencing reads of cellular component target library members.

In some embodiments, each of the plurality of sequencing reads of cellular component target library members, comprise (1) a molecular label sequence, and/or (2) at least a portion of the unique identifier sequence. In some embodiments, the cellular component-binding reagent specific oligonucleotide comprises a second molecular label. In some embodiments, at least ten of the plurality of cellular component-binding reagent specific oligonucleotides comprise different second molecular label sequences. In some embodiments, the second molecular label sequences of at least two cellular component-binding reagent specific oligonucleotides are different, and wherein the unique identifier sequences of the at least two cellular component-binding reagent specific oligonucleotides are identical. In some embodiments, the second molecular label sequences of at least two cellular component-binding reagent specific oligonucleotides are different, and wherein the unique identifier sequences of the at least two cellular component-binding reagent specific oligonucleotides are different. In some embodiments, the number of unique first molecular label sequences associated with the unique identifier sequence for the cellular component-binding reagent capable of specifically binding to the at least one cellular component target in the sequencing data indicates the number of copies of the at least one cellular component target in the one or more single cells. In some embodiments, the number of unique second molecular label sequences associated with the unique identifier sequence for the cellular component-binding reagent capable of specifically binding to the at least one cellular component target in the sequencing data indicates the number of copies of the at least one cellular component target in the one or more single cells.

The method can comprise: after contacting the plurality of cellular component-binding reagents with the first plurality of cells associated with the receptor detection constructs, removing one or more cellular component-binding reagents of the plurality of cellular component-binding reagents that are not contacted with the first plurality of cells associated with the receptor detection constructs. In some embodiments, removing the one or more cellular component-binding reagents not contacted with the first plurality of cells associated with the receptor detection constructs comprises: removing the one or more cellular component-binding reagents not contacted with the respective at least one of the plurality of cellular component targets.

In some embodiments, the target-binding region comprises a poly(dT) region and wherein the cellular component-binding reagent specific oligonucleotide comprises a poly(dA) region. In some embodiments, the cellular component-binding reagent specific oligonucleotide comprises an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. In some embodiments, the cellular component-binding reagent specific oligonucleotide is associated with the cellular component-binding reagent through a linker. In some embodiments, the cellular component-binding reagent specific oligonucleotide is configured to be detachable from the cellular component-binding reagent. The method can comprise: dissociating the cellular component-binding reagent specific oligonucleotide from the cellular component-binding reagent. In some embodiments, the linker comprises a carbon chain. In some embodiments, the carbon chain comprises 2-30 carbons, for example 12 carbons. In some embodiments, the linker comprises 5' amino modifier C12 (5AmMC12), or a derivative thereof. In some embodiments, the cellular component target comprises a protein target. In some embodiments, the cellular component-binding reagent comprises an antibody or fragment thereof. In some embodiments, the cellular component target comprises a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. In some embodiments, the cellular component-binding reagent comprises an antibody or fragment thereof. In some embodiments, the cellular component target is on a cell surface. In some embodiments, contacting the plurality of receptor detection constructs with the plurality of cells to form the first plurality of cells comprises removing one or more cells not bound to one or more receptor detection constructs. In some embodiments, removing one or more cells not bound to one or more receptor detection constructs comprises selecting cells bound to one or more receptor detection constructs.

In some embodiments, the receptor detection constructs comprise one or more additional labels, wherein selecting cells bound to one or more receptor detection constructs comprises flow cytometry and/or selecting cells based on the presence of the one or more additional labels. In some embodiments, the one or more additional labels comprise a fluorescent label. In some embodiments, removing the one or more receptor-binding reagents not contacted with the first plurality of cells associated with the receptor detection constructs comprises: removing the one or more receptor-binding reagents not contacted with the receptor. In some embodiments, the receptor-binding reagent specific oligonucleotide comprises a second universal sequence. In some embodiments, generating the sequencing library comprises: amplifying the plurality of barcoded receptor-binding reagent specific oligonucleotides, or products thereof, using a primer capable of hybridizing to the first universal sequence, or a complement thereof, and a primer capable of hybridizing to the second universal sequence, or a complement thereof, to generate a plurality of amplified barcoded receptor-binding reagent specific oligonucleotides, wherein the plurality of receptor library members comprise the plurality of amplified barcoded receptor-binding reagent specific oligonucleotides, or products thereof. In some embodiments, amplifying the plurality of barcoded receptor-binding reagent specific oligonucleotides comprises adding sequences of binding sites of sequencing primers and/or sequencing adaptors, complementary sequences thereof, and/or portions thereof, to the plurality of barcoded receptor-binding reagent specific oligonucleotides.

In some embodiments, each of the plurality of sequencing reads of receptor library members, comprise (1) a molecular label sequence, and/or (2) at least a portion of the unique receptor identifier sequence. In some embodiments, each of the plurality of sequencing reads of receptor library members, comprise a cell label sequence. In some embodiments, each unique cell label sequence indicates a single cell of the second plurality of cells. The method can comprise: determining the number of copies of the receptor in the one or more single cells based on the plurality of sequencing reads of receptor library members. The method can comprise: determining the identity of the receptor-binding reagent bound to the one or more single cells based on the plurality of sequencing reads of receptor library members. The method can comprise: determining the identity of the receptor in the one or more single cells based on the plurality of sequencing reads of receptor library members. In some embodiments, the receptor-binding reagent specific oligonucleotide comprises a third molecular label. In some embodiments, at least ten of the plurality of receptor-binding reagent specific oligonucleotides comprise different third molecular label sequences. In some embodiments, the third molecular label sequences of at least two receptor-binding reagent specific oligonucleotides are different, and wherein the unique receptor identifier sequences of the at least two receptor-binding reagent specific oligonucleotides are identical. In some embodiments, the third molecular label sequences of at least two receptor-binding reagent specific oligonucleotides are different, and wherein the unique receptor identifier sequences of the at least two receptor-binding reagent specific oligonucleotides are different. In some embodiments, the number of unique first molecular label sequences associated with the unique receptor identifier sequence for the receptor-binding reagent capable of specifically binding to the at least one receptor target in the sequencing data indicates the number of copies of the receptor in the one or more single cells. In some embodiments, the number of unique third molecular label sequences associated with the unique receptor identifier sequence for the receptor-binding reagent capable of specifically binding to the at least one receptor in the sequencing data indicates the number of copies of the receptor in the one or more single cells. In some embodiments, receptor-binding reagent specific oligonucleotides associated with identical receptor-binding reagents comprise an identical unique receptor identifier sequence, and wherein receptor-binding reagent specific oligonucleotides associated with different receptor-binding reagents comprise different unique receptor identifier sequences.

In some embodiments, the receptor-binding reagent specific oligonucleotide comprises DNA, RNA, a locked nucleic acid (LNA), a peptide nucleic acid (PNA), an LNA/PNA chimera, an LNA/DNA chimera, a PNA/DNA chimera, or any combination thereof. In some embodiments, the receptor-binding reagent specific oligonucleotide is about 10 nucleotides to about 100 nucleotides in length. In some embodiments, the receptor comprises a cluster of differentiation (CD) molecule. In some embodiments, the receptor comprises an immune receptor (e.g., a T cell receptor (TCR)). In some embodiments, the unique receptor identifier sequence is about 3 nucleotides to about 100 nucleotides in length. In some embodiments, the target-binding region comprises a poly(dT) region and wherein the receptor-binding reagent specific oligonucleotide comprises a poly(dA) region. In some embodiments, the receptor-binding reagent specific oligonucleotide comprises an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. In some embodiments, the receptor-binding reagent specific oligonucleotide is associated with the receptor-binding reagent through a linker. In some embodiments, the receptor-binding reagent specific oligonucleotide is configured to be detachable from the receptor-binding reagent. The method can comprise: dissociating the receptor-binding reagent specific oligonucleotide from the receptor-binding reagent. In some embodiments, the linker comprises a carbon chain. In some embodiments, the carbon chain comprises 2-30 carbons, and further optionally the carbon chain comprises 12 carbons. In some embodiments, the linker comprises 5' amino modifier C12 (5AmMC12), or a derivative thereof.

The plurality of receptor detection constructs can comprise one or more MHC multimers, and wherein the two or more receptor-binding reagents comprise two or more MHC-peptide complexes. An MHC multimer can comprise $(a\text{-}b\text{-}P)_n$, wherein n>1, wherein polypeptides a and b together form a functional MHC protein capable of binding peptide P, and (a-b-P) is a MHC-peptide complex formed when peptide P binds to the functional MHC protein. In some embodiments, each MHC-peptide complex of a MHC multimer is associated with one or more multimerization domains. In some embodiments, the plurality of receptor detection constructs comprises 2 MHC multimers, 3 MHC multimers, 4 MHC multimers, 5 MHC multimers, 6 MHC multimers, 7 MHC multimers, 8 MHC multimers, 9 MHC multimers, 10 MHC multimers, 11 MHC multimers, 12 MHC multimers, 13 MHC multimers, 14 MHC multimers, 15 MHC multimers, 16 MHC multimers, 17 MHC multimers, 18 MHC multimers, 19 MHC multimers, or 20 MHC multimers. In some embodiments, the individual antigenic peptides P of each MHC-peptide complex of said MHC multimers are identical or different. In some embodiments, the plurality of receptor detection constructs comprises one or more negative control MHC multimers. In some embodiments, the one or more negative control MHC multimers wherein each MHC multimer comprises a negative control peptide P. In some embodiments, said negative control peptide P is a nonsense peptide. In some embodiments, said one or more negative control MHC multimers are empty MHC multimers. In some embodiments, the plurality of receptor detection constructs comprises one or more positive control MHC multimers wherein each MHC multimer comprises a positive control peptide P. In some embodiments, the value of n of said one or more MHC multimers comprising $(a\text{-}b\text{-}P)_n$ is $1<n\geq 1000$. In some embodiments, the value of n is between 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-35, 35-40, 40-45, 45-50, 50-55, 55-60, 60-65, 65-70, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-325, 325-350, 350-375, 375-400, 400-450, 450-500, 500-550, 550-600, 600-650, 650-700, 700-750, 750-800, 800-850, 850-900, 900-950, or 950-1000. In some embodiments, said MHC protein is MHC Class I. In some embodiments, said MHC protein is MHC Class I, MHC class II, MR1, CD1, or a MHC-like molecule, and the antigenic peptides P are selected from the group consisting of 8-, 9-, 10-, 11-, and 12-mer peptides that binds to MHC Class I, MHC class II, MR1, CD1, or the MHC-like molecule.

In some embodiments, the association between the one or more of each MHC protein or MHC-peptide complex of a multimeric MHC, and the one or more multimerization domains, is a covalent association and/or a non-covalent association. In some embodiments, the one or more multimerization domains comprises one or more multimerization domain connector molecules. In some embodiments, one or more of each MHC protein or MHC-peptide complex of a multimeric MHC comprises one or more MHC connector molecules. In some embodiments, the one or more multimerization domain connector molecules comprises one or more streptavidins and/or one or more avidins, or any derivatives thereof. In some embodiments, the one or more streptavidins comprises one or more tetrameric streptavidin variants or one or more monomeric streptavidin variants. The one or more MHC connector molecules can be biotin. In some embodiments, one or more of each MHC protein or MHC-peptide complex of a MHC multimer is associated with one or more multimerization domains via a streptavidin-biotin linkage or an avidin-biotin linkage. In some embodiments, one or more of each MHC protein or MHC-peptide complex of a MHC multimer is associated with one or more multimerization domains by a linker moiety. In some embodiments, one or more of each MHC protein or MHC-peptide complex of a MHC multimer is associated with one or more multimerization domains by a natural dimerization and/or a protein-protein interaction. In some embodiments, the natural dimerization and/or a protein-protein interaction is selected from the group consisting of leucine zipper e.g. leucine zipper domain of AP-1, Fos/Jun interactions, acid/base coiled coil structure based interactions (e.g. helices), antibody/antigen interactions, polynucleotide-polynucleotide interactions e.g. DNA/DNA, DNA/PNA, DNA/RNA, PNA/PNA, LNA/DNA; synthetic molecule-synthetic molecule interactions and protein-small molecule interactions, IgG dimeric protein, IgM multivalent protein, chelate/metal ion-bound chelate, strep immunoglobulins, antibodies (monoclonal, polyclonal, and recombinant), antibody fragments and derivatives thereof, hexahis (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

In some embodiments, the one or more multimerization domains comprises (i) one or more scaffolds; (ii) one or more carriers; (iii) at least one scaffold and at least one carrier; and/or (iv) one or more optionally substituted organic molecules. In some embodiments, the optionally substituted organic molecule comprises one or more functionalized cyclic structures. In some embodiments, the functionalized cyclic structures comprise benzene rings. In some embodiments, the optionally substituted organic molecule comprises a scaffold molecule comprising at least three reactive groups, or at least three sites suitable for non-covalent attachment. In some embodiments, the one or more multimerization domains comprises one or more biological cells and/or cell-like structures. In some embodiments, the one or more multimerization domains comprises one or more membranes. In some embodiments, the one or more membranes comprises liposomes or micelles. In some embodiments, the one or more multimerization domains comprises one or more polymers (e.g., one or more synthetic polymers). In some embodiments, the one or more polymers comprise polysaccharides.

The polysaccharide can comprise one or more dextran moieties. In some embodiments, the one or more dextran moieties are (i) covalently attached to one or more MHC peptide complexes; (ii) non-covalently attached to one or more MHC peptide complexes; and/or (iii) modified. The one or more dextran moieties can comprise one or more amino-dextrans. The one or more amino-dextrans can be modified with divinyl sulfone. In some embodiments, the one or more dextran moieties comprises one or more dextrans with a molecular weight of from about 1,000 to 50,000 Da. In some embodiments, the one or more dextran moieties comprises one or more dextrans with a molecular weight of from about 50,000 to 150,000 Da (e.g., from about 50,000 to 60,000, from about 60,000 to 70,000, from about 70,000 to 80,000, from about 80,000 to 90,000, from about 90,000 to 100,000, from about 100,000 to 110,000, from about 110,000 to 120,000, from about 120,000 to 130,000, from about 130,000 to 140,000, or from about 140,000 to 150,000 Da). In some embodiments, the one or more dextran moieties comprises one or more dextrans with a molecular weight of from about 150,000 Da to 270,000 Da. The one or more dextran moieties can be linear and/or branched.

In some embodiments, the one or more synthetic polymers comprise PNA, polyamide, PEG, or any combination thereof. In some embodiments, the one or more multimerization domains comprises one or more entities selected from the group consisting of an IgG domain, a coiled-coil polypeptide structure, a DNA duplex, a nucleic acid duplex, PNA-PNA, PNA-DNA and DNA-RNA. In some embodiments, the one or more multimerization domains comprises an antibody. In some embodiments, the antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody and fusion antibody. In some embodiments, the one or more multimerization domains comprises one or more small organic scaffold molecules or small organic molecules. In some embodiments, the one or more small organic molecules comprises one or more steroids, one or more peptides, and/or one or more aromatic organic molecules. In some embodiments, the one or more aromatic organic molecules comprises one or more one or more dicyclic structures, one or more polycyclic structures or one or more monocyclic structures; optionally the one or more monocyclic structures comprises one or more optionally functionalized or substituted benzene rings. In some embodiments, the one or more multimerization domains comprises one or more: (i) monomeric molecules able to polymerize; (ii) biological polymers such as one or more proteins; (iii) small molecule scaffolds; (iv) supramolecular structure(s) such as one or more nanoclusters; and/or (v) protein complexes.

The one or more multimerization domains can comprise one or more beads. In some embodiments, the one or more beads comprise one or more beads that carry electrophilic groups e.g., divinyl sulfone activated polysaccharide, polystyrene beads that have been functionalized with tosyl-activated esters, magnetic polystyrene beads functionalized with tosyl-activated esters, and beads where MHC complexes have been covalently immobilized to these by reaction of nucleophiles comprised within the MHC complex with the electrophiles of the beads. In some embodiments, the one or more beads are selected from the groups consisting of sepharose beads, sephacryl beads, polystyrene beads, agarose beads, polysaccharide beads, polycarbamate beads and any other kind of beads that can be suspended in an aqueous buffer. In some embodiments, the multimerization domain comprises one or more compounds selected from agarose, sepharose, resin beads, glass beads, pore-glass beads, glass particles coated with a hydrophobic polymer, chitosan-coated beads, SH beads, latex beads .spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally cross-linked with N-N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

The one or more multimerization domains can comprise a dimerization domain, a trimerization domain, a tetramerization domain, a pentamerization domain, or a hexamerization domain. In some embodiments, the one or more multimerization domains comprises a polymer structure to which is attached one or more scaffolds. In some embodiments, the polymer structure comprises a polysaccharide. In some embodiments, the polysaccharide comprises one or more dextran moieties. In some embodiments, the one or more multimerization domains comprises a polyamide, a polyethylene glycol, a polysaccharide, a sepharose, or any combination thereof. In some embodiments, the one or more multimerization domains comprises a carboxy methyl dextran, a dextran polyaldehyde, a carboxymethyl dextran lactone, a cyclodextrin, or any combination thereof. In some embodiments, the one or more multimerization domains have a molecular weight of less than 1,000 Da, of from 1,000 Da to less than 10,000 Da, of from 10,000 Da to less than 100,000 Da, of from 100,000 Da to less than 1,000,000 Da, or of more than 1,000,000 Da. In some embodiments, said one or more MEW multimers further comprise one or more scaffolds, carriers and/or linkers selected from the group consisting of streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). In some embodiments, said MHC multimer comprises a plurality of identical or different multimerization domains linked by a multimerization domain linking moiety. In some embodiments, said MHC multimer comprises a first multimerization domain linked to a second multimerization domain.

The one or more MHC multimers can comprise one or more labels. The one or more labels can comprise the receptor-binding reagent specific oligonucleotide. In some embodiments, the one or more labels comprises the receptor-binding reagent specific oligonucleotide and one or more additional labels. In some embodiments, the one or more additional labels is a peptide label, a fluorophore label, heavy metal labels, isotope labels, radiolabels, radionuclide, stable isotopes, chains of isotopes and single atoms, a chemiluminescent label, a bioluminescent label, a radioactive label, an enzyme label, a DNA fluorescent stain, a lanthanide, a ionophore, a chelating chemical compound binding to specific ions, or any combination thereof. In some embodiments, the one or more labels comprise covalently attached labels and/or non-covalently attached labels. In some embodiments, the one or more labels are attached to: (i) the MHC polypeptide a; (ii) the MHC polypeptide b; (iii) the peptide P; (iv) the one or more multimerization domains; and/or (v) $(a\text{-}b\text{-}P)_n$. In some embodiments, the one or more labels is attached to $(a\text{-}b\text{-}P)_n$ via a streptavidin-biotin linkage.

The one or more additional labels can be a fluorophore label. In some embodiments, the fluorophore label is fluorescein isothiocyanate, rhodamine, phycoerythrin, phycocyanin, allophycocyanin, o-phthaldehyde, fluorescamine; 2-(4'-maleimidylanilino)naphthalene-6-sulfonic acid, sodium salt; 5-((((2-iodoacetyl)amino)ethyl)amino) naphthalene-1-sulfonic acid; Pyrene-1-butanoic acid; AlexaFluor 350 (7-amino-6-sulfonic acid-4-methyl coumarin-3-acetic acid; AMCA (7-amino-4-methyl coumarin-3-acetic acid); 7-hydroxy-4-methyl coumarin-3-acetic acid; Marina Blue (6,8-difluoro-7-hydroxy-4-methyl coumarin-3-acetic acid); 7-dimethylamino-coumarin-4-acetic acid; Fluorescamin-N-butyl amine adduct; 7-hydroxy-coumarine-3-carboxylic acid; CascadeBlue (pyrene-trisulphonic acid acetyl azide; Cascade Yellow; Pacific Blue (6,8 difluoro-7-hydroxy coumarin-3-carboxylic acid; 7-diethylamino-coumarin-3-carboxylic acid; N-(((4-azidobenzoyl)amino)ethyl)-4-amino-3,6-disulfo-1,8-naphthalimide, dipotassium salt; Alexa Fluor 430; 3-perylenedodecanoic acid; 8-hydroxypyrene-1,3,6-trisulfonic acid, trisodium salt; 12-(N-(7-nitrobenz-2-oxa-1,3-diazol-4-yl)amino)dodecanoic acid; N,N'-dimethyl-N-(iodoacetyl)-N'-(7-nitrobenz-2-oxa-1,3-diazol-4-yl) ethylenediamine; Oregon Green 488 (difluoro carboxy fluorescein); 5-iodoacetamidofluorescein; propidium iodide-DNA adduct; Carboxy fluorescein, Fluor dyes, Pacific Blue™, Pacific Orange™, Cascade Yellow™; AlexaFluor® (AF), AF405, AF488, AF500, AF514, AF532, AF546, AF555, AF568, AF594, AF610, AF633, AF635, AF647, AF680, AF700, AF710, AF750, AF800; Quantum Dot based dyes, QDot® Nanocrystals (Invitrogen, MolecularProbs), Qdot®525, Qdot®565, Qdot®585, Qdot®605, Qdot®655, Qdot®705, Qdot®800; DyLight™ Dyes (Pierce) (DL); DL549, DL649, DL680, DL800; Fluorescein (Flu) or any derivate of that, such as FITC; Cy-Dyes, Cy2, Cy3, Cy3.5, Cy5, Cy5.5, Cy7; Fluorescent Proteins, RPE, PerCp, APC, Green fluorescent proteins; GFP and GFP derivated mutant proteins; BFP.CFP, YFP, DsRed, T1, Dimer2, mRFP1, MBanana, mOrange, dTomato, tdTomato, mTangerine, mStrawberry, mCherry; Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, APC-Cy5.5, or a combination thereof.

In some embodiments, the one or more additional labels is capable of absorption of light (e.g., a chromophore and/or a dye). In some embodiments, the one or more additional labels is capable of emission of light after excitation, optionally one or more fluorochromes, further optionally the one or more fluorochromes is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800; selected from the Quantum Dot (Qdot®) based dye family, which include Qdot®525, Qdot®565, Qdot®585, Qdot®605, Qdot®655, Qdot®705, Qdot®800; selected from the DyLight™ Dyes (DL) family, which include DL549, DL649, DL680, DL800; selected from the family of Small fluorescing dyes, which include FITC, Pacific Blue™, Pacific Orange™, Cascade Yellow™, Marina blue™, DSred, DSred-2, 7-AAD, TO-Pro-3; selected from the family of Cy-Dyes, which include Cy2, Cy3, Cy3.5, Cy5, Cy5.5, Cy7; selected from the family of Phycobili Proteins, which include R-Phycoerythrin (RPE), PerCP, Allophycocyanin (APC), B-Phycoerythrin, C-Phycocyanin; selected from the family of Fluorescent Proteins, which include (E) GFP and GFP ((enhanced) green fluorescent protein) derived mutant proteins; BFP.CFP, YFP, DsRed, T1, Dimer2, mRFP1, MBanana, mOrange, dTomato, tdTomato, mTangerine; selected from the family of Tandem dyes with RPE, which include RPE-Cy5, RPE-Cy5.5, RPE-Cy7, RPE-AlexaFluor® tandem conjugates; RPE-Alexa610, RPE-TxRed; selected from the family of Tandem dyes with APC, which include APC-Aleca600, APC-Alexa610, APC-Alexa750, APC-Cy5, APC-Cy5.5; selected from the family of Calcium dyes, which include lndo-1-$Ca^{2+}$ lndo-1-$Ca^{2+}$.

The MHC multimer can comprise one or more further polypeptides in addition to a and b. In some embodiments, one of the polypeptides of the MHC-peptide complex is a heavy chain polypeptide. In some embodiments, one of the polypeptides of the MHC-peptide complex is a b2M polypeptide. In some embodiments, (i) P is chemically modified; (ii) P is pegylated, phosphorylated and/or glycosylated; (iii) one of the amino acid residues of the peptide P is substituted with another amino acid; (iv) a and b are both full-length peptides; (v) a is a full-length peptide; (vi) b is a full-length peptide; (vii) a is truncated; (viii) b is truncated; (ix) a and b are both truncated; (x) a is covalently linked to b; (xi) a is covalently linked to P; (xii) b is covalently linked to P; (xiii) a, b and P are all covalently linked; (xiv) a is non-covalently linked to b; (xv) a is non-covalently linked to P; (xvi) b is non-covalently linked to P; (xvii) a, b and P are all non-covalently linked; (xviii) a is not included in the (a-b-P) complex; (xix) b is not included in the (a-b-P) complex; and/or (xx) P is not included in the (a-b-P) complex. In some embodiments, the MHC multimer comprises one or more stability-increasing components (e.g., HEG and/or TEG).

The method can comprise: associating a T cell receptor (TCR) receptor in the one or more single cells with the peptide P based on the plurality of sequencing reads of receptor library members. The method can comprise: measuring the presence, frequency, number, activity and/or state of T cells specific for a peptide P, thereby detecting an antigen-specific T cell response.

In some embodiments, the first universal sequence, the second universal sequence, the third universal sequence, and/or the fourth universal sequence are the same. In some embodiments, the first universal sequence, the second universal sequence, the third universal sequence, and/or the fourth universal sequence are different. In some embodiments, the first universal sequence, the second universal sequence, the third universal sequence, and/or the fourth universal sequence comprise the binding sites of sequencing primers and/or sequencing adaptors, complementary sequences thereof, and/or portions thereof. In some embodiments, the sequencing adaptors comprise a P5 sequence, a P7 sequence, complementary sequences thereof, and/or portions thereof. In some embodiments, the sequencing primers comprise a Read 1 sequencing primer, a Read 2 sequencing primer, complementary sequences thereof, and/or portions thereof.

The method can comprise: physically separating one or more of (i) barcoded nucleic acid molecules, (ii) barcoded receptor-binding reagent specific oligonucleotides, and (iii) barcoded cellular component-binding reagent specific oligonucleotides from one or more of (i) barcoded nucleic acid molecules, (ii) barcoded receptor-binding reagent specific oligonucleotides, and (iii) barcoded cellular component-binding reagent specific oligonucleotides. In some embodiments, physically separating comprises use of one or more size selection reagents. In some embodiments, the plurality of barcoded receptor-binding reagent specific oligonucleotides and the plurality barcoded cellular component-binding reagent specific oligonucleotides are amplified separately.

The second universal sequence and the third universal sequence can be different. In some embodiments, the second universal sequence is less than about 85% identical to the third universal sequence. In some embodiments, the second universal sequence comprises a sequence at least about 85% identical to SEQ ID NO: 1 (GGAGGGAGGT-TAGCGAAGGT). In some embodiments, amplifying the plurality of barcoded receptor-binding reagent specific oligonucleotides, or products thereof, does not comprise amplifying the plurality of barcoded cellular component-binding reagent specific oligonucleotides, or products thereof. In some embodiments, generating the sequencing library comprises generating a sequencing mixture comprising (i) nucleic acid target library members, (ii) cellular component target library members, and/or (iii) receptor library members. In some embodiments, generating a sequencing mixture comprises mixing (i) nucleic acid target library members, (ii) cellular component target library members, and/or (iii) receptor library members at a predetermined ratio. In some embodiments, the (i) nucleic acid target library members, (ii) cellular component target library members, and/or (iii) receptor library members are physically separate from one another prior to generating the sequencing mixture. In some embodiments, the sequencing mixture comprises a predetermined ratio of (i) nucleic acid target library members, (ii) cellular component target library members, and/or (iii) receptor library members.

In some embodiments, the predetermined ratio of cellular component target library members to receptor library members is about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. In some embodiments, the predetermined ratio of cellular component target library members to receptor library members is configured to achieve a ratio of sequencing reads of cellular component target library members to sequencing reads of receptor library members that is about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. In some embodiments, the ratio of sequencing reads of cellular component target library members to sequencing reads of receptor library members is about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. In some embodiments, the ratio of sequencing reads of cellular component target library members to sequencing reads of receptor library members is at least about 2-fold lower as compared to a method wherein: (i) the plurality of barcoded receptor-binding reagent specific oligonucleotides and the plurality barcoded cellular component-binding reagent specific oligonucleotides are amplified together; (ii) the second universal sequence and third universal sequence are the same; and/or (iii) the sequencing mixture does not comprise a predetermined ratio of cellular component target library members to receptor library members.

Disclosed herein include kits. In some embodiments, the kit comprises: a plurality of receptor detection constructs, wherein a receptor detection construct comprises two or more receptor-binding reagents, wherein a receptor-binding reagent is capable of specifically binding to a receptor, and wherein each of the receptor detection constructs comprises a receptor-binding reagent specific oligonucleotide comprising a unique receptor identifier sequence for the receptor-binding reagent. The kit can comprise: a plurality of cellular component-binding reagents, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to a cellular component target. wherein the receptor-binding reagent specific oligonucleotide comprises a second universal sequence, wherein the cellular component-binding reagent specific oligonucleotide comprises a third universal sequence, wherein the second universal sequence and the third universal sequence are different. In some embodiments, the second universal sequence is less than about 85% identical to the third universal sequence.

The kit can comprise: a plurality of oligonucleotide barcodes, wherein each of the plurality of oligonucleotide barcodes comprises a first universal sequence, a molecular label and a target-binding region, and wherein at least 10 of the plurality of oligonucleotide barcodes comprise different molecular label sequences. In some embodiments, the plurality of oligonucleotide barcodes are associated with a solid support. In some embodiments, the target-binding region comprises a gene-specific sequence, an oligo(dT) sequence, a random multimer, or any combination thereof. The kit can comprise: a reverse transcriptase. In some embodiments, the reverse transcriptase comprises a viral reverse transcriptase, and further optionally the viral reverse transcriptase is a murine leukemia virus (MLV) reverse transcriptase or a Moloney murine leukemia virus (MMLV) reverse transcriptase. The kit can comprise: a DNA polymerase lacking at least one of 5' to 3' exonuclease activity and 3' to 5' exonuclease activity, (e.g., a Klenow Fragment). The kit can comprise: a buffer, a cartridge, or both. The kit can comprise: one or more reagents for a reverse transcription reaction and/or an amplification reaction. In some embodiments, the plurality of oligonucleotide barcodes each comprise a cell label. In some embodiments, each cell label of the plurality of oligonucleotide barcodes comprises at least 6 nucleotides. In some embodiments, oligonucleotide barcodes of the plurality of oligonucleotide barcodes associated with the same solid support comprise the same cell label. In some embodiments, oligonucleotide barcodes of the plurality of oligonucleotide barcodes associated with different solid supports comprise different cell labels.

The solid support can comprise a synthetic particle, a planar surface, or a combination thereof. In some embodiments, at least one oligonucleotide barcode of the plurality of oligonucleotide barcodes is immobilized or partially immobilized on the synthetic particle, or at least one oligonucleotide barcode of the plurality of oligonucleotide barcodes is enclosed or partially enclosed in the synthetic particle. In some embodiments, the synthetic particle is disruptable (e.g, a disruptable hydrogel particle). In some embodiments, the synthetic particle comprises a bead. The bead can be a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, each oligonucleotide barcode of the plurality of oligonucleotide barcodes comprises a linker functional group. In some embodiments, the synthetic particle comprises a solid support functional group. In some embodiments, the support functional group and the linker functional group are associated with each other, and optionally the linker functional group and the support functional group are individually selected from the group consisting of C6, biotin, streptavidin, primary amine(s), aldehyde(s), ketone(s), and any combination thereof.

The kit can comprise: one or more primers comprising the first universal sequence, first universal sequence, and/or third universal sequence. In some embodiments, the second universal sequence comprises a sequence at least about 85% identical to SEQ ID NO: 1 (GGAGGGAGGTTAGCGAAGGT). In some embodiments, the target-binding region comprises a poly(dT) region and wherein the cellular component-binding reagent specific oligonucleotide comprises a poly(dA) region. In some embodiments, the cellular component-binding reagent specific oligonucleotide comprises an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. In some embodiments, the cellular component-binding reagent specific oligonucleotide is associated with the cellular component-binding reagent through a linker. In some embodiments, the cellular component-binding reagent specific oligonucleotide is configured to be detachable from the cellular component-binding reagent. In some embodiments, the linker comprises a carbon chain. In some embodiments, the carbon chain comprises 2-30 carbons, for example 12 carbons. In some embodiments, the linker comprises 5' amino modifier C12 (5AmMC12), or a derivative thereof.

In some embodiments, the cellular component target comprises a protein target. In some embodiments, the cellular component-binding reagent comprises an antibody or fragment thereof. In some embodiments, the cellular component target comprises a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. In some embodiments, the cellular component-binding reagent comprises an antibody or fragment thereof. In some embodiments, the cellular component target is on a cell surface.

In some embodiments, the receptor-binding reagent specific oligonucleotide comprises a third molecular label and/or the cellular component-binding reagent specific oligonucleotide comprises a second molecular label. In some embodiments, the receptor-binding reagent specific oligonucleotide is about 10 nucleotides to about 100 nucleotides in length. In some embodiments, the receptor comprises a cluster of differentiation (CD) molecule. In some embodiments, the receptor comprises an immune receptor (e.g., a T cell receptor (TCR)). In some embodiments, the unique receptor identifier sequence is about 3 nucleotides to about 100 nucleotides in length. In some embodiments, the target-binding region comprises a poly(dT) region and wherein the receptor-binding reagent specific oligonucleotide comprises a poly(dA) region. In some embodiments, the receptor-binding reagent specific oligonucleotide comprises an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. In some embodiments, the receptor-binding reagent specific oligonucleotide is associated with the receptor-binding reagent through a linker. In some embodiments, the receptor-binding reagent specific oligonucleotide is configured to be detachable from the receptor-binding reagent. In some embodiments, the linker comprises a carbon chain. In some embodiments, the carbon chain comprises 2-30 carbons, for example 12 carbons. In some embodiments, the linker comprises 5' amino modifier C12 (5AmMC12), or a derivative thereof.

In some embodiments, the plurality of receptor detection constructs comprises one or more MHC multimers, and wherein the two or more receptor-binding reagents comprise two or more MHC-peptide complexes. In some embodiments, an MHC multimer comprises $(a\text{-}b\text{-}P)_n$, wherein $n>1$, wherein polypeptides a and b together form a functional MHC protein capable of binding peptide P, and (a-b-P) is a MHC-peptide complex formed when peptide P binds to the functional MHC protein. In some embodiments, each MHC-peptide complex of a MHC multimer is associated with one or more multimerization domains. In some embodiments, the plurality of receptor detection constructs comprises 2 MHC multimers, 3 MHC multimers, 4 MHC multimers, 5 MHC multimers, 6 MHC multimers, 7 MHC multimers, 8 MHC multimers, 9 MHC multimers, 10 MHC multimers, 11 MHC multimers, 12 MHC multimers, 13 MHC multimers, 14 MHC multimers, 15 MHC multimers, 16 MHC multimers, 17 MHC multimers, 18 MHC multimers, 19 MHC multimers, or 20 MHC multimers. In some embodiments, the individual antigenic peptides P of each MHC-peptide complex of said MHC multimers are identical or different. In some embodiments, the plurality of receptor detection constructs comprises one or more negative control MHC multimers. In some embodiments, the one or more negative control MHC multimers wherein each MHC multimer comprises a negative control peptide P. In some embodiments, said negative control peptide P is a nonsense peptide. In some embodiments, said one or more negative control MHC multimers are empty MHC multimers. In some embodiments, the plurality of receptor detection constructs comprises one or more positive control MHC multimers wherein each MHC multimer comprises a positive control peptide P. In some embodiments, the value of n of said one or more MHC multimers comprising $(a\text{-}b\text{-}P)_n$ is $1<n\geq1000$. In some embodiments, the value of n is between 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-35, 35-40, 40-45, 45-50, 50-55, 55-60, 60-65, 65-70, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-325, 325-350, 350-375, 375-400, 400-450, 450-500, 500-550, 550-600, 600-650, 650-700, 700-750, 750-800, 800-850, 850-900, 900-950, or 950-1000. In some embodiments, said MHC protein is MHC Class I, MHC class II, MR1, CD1, or a MHC-like molecule. In some embodiments, said MHC protein is MHC Class I and the antigenic peptides P are selected from the group consisting of 8-, 9-, 10-, 11-, and 12-mer peptides that binds to MHC Class I, MHC class II, MR1, CD1, or a MHC-like molecule.

In some embodiments, the association between the one or more of each MHC protein or MHC-peptide complex of a multimeric MHC, and the one or more multimerization domains, is a covalent association and/or a non-covalent association. In some embodiments, the one or more multimerization domains comprises one or more multimerization domain connector molecules. In some embodiments, one or more of each MHC protein or MHC-peptide complex of a multimeric MHC comprises one or more MHC connector molecules. In some embodiments, the one or more multimerization domain connector molecules comprises one or more streptavidins and/or one or more avidins, or any derivatives thereof. In some embodiments, the one or more streptavidins comprises one or more tetrameric streptavidin variants or one or more monomeric streptavidin variants. The one or more MHC connector molecules can be biotin. In some embodiments, one or more of each MHC protein or MHC-peptide complex of a MHC multimer is associated with one or more multimerization domains via a streptavidin-biotin linkage or an avidin-biotin linkage. In some embodiments, one or more of each MHC protein or MHC-peptide complex of a MHC multimer is associated with one or more multimerization domains by a linker moiety. In some embodiments, one or more of each MHC protein or MHC-peptide complex of a MHC multimer is associated with one or more multimerization domains by a natural dimerization and/or a protein-protein interaction. In some embodiments, the natural dimerization and/or a protein-protein interaction is selected from the group consisting of leucine zipper e.g. leucine zipper domain of AP-1, Fos/Jun interactions, acid/base coiled coil structure based interactions (e.g. helices), antibody/antigen interactions, polynucleotide-polynucleotide interactions e.g. DNA/DNA, DNA/PNA, DNA/RNA, PNA/PNA, LNA/DNA; synthetic molecule-synthetic molecule interactions and protein-small molecule interactions, IgG dimeric protein, IgM multivalent protein, chelate/metal ion-bound chelate, strep immunoglobulins, antibodies (monoclonal, polyclonal, and recombinant), antibody fragments and derivatives thereof, hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g., Con A (*Canavalia ensiformis*) or WGA (wheat germ agglutinin) and tetranectin or Protein A or G (antibody affinity).

In some embodiments, the one or more multimerization domains comprises (i) one or more scaffolds; (ii) one or more carriers; (iii) at least one scaffold and at least one carrier; and/or (iv) one or more optionally substituted organic molecules. In some embodiments, the optionally substituted organic molecule comprises one or more functionalized cyclic structures. In some embodiments, the functionalized cyclic structures comprise benzene rings. In some embodiments, the optionally substituted organic molecule comprises a scaffold molecule comprising at least three reactive groups, or at least three sites suitable for non-covalent attachment. In some embodiments, the one or more multimerization domains comprises one or more biological cells and/or cell-like structures. In some embodiments, the one or more multimerization domains comprises one or more membranes. In some embodiments, the one or more membranes comprises liposomes or micelles. In some embodiments, the one or more multimerization domains comprises one or more polymers. In some embodiments, one or more synthetic polymers. In some embodiments, the one or more polymers are selected from the group consisting of polysaccharides.

In some embodiments, the polysaccharide comprises one or more dextran moieties. In some embodiments, the one or more dextran moieties are (i) covalently attached to one or more MHC peptide complexes; (ii) non-covalently attached to one or more MHC peptide complexes; and/or (iii) modified. In some embodiments, the one or more dextran moieties comprises one or more amino-dextrans. In some embodiments, the one or more amino-dextrans are modified with divinyl sulfone. In some embodiments, the one or more dextran moieties comprises one or more dextrans with a molecular weight of from about 1,000 to 50,000 Da. In some embodiments, the one or more dextran moieties comprises one or more dextrans with a molecular weight of from about 50,000 to 150,000 Da. In some embodiments, the one or more dextran moieties comprises one or more dextrans with a molecular weight of from about 150,000-270,000 Da. In some embodiments, the one or more dextran moieties are linear and/or branched.

In some embodiments, the one or more synthetic polymers comprise PNA, polyamide, PEG, or any combination thereof. In some embodiments, the one or more multimerization domains comprises one or more entities selected from the group consisting of an IgG domain, a coiled-coil polypeptide structure, a DNA duplex, a nucleic acid duplex, PNA-PNA, PNA-DNA and DNA-RNA. In some embodiments, the one or more multimerization domains comprises an antibody. In some embodiments, the antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody and fusion antibody. In some embodiments, the one or more multimerization domains comprises one or more small organic scaffold molecules or small organic molecules. In some embodiments, the one or more small organic molecules comprises one or more steroids, one or more peptides, and/or one or more aromatic organic molecules. In some embodiments, the one or more aromatic organic molecules comprises one or more one or more dicyclic structures, one or more polycyclic structures or one or more monocyclic structures; optionally the one or more monocyclic structures comprises one or more optionally functionalized or substituted benzene rings. In some embodiments, the one or more multimerization domains comprises one or more: (i) monomeric molecules able to polymerize; (ii) biological polymers such as one or more proteins; (iii) small molecule scaffolds; (iv) supramolecular structure(s) such as one or more nanoclusters; and/or (v) protein complexes.

In some embodiments, the one or more multimerization domains comprises one or more beads. In some embodiments, the one or more beads are selected from the group consisting of beads that carry electrophilic groups e.g. divinyl sulfone activated polysaccharide, polystyrene beads that have been functionalized with tosyl-activated esters, magnetic polystyrene beads functionalized with tosyl-activated esters, and beads where MHC complexes have been covalently immobilized to these by reaction of nucleophiles comprised within the MHC complex with the electrophiles of the beads. In some embodiments, the one or more beads are selected from the groups consisting of sepharose beads, sephacryl beads, polystyrene beads, agarose beads, polysaccharide beads, polycarbamate beads and any other kind of beads that can be suspended in an aqueous buffer. In some embodiments, the multimerization domain comprises one or more compounds selected from the group consisting of agarose, sepharose, resin beads, glass beads, pore-glass beads, glass particles coated with a hydrophobic polymer, chitosan-coated beads, SH beads, latex beads .spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone) PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptavidin-monomer coated beads, streptavidin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally cross-linked with N-N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan. In some embodiments, the one or more multimerization domains comprises a dimerization domain, a trimerization domain, a tetramerization domain, a pentamerization domain, or a hexamerization domain.

In some embodiments, the one or more multimerization domains comprises a polymer structure to which is attached one or more scaffolds. In some embodiments, the polymer structure comprises a polysaccharide. In some embodiments, the polysaccharide comprises one or more dextran moieties. In some embodiments, the one or more multimerization domains comprises a polyamide, a polyethylene glycol, a polysaccharide, a sepharose, or any combination thereof. In some embodiments, the one or more multimerization domains comprises a carboxy methyl dextran, a dextran polyaldehyde, a carboxymethyl dextran lactone, a cyclodextrin, or any combination thereof. In some embodiments, the one or more multimerization domains have a molecular weight of less than 1,000 Da, of from 1,000 Da to less than 10,000 Da, of from 10,000 Da to less than 100,000 Da, of from 100,000 Da to less than 1,000,000 Da, or of more than 1,000,000 Da. In some embodiments, said one or more MHC multimers further comprise one or more scaffolds, carriers and/or linkers selected from the group consisting of streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). In some embodiments, said MHC multimer comprises a plurality of identical or different multimerization domains linked by a multimerization domain linking moiety. In some embodiments, said MHC multimer comprises a first multimerization domain linked to a second multimerization domain.

The one or more MHC multimers can comprise one or more labels. In some embodiments, the one or more labels comprises the receptor-binding reagent specific oligonucleotide. In some embodiments, the one or more labels comprises the receptor-binding reagent specific oligonucleotide and one or more additional labels. In some embodiments, the one or more additional labels comprise a peptide label, a fluorophore label, heavy metal labels, isotope labels, radiolabels, radionuclide, stable isotopes, chains of isotopes and single atoms, a chemiluminescent label, a bioluminescent label, a radioactive label, an enzyme label, a DNA fluorescent stain, a lanthanide, a ionophore, a chelating chemical compound binding to specific ions, or any combination thereof. In some embodiments, the one or more labels comprise covalently attached labels and/or non-covalently attached labels. In some embodiments, the one or more labels are attached to: (i) the MHC polypeptide a; (ii) the MHC polypeptide b; (iii) the peptide P; (iv) the one or more multimerization domains; and/or (v) $(a\text{-}b\text{-}P)_n$. In some embodiments, the one or more labels is attached to $(a\text{-}b\text{-}P)_n$ via a streptavidin-biotin linkage.

In some embodiments, the one or more additional labels is a fluorophore label. In some embodiments, the fluorophore label is selected from the group comprising fluorescein isothiocyanate, rhodamine, phycoerythrin, phycocyanin, allophycocyanin, o-phthaldehyde, fluorescamine; 2-(4'-maleimidylanilino)naphthalene-6-sulfonic acid, sodium salt; 5-((((2-iodoacetyl)amino)ethyl)amino) naphthalene-1-sulfonic acid; Pyrene-1-butanoic acid; AlexaFluor 350 (7-amino-6-sulfonic acid-4-methyl coumarin-3-acetic acid; AMCA (7-amino-4-methyl coumarin-3-acetic acid); 7-hydroxy-4-methyl coumarin-3-acetic acid; Marina Blue (6,8-difluoro-7-hydroxy-4-methyl coumarin-3-acetic acid); 7-dimethylamino-coumarin-4-acetic acid; Fluorescamin-N-butyl amine adduct; 7-hydroxy-coumarine-3-carboxylic acid; CascadeBlue (pyrene-trisulphonic acid acetyl azide; Cascade Yellow; Pacific Blue (6,8 difluoro-7-hydroxy coumarin-3-carboxylic acid; 7-diethylamino-coumarin-3-carboxylic acid; N-(((4-azidobenzoyl)amino)ethyl)-4-amino-3,6-disulfo-1,8-naphthalimide, dipotassium salt; Alexa Fluor 430; 3-perylenedodecanoic acid; 8-hydroxypyrene-1,3,6-trisulfonic acid, trisodium salt; 12-(N-(7-nitrobenz-2-oxa-1,3-diazol-4-yl)amino)dodecanoic acid; N,N'-dimethyl-N-(iodoacetyl)-N'-(7-nitrobenz-2-oxa-1,3-diazol-4-yl) ethylenediamine; Oregon Green 488 (difluoro carboxy fluorescein); 5-iodoacetamidofluorescein; propidium iodide-DNA adduct; Carboxy fluorescein, Fluor dyes, Pacific Blue™, Pacific Orange™, Cascade Yellow™; AlexaFluor® (AF), AF405, AF488, AF500, AF514, AF532, AF546, AF555, AF568, AF594, AF610, AF633, AF635, AF647, AF680, AF700, AF710, AF750, AF800; Quantum Dot based dyes, QDot® Nanocrystals (Invitrogen, MolecularProbs), Qdot®525, Qdot®565, Qdot®585, Qdot®605, Qdot®655, Qdot®705, Qdot®800; DyLight™ Dyes (Pierce) (DL); DL549, DL649, DL680, DL800; Fluorescein (Flu) or any derivate of that, such as FITC; Cy-Dyes, Cy2, Cy3, Cy3.5, Cy5, Cy5.5, Cy7; Fluorescent Proteins, RPE, PerCp, APC, Green fluorescent proteins; GFP and GFP derivated mutant proteins; BFP.CFP, YFP, DsRed, T1, Dimer2, mRFP1, MBanana, mOrange, dTomato, tdTomato, mTangerine, mStrawberry, mCherry; Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, and APC-Cy5.5.

In some embodiments, the one or more additional labels is capable of absorption of light (e.g., a chromophore and/or a dye). In some embodiments, the one or more additional labels is capable of emission of light after excitation, optionally one or more fluorochromes, further optionally the one or more fluorochromes is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800; selected from the Quantum Dot (Qdot®) based dye family, which include Qdot®525, Qdot®565, Qdot®585, Qdot®605, Qdot®655, Qdot®705, Qdot®800; selected from the DyLight™ Dyes (DL) family, which include DL549, DL649, DL680, DL800; selected from the family of Small fluorescing dyes, which include FITC, Pacific Blue™, Pacific Orange™, Cascade Yellow™, Marina blue™, DSred, DSred-2, 7-AAD, TO-Pro-3; selected from the family of Cy-Dyes, which include Cy2, Cy3, Cy3.5, Cy5, Cy5.5, Cy7; selected from the family of Phycobili Proteins, which include R-Phycoerythrin (RPE), PerCP, Allophycocyanin (APC), B-Phycoerythrin, C-Phycocyanin; selected from the family of Fluorescent Proteins, which include (E) GFP and GFP ((enhanced) green fluorescent protein) derived mutant proteins; BFP.CFP, YFP, DsRed, T1, Dimer2, mRFP1, MBanana, mOrange, dTomato, tdTomato, mTangerine; selected from the family of Tandem dyes with RPE, which include RPE-Cy5, RPE-Cy5.5, RPE-Cy7, RPE-AlexaFluor® tandem conjugates; RPE-Alexa610, RPE-TxRed; selected from the family of Tandem dyes with APC, which include APC-Aleca600, APC-Alexa610, APC-Alexa750, APC-Cy5, APC-Cy5.5; selected from the family of Calcium dyes, which include Indo-1-$Ca^{2+}$ Indo-2-$Ca^{2+}$.

In some embodiments, the MHC multimer comprises one or more further polypeptides in addition to a and b. In some embodiments, one of the polypeptides of the MHC-peptide complex is a heavy chain polypeptide. In some embodiments, one of the polypeptides of the MHC-peptide complex is a b2M polypeptide. In some embodiments, (i) P is chemically modified; (ii) P is pegylated, phosphorylated and/or glycosylated; (iii) one of the amino acid residues of the peptide P is substituted with another amino acid; (iv) a and b are both full-length peptides; (v) a is a full-length peptide; (vi) b is a full-length peptide; (vii) a is truncated; (viii) b is truncated; (ix) a and b are both truncated; (x) a is covalently linked to b; (xi) a is covalently linked to P; (xii) b is covalently linked to P; (xiii) a, b and P are all covalently linked; (xiv) a is non-covalently linked to b; (xv) a is non-covalently linked to P; (xvi) b is non-covalently linked to P; (xvii) a, b and P are all non-covalently linked; (xviii) a is not included in the (a-b-P) complex; (xix) b is not included in the (a-b-P) complex; and/or (xx) P is not included in the (a-b-P) complex. In some embodiments, the MHC multimer comprises one or more stability-increasing components (e.g., HEG and/or TEG).

BRIEF DESCRIPTION OF THE DRAWINGS

FIG. 9A depicts a non-limiting exemplary Immudex dCODE Dextramer design compatible with BD Rhapsody System. FIG. 9B depicts a non-limiting exemplary BD Rhapsody System targeted workflow with dCODE Dextramer. FIG. 9C depicts non-limiting exemplary beads with hybridized mRNA and dCODE retrieved from cartridge. FIGS. 9D-9F depict a non-limiting exemplary experimental design: Human PBMCs stained with 3 Dextramers.

FIG. 12A depicts a Bioanalyzer trace of both the RiO dCODE® and AbSeg™ library PCR1 amplicons (peak 166 bp). FIG. 12B depicts a Bioanalyzer trace the RiO dCODE® library PCR2 amplicons (peak approximately 190 bp). FIGS. 12C-12D depict Bioanalyzer traces of the final library (indexing PCR) preps for Abseq (FIG. 12C; peak 265 bp) and RiO dCODE dextramers (FIG. 12D; peak approximately 290 bp).

DETAILED DESCRIPTION

Figure 1:
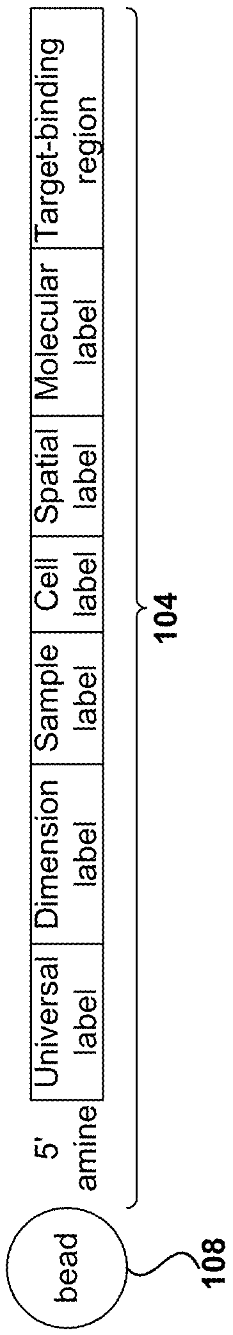
FIG. 1 illustrates a non-limiting exemplary barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding, such as the Precise™ assay (Cellular Research, Inc. (Palo Alto, CA)) and Rhapsody™ assay (Becton, Dickinson and Company (Franklin Lakes, NJ)), can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular label sequences on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular label sequences, and the numbers of mRNA molecules.

Disclosed herein include methods. In some embodiments, the method comprises: contacting a plurality of receptor detection constructs with a plurality of cells to form a first plurality of cells associated with the receptor detection constructs, wherein the plurality of cells comprise a plurality of cellular component targets and copies of a nucleic acid target, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: barcoding copies of the nucleic acid target of the plurality of cells with the plurality of oligonucleotide barcodes to generate a plurality of barcoded nucleic acid molecules each comprising a sequence complementary to at least a portion of the nucleic acid target. The method can comprise: generating a sequencing library comprising a plurality of nucleic acid target library members, a plurality of cellular component target library members, and a plurality of receptor library members, wherein generating the sequencing library comprises: attaching sequencing adaptors to the plurality of barcoded nucleic acid molecules, or products thereof, to generate the plurality of nucleic acid target library members; and attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of nucleic acid target library members, a plurality of sequencing reads of cellular component target library members, and a plurality of sequencing reads of receptor library members.

Disclosed herein include methods. In some embodiments, the method comprises: contacting a plurality of receptor detection constructs with a plurality of cells to form a first plurality of cells associated with the receptor detection constructs, wherein the plurality of cells comprise a plurality of cellular component targets, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: generating a sequencing library comprising a plurality of cellular component target library members and a plurality of receptor library members, wherein generating the sequencing library comprises: attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of cellular component target library members and a plurality of sequencing reads of receptor library members.

Disclosed herein include kits. In some embodiments, the kit comprises: a plurality of receptor detection constructs, wherein a receptor detection construct comprises two or more receptor-binding reagents, wherein a receptor-binding reagent is capable of specifically binding to a receptor, and wherein each of the receptor detection constructs comprises a receptor-binding reagent specific oligonucleotide comprising a unique receptor identifier sequence for the receptor-binding reagent. The kit can comprise: a plurality of cellular component-binding reagents, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to a cellular component target. wherein the receptor-binding reagent specific oligonucleotide comprises a second universal sequence, wherein the cellular component-binding reagent specific oligonucleotide comprises a third universal sequence, wherein the second universal sequence and the third universal sequence are different. In some embodiments, the second universal sequence is less than about 85% identical to the third universal sequence.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adaptors can be linear. The adaptors can be pre-adenylated adaptors. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adaptor can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adaptors can comprise identical and/or universal nucleic acid sequences and the 3' adaptors can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adaptors (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, a "complementary" sequence can refer to a "complement" or a "reverse complement" of a sequence. It is understood from the disclosure that if a molecule can hybridize to another molecule it may be complementary, or partially complementary, to the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid can include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* LI.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

"8 mers" are peptides consisting of 8 amino acids. "9 mers" are peptides consisting of 9 amino acids. "10 mers" are peptides consisting of 10 amino acids. "11 mers" are peptides consisting of 11 amino acids. "12 mers" are peptides consisting of 13 amino acids.

An "amino acid residue" can be a natural or non-natural amino acid residue linked by peptide bonds or bonds different from peptide bonds. The amino acid residues can be in D-configuration or L-configuration. An amino acid residue comprises an amino terminal part (NH2) and a carboxy terminal part (COOH) separated by a central part comprising a carbon atom, or a chain of carbon atoms, at least one of which comprises at least one side chain or functional group. NH2 refers to the amino group present at the amino terminal end of an amino acid or peptide, and COOH refers to the carboxy group present at the carboxy terminal end of an amino acid or peptide. The generic term amino acid comprises both natural and non-natural amino acids as are known to the skilled person. Also, non-natural amino acid residues include, but are not limited to, modified amino acid residues, L-amino acid residues, and stereoisomers of D-amino acid residues.

Anchor amino acid: Anchor amino acid is used interchangeably herein with anchor residue and is an amino acid of antigenic peptide having amino acid sidechains that bind into pockets lining the peptide-binding groove of MHC molecules thereby anchoring the peptide to the MHC molecule. Anchor residues being responsible for the main anchoring of peptide to MHC molecule are called primary anchor amino acids. Amino acids contributing to the binding of antigenic peptide to MHC molecule but in a lesser extent than primary anchor amino acids are called secondary anchor amino acids.

Anchor motif: The pattern of anchor residues in an antigenic peptide binding a certain MHC molecule. Peptides binding different MHC molecules have different anchor motifs defined by the patterns of anchor residues in the peptide sequence.

Anchor residue: Anchor residue is used interchangeably herein with anchor amino acid Anchor position: The position of an anchor amino acid in antigenic peptide sequence. For MHC II the anchor positions is defined in the 9-mer core motif.

Antigen presenting cell: An antigen-presenting cell (APC) as used herein is a cell that displays foreign antigen complexed with MHC on its surface.

Antigenic peptide, Antigenic peptide P: Used interchangeably with P, binding peptide, peptide epitope P or simply epitope. Any peptide molecule that is bound or able to bind into the binding groove of an MHC molecule.

Antigenic polypeptide: A polypeptide or protein expressed in an organism that contains one or more antigenic peptides.

Aptamer: the term aptamer as used herein is defined as oligonucleic acid or peptide molecules that bind a specific target molecule. Aptamers are usually created by selecting them from a large random sequence pool, but natural aptamers also exist. Aptamers can be divided into DNA amtamers, RNA aptamers and peptide aptamers.

Avidin: Avidin as used herein is a glycoprotein found in the egg white and tissues of birds, reptiles and amphibians. It contains four identical subunits having a combined mass of 67,000-68,000 daltons. Each subunit consists of 128 amino acids and binds one molecule of biotin. Biologically active molecule: A biologically active molecule is a molecule having itself a biological activity/effect or is able to induce a biological activity/effect when administered to a biological system. Biologically active molecules include adjuvants, immune targets (e.g. antigens), enzymes, regulators of receptor activity, receptor ligands, immune potentiators, drugs, toxins, cytotoxic molecules, co-receptors, proteins and peptides in general, sugar moieties, lipid groups, nucleic acids including siRNA, nanoparticles, small molecules.

Biotin: Biotin, as used herein, is also known as vitamin H or $B_7$. Niotin has the chemical formula $C_{10}H_{16}N_2O_3S$.

Bispecific capture molecule: Molecule that have binding specificities for at least two different antigens. The molecule can also be trispecific or multispecific.

Carrier: A carrier as used herein can be any type of molecule that is directly or indirectly associated with the MHC peptide complex. In this disclosure, a carrier will typically refer to a functionalized polymer (e.g. dextran) that is capable of reacting with MHC-peptide complexes, thus covalently attaching the MHC-peptide complex to the carrier, or that is capable of reacting with scaffold molecules (e.g. streptavidin), thus covalently attaching streptavidin to the carrier; the streptavidin then may bind MHC-peptide complexes. Carrier and scaffold are used interchangeably herein where scaffold typically refers to smaller molecules of a multimerization domain and carrier typically refers to larger molecule and/or cell like structures.

Coiled-coil polypeptide: Used interchangeably with coiled-coil peptide and coiled-coil structure. The term coiled-coil polypeptide as used herein is a structural motif in proteins, in which 2-7 alpha-helices are coiled together like the strands of a rope Dextran: the term dextran as used herein is a complex, branched polysaccharide made of many glucose molecules joined into chains of varying lengths. The straight chain consists of a1→6 glycosidic linkages between glucose molecules, while branches begin from a1→3 linkages (and in some cases, a1→2 and a1→4 linkages as well).

Folding: in vitro or in vivo folding of proteins in a tertiary structure.

Immune monitoring: Immune monitoring provided herein refers to testing of immune status in the diagnosis and therapy of infectious disease. It also refers to testing of immune status before, during and after vaccination procedures.

Immune monitoring process: a series of one or more immune monitoring analysis.

Label: Label herein is used interchangeable with labeling molecule. Label as described herein is an identifiable substance that is detectable in an assay and that can be attached to a molecule creating a labeled molecule. The behavior of the labeled molecule can then be studied.

Labelling: Labelling herein means attachment of a label to a molecule.

Linker molecule: Linker molecule and linker is used interchangeable herein. A linker molecule is a molecule that covalently or non-covalently connects two or more molecules, thereby creating a larger complex consisting of all molecules including the linker molecule.

Immuno profiling: Immuno profiling as used herein defines the profiling of an individual's antigen-specific T-cell repertoire.

Marker: Marker is used interchangeably with marker molecule herein. A marker is molecule that specifically associates covalently or non-covalently with a molecule belonging to or associated with an entity.

MHC I is used interchangeably herein with MHC class I and denotes the major histocompatibility complex class I. MHC II is used interchangeably herein with MHC class II and denotes the major histocompatibility complex class I.

MHC molecule: a MHC molecule as used everywhere herein is defined as any MHC class I molecule or MHC class II molecule as defined herein, including a MHC class I molecule. A "MHC Class I molecule" as used everywhere herein is used interchangeably with MHC I molecule and is defined as a molecule which comprises 1-3 subunits, including a MHC I heavy chain, a MHC I heavy chain combined with a MHC I beta2microglobulin chain, a MHC I heavy chain combined with MHC I beta2microglobulin chain through a flexible linker, a MHC I heavy chain combined with an antigenic peptide, a MHC I heavy chain combined with an antigenic peptide through a linker, a MHC I heavy chain/MHC I beta2microglobulin dimer combined with an antigenic peptide, and a MHC I heavy chain/MHC I beta2microglobulin dimer combined with an antigenic peptide through a flexible linker to the heavy chain or beta2microglobulin. The MHC I molecule chains can be changed by substitution of single or by cohorts of native amino acids, or by inserts, or deletions to enhance or impair the functions attributed to said molecule. MHC complex: MHC complex is herein used interchangeably with MHC-peptide complex, and defines any MHC I and/or MHC II molecule combined with antigenic peptide unless it is specified that the MHC complex is empty, i.e. is not complexed with antigenic peptide MHC Class I like molecules (including non-classical MHC Class I molecules) include CD1d, HLA E, HLA G, HLA F, HLA H, MIC A, MIC B, ULBP-1, ULBP-2, and ULBP-3.

A "peptide free MHC Class I molecule" is used interchangeably herein with "peptide free MHC I molecule" and as used everywhere herein is meant to be a MHC Class I molecule as defined above with no peptide. Peptide free MHC Class molecules are also called "empty" MHC molecules.

The MHC molecule may suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

In general, the term "MHC molecule" is intended to include all alleles. By way of example, in humans e.g. HLA A, HLA B, HLA C, HLA D, HLA E, HLA F, HLA G, HLA H, HLA DR, HLA DQ and HLA DP alleles are of interest shall be included, and in the mouse system, H-2 alleles are of interest shall be included. Likewise, in the rat system RT1-alleles, in the porcine system SLA-alleles, in the bovine system BoLA, in the avian system e.g. chicken-B alleles, are of interest shall be included.

"MHC complexes" and "MHC constructs" are used interchangeably herein.

By the terms "MHC complexes" and "MHC multimers" as used herein are meant such complexes and multimers thereof, which are capable of performing at least one of the functions attributed to said complex or multimer. The terms include both classical and non-classical MHC complexes. The meaning of "classical" and "non-classical" in connection with MHC complexes is well known to the person skilled in the art. Non-classical MHC complexes are subgroups of MHC-like complexes. The term "MHC complex" includes MHC Class I molecules, MHC Class II molecules, as well as MHC-like molecules (both Class I and Class II), including the subgroup non-classical MHC Class I and Class II molecules.

MHC multimer: The terms "MHC multimer", "MHC-multimer", "MHCmer" and "MHC'mer" herein are used interchangeably, to denote a complex comprising more than one MHC-peptide complexes, held together by covalent or non-covalent bonds.

Multimerization domain: A multimerization domain is a molecule, a complex of molecules, or a solid support, to which one or more MHC or MHC-peptide complexes can be attached. A multimerization domain consist of one or more carriers and/or one or more scaffolds and may also contain one or more linkers connecting carrier to scaffold, carrier to carrier, scaffold to scaffold. The multimerization domain may also contain one or more linkers that can be used for attachment of MHC complexes and/or other molecules to the multimerization domain. Multimerization domains thus include IgG, streptavidin, avidin, streptactin, micelles, cells, polymers, dextran, polysaccharides, beads and other types of solid support, and small organic molecules carrying reactive groups or carrying chemical motifs that can bind MHC complexes and other molecules; such as identified in detail herein elsewhere One or more" as used everywhere herein is intended to include one and a plurality. This applies e.g., to the MHC peptide complex and the binding entity. When a plurality of MHC peptide complexes is attached to the multimerization domain, such as a scaffold or a carrier molecule, the number of MHC peptide complexes need only be limited by the capacity of the multimerization domain.

Scaffold: A scaffold is typically an organic molecule carrying reactive groups, capable of reacting with reactive groups on a MHC-peptide complex. Particularly small organic molecules of cyclic structure (e.g. functionalized cycloalkanes or functionalized aromatic ring structures) are termed scaffolds. Scaffold and carrier are used interchangeably herein where scaffold typically refers to smaller molecules of a multimerization domain and carrier typically refers to larger molecule and/or cell like structures.

Staining: specific or unspecific labelling of cells by binding labelled molecules to defined proteins or other structures on the surface of cells or inside cells. The cells are either in suspension or part of a tissue. The labelled molecules can be MHC multimers, antibodies or similar molecules capable of binding specific structures on the surface of cells.

Streptavidin: Streptavidin as used herein is a tetrameric protein purified from the bacterium *Streptomyces avidinii*. Streptavidin is widely use in molecular biology through its extraordinarily strong affinity for biotin.

Barcodes

Barcoding, such as stochastic barcoding, has been described in, for example, Fu et al., *Proc Natl Acad Sci U.S.A.,* 2011 May 31,108(22):9026-31; US2011/0160078; Fan et al., *Science,* 2015, 347(6222):1258367; US2015/0299784; and WO2015/031691; the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% or at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides, between about 10 to about 150 nucleotides, or between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% or at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides, about 10 to about 150 nucleotides, or between about 20 to about 125 nucleotides, in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about, 60%, 70%, 80%, 85%, 90%, 95%, 97%, 99%, or 100%. For example, at least 60% or at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides, between about 10 to about 150 nucleotides, or between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead). In some embodiments, the unique molecular label sequence is partially or entirely encompassed by a particle (e.g., a hydrogel bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For barcoding (e.g., stochastic barcoding) using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, a poly(dA) sequence, a poly(dT) sequence, a poly(dG) sequence, a poly(dC) sequence, or a combination thereof. For example, the target binding region can be an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least, at least about, at most, or at most about, 5, 10, 15, 20, 25, 30, 35, 40, 45, 50 or more nucleotides in length. In some embodiments, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be disruptable (e.g., dissolvable, degradable). For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle)

(PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead can be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
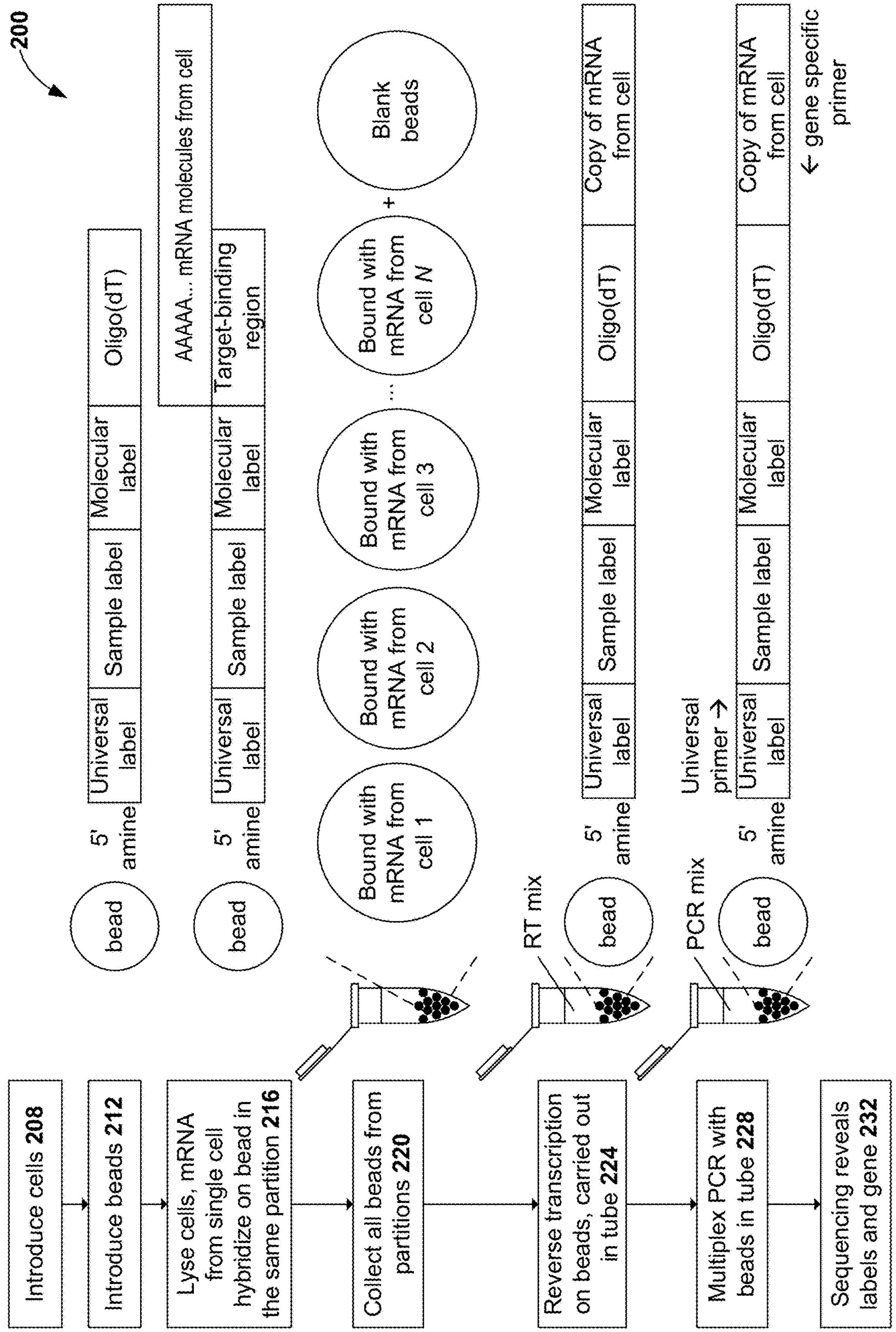
FIG. 2 shows a non-limiting exemplary workflow of barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms “tethered,” “attached,” and “immobilized,” are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, 100%, 150%, 200%, 250%, or 300% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic or hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. A microwell can entrap one or more cells, or entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. In some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least, at least about, at most, or at most about, 1, 2, 3, 4, 5, 6, 7, 8, 9, or 10. In some embodiments, the pH of the lysis buffer is about 7.5. The lysis buffer can comprise a salt (e.g., LiCl). The concentration of salt in the lysis buffer can be at least, at least about, at most, or at most about, 0.1, 0.5, or 1 M. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least, at least about, at most, or at most about, 0.0001%, 0.0005%, 0.001%, 0.005%, 0.01%, 0.05%, 0.1%, 0.5%, 1%, 2%, 3%, 4%, 5%, 6%, or 7%. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least, at least about, at most, or at most about, 1, 5, 10, 15, or 20 mM. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least, at least about, at most, or at most about, 100000, 200000, 300000, 400000, 500000, 600000, or 700000 target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription or Nucleic Acid Extension

The disclosure provides for a method to create a target-barcode conjugate using reverse transcription (e.g., at block 224 of FIG. 2) or nucleic acid extension. The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of an mRNA molecule to a labeled-RNA molecule can occur by the addition of a reverse transcription primer. In some embodiments, the reverse transcription primer is an oligo(dT)

primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, a target is a cDNA molecule. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

Reverse transcription can occur repeatedly to produce multiple labeled-cDNA molecules. The methods disclosed herein can comprise conducting at least, at least about, at most, or at most about, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, or comprise about 1, 2, 3, 4, 5, 6, 7, 8, 9, 10, 11, 12, 13, 14, or 15 or more nucleotides. The one or more primers can at least, at least about, at most, or at most about 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least, at least about, at most, or at most about, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers, at least 960 or more custom primers, or at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least, at least about, at most, or at most about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by PCR. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods, for example any of the non-PCR based methods as described herein (e.g., MDA, TMA, NASBA, SDA, real-time SDA, rolling circle amplification, or circle-to-circle amplification, multiple cycles of DNA-dependent RNA polymerase-driven RNA transcription amplification or RNA-directed DNA synthesis and transcription to amplify DNA or RNA targets, LCR, Qβ, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and RAM).

In some embodiments, the methods disclosed herein further comprise conducting a nested polymerase chain reaction on the amplified amplicon (e.g., target). The amplicon can be double-stranded molecule. The double-stranded (ds) molecule can comprise a dsRNA molecule, a dsDNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least, at least about, at most, or at most about, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, PNA, morpholino and LNA, as well as GNA and TNA. Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers, at least one or more control primers, at least one or more housekeeping gene primers, or a combination thereof. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
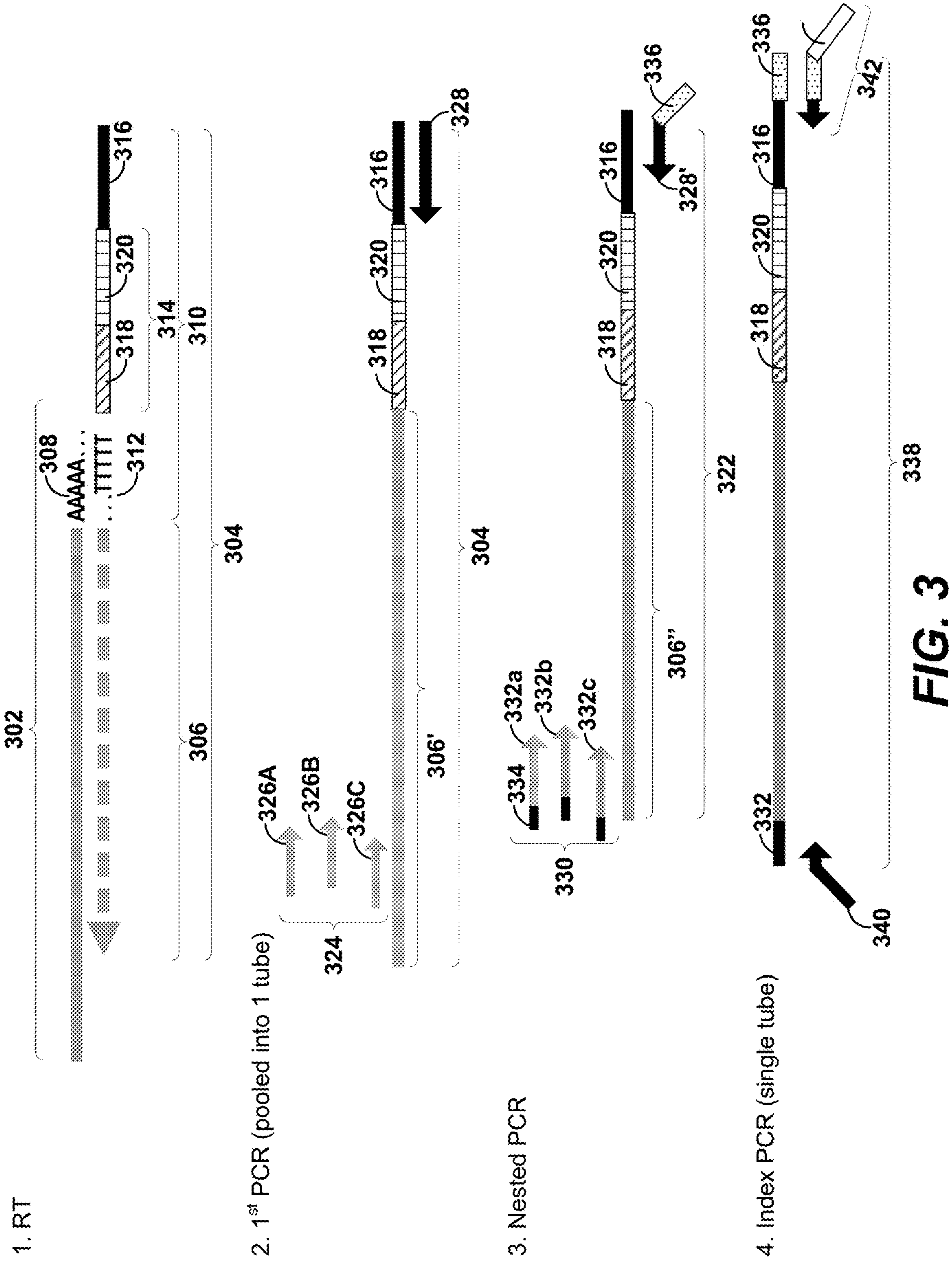
FIG. 3 is a schematic illustration showing a non-limiting exemplary process for generating an indexed library of targets barcoded at the 3'-ends from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label sequence, a cell label sequence, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label sequence can include 3 to 20 nucleotides. In some embodiments, the molecular label sequence can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a 1st PCR primer pool and a 1st universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{11}$, $10^{14}$, $10^{15}$, $10^{20}$, or a number or a range between any of these values, multiplex primers in a single reaction volume. Amplification can comprise using a 1st PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a 2nd universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332*a-c* and a 2nd universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the 2nd universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Multiomic Characterization of Single Cell Populations Utilizing Sensitive Receptor-Binding Reagent Specific Oligonucleotides and Cellular Component-Binding Reagent Specific Oligonucleotides There are provided, in some embodiments, methods, compositions, systems, and kits for the generation of dCODE Dextramer libraries, cellular component binding reagent specific oligonucleotide (e.g., AbSeq, protein profiling) libraries and/or mRNA single cell libraries. There are provided, in some embodiments, a unique primer design for compatibility of Immudex dextramer technology with the BD Rhapsody system. The disclosed methods and compositions, in some embodiments, allow separate next generation sequencing library preparations of highly expressed AbSeq antibodies versus low expressed dextramers that can enable users to reduce sequencing costs to detect dextramer molecules.

Figure 4A:
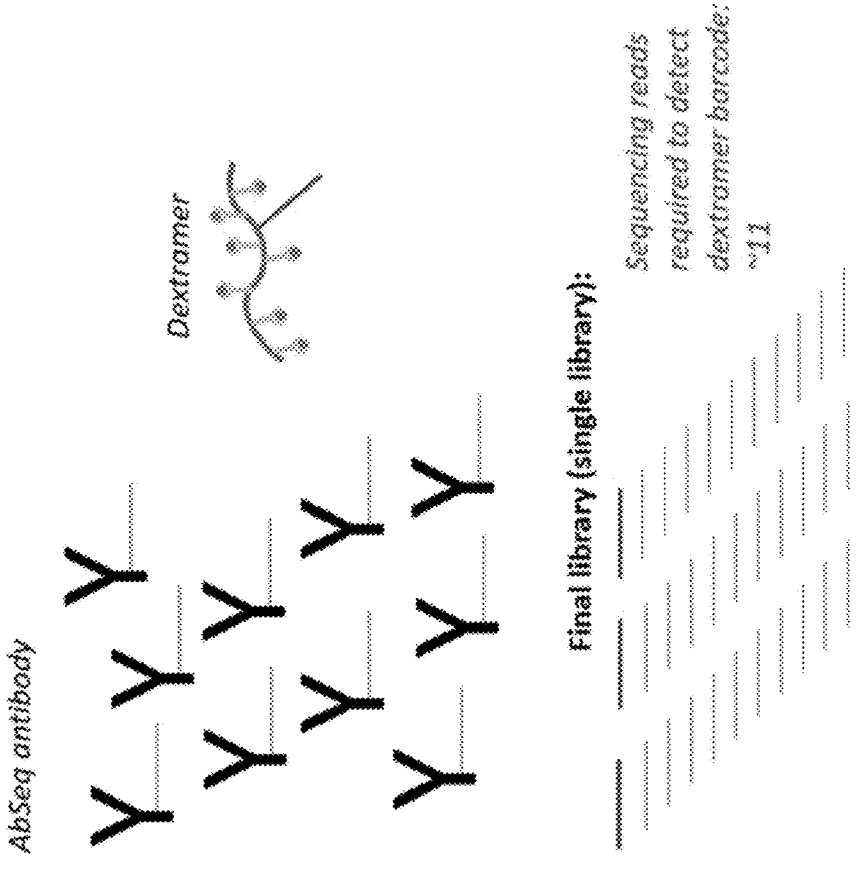
FIGS. 4A-4B depict a non-limiting exemplary schematics of AbSeq and Dextramer sequencing libraries generated without the use of a unique primer (FIG. 4A) and with the use of a unique primer (FIG. 4B).
Figure 4B:
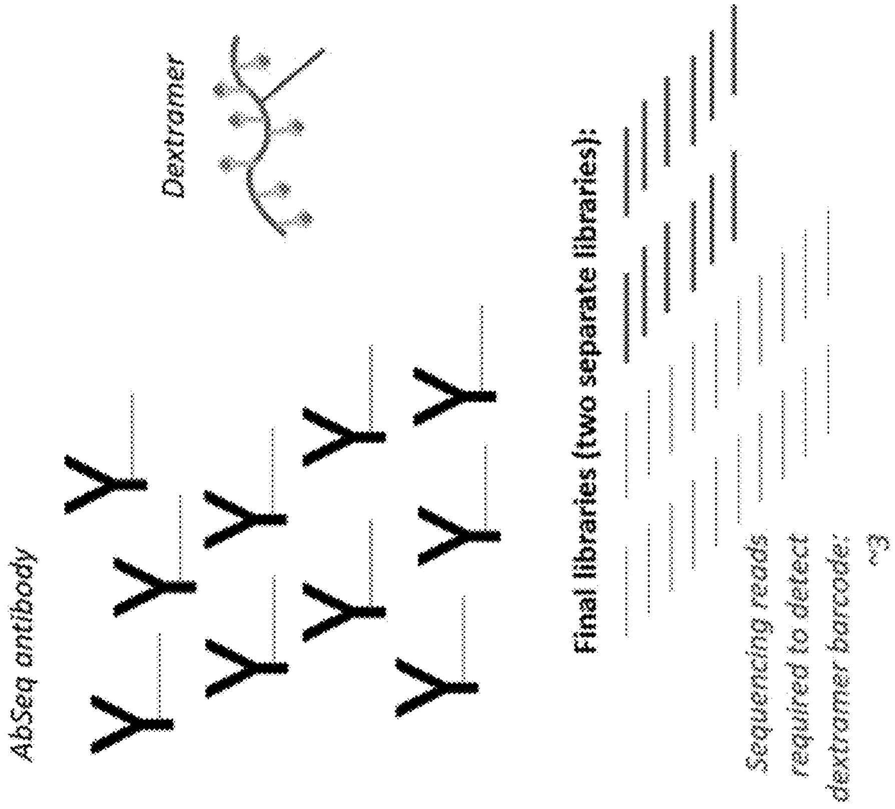
Figure 5:
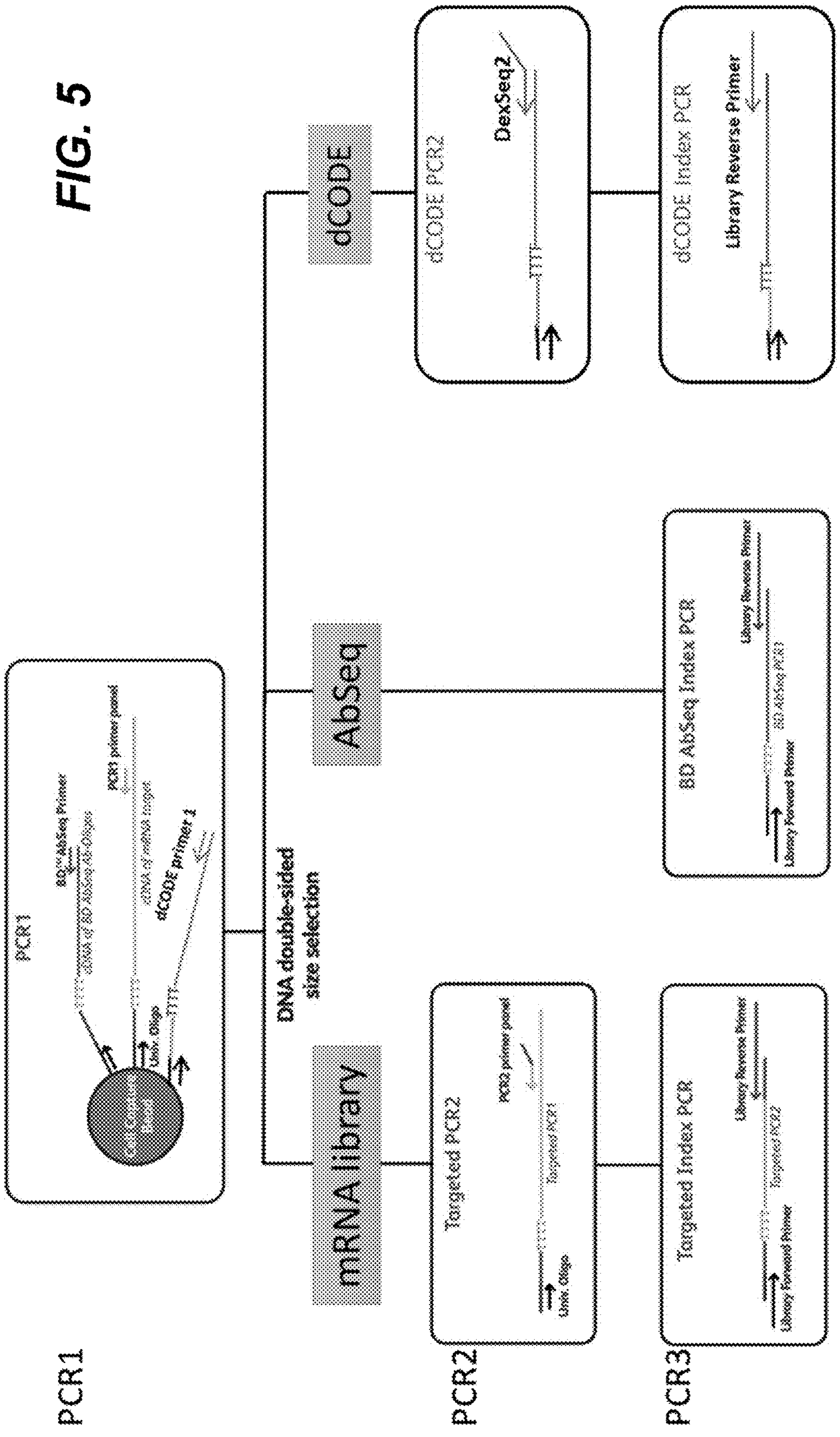
FIG. 5 depicts a non-limiting exemplary schematic workflow of the compositions and methods provided herein.

Immudex dextramers have been used to profile TCR/MHC/peptide complexes using currently available platforms wherein users amplify the dextramer signal using the same primer as is used for the protein library. Disclosed herein include methods, compositions, and kits enabling the use of dextramers on the BD Rhapsody platform. In some embodiments, the disclosed methods and compositions employ a novel primer to amplify the dextramer barcode library. In contrast to the aforementioned currently available methods, the methods provided herein can employ separate primers for the preparation of the protein library ("AbSeq") and the dextramer library. Without being bound by any particular theory, the ratio of products in a library is fixed when all products are amplified using the same amplification handle ("primer"). Using a separate primer allows the user to adjust the ratio of products which can substantially decrease sequencing costs to attain the same resolution. This can be applied to adjusting ratios of dextramer:protein as disclosed herein. FIGS. 4A-4B depicts a non-limiting exemplary schematics of AbSeq and Dextramer sequencing libraries generated without the use of a unique primer (FIG. 4A) and with the use of a unique primer (FIG. 4B). When dextramer and protein barcodes are amplified together (e.g., using the same primers) the relative ratio of each marker cannot be adjusted. For example, if protein A is expressed 10,000 fold higher than dextramer A, the ratio of the barcodes will be 10,000:1. This leads to high sequencing cost, as all 10,000 copies of the protein A barcode must be sequenced to see a single copy of the dextramer A barcode. The use of a unique primer for the dextramer library separate from the AbSeq library allows the user to generate two separate amplified products for sequencing (the AbSeq library and the dextramer library). This means the relative ratios can be adjusted during sequencing input which can allow the user to see the low-expressed dextramer barcode without sequencing all molecules of the protein barcodes. In some embodiments provided herein, PCR1 amplification of capture bead bound cDNA is performed using mRNA target primers, dCODE primers, and AbSeq primers (e.g., as shown in FIG. 5). The dCODE dextramer oligonucleotides (e.g., receptor-binding reagent specific oligonucleotides) and AbSeq protein profiling oligonucleotides (e.g., cellular component-binding reagent specific oligonucleotides) can comprise different amplification handles (e.g., a second universal sequence versus a third universal sequence, respectively). The BD AbSeq and dCODE® PCR1 products can separated from the mRNA targeted PCR1 products (e.g., by double-sided size selection). The dCODE® library can be copurified with the AbSeq library from PCR1. The dCODE® and BD Rhapsody mRNA targeted PCR1 products can undergo PCR2 amplification. The dCODE, AbSeq and mRNA libraries can undergo separate index PCR with library index primers. After index PCR, the dCODE®, BD Rhapsody mRNA and BD AbSeq libraries can be combined for sequencing (e.g., at predetermined ratios of each indexed library).

Disclosed herein includes methods, composition, kits and systems for using dextramers in single cell analysis. In some embodiments, primers are configured to allow dextramers to be used with a single cell analysis system (e.g., BD Rhapsody™ system), enabling separate next generation sequencing library preparations of highly expressed AbSeq™ antibodies versus low expressed dextramers that can enable users to reduce sequencing costs to detect dextramer molecules.

Dextramers, for example dextramers from Immudex, have been used to profile TCR/MHC/peptide complexes. dCODE Dextramers™ by Immundex and the uses thereof have been described in WO 2015/185067, WO 2015/188839 and WO 2002/072631, each of which is hereby expressly incorporated by reference in its entirety. The methods, systems, kits and compositions disclosed herein can enable use of dextramers for single cell analysis, e.g., BD Rhapsody™ system. In some embodiments, one or more primer are configured to amplify the dextramer barcode library. In some embodiments, the same primer can be used to amplify the dextramer signal, for example, for the protein library. In some embodiments, separate primers are used to amplify the protein library ("AbSeq") and the dextramer library, respectively. A non-limiting example of how dextramers can be used in single cell analysis is shown in Example 2 which illustrates multiomic characterization of T cell populations at the single cell level utilizing sensitive dCODE Dextramer® and BD® AbSeq Ab-Oligos on the BD Rhapsody™ Single-Cell Analysis System. Example 1 describes a non-limiting example of staining procedure using dextramers (e.g., dCODE Dextramers) in BD Rhapsody™ Single Cell Analysis System. Example 1 describes a non-limiting example of the procedure for using dextramers (e.g., dCODE Dextramers) in BD Rhapsody™ Single Cell Analysis System in preparing targeted mRNA library.

Disclosed herein include methods. In some embodiments, the method comprises: contacting a plurality of receptor detection constructs with a plurality of cells to form a first plurality of cells associated with the receptor detection constructs, wherein the plurality of cells comprise a plurality of cellular component targets and copies of a nucleic acid target, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: barcoding copies of the nucleic acid target of the plurality of cells with the plurality of oligonucleotide barcodes to generate a plurality of barcoded nucleic acid molecules each comprising a sequence complementary to at least a portion of the nucleic acid target. The method can comprise: generating a sequencing library comprising a plurality of nucleic acid target library members, a plurality of cellular component target library members, and a plurality of receptor library members, wherein generating the sequencing library comprises: attaching sequencing adaptors to the plurality of barcoded nucleic acid molecules, or products thereof, to generate the plurality of nucleic acid target library members; and attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of nucleic acid target library members, a plurality of sequencing reads of cellular component target library members, and a plurality of sequencing reads of receptor library members.

The method disclosed herein can comprise: contacting a plurality of receptor detection constructs with a plurality of cells to form a first plurality of cells associated with the receptor detection constructs, wherein the plurality of cells comprise a plurality of cellular component targets, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent. The method can comprise: contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets. The method can comprise: barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence. The method can comprise: barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence. The method can comprise: generating a sequencing library comprising a plurality of cellular component target library members and a plurality of receptor library members, wherein generating the sequencing library comprises: attaching sequencing adaptors to the plurality of barcoded cellular component-binding reagent specific oligonucleotides, or products thereof, to generate the plurality of cellular component target library members; and attaching sequencing adaptors to the plurality of barcoded receptor-binding reagent specific oligonucleotides, or products thereof, to generate the plurality of receptor library members. The method can comprise: obtaining sequencing data comprising a plurality of sequencing reads of cellular component target library members and a plurality of sequencing reads of receptor library members.

Barcoding copies of the nucleic acid target of the plurality of cells with the plurality of oligonucleotide barcodes can comprise: contacting copies of the nucleic acid target of the plurality of cells with the plurality of oligonucleotide barcodes, wherein each oligonucleotide barcode of the plurality of oligonucleotide barcodes comprises a first universal sequence, a first molecular label, and a target-binding region capable of hybridizing to the nucleic acid target; and extending the plurality of oligonucleotide barcodes hybridized to the copies of the nucleic acid target to generate a plurality of barcoded nucleic acid molecules each comprising a sequence complementary to the at least a portion of the nucleic acid target.

Barcoding the cellular component-binding reagent specific oligonucleotides with the plurality of oligonucleotide barcodes can comprise: contacting the cellular component-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the cellular component-binding reagent specific oligonucleotides; and extending the plurality of oligonucleotide barcodes hybridized to the cellular component-binding reagent specific oligonucleotides to generate a plurality of barcoded cellular component-binding reagent specific oligonucleotides each comprising a sequence complementary to at least a portion of the unique identifier sequence.

Barcoding the receptor-binding reagent specific oligonucleotides with the plurality of oligonucleotide barcodes can comprise: contacting receptor-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the receptor-binding reagent specific oligonucleotide; and extending the plurality of oligonucleotide barcodes hybridized to the receptor-binding reagent specific oligonucleotides to generate a plurality of barcoded receptor-binding reagent specific oligonucleotides each comprising a sequence complementary to at least a portion of the unique receptor identifier sequence. The target-binding region can comprise a capture sequence. In some embodiments, (i) the cellular component-binding reagent specific oligonucleotides comprise a sequence complementary to the capture sequence configured to capture the cellular component-binding reagent specific oligonucleotide and/or (ii) the receptor-binding reagent specific oligonucleotides comprise a sequence complementary to the capture sequence configured to capture the receptor-binding reagent specific oligonucleotides. In some embodiments, (i) each barcoded nucleic acid molecule of the plurality of barcoded nucleic acid molecules comprise a first universal sequence and a first molecular label; (ii) each barcoded cellular component-binding reagent specific oligonucleotide of the plurality of barcoded cellular component-binding reagent specific oligonucleotides comprise a first universal sequence and a first molecular label; and/or (iii) each barcoded receptor-binding reagent specific oligonucleotide of the plurality of barcoded receptor-binding reagent specific oligonucleotides comprise a first universal sequence and a first molecular label.

The second plurality of cells can comprise one or more single cells. The method can comprise: prior to (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes: partitioning the second plurality of cells to a plurality of partitions, wherein a partition of the plurality of partitions comprises a single cell from the second plurality of cells; and in the partition comprising the single cell, (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes. The partition can be a well or a droplet. The plurality of oligonucleotide barcodes can be associated with a solid support, the method comprising associating the solid support with the single cell in the partition, and wherein a partition of the plurality of partitions comprises a single solid support. The method can comprise: lysing the single cell after the partitioning step and before the contacting step. Lysing the single cell can comprise heating, contacting with a detergent, changing the pH, or any combination thereof. The plurality of cells can comprise T cells, B cells, tumor cells, myeloid cells, blood cells, normal cells, fetal cells, maternal cells, or a mixture thereof. At least 10 of the plurality of oligonucleotide barcodes can comprise different first molecular label sequences. The plurality of oligonucleotide barcodes each can comprise a cell label. Each cell label of the plurality of oligonucleotide barcodes can comprise at least 6 nucleotides. Oligonucleotide barcodes of the plurality of oligonucleotide barcodes associated with the same solid support can comprise the same cell label. Oligonucleotide barcodes of the plurality of oligonucleotide barcodes associated with different solid supports can comprise different cell labels. The target-binding region can comprise a poly (dT) region, a random sequence, a target-specific sequence, or a combination thereof.

The solid support can comprise a synthetic particle, a planar surface, or a combination thereof. At least one oligonucleotide barcode of the plurality of oligonucleotide barcodes can be immobilized or partially immobilized on the synthetic particle, or at least one oligonucleotide barcode of the plurality of oligonucleotide barcodes can be enclosed or partially enclosed in the synthetic particle. The synthetic particle can be disruptable (e.g., a disruptable hydrogel particle). The synthetic particle can comprise a bead (e.g., the bead can be a sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. Each oligonucleotide barcode of the plurality of oligonucleotide barcodes can comprise a linker functional group. The synthetic particle can comprise a solid support functional group. The support functional group and the linker functional group can be associated with each other. The linker functional group and the support functional group can be individually selected from the group consisting of C6, biotin, streptavidin, primary amine(s), aldehyde(s), ketone(s), and any combination thereof.

Generating the sequencing library can comprise: contacting random primers with the plurality of barcoded nucleic acid molecules, wherein each of the random primers comprises a fourth universal sequence, or a complement thereof; and extending the random primers hybridized to the plurality of barcoded nucleic acid molecules to generate a first plurality of extension products. The method can comprise: amplifying the first plurality of extension products using primers capable of hybridizing to the first universal sequence or complements thereof, and primers capable of hybridizing the fourth universal sequence or complements thereof, thereby generating a first plurality of barcoded amplicons, wherein the plurality of nucleic acid target library members comprise the first plurality of barcoded amplicons, or products thereof. Amplifying the first plurality of extension products can comprise adding sequences of binding sites of sequencing primers and/or sequencing adaptors, complementary sequences thereof, and/or portions thereof, to the first plurality of extension products. The method can comprise: determining the copy number of the nucleic acid target in each of the one or more single cells based on the number of first molecular labels with distinct sequences associated with the first plurality of barcoded amplicons, or products thereof.

Generating the sequencing library can comprise: amplifying the first plurality of barcoded amplicons using primers capable of hybridizing to the first universal sequence or complements thereof, and primers capable of hybridizing the fourth universal sequence or complements thereof, thereby generating a second plurality of barcoded amplicons; wherein the plurality of nucleic acid target library members comprise the second plurality of barcoded amplicons, or products thereof. Amplifying the first plurality of barcoded amplicons can comprise adding sequences of binding sites of sequencing primers and/or sequencing adaptors, complementary sequences thereof, and/or portions thereof, to the first plurality of barcoded amplicons. The method can comprise: determining the copy number of the nucleic acid target in each of the one or more single cells based on the number of first molecular labels with distinct sequences associated with the second plurality of barcoded amplicons, or products thereof. The first plurality of barcoded amplicons and/or the second plurality of barcoded amplicons can comprise whole transcriptome amplification (WTA) products.

Generating the sequencing library can comprise: synthesizing a third plurality of barcoded amplicons using the plurality of barcoded nucleic acid molecules as templates to generate a third plurality of barcoded amplicons, wherein the plurality of nucleic acid target library members comprise the third plurality of barcoded amplicons, or products thereof. Synthesizing the third plurality of barcoded amplicons can comprise PCR amplification using primers capable of hybridizing to the first universal sequence, or a complement thereof, and a target-specific primer. Synthesizing the third plurality of barcoded amplicons can comprise adding sequences of binding sites of sequencing primers and/or sequencing adaptors, complementary sequences thereof, and/or portions thereof, to barcoded nucleic acid molecules. The method can comprise: determining the copy number of the nucleic acid target in each of the one or more single cells based on the number of first molecular labels with distinct sequences associated with the third plurality of barcoded amplicons, or products thereof. In some embodiments, the target-specific primer specifically hybridizes to an immune receptor. In some embodiments, the target-specific primer specifically hybridizes to a constant region of an immune receptor, a variable region of an immune receptor, a diversity region of an immune receptor, the junction of a variable region and diversity region of an immune receptor, or a combination thereof. The immune receptor can be a T cell receptor (TCR) and/or a B cell receptor (BCR) receptor. The TCR can comprise TCR alpha chain, TCR beta chain, TCR gamma chain, TCR delta chain, or any combination thereof. The BCR receptor can comprise BCR heavy chain and/or BCR light chain. Each of the plurality of sequencing reads of the plurality of barcoded nucleic acid molecules, or products thereof, can comprise (1) a molecular label sequence, and/or (2) a subsequence of the nucleic acid target. The method can comprise: determining the copy number of the nucleic acid target in each of the one or more single cells based on the plurality of sequencing reads of nucleic acid target library members. Determining the copy number of the nucleic acid target in each of the one or more single cells can comprise determining the copy number of the nucleic acid target in each of the one or more single cells based on the number of first molecular labels with distinct sequences, complements thereof, or a combination thereof, associated with the one or more nucleic acid target library members, or products thereof. The plurality of barcoded nucleic acid molecules can comprise barcoded deoxyribonucleic acid (DNA) molecules, barcoded ribonucleic acid (RNA) molecules, or a combination thereof. The nucleic acid target can comprise a nucleic acid molecule (e.g., ribonucleic acid (RNA), messenger RNA (mRNA), microRNA, small interfering RNA (siRNA), RNA degradation product, RNA comprising a poly(A) tail, or any combination thereof). In some embodiments, the mRNA encodes an immune receptor.

The cellular component-binding reagent specific oligonucleotide can comprise a third universal sequence. Generating the sequencing library can comprise: amplifying the plurality of barcoded cellular component-binding reagent specific oligonucleotides, or products thereof, using a primer capable of hybridizing to the first universal sequence, or a complement thereof, and a primer capable of hybridizing to the third universal sequence, or a complement thereof, to generate a plurality of amplified barcoded cellular component-binding reagent specific oligonucleotides, wherein the plurality of cellular component target library members comprise the plurality of amplified barcoded cellular component-binding reagent specific oligonucleotides, or products thereof. Amplifying the plurality of barcoded cellular component-binding reagent specific oligonucleotides can comprise adding sequences of binding sites of sequencing primers and/or sequencing adaptors, complementary sequences thereof, and/or portions thereof, to the plurality of barcoded cellular component-binding reagent specific oligonucleotides. The method can comprise: determining the number of copies of at least one cellular component target of the plurality of cellular component targets in the one or more single cells based on the plurality of sequencing reads of cellular component target library members.

Each of the plurality of sequencing reads of cellular component target library members, can comprise (1) a molecular label sequence, and/or (2) at least a portion of the unique identifier sequence. The cellular component-binding reagent specific oligonucleotide can comprise a second molecular label. At least ten of the plurality of cellular component-binding reagent specific oligonucleotides can comprise different second molecular label sequences. In some embodiments, the second molecular label sequences of at least two cellular component-binding reagent specific oligonucleotides are different, and wherein the unique identifier sequences of the at least two cellular component-binding reagent specific oligonucleotides are identical. In some embodiments, the second molecular label sequences of at least two cellular component-binding reagent specific oligonucleotides are different, and wherein the unique identifier sequences of the at least two cellular component-binding reagent specific oligonucleotides are different. In some embodiments, the number of unique first molecular label sequences associated with the unique identifier sequence for the cellular component-binding reagent capable of specifically binding to the at least one cellular component target in the sequencing data indicates the number of copies of the at least one cellular component target in the one or more single cells. In some embodiments, the number of unique second molecular label sequences associated with the unique identifier sequence for the cellular component-binding reagent capable of specifically binding to the at least one cellular component target in the sequencing data indicates the number of copies of the at least one cellular component target in the one or more single cells.

The method can comprise: after contacting the plurality of cellular component-binding reagents with the first plurality of cells associated with the receptor detection constructs, removing one or more cellular component-binding reagents of the plurality of cellular component-binding reagents that are not contacted with the first plurality of cells associated with the receptor detection constructs. In some embodiments, removing the one or more cellular component-binding reagents not contacted with the first plurality of cells associated with the receptor detection constructs can comprise: removing the one or more cellular component-binding reagents not contacted with the respective at least one of the plurality of cellular component targets.

The target-binding region can comprise a poly(dT) region and the cellular component-binding reagent specific oligonucleotide can comprise a poly(dA) region. The cellular component-binding reagent specific oligonucleotide can comprise an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. The cellular component-binding reagent specific oligonucleotide can be associated with the cellular component-binding reagent through a linker. The cellular component-binding reagent specific oligonucleotide can be configured to be detachable from the cellular component-binding reagent. The method can comprise: dissociating the cellular component-binding reagent specific oligonucleotide from the cellular component-binding reagent. The linker can comprise a carbon chain. The carbon chain can comprise 2-30 carbons, and further optionally the carbon chain can comprise 12 carbons. The linker can comprise 5' amino modifier C12 (5AmMC12), or a derivative thereof. The cellular component target can comprise a protein target. The cellular component-binding reagent can comprise an antibody or fragment thereof. The cellular component target can comprise a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. The cellular component-binding reagent can comprise an antibody or fragment thereof. The cellular component target can be on a cell surface.

Contacting the plurality of receptor detection constructs with the plurality of cells to form the first plurality of cells can comprise removing one or more cells not bound to one or more receptor detection constructs. Removing one or more cells not bound to one or more receptor detection constructs can comprise selecting cells bound to one or more receptor detection constructs. The receptor detection constructs can comprise one or more additional labels, wherein selecting cells bound to one or more receptor detection constructs comprises flow cytometry and/or selecting cells based on the presence of the one or more additional labels.

The one or more additional labels can comprise a fluorescent label. Removing the one or more receptor-binding reagents not contacted with the first plurality of cells associated with the receptor detection constructs can comprise: removing the one or more receptor-binding reagents not contacted with the receptor.

The receptor-binding reagent specific oligonucleotide can comprise a second universal sequence. Generating the sequencing library can comprise: amplifying the plurality of barcoded receptor-binding reagent specific oligonucleotides, or products thereof, using a primer capable of hybridizing to the first universal sequence, or a complement thereof, and a primer capable of hybridizing to the second universal sequence, or a complement thereof, to generate a plurality of amplified barcoded receptor-binding reagent specific oligonucleotides, wherein the plurality of receptor library members comprise the plurality of amplified barcoded receptor-binding reagent specific oligonucleotides, or products thereof. Amplifying the plurality of barcoded receptor-binding reagent specific oligonucleotides can comprise adding sequences of binding sites of sequencing primers and/or sequencing adaptors, complementary sequences thereof, and/or portions thereof, to the plurality of barcoded receptor-binding reagent specific oligonucleotides.

Each of the plurality of sequencing reads of receptor library members, can comprise (1) a molecular label sequence, and/or (2) at least a portion of the unique receptor identifier sequence. Each of the plurality of sequencing reads of receptor library members, can comprise a cell label sequence. In some embodiments, each unique cell label sequence indicates a single cell of the second plurality of cells. The method can comprise: determining the number of copies of the receptor in the one or more single cells based on the plurality of sequencing reads of receptor library members. The method can comprise: determining the identity of the receptor-binding reagent bound to the one or more single cells based on the plurality of sequencing reads of receptor library members. The method can comprise: determining the identity of the receptor in the one or more single cells based on the plurality of sequencing reads of receptor library members.

The receptor-binding reagent specific oligonucleotide can comprise a third molecular label. At least ten of the plurality of receptor-binding reagent specific oligonucleotides can comprise different third molecular label sequences. In some embodiments, the third molecular label sequences of at least two receptor-binding reagent specific oligonucleotides are different, and wherein the unique receptor identifier sequences of the at least two receptor-binding reagent specific oligonucleotides are identical. In some embodiments, the third molecular label sequences of at least two receptor-binding reagent specific oligonucleotides are different, and wherein the unique receptor identifier sequences of the at least two receptor-binding reagent specific oligonucleotides are different. In some embodiments, the number of unique first molecular label sequences associated with the unique receptor identifier sequence for the receptor-binding reagent capable of specifically binding to the at least one receptor target in the sequencing data indicates the number of copies of the receptor in the one or more single cells. In some embodiments, the number of unique third molecular label sequences associated with the unique receptor identifier sequence for the receptor-binding reagent capable of specifically binding to the at least one receptor in the sequencing data indicates the number of copies of the receptor in the one or more single cells. Receptor-binding reagent specific oligonucleotides associated with identical receptor-binding reagents can comprise an identical unique receptor identifier sequence, and receptor-binding reagent specific oligonucleotides associated with different receptor-binding reagents can comprise different unique receptor identifier sequences.

The receptor-binding reagent specific oligonucleotide can comprise DNA, RNA, a locked nucleic acid (LNA), a peptide nucleic acid (PNA), an LNA/PNA chimera, an LNA/DNA chimera, a PNA/DNA chimera, or any combination thereof. The receptor-binding reagent specific oligonucleotide can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The receptor can comprise a cluster of differentiation (CD) molecule. The receptor can comprise an immune receptor (e.g., a T cell receptor (TCR)). The unique receptor identifier sequence can be about 3 nucleotides to about 100 nucleotides in length. The target-binding region can comprise a poly(dT) region and the receptor-binding reagent specific oligonucleotide can comprise a poly(dA) region. The receptor-binding reagent specific oligonucleotide can comprise an alignment sequence adjacent to the poly(dA) region. In some embodiments, (a) the alignment sequence comprises a guanine, a cytosine, a thymine, a uracil, or a combination thereof; (b) the alignment sequence comprises a poly(dT) sequence, a poly(dG) sequence, a poly(dC) sequence, a poly(dU) sequence, or a combination thereof; and/or (c) the alignment sequence is 5' to the poly(dA) region. The receptor-binding reagent specific oligonucleotide can be associated with the receptor-binding reagent through a linker. The receptor-binding reagent specific oligonucleotide can be configured to be detachable from the receptor-binding reagent. The method can comprise: dissociating the receptor-binding reagent specific oligonucleotide from the receptor-binding reagent. The linker can comprise a carbon chain. The carbon chain can comprise 2-30 carbons, and further optionally the carbon chain can comprise 12 carbons. The linker can comprise 5' amino modifier C12 (5AmMC12), or a derivative thereof.

The plurality of receptor detection constructs can comprise one or more MHC multimers, and wherein the two or more receptor-binding reagents comprise two or more MHC-peptide complexes. A MHC multimer can comprise $(a\text{-}b\text{-}P)_n$, wherein n>1, wherein polypeptides a and b together form a functional MHC protein capable of binding peptide P, and (a-b-P) is a MHC-peptide complex formed when peptide P binds to the functional MHC protein. Each MHC-peptide complex of a MHC multimer can be associated with one or more multimerization domains. The plurality of receptor detection constructs can comprise at least, or at most, 2 MHC multimers, 3 MHC multimers, 4 MHC multimers, 5 MHC multimers, 6 MHC multimers, 7 MHC multimers, 8 MHC multimers, 9 MHC multimers, 10 MHC multimers, 11 MHC multimers, 12 MHC multimers, 13 MHC multimers, 14 MHC multimers, 15 MHC multimers, 16 MHC multimers, 17 MHC multimers, 18 MHC multimers, 19 MHC multimers, or 20 MHC multimers. The individual antigenic peptides P of each MHC-peptide complex of said MHC multimers can be identical or different.

The plurality of receptor detection constructs can comprise one or more negative control MHC multimers. The one or more negative control MHC multimers wherein each MHC multimer can comprise a negative control peptide P. Said negative control peptide P can be a nonsense peptide. Said one or more negative control MHC multimers can be empty MHC multimers. The plurality of receptor detection constructs can comprise one or more positive control MHC multimers wherein each MHC multimer can comprise a positive control peptide P.

The value of n of said one or more MHC multimers comprising $(a\text{-}b\text{-}P)_n$ can be $1<n\geq1000$. The value of n can be between 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-35, 35-40, 40-45, 45-50, 50-55, 55-60, 60-65, 65-70, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-325, 325-350, 350-375, 375-400, 400-450, 450-500, 500-550, 550-600, 600-650, 650-700, 700-750, 750-800, 800-850, 850-900, 900-950, or 950-1000, or a number or a range between any of these values. Said MHC protein can be MHC Class I. Said MHC protein can be MHC Class I and the antigenic peptides P can be a 8-, 9-, 10-, 11-, or 12-mer peptide that binds to MHC Class I.

The association between the one or more of each MHC protein or MHC-peptide complex of a multimeric MHC, and the one or more multimerization domains, can be a covalent association and/or a non-covalent association. The one or more multimerization domains can comprise one or more multimerization domain connector molecules. One or more of each MHC protein or MHC-peptide complex of a multimeric MHC can comprise one or more MHC connector molecules. The one or more multimerization domain connector molecules can comprise one or more streptavidins and/or one or more avidins, or any derivatives thereof. The one or more streptavidins can comprise one or more tetrameric streptavidin variants or one or more monomeric streptavidin variants. The one or more MHC connector molecules can be biotin. One or more of each MHC protein or MHC-peptide complex of a MHC multimer can be associated with one or more multimerization domains via a streptavidin-biotin linkage or an avidin-biotin linkage. One or more of each MHC protein or MHC-peptide complex of a MHC multimer can be associated with one or more multimerization domains by a linker moiety. One or more of each MHC protein or MHC-peptide complex of a MHC multimer can be associated with one or more multimerization domains by a natural dimerization and/or a protein-protein interaction. The natural dimerization and/or a protein-protein interaction can be selected from the group consisting of leucine zipper e.g. leucine zipper domain of AP-1, Fos/Jun interactions, acid/base coiled coil structure based interactions (e.g. helices), antibody/antigen interactions, polynucleotide-polynucleotide interactions e.g. DNA/DNA, DNA/PNA, DNA/RNA, PNA/PNA, LNA/DNA; synthetic molecule-synthetic molecule interactions and protein-small molecule interactions, IgG dimeric protein, IgM multivalent protein, chelate/metal ion-bound chelate, strep immunoglobulins, antibodies (monoclonal, polyclonal, and recombinant), antibody fragments and derivatives thereof, hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

The one or more multimerization domains can comprise (i) one or more scaffolds; (ii) one or more carriers; (iii) at least one scaffold and at least one carrier; and/or (iv) one or more optionally substituted organic molecules. The optionally substituted organic molecule can comprise one or more functionalized cyclic structures. The functionalized cyclic structures can comprise benzene rings. The optionally substituted organic molecule can comprise a scaffold molecule comprising at least three reactive groups, or at least three sites suitable for non-covalent attachment. The one or more multimerization domains can comprise one or more biological cells and/or cell-like structures. The one or more multimerization domains can comprise one or more membranes. The one or more membranes can comprise liposomes or micelles. The one or more multimerization domains can comprise one or more polymers (e.g., one or more synthetic polymers).

The one or more polymers can be selected from the group consisting of polysaccharides. The polysaccharide can comprise one or more dextran moieties. The one or more dextran moieties can be (i) covalently attached to one or more MHC peptide complexes; (ii) non-covalently attached to one or more MHC peptide complexes; and/or (iii) modified. The one or more dextran moieties can comprise one or more amino-dextrans. The one or more amino-dextrans can be modified with divinyl sulfone. The one or more dextran moieties can comprise one or more dextrans with a molecular weight of from about 1,000 to 50,000 Da (e.g., from about 1,000 to 5,000, from about 5,000 to 10,000, from about 10,000 to 15,000, from about 15,000 to 20,000, from about 20,000 to 25,000, from about 25,000 to 30,000, from about 30,000 to 35,000, from about 35,000 to 40,000, from about 40,000 to 45,000, or from about 45,000 to 50,000 Da, or a number or a range between any of these values). The one or more dextran moieties can comprise one or more dextrans with a molecular weight of from about 50,000 to 150,000 Da (e.g., from about 50,000 to 60,000, from about 60,000 to 70,000, from about 70,000 to 80,000, from about 80,000 to 90,000, from about 90,000 to 100,000, from about 100,000 to 110,000, from about 110,000 to 120,000, from about 120,000 to 130,000, from about 130,000 to 140,000, or from about 140,000 to 150,000 Da). The one or more dextran moieties can comprise one or more dextrans with a molecular weight of from about 150,000-270,000 Da (e.g., from about 150,000 to 160,000, from about 160,000 to 170,000, from about 170,000 to 180,000, from about 180,000 to 190,000, from about 190,000 to 200,000, from about 200,000 to 210,000, from about 210,000 to 220,000, from about 220,000 to 230,000, from about 230,000 to 240,000, from about 240,000 to 250,000, from about 250,000 to 260,000, from about 260,000 to 270,000, from about 270,000 to 280,000, from about 280,000 to 290,000, from about 290,000 to 300,000, from about 300,000 to 310,000 from about 310,000 to 320,000, from about 320,000 to 330,000 from about 330,000 to 340,000, from about 340,000 to 350,000 from about 350,000 to 360,000, from about 360,000 to 370,000 from about 370,000 to 380,000, from about 380,000 to 390,000, from about 390,000 to 400,000, from about 400,000 to 410,000, from about 410,000 to 420,000, from about 420,000 to 430,000, from about 430,000 to 440,000, from about 440,000 to 450,000, from about 450,000 to 460,000, from about 460,000 to 470,000, from about 470,000 to 480,000, from about 480,000 to 490,000, from about 490,000 to 500,000, from about 500,000 to 550,000, from about 550,000 to 600,000, from about 600,000 to 650,000, from about 650,000 to 700,000, from about 700,000 to 750,000, from about 750,000 to 800,000, from about 800,000 to 850,000, from about 850,000 to 900,000, from about 900,000 to 950,000, or from about 950,000 to 1,000,000 Da, or a number or a range between any of these values). The one or more dextran moieties can be linear and/or branched.

The one or more synthetic polymers can comprise PNA, polyamide, PEG, or any combination thereof. The one or more multimerization domains can comprise one or more entities selected from the group consisting of an IgG domain, a coiled-coil polypeptide structure, a DNA duplex, a nucleic acid duplex, PNA-PNA, PNA-DNA and DNA-RNA. The one or more multimerization domains can comprise an antibody. The antibody can be selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody and fusion antibody. The one or more multimerization domains can comprise one or more small organic scaffold molecules or small organic molecules. The one or more small organic molecules can comprise one or more steroids, one or more peptides, and/or one or more aromatic organic molecules. The one or more aromatic organic molecules can comprise one or more one or more dicyclic structures, one or more polycyclic structures or one or more monocyclic structures; optionally the one or more monocyclic structures can comprise one or more optionally functionalized or substituted benzene rings. The one or more multimerization domains can comprise one or more: (i) monomeric molecules able to polymerize; (ii) biological polymers such as one or more proteins; (iii) small molecule scaffolds; (iv) supramolecular structure(s) such as one or more nanoclusters; and/or (v) protein complexes. The one or more multimerization domains can comprise one or more beads. The one or more beads can be selected from the group consisting of beads that carry electrophilic groups e.g. divinyl sulfone activated polysaccharide, polystyrene beads that have been functionalized with tosyl-activated esters, magnetic polystyrene beads functionalized with tosyl-activated esters, and beads where MHC complexes have been covalently immobilized to these by reaction of nucleophiles comprised within the MHC complex with the electrophiles of the beads. The one or more beads can be selected from the groups consisting of sepharose beads, sephacryl beads, polystyrene beads, agarose beads, polysaccharide beads, polycarbamate beads and any other kind of beads that can be suspended in an aqueous buffer.

The multimerization domain can comprise one or more compounds selected from the group consisting of agarose, sepharose, resin beads, glass beads, pore-glass beads, glass particles coated with a hydrophobic polymer, chitosan-coated beads, SH beads, latex beads. spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone) PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, poly-acrylamide beads, dimethylacrylamide beads optionally cross-linked with N-N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

The one or more multimerization domains can comprise a dimerization domain, a trimerization domain, a tetramerization domain, a pentamerization domain, or a hexamerization domain. The one or more multimerization domains can comprise a polymer structure to which can be attached one or more scaffolds. The polymer structure can comprise a polysaccharide. The polysaccharide can comprise one or more dextran moieties. The one or more multimerization domains can comprise a polyamide, a polyethylene glycol, a polysaccharide, a sepharose, or any combination thereof. The one or more multimerization domains can comprise a carboxy methyl dextran, a dextran polyaldehyde, a carboxymethyl dextran lactone, a cyclodextrin, or any combination thereof. In some embodiments, the one or more multimerization domains have a molecular weight of less than 1,000 Da, of from 1,000 Da to less than 10,000 Da, of from 10,000 Da to less than 100,000 Da, of from 100,000 Da to less than 1,000,000 Da, or of more than 1,000,000 Da, or a number or a range between any of these values. Said one or more MHC multimers further can comprise one or more scaffolds, carriers and/or linkers selected from the group consisting of streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Said MHC multimer can comprise a plurality of identical or different multimerization domains linked by a multimerization domain linking moiety. Said MHC multimer can comprise a first multimerization domain linked to a second multimerization domain.

Said one or more MHC multimers can comprise one or more labels. The one or more labels can comprise the receptor-binding reagent specific oligonucleotide. The one or more labels can comprise the receptor-binding reagent specific oligonucleotide and one or more additional labels. The one or more additional labels can be selected from the group comprising a peptide label, a fluorophore label, heavy metal labels, isotope labels, radiolabels, radionuclide, stable isotopes, chains of isotopes and single atoms, a chemiluminescent label, a bioluminescent label, a radioactive label, an enzyme label, a DNA fluorescent stain, a lanthanide, a ionophore, a chelating chemical compound binding to specific ions, or any combination thereof. The one or more labels can comprise covalently attached labels and/or non-covalently attached labels. The one or more labels can be attached to: (i) the MHC polypeptide a; (ii) the MHC polypeptide b; (iii) the peptide P; (iv) the one or more multimerization domains; and/or (v) $(a\text{-}b\text{-}P)_n$. The one or more labels can be attached to $(a\text{-}b\text{-}P)_n$ via a streptavidin-biotin linkage. The one or more additional labels can be a fluorophore label. The fluorophore label can be selected from the group comprising fluorescein isothiocyanate, rhodamine, phycoerythrin, phycocyanin, allophycocyanin, o-phthaldehyde, fluorescamine; 2-(4'-maleimidylanilino) naphthalene-6-sulfonic acid, sodium salt; 5-((((2-iodoacetyl)amino)ethyl)amino) naphthalene-1-sulfonic acid; Pyrene-1-butanoic acid; AlexaFluor 350 (7-amino-6-sulfonic acid-4-methyl coumarin-3-acetic acid; AMCA (7-amino-4-methyl coumarin-3-acetic acid); 7-hydroxy-4-methyl coumarin-3-acetic acid; Marina Blue (6,8-difluoro-7-hydroxy-4-methyl coumarin-3-acetic acid); 7-dimethylamino-coumarin-4-acetic acid; Fluorescamin-N-butyl amine adduct; 7-hydroxy-coumarine-3-carboxylic acid; Cascade-Blue (pyrene-trisulphonic acid acetyl azide; Cascade Yellow; Pacific Blue (6,8 difluoro-7-hydroxy coumarin-3-carboxylic acid; 7-diethylamino-coumarin-3-carboxylic acid; N-(((4-azidobenzoyl)amino)ethyl)-4-amino-3,6-disulfo-1,8-naphthalimide, dipotassium salt; Alexa Fluor 430; 3-perylenedodecanoic acid; 8-hydroxypyrene-1,3,6-trisulfonic acid, trisodium salt; 12-(N-(7-nitrobenz-2-oxa-1,3-diazol-4-yl)amino)dodecanoic acid; N,N'-dimethyl-N-(iodoacetyl)-N'-(7-nitrobenz-2-oxa-1,3-diazol-4-yl) ethylenediamine; Oregon Green 488 (difluoro carboxy fluorescein); 5-iodoacetamidofluorescein; propidium iodide-DNA adduct; Carboxy fluorescein, Fluor dyes, Pacific Blue™, Pacific Orange™, Cascade Yellow™; AlexaFluor® (AF), AF405, AF488, AF500, AF514, AF532, AF546, AF555, AF568, AF594, AF610, AF633, AF635, AF647, AF680, AF700, AF710, AF750, AF800; Quantum Dot based dyes, QDot® Nanocrystals (Invitrogen, MolecularProbs), Qdot®525, Qdot®565, Qdot®585, Qdot®605, Qdot®655, Qdot®705, Qdot®800; DyLight™ Dyes (Pierce) (DL); DL549, DL649, DL680, DL800; Fluorescein (Flu) or any derivate of that, such as FITC; Cy-Dyes, Cy2, Cy3, Cy3.5, Cy5, Cy5.5, Cy7; Fluorescent Proteins, RPE, PerCp, APC, Green fluorescent proteins; GFP and GFP derivated mutant proteins; BFP.CFP, YFP, DsRed, T1, Dimer2, mRFP1, MBanana, mOrange, dTomato, tdTomato, mTangerine, mStrawberry, mCherry; Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5, and APC-Cy5.5.

The one or more additional labels can be capable of absorption of light (e.g., a chromophore and/or a dye). In some embodiments, the one or more additional labels is capable of emission of light after excitation, optionally one or more fluorochromes, further optionally the one or more fluorochromes is selected from the AlexaFluor® (AF) family, which include AF®350, AF405, AF430, AF488, AF500, AF514, AF532, AF546, AF555, AF568, AF594, AF610, AF633, AF635, AF647, AF680, AF700, AF710, AF750 and AF800; selected from the Quantum Dot (Qdot®) based dye family, which include Qdot®525, Qdot®565, Qdot®585, Qdot®605, Qdot®655, Qdot®705, Qdot®800; selected from the DyLight™ Dyes (DL) family, which include DL549, DL649, DL680, DL800; selected from the family of Small fluorescing dyes, which include FITC, Pacific Blue™, Pacific Orange™, Cascade Yellow™, Marina blue™, DSred, DSred-2, 7-AAD, TO-Pro-3; selected from the family of Cy-Dyes, which include Cy2, Cy3, Cy3.5, Cy5, Cy5.5, Cy7; selected from the family of Phycobili Proteins, which include R-Phycoerythrin (RPE), PerCP, Allophycocyanin (APC), B-Phycoerythrin, C-Phycocyanin; selected from the family of Fluorescent Proteins, which include (E) GFP and GFP ((enhanced) green fluorescent protein) derived mutant proteins; BFP.CFP, YFP, DsRed, T1, Dimer2, mRFP1, MBanana, mOrange, dTomato, tdTomato, mTangerine; selected from the family of Tandem dyes with RPE, which include RPE-Cy5, RPE-Cy5.5, RPE-Cy7, RPE-AlexaFluor® tandem conjugates; RPE-Alexa610, RPE-TxRed; selected from the family of Tandem dyes with APC, which include APC-Aleca600, APC-Alexa610, APC-Alexa750, APC-Cy5, APC-Cy5.5; selected from the family of Calcium dyes, which include lndo-1-$Ca^{2+}$ lndo-2-$Ca^{2+}$.

The MHC multimer can comprise one or more further polypeptides in addition to a and b. One of the polypeptides of the MHC-peptide complex can be a heavy chain polypeptide. One of the polypeptides of the MHC-peptide complex can be a b2M polypeptide. In some embodiments, (i) P is chemically modified; (ii) P is pegylated, phosphorylated and/or glycosylated; (iii) one of the amino acid residues of the peptide P is substituted with another amino acid; (iv) a and b are both full-length peptides; (v) a is a full-length peptide; (vi) b is a full-length peptide; (vii) a is truncated; (viii) b is truncated; (ix) a and b are both truncated; (x) a is covalently linked to b; (xi) a is covalently linked to P; (xii) b is covalently linked to P; (xiii) a, b and P are all covalently linked; (xiv) a is non-covalently linked to b; (xv) a is non-covalently linked to P; (xvi) b is non-covalently linked to P; (xvii) a, b and P are all non-covalently linked; (xviii) a is not included in the (a-b-P) complex; (xix) b is not included in the (a-b-P) complex; and/or (xx) P is not included in the (a-b-P) complex. The MHC multimer can comprise one or more stability-increasing components (e.g., HEG and/or TEG).

The method can comprise: associating a T cell receptor (TCR) receptor in the one or more single cells with the peptide P based on the plurality of sequencing reads of receptor library members. The method can comprise: measuring the presence, frequency, number, activity and/or state of T cells specific for a peptide P, thereby detecting an antigen-specific T cell response.

The first universal sequence, the second universal sequence, the third universal sequence, and/or the fourth universal sequence can be the same. The first universal sequence, the second universal sequence, the third universal sequence, and/or the fourth universal sequence can be different. The first universal sequence, the second universal sequence, the third universal sequence, and/or the fourth universal sequence can comprise the binding sites of sequencing primers and/or sequencing adaptors, complementary sequences thereof, and/or portions thereof. The sequencing adaptors can comprise a P5 sequence, a P7 sequence, complementary sequences thereof, and/or portions thereof. The sequencing primers can comprise a Read 1 sequencing primer, a Read 2 sequencing primer, complementary sequences thereof, and/or portions thereof.

The method can comprise: physically separating one or more of (i) barcoded nucleic acid molecules, (ii) barcoded receptor-binding reagent specific oligonucleotides, and (iii) barcoded cellular component-binding reagent specific oligonucleotides from one or more of (i) barcoded nucleic acid molecules, (ii) barcoded receptor-binding reagent specific oligonucleotides, and (iii) barcoded cellular component-binding reagent specific oligonucleotides. In some embodiments, physically separating can comprise use of one or more size selection reagents.

The plurality of barcoded receptor-binding reagent specific oligonucleotides and the plurality barcoded cellular component-binding reagent specific oligonucleotides can be amplified separately. The second universal sequence and the third universal sequence can be different. The second universal sequence can be less than about 85% (e.g., 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or a number or a range between any two of these values) identical to the third universal sequence. The second universal sequence can comprise a sequence at least about 85% identical to SEQ ID NO: 1 (GGAGGGAGGTTAGCGAAGGT). In some embodiments, amplifying the plurality of barcoded receptor-binding reagent specific oligonucleotides, or products thereof, does not comprise amplifying the plurality of barcoded cellular component-binding reagent specific oligonucleotides, or products thereof.

In some embodiments, generating the sequencing library can comprise generating a sequencing mixture comprising (i) nucleic acid target library members, (ii) cellular component target library members, and/or (iii) receptor library members. In some embodiments, generating a sequencing mixture can comprise mixing (i) nucleic acid target library members, (ii) cellular component target library members, and/or (iii) receptor library members at a predetermined ratio. The (i) nucleic acid target library members, (ii) cellular component target library members, and/or (iii) receptor library members can be physically separate from one another prior to generating the sequencing mixture. The sequencing mixture can comprise a predetermined ratio of (i) nucleic acid target library members, (ii) cellular component target library members, and/or (iii) receptor library members. The predetermined ratio of cellular component target library members to receptor library members can be about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. The predetermined ratio of cellular component target library members to receptor library members can be configured to achieve a ratio of sequencing reads of cellular component target library members to sequencing reads of receptor library members that can be about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1, a number or a range between any two of the values. The ratio of sequencing reads of cellular component target library members to sequencing reads of receptor library members can be about 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values.

The ratio of sequencing reads of cellular component target library members to sequencing reads of receptor library members can be at least about 2-fold lower (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) as compared to a method wherein: (i) the plurality of barcoded receptor-binding reagent specific oligonucleotides and the plurality barcoded cellular component-binding reagent specific oligonucleotides are amplified together; (ii) the second universal sequence and third universal sequence are the same; and/or (iii) the sequencing mixture does not comprise a predetermined ratio of cellular component target library members to receptor library members.

Protein Profiling and Sample Indexing

The nucleic acid target can comprise a nucleic acid molecule, such as, for example, ribonucleic acid (RNA), messenger RNA (mRNA), microRNA, small interfering RNA (siRNA), RNA degradation product, RNA comprising a poly(A) tail, or any combination thereof. The nucleic acid target can comprise a sample indexing oligonucleotide. The sample indexing oligonucleotide can comprise a sample indexing sequence. The sample indexing sequences of at least two sample indexing compositions of a plurality of sample indexing compositions provided herein can comprise different sequences. The nucleic acid target can comprise a cellular component-binding reagent specific oligonucleotide. A cellular component-binding reagent specific oligonucleotide can comprise a unique identifier sequence for a cellular component-binding reagent. In some embodiments of the methods and compositions provided herein the nucleic acid target is a binding reagent oligonucleotide (e.g., antibody oligonucleotide ("AbOligo" or "AbO"), binding reagent oligonucleotide, cellular component-binding reagent specific oligonucleotide, sample indexing oligonucleotide). Some embodiments disclosed herein provide a plurality of compositions each comprising a cellular component binding reagent (such as a protein binding reagent) that is conjugated with an oligonucleotide (e.g., a binding reagent oligonucleotide), wherein the oligonucleotide comprises a unique identifier for the cellular component binding reagent that it is conjugated with. Cellular component binding reagents (such as barcoded antibodies) and their uses (such as sample indexing of cells) have been described in US2018/0088112 and US2018/0346970; the content of each of these is incorporated herein by reference in its entirety.

Systems, methods, compositions, and kits for determining protein expression and gene expression simultaneously, as well as for sample indexing, are also described in US 2020/0232032, the content of which is incorporated herein by reference in its entirety. In some such embodiments, an oligonucleotide associated with a cellular component-binding reagent (e.g., an antibody) comprises one or more of a unique molecular label sequence, a primer adapter, antibody-specific barcode sequence, an alignment sequence, and/or a poly(A) sequence. In some embodiments, the oligonucleotide is associated with the cellular component-binding reagent via a linker (e.g., 5AmMC12).

Immune Repertoire Profiling

Disclosed herein includes systems, methods, compositions, and kits for attachment of barcodes (e.g., stochastic barcodes) with molecular labels (or molecular indices) to the 5'-ends of nucleic acid targets being barcoded or labeled (e.g., deoxyribonucleic acid molecules, and ribonucleic acid molecules). The 5'-based transcript counting methods disclosed herein can complement, or supplement, for example, 3'-based transcript counting methods (e.g., Rhapsody™ assay (Becton, Dickinson and Company, Franklin Lakes, NJ), Chromium™ Single Cell 3' Solution (10× Genomics, San Francisco, CA)). The barcoded nucleic acid targets can be used for sequence identification, transcript counting, alternative splicing analysis, mutation screening, and/or full length sequencing in a high throughput manner. Transcript counting on the 5'-end (5' relative to the target nucleic acid targets being labeled) can reveal alternative splicing isoforms and variants (including, but not limited to, splice variants, single nucleotide polymorphisms (SNPs), insertions, deletions, substitutions) on, or closer to, the 5'-ends of nucleic acid molecules. In some embodiments, the method can involve intramolecular hybridization. Methods for determining the sequences of a nucleic acid target (e.g., the V(D)J region of an immune receptor) using 5' barcoding and/or 3' barcoding are described in US2020/0109437; the content of which is incorporated herein by reference in its entirety. Systems, methods, compositions, and kits for molecular barcoding on the 5'-end of a nucleic acid target have been described in US2019/0338278, the content of which is incorporated herein by reference in its entirety. The systems, methods, compositions, and kits for 5'-based gene expression profiling provided herein can, in some embodiments, be employed in concert with random priming and extension (RPE)-based whole transcriptome analysis methods and compositions have been described in US2020/0149037; the content of which is incorporated herein by reference in its entirety.

Design and Generation of Antigenic Peptides

Antigenic peptides disclosed herein may be used in the disclosed processes as part of MHC multimers disclosed herein. The features of and principles for design and generation of antigenic peptides provided herein will be described in more detail in the following.

MHC class 1 protein typically binds octa-, nona-, deca- or ondecamer (8-, 9-, 10-, 11-mer) peptides in their peptide binding groove, in some instances up to 12mer peptides. The individual MHC class 1 alleles have individual preferences for the peptide length within the given range. MHC class 2 proteins typically bind peptides with a total length of 13-18 amino acids, comprising a 9'-mer core motif containing the important amino acid anchor residues. However the total length is not strictly defined, as opposed to most MHC class 1 molecules.

For some of the MHC alleles the optimal peptide length and the preferences for specific amino acid residues in the so called anchor positions are known.

To identify high-affinity binding peptides derived from a specific protein for a given MHC allele it is necessary to systematically work through the amino acid sequence of the protein to identify the putative high-affinity binding peptides. Although a given peptide is a binder it is not necessarily a functional T-cell epitope. Functionality needs to be confirmed by a functional analysis e.g. ELISPOT, CTL killing assay or flow cytometry assay as described elsewhere herein.

The antigenic peptides can, in some embodiments, be generated by computational prediction e.g. using NetMHC or by selection of specific 8, 9, 10, 11, 12-mer amino acid sequences. The binding affinity of the peptides can for some MHC molecules be predicted in currently available databases.

Design of Binding Peptides, P

The first step in the design of binding peptides P is obtaining the amino acid sequence of the protein or antigenic polypeptide of interest.

In many cases the amino acid sequence of the protein from which antigenic peptides have to be identified from are known. However, when only the genomic DNA sequences are known, i.e. the reading frame and direction of transcription of the genes is unknown, the DNA sequence needs to be translated in all three reading frames in both directions leading to a total of six amino acid sequences for a given genome.

From these amino acid sequences binding peptides can then be identified as described below. In organisms having intron/exon gene structure the present approach must be modified accordingly, to identify peptide sequence motifs that are derived by combination of amino acid sequences derived partly from two separate introns. cDNA sequences can be translated into the actual amino acid sequences to allow peptide identification. In cases where the protein sequence is known, these can directly be used to predict peptide epitopes.

Binding peptide sequences can be predicted from any protein sequence by either a total approach, generating binding peptide sequences for potentially any MHC allele, or by a directed approach, identifying a subset of binding peptides with certain preferred characteristics such as affinity for MHC protein, specificity for MHC protein, likelihood of being formed by proteolysis in the cell, and other important characteristics.

Design of MHC Class 1 Binding Peptide Sequence

Many parameters influence the design of the individual binding peptide, P, as well as the choice of the set of binding peptides to be used in a particular application.

Important characteristics of the MHC-peptide complex are physical and chemical (e.g. proteolytic) stability. The relevance of these parameters must be considered for the production of the antigenic peptides, P, the MHC-peptide complexes and the MHC multimers, as well as for their use in a given application. As an example, the stability of the MHC-peptide complex in assay buffer (e.g. PBS), in blood, or in the body can be very important for a particular application.

In the interaction of the MHC-peptide complex with the TCR, a number of additional characteristics must be considered, including binding affinity and specificity for the TCR, degree of cross-talk, undesired binding or interaction with other TCRs. Finally, a number of parameters must be considered for the interaction of MHC-peptide complexes, MHC multimers or antigenic peptides with the sample or individual it is being applied to. These include immunogenicity, allergenicity, as well as side effects resulting from un-desired interaction with "wrong" T cells, including cross-talk with e.g. autoimmune diseases and un-desired interaction with other cells than antigen-specific T cells.

For some applications, e.g. immuno-profiling of an individual's immune response focused on one antigen, it is advantageous that all possible binding peptides of that antigen are included in the application (i.e. the "total approach" for the design of binding peptides described below). For other applications, it may be adequate to include a few or just one binding peptide for each of the HLA-alleles included in the application (i.e. the "directed approach" whereby only the most potent binding peptides can be included). Personalized diagnostics, therapeutics and vaccines will often fall in-between these two extremes, as it will only be necessary to include a few or just one binding peptide in e.g. a vaccine targeting a given individual, but the specific binding peptide may have to be picked from binding peptides designed by the total approach, and identified through the use of immuno-profiling studies involving all possible binding peptides. The principles of immuno-profiling is described elsewhere herein.

a) Total Approach

The MHC class 1 binding peptide, P, prediction is done as follows using the total approach. The actual protein sequence is split up into 8-, 9-, 10-, and 11-mer peptide sequences. This is performed by starting at amino acid position 1 identifying the first 8-mer; then move the start position by one amino acid identifying the second 8-mer; then move the start position by one amino acid, identifying the third 8-mer. This procedure continues by moving start position by one amino acid for each round of peptide identification. Generated peptides will be amino acid position 1-8, 2-9, 3-10 etc. This procedure can be carried out manually or by means of a software program (such as disclosed in FIG. 2 of WO 2009/106073). This procedure is then repeated in an identical fashion for 9-, 10, 11- and 12-mers, respectively.

b) Directed Approach

The directed approach identifies a preferred subset of binding peptides, P, from the binding peptides generated in the total approach. This preferred subset is of particularly value in a given context. One way to select subsets of antigenic peptides (P) is to use consensus sequences to choose a set of relevant binding peptides able to bind the individual MHC allele and that will suit the "average" individual. Such consensus sequences often solely consider the affinity of the binding peptide for the MHC protein; in other words, a subset of binding peptides is identified where the designed binding peptides have a high probability of forming stable MHC-peptide complexes, but where it is uncertain whether this MHC-peptide complex is of high relevance in a population, and more uncertain whether this MHC-peptide complex is of high relevance in a given individual.

For class I MHC-alleles, the consensus sequence for a binding peptide is generally given by the formula X1-X2-X3-X4- . . . -Xn, where n equals 8, 9, 10, or 11, and where X represents one of the twenty naturally occurring amino acids, optionally modified as described elsewhere in this application. X1-Xn can be further defined. Thus certain positions in the consensus sequence are more likely to contribute to binding to a given MHC molecule than others.

Antigenic peptide-binding by MHC I is accomplished by interaction of specific amino acid side chains of the antigenic peptide with discrete pockets within the peptide binding groove of the MHC molecule. The peptide-binding groove is formed by the a1 and a2 domains of the MHC I heavy chain and contains six pockets denoted A, B, C, D, E, F. For human HLA molecules the main binding energy associating antigenic peptide to MHC I is provided by interaction of amino acids in position 2 and at the c-terminus of the antigenic peptide with the B and F binding pockets of the MHC I molecule. The amino acids of the antigenic peptide being responsible for the main anchoring of the peptide to the MHC molecule are in the following called primary anchor amino acids and the motif they form for primary anchor motif. Other amino acid side chains of an antigenic peptide may also contribute to the anchoring of the antigenic peptide to the MHC molecule but to a lesser extent. Such amino acids are often referred to as secondary anchor amino acids and form a secondary anchor motif.

Different HLA alleles have different amino acids lining the various pockets of the peptide-binding groove enabling the various alleles to bind unique repertoires of antigenic peptides with specific anchor amino acid motifs. Thus for a selected consensus sequence certain positions are the so-called anchor positions and the selection of useful amino acids for these positions is limited to those able to fit into the corresponding binding pockets in the HLA molecule. For example for peptides binding HLA-A*02, X2 and X9 are primary anchor positions docking into the B and F pocket of the HLA molecule respectively, and useful amino acids at these two positions in the binding peptide are preferable limited to leucine or methionine for X2 and to valine or leucine at position X9. In contrast the primary anchor positions of peptides binding HLA-B*08 are X3, X5 and X9 and the corresponding preferred amino acids at these positions are lysine at position X3, lysine or arginine at position X5 and leucine at position X9.

The different HLA alleles can be grouped into clusters or supertypes where the alleles of the supertype share peptide-binding pocket similarities in that they are able to recognize the same type of antigenic peptide primary anchor motif. Therefore antigenic peptides can be selected on their ability to bind a given HLA molecule or a given HLA supertype on the basis of their amino acid sequence, e.g. the identity of the primary anchor motif.

Antigenic peptide primary anchor motifs of special interest are listed in Table 1, where examples of useful amino acids binding in pocket B and pocket F are shown as one letter code.

TABLE 1

HLA I supertype families and their antigenic peptide anchor motifs

| | Anchor motif | | | | |
|---|---|---|---|---|---|
| Supertype | B pocket specificity | Example aa B pocket | F pocket specificity | Example aa F pocket | Example of HLA alleles |
| A01 | Small and aliphatic | A, T, S, V, L, I, M, Q | Aromatic and large hydrophobic | F, W, Y, L, I, M | A*0101, A*2601, A*2602, A*2603, A*3002, A*3003, A*3004, A*3201 |
| A01/A03 | Small and aliphatic | A, T, S, V, L, I, M, Q | Aromatic and basic | Y, R, K | A*3001, A*3201, A*7401 |
| A01/A24 | Small, aliphatic and aromatic | A, S, T, V, L, I, M, Q, F, W, Y | Aromatic and large hydrophobic | F, W, Y, L, I, M | A*2902 |
| A02 | Small and aliphatic | A, T, S, V, L, I, M, Q | Aliphatic and small hydrophobic | L, I, V, M, Q, A | A*0201, A*0202, A*0203, A*0204, A*0205, A*0206, A*0207, A*0214, A*0217, A*6802, A*6901 |
| A03 | Small and aliphatic | A, T, S, V, L, I, M, Q | Basic | R, H, K | A*0301, A*1101, A*3101, A*3301, A*3303, A*6601, A*6801, A*7401 |
| A24 | Aromatic and aliphatic | F, W, Y, L, I, V, M, Q | Aromatic, aliphatic and hydrophobic | F, W, Y, L, I, V, M, Q, A | A*2301, A*2402 |
| B07 | Proline | P | Aromatic, aliphatic and hydrophobic | F, W, Y, L, I, V, M, Q, A | B*0702, B*0703, B*0705, B*1508, B*3501, B*3503, B*4201, B*5101, B*5102, B*5103, B*5301, B*5401, B*5501, B*5502, B*5601, B*6701, B*7801 |
| B08 | Undefined | | Aromatic, aliphatic and hydrophobic | F, W, Y, L, I, V, M, Q, A | B*0801, B*0802 |
| B27 | Basic | R, H, K | Aromatic, aliphatic, basic and hydrophobic | F, W, Y, L, I, V, M, Q, A, R, H, K | B*1402, B*1503, B*1509, B*1510, B*1518, B*2702, B*2703, B*2704, B*2705, B*2706, B*2707, B*2709, B*3801, B*3901, B*3902, B*3909, B*4801, B*7301 |
| B44 | Acidic | D, E | Aromatic, aliphatic and hydrophobic | F, W, Y, L, I, V, M, Q, A | B*1801, B*3701, B*4001, B*4002, B*4006, B*4402, B*4403, B*4501 |
| B58 | Small | A, S, T | Aromatic, aliphatic and hydrophobic | F, W, Y, L, I, V, M, Q, A | B*1516, B*1517, B*5701, B*5702, B*5801, B*5802 |
| B62 | Aliphatic | L, I, V, M, Q | Aromatic, aliphatic and hydrophobic | F, W, Y, L, I, V, M, Q, A | B*1501, B*1502, B*1512, B*1513, B*4501, B*4601, B*5201 |

Antigenic peptides P able to bind a given MHC molecule do not necessarily have primary anchor amino acid residues compatible with both main anchoring pockets of the MHC molecule but may have one or no primary anchor amino acids suitable for binding the MHC molecule in question. However, having the preferred primary anchor motif for a given MHC allele increases the affinity of the antigenic peptide for that given allele and thereby the likelihood of making a stable and useful MHC-peptide molecule.

Therefore, in some embodiments, antigenic peptides can be identified and selected on their ability to bind a given HLA or other MHC molecule based on what amino acids they have at primary anchor positions and/or secondary anchor positions.

Software programs are available that use neural networks or established binding preferences to predict the interaction of specific binding peptides with specific MHC class I alleles. Another useful parameter for prediction and selection of useful antigenic peptides are the probability of the binding peptide in question to be generated in vivo by the proteolytic machinery inside cells. For example for a given antigen the combined action of endosolic, cytosolic and membrane bound protease activities as well as the TAP1 and TAP2 transporter specificities can be taken into consideration. However, the proteolytic activity varies a lot among individuals, and for personalized diagnostics, treatment or vaccination it may be desirable to disregard these general proteolytic data.

In some embodiments, the identification of the antigenic peptides P comprises prediction of a theoretical binding affinity of the peptide P to the one or more MHC Class I alleles with a binding affinity threshold (nM) (or simply 'affinity threshold'). In some embodiments, the identification of the antigenic peptides P comprises prediction of a theoretical binding affinity of the peptide P to the MHC Class I molecules with an affinity threshold of 1000 nM (binder), 500 nM (weak binder) or 50 nM (strong binder).

Using the above described principles individual peptides or a subset of peptides able to bind one or more types of MHC molecules and make stable MHC-peptide complexes can be identified. The identified peptides can then be tested for biological relevance in functional assays such as interferon amma release assays (e.g. ELISPOT), cytotoxicity assays (e.g. CTL killing assays) or using other methods as described elsewhere herein. Alternatively or complementary hereto the ability of the identified antigenic peptides to bind selected MHC molecules may be determined in binding assays like Biacore measurement, competition assays or other assays useful for measurement of binding of peptide to MHC molecules, known by skilled persons.

Antigenic Peptides P with Amino Acid Substitutions

Antigenic peptides of interest can be modified, e.g., antigenic peptides P can have one or more amino acid substitutions, such as 1, 2, 3, 4, 5, 6, 7, or 8 amino acid substitutions. The one or more amino acid substitutions can be within the amino acid anchor motif, outside the amino acid anchor motif, or both. In some embodiments, the one or more amino acid substitutions are within the 9-mer core motif. In some embodiments, the one or more amino acid substitutions are outside the 9-mer core motif.

In some embodiments, these amino acid substitutions comprise substitution with an "equivalent amino acid residue". An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers, in some embodiments, to the following classes: 1) HRK, 2) DENQ, 3) C, 4) STPAG, 5) MILV and 6) FYW. Within the meaning of the term "equivalent amino acid substitution" as applied herein, one amino acid may be substituted for another, in some embodiments, within the groups of amino acids indicated herein below:

Amino acids having polar side chains (Asp, Glu, Lys, Arg, His, Asn, Gin, Ser, Thr, Tyr, and Cys)

Amino acids having non-polar side chains (Gly, Ala, Val, Leu, lie, Phe, Trp, Pro, and Met)

Amino acids having aliphatic side chains (Gly, Ala Val, Leu, lie)

Amino acids having cyclic side chains (Phe, Tyr, Trp, His, Pro)

Amino acids having aromatic side chains (Phe, Tyr, Trp)

Amino acids having acidic side chains (Asp, Glu)

Amino acids having basic side chains (Lys, Arg, His)

Amino acids having amide side chains (Asn, Gin)

Amino acids having hydroxy side chains (Ser, Thr)

Amino acids having sulphor-containing side chains (Cys, Met),

Neutral, weakly hydrophobic amino acids (Pro, Ala, Gly, Ser, Thr)

Hydrophilic, acidic amino acids (Gin, Asn, Glu, Asp), and

Hydrophobic amino acids (Leu, lie, Val)

A Venn diagram is another method for grouping of amino acids according to their properties (Livingstone & Barton, CABIOS, 9, 745-756, 1993). In some embodiments, one or more amino acids may be substituted with another within the same Venn diagram group.

In some embodiments, these amino acid substitutions comprise substitution with a "non-equivalent amino acid residue". Non-equivalent amino acid residues are amino acid residues with dissimilar properties to the properties of the amino acid they substitute according to the groupings described above.

In some embodiments, the modified antigenic peptide P comprises an anchor motif selected from the group of HLA motifs included in Table 1 herein above; such as comprises a primary anchoring amino acid residue in amino acid position 2 and/or 9 in accordance with Table 1 herein above. In some embodiments, the modified antigenic peptide P comprises a substitution of the amino acid residue in position 2 with an amino acid residue selected from the group consisting of: i) alanine, threonine, serine, valine, leucine, isoleucine, methionine, glutamine, phenylalanine, tryptophan and tyrosine; ii) alanine, threonine, serine, valine, leucine, isoleucine, methionine and glutamine iii) arginine, histidine and lysine; iv) aspartic acid and glutamic acid, or v) alanine, threonine and serine.

In some embodiments, the antigenic peptide P or modified antigenic peptide P comprises a substitution of the amino acid residue in position 9 or 10 with an amino acid residue selected from the group consisting of: i) phenylalanine, tryptophan, tyrosine, leucine, isoleucine, valine, glutamine, alanine, argentine, histidine, lysine and methionine; ii) phenylalanine, tryptophan, tyrosine, leucine, isoleucine, valine, glutamine, alanine and methionine; iii) leucine, isoleucine, valine, glutamine, alanine and methionine; iv) phenylalanine, tryptophan, tyrosine, leucine, isoleucine and methionine v) glutamine and alanine, and vi) tyrosine, arginine and lysine.

In some embodiments, the amino acid substitutions increases the affinity of the peptide for the MHC molecule and thereby increase the stability of the MHC-peptide complex.

In some embodiments, the amino acid substitutions decreases the affinity of the peptide for the MHC molecule and thereby increase the stability of the MHC-peptide complex. In some embodiments, the amino acid substitutions increases the overall affinity of one or more T-cell receptors for the MHC-peptide complex containing the modified antigenic peptide. In some embodiments, the amino acid substitutions decreases the overall affinity of one or more T-cell receptors for the MHC-peptide complex containing the modified antigenic peptide.

Antigenic Peptides P Fragments

The one or more antigenic peptides In some embodiments, comprise or consist of a fragment of one or more antigenic peptides, such as a fragment consisting of 1, 2, 3, 4, 5, 6, 7, 8, 9, 10, 11 or 12 amino acids of said one or more antigenic peptide P.

Other Peptide Modifications

In addition to the binding peptides designed by the total approach and/or directed approach, homologous peptides and peptides that have been modified in the amino acid side chains or in the backbone can be used as binding peptides.

In some embodiments, the antigenic peptides disclosed herein are modified by one or more type(s) of post-translational modifications such as one or more of the post-translational modifications disclosed herein elsewhere. The same or different types of post-translational modification can occur on one or more amino acids in the antigenic peptide.

total approach, i.e. have an amino acid sequence identity greater than e.g. more than 90%, more than 80%, or more than 70%, or more than 60%, to one or two binding peptides derived by the total approach, they may be good candidates. Identity is often most important for the anchor residues.

A MHC binding peptide may be of split- or combinatorial epitope origin i.e. formed by linkage of peptide fragments derived from two different peptide fragments and/or proteins. Such peptides can be the result of either genetic recombination on the DNA level or due to peptide fragment association during the complex break down of proteins during protein turnover. Possibly it could also be the result of faulty reactions during protein synthesis i.e. caused by some kind of mixed RNA handling. A kind of combinatorial peptide epitope can also be seen if a portion of a longer peptide make a loop out leaving only the terminal parts of the peptide bound in the groove.

Uncommon, Artificial and Chemically Modified Amino Acids

Peptides having un-common amino acids, such as selenocysteine and pyrrolysine, may be bound in the MHC groove as well. Artificial amino acids e.g. having the isomeric D-form may also make up isomeric D-peptides that can bind in the binding groove of the MHC molecules. Bound peptides may also contain amino acids that are chemically modified or being linked to reactive groups that can be activated to induce changes in or disrupt the peptide. Example post-translational modifications are shown below. However, chemical modifications of amino acid side chains or the peptide backbone can also be performed.

Any of the modifications can be found individually or in combination at any position of the peptide, e.g. position 1, 2, 3, 4, 5, 6, etc. up to n.

TABLE 2

Post-translational modification of peptides

| | Protein primary structure and posttranslational modifications |
|---|---|
| N-terminus | Acetylation, Formylation, Pyroglutamate, Methylation, Glycation, Myristoylation (Gly), carbamylation |
| C-terminus | Amidation, Glycosyl phosphatidylinositol (GPI), O-methylation, Glypiation, Ubiquitination, Sumoylation |
| Lysine | Methylation, Acetylation, Acylation, Hydroxylation, Ubiquitination, SUMOylation, Desmosine formation, ADP-ribosylation, Deamination and Oxidation to aldehyde |
| Cysteine | Disulfide bond, Prenylation, Palmitoylation |
| Serine/Threonine | Phosphorylation, Glycosylation |
| Tyrosine | Phosphorylation, Sulfation, Porphyrin ring linkage, Flavin linkage GFP prosthetic group (Thr-Tyr-Gly sequence) formation, Lysine tyrosine quinone (LTQ) formation, Topaquinone (TPQ) formation |
| Asparagine | Deamidation, Glycosylation |
| Aspartate | Succinimide formation |
| Glutamine | Transglutamination |
| Glutamate | Carboxylation, Methylation, Polyglutamylation, Polyglycylation |
| Arginine | Citrullination, Methylation |
| Proline | Hydroxylation |

Thus, in some embodiments, any one amino acid may be modified once, twice or three times with the same or different types of modifications. Furthermore, said identical and/or different modification may be present on 1, 2, 3, 4, 5, 6, 7, 8, 9, 10, 11 or 12 of the amino acid residues of the binding peptide disclosed herein.

Homologous Peptides

Homologues MHC peptide sequences may arise from the existence of multiple strongly homologous alleles, from small insertions, deletions, inversions or substitutions. If they are sufficiently homologous to peptides derived by the Post Translationally Modified Peptides The amino acids of the antigenic peptides, P, can also be modified in various ways dependent on the amino acid in question, or the modification can affect the amino- or carboxy-terminal end of the peptide (see Table 2 immediately herein above). Such peptide modifications occur naturally as the result of post-translational processing of the parental protein. A non-exhaustive description of the major post-translational modifications is given below, divided into three main types listed below (a, b, c).

a) Modifications that Add a Chemical Moiety to the Binding Peptide, P:

Acetylation, the addition of an acetyl group, usually at the N-terminus of the protein. Alkylation, the addition of an alkyl group (e.g. methyl, ethyl).

Methylation, the addition of a methyl group, usually at lysine or arginine residues is a type of alkylation. Demethylation involves the removal of a methyl-group.

Amidation at C-terminus.

Biotinylation, acylation of conserved lysine residues with a biotin appendage formylation.

Gamma-carboxylation dependent on Vitamin K.

Glutamylation, covalent linkage of glutamic acid residues to tubulin and some other proteins by means of tubulin polyglutamylase. Glycosylation, the addition of a glycosyl group to either asparagine, hydroxylysine, serine, or threonine, resulting in a glycoprotein. Distinct from glycation, which is regarded as a nonenzymatic attachment of sugars.

Glycylation, covalent linkage of one to more than 40 glycine residues to the tubulin C-terminal tail.

Heme moiety may be covalently attached.

Hydroxylation, is any chemical process that introduces one or more hydroxyl groups (—OH) into a compound (or radical) thereby oxidizing it. The principal residue to be hydroxylated is Proline. The hydroxilation occurs at the $C^{Y}$ atom, forming hydroxyproline (Hyp). In some cases, proline may be hydroxylated instead on its $C^{P}$ atom. Lysine may also be hydroxylated on its $C^{6}$ atom, forming hydroxylysine (Hyl). Iodination.

Isoprenylation, the addition of an isoprenoid group (e.g. farnesol and geranylgeraniol).

Lipoylation, attachment of a lipoate functionality, as in prenylation, GPI anchor formation, myristoylation, farnesylation, geranylation.

Nucleotides or derivatives thereof may be covalently attached, as in ADP-ribosylation and flavin attachment.

Oxidation, lysine can be oxidized to aldehyde.

Pegylation, addition of poly-ethylen-glycol groups to a protein. Typical reactive amino acids include lysine, cysteine, histidine, arginine, aspartic acid, glutamic acid, serine, threonine, tyrosine. The N-terminal amino group and the C-terminal carboxylic acid can also be used Phosphatidylinositol may be covalently attached.

Phosphopantetheinylation, the addition of a 4'-phosphopantetheinyl moiety from coenzyme A, as in fatty acid, polyketide, non-ribosomal peptide and leucine biosynthesis.

Phosphorylation, the addition of a phosphate group, usually to serine, tyrosine, threonine or histidine.

Pyroglutamate formation as a result of N-terminal glutamine self-attack, resulting in formation of a cyclic pyroglutamate group.

Racemization of proline by prolyl isomerase.

tRNA-mediated addition of amino acids such as arginylation.

Sulfation, the addition of a sulfate group to a tyrosine.

Selenoylation (co-translational incorporation of selenium in selenoproteins).

b) Modification that Adds Protein or Peptide:

ISGylation, the covalent linkage to the ISG15 protein (Interferon-Stimulated Gene 15).

SUMOylation, the covalent linkage to the SUMO protein (Small Ubiquitin-related Modifier).

Ubiquitination, the covalent linkage to the protein ubiquitin.

c) Modification that Converts One or More Amino Acids to Different Amino Acids:

Citrullination, or deimination the conversion of arginine to citrulline.

Deamidation, the conversion of glutamine to glutamic acid or asparagine to aspartic acid.

The peptide modifications can occur as modification of a single amino acid or more than one i.e. alone or in combinations. Modifications can be present on any position within the peptide i.e. on position 1, 2, 3, 4, 5, etc. for the entire length of the peptide P.

Sources of Binding Peptides

A) from Natural Sources

The binding peptides can be obtained from natural sources by enzymatic digestion or proteolysis of natural proteins or proteins derived by in vitro translation of mRNA. Binding peptides may also be eluted from the MHC binding groove.

B) From Recombinant Sources 1) as Monomeric or Multimeric Peptide

Alternatively peptides can be produced recombinantly by transfected cells either as monomeric antigenic peptides or as multimeric (concatemeric) antigenic peptides. Optionally, the Multimeric antigenic peptides are cleaved to form monomeric antigenic peptides before binding to MHC protein.

2) As Part of a Bigger Recombinant Protein

Binding peptides may also constitute a part of a bigger recombinant protein e.g. consisting of;

2a) for MHC Class 1 Binding Peptides;

Peptide-linker^2m, b2hi being full length or truncated; Peptide-linker-MHC class 1 heavy chain, the heavy chain being full length or truncated. Most importantly the truncated class I heavy chain will consist of the extracellular part i.e the a1, D a2, and a domains. The heavy chain fragment may also only contain the a1 and a2 domains, or a1 domain alone, or any fragment or full length b2hi or heavy chain attached to a designer domain(s) or protein fragment(s).

C) From Chemical Synthesis

MHC binding peptide may also be chemically synthesized by solid phase or fluid phase synthesis, according to standard protocols.

Comprehensive collections of antigenic peptides, derived from one antigen, may be prepared by a modification of the solid phase synthesis protocol.

The protocol for the synthesis of the full-length antigen on solid support is modified by adding a partial cleavage step after each coupling of an amino acid. Thus, the starting point for the synthesis is a solid support to which has been attached a cleavable linker. Then the first amino acid X1 (corresponding to the C-terminal end of the antigen) is added and a coupling reaction performed. The solid support now carries the molecule "Nnker-X1". After washing, a fraction (e.g. 10%) of the cleavable linkers are now cleaved, to release into solution X1. The supernatant is transferred to a collection container. Additional solid support carrying a cleavable linker is added, e.g. corresponding to 10% of the initial amount of solid support.

Then the second amino acid X2 is added and coupled to X1 or the cleavable linker, to form on solid support the molecules"Nnker-X2" and"Nnker-X1-X2". After washing, a fraction (e.g. 10%) of the cleavable linker is cleaved, to release into solution X2 and X1-X2. The supernatant is collected into the collection container, which therefore now contains X1, X2, and X1-X2. Additional solid support carrying a cleavable linker is added, e.g. corresponding to 10% of the initial amount of solid support.

Then the third amino acid X3 is added and coupled to X2 or the cleavable linker, to form on solid support the molecules"Nnker-X3", "Nnker-X2-X3" and"Nnker-X1-X2-X3". After washing, a fraction (e.g. 10%) of the cleavable linker is cleaved, to release into solution X3, X2-X3 and X1-X2-X3. The supernatant is collected into the collection container, which therefore now contains X1, X2, X3, X1-X2, X2-X3 and X1-X2-X3. Additional solid support carrying a cleavable linker is added, e.g. corresponding to 10% of the initial amount of solid support. This step-wise coupling and partial cleavage of the linker is continued until the N-terminal end of the antigen is reached. The collection container will now contain a large number of peptides of different length and sequence. In the present example where a 10% partial cleavage was employed, a large fraction of the peptides will be 8'-mers, 9'-mers, 10'-mers and 10-mers, corresponding to class I antigenic peptides. As an example, for a 100 amino acid antigen the 8'-mers will consist of the sequences X1-X2-X3-X4-X5-X6-X7-X8, X2-X3-X4-X5-X6-X7-X8-X9, X93-X94-X95-X96-X97-X98-X99-X100.

Optionally, after a number of coupling and cleavage steps or after each coupling and cleavage step, the used (inactivated) linkers on solid support can be regenerated, in order to maintain a high fraction of linkers available for synthesis. The collection of antigenic peptides can be used as a pool for e.g. the display by APCs to stimulate CTLs in ELISPOT assays, or the antigenic peptides may be mixed with one or more MEW alleles, to form a large number of different MHC-peptide complexes which can e.g. be used to form a large number of different MHC multimers which can e.g. be used in flow cytometry experiments.

Choice of MEW Allele for Generation of MHC Monomers and MEW Multimers

More than 600 MEW alleles (class 1 and 2) are known in humans; for many of these, the peptide binding characteristics are known. FIG. 3 of WO 2009/106073 presents a list of the HLA class 1 alleles. The frequency of the different HLA alleles varies considerably, also between different ethnic groups—as illustrated for top 30 HLA class I alleles (e.g. FIG. 4 in WO 2009/106073). Thus it is of outmost importance to carefully select the MEW alleles that corresponds to the population that one wish to study.

The MEW protein can be selected from the group of HLA alleles consisting of: A*0201, C*0701, A*0101, A*0301, C*0702, C*0401, B*4402, B*0702, B*0801, C*0501, C*0304, C*0602, A*1101, B*4001, A*2402, B*3501, C*0303, B*5101, C*1203, B*1501, A*2902, A*2601, A*3201, C*0802, A*2501, B*5701, B*1402, C*0202, B*1801, B 403, C*0401, C*0701, C*0602, A*0201, A*2301, C*0202, A*0301, C*0702, B*5301, B*0702, C*1601, B*1503, B*5801, A*6802, C*1701, B 501, B*4201, A*3001, B*3501, A*0101, C*0304, A*3002, B*0801, A*3402, A*7401, A*3303, C*1801, A*2902, B 403, B*4901, A*0201, C*0401, A*2402, C*0702, C*0701, C*0304, A*0301, B*0702, B*3501, C*0602, C*0501, A*0101, A*1101, B*5101, C*1601, B 403, C*0102, A*2902, C*0802, B*1801, A*3101, B*5201, B*1402, C*0202, C*1203, A*2601, A*6801, B*0801, A*3002, B 402, A*1101, A*2402, C*0702, C*0102, A*3303, C*0801, C*0304, A*0201, B 001, C*0401, B*5801, B 601, B*5101, C*0302, B*3802, A*0207, B*1501, A*0206, C*0303, B*1502, A*0203, B 403, C*1402, B*3501, C*0602, B*5401, B*1301, B*4002, B*5502 and A*2601. In some embodiments, the MEW protein is selected from the group of HLA alleles consisting of: HLA-A*A0101, A0201, A0301, A1101, A2402, A2501, A2601, A2902, A3101, A3201, A6801, B0702, B0801, B1503, B1801, B3501, B4002, B4402, B4501 and B5101.

Loading of the Peptide into the MHC Multimer

Loading of the peptides into the MHCmer MHC class 1 can be performed in a number of ways depending on the source of the peptide and the MHC, and depending on the application.

The antigenic peptide may be added to the other peptide chain(s) at different times and in different forms, as follows a) Loading of antigenic peptide during MHC complex folding:

a. Antigenic peptide is added as a free peptide MHC class I molecules are most often loaded with peptide during assembly in vitro by the individual components in a folding reaction i.e. consisting of purified recombinant heavy chain a with the purified recombinant b2 microglobulin and a peptide or a peptide mix.

b. Antigenic peptide is part of a recombinant protein construct

Alternatively the peptide to be folded into the binding groove can be encoded together with e.g. the a heavy chain or fragment hereof by a gene construct having the structure, heavy chain-flexible linker-peptide. This recombinant molecule is then folded in vitro with p2-microglobulin.

b) Antigenic peptide replaces another antigenic peptide by an exchange reaction: a. Exchange reaction "in solution"

Loading of desired peptide can also be made by an in vitro exchange reaction where a peptide already in place in the binding groove are being exchanged by another peptide species.

b. Exchange reaction "in situ"

Peptide exchange reactions can also take place when the parent molecule is attached to other molecules, structures, surfaces, artificial or natural membranes and nano-particles.

c. Aided exchange reaction.

This method can be refined by making the parent construct with a peptide containing a meta-stable amino acid analogue that is split by either light or chemically induction thereby leaving the parent structure free for access of the desired peptide in the binding groove.

d. Display by in vivo loading

Loading of MHC class I molecules expressed on the cell surface with the desired peptides can be performed by an exchange reaction. Alternatively cells can be transfected by the peptides themselves or by the mother proteins that are then being processed leading to an in vivo analogous situation where the peptides are bound in the groove during the natural cause of MHC expression by the transfected cells. In the case of professional antigen presenting cells e.g. dendritic cells, macrophages, Langerhans cells, the proteins and peptides can be taken up by the cells themselves by phagocytosis and then bound to the MHC complexes the natural way and expressed on the cell surface in the correct MHC context.

MHC Multimers

In some embodiments, the MHC multimer is between 50,000 Da and 1,000,000 Da, such as from 50,000 to 980,000 Da (e.g., from 50,000 to 960,000; 50,000 to 940,000; from 50,000 to 920,000; from 50,000 to 900,000; from 50,000 to 880,000; from 50,000 to 860,000; from 50,000 to 840,000; from 50,000 to 820,000; from 50,000 to 800,000; from 50,000 to 780,000; from 50,000 to 760,000; from 50,000 to 740,000; from 50,000 to 720,000; from 50,000 to 700,000; from 50,000 to 680,000; 50,000 to 660,000; from 50,000 to 640,000; from 50,000 to 620,000; from 50,000 to 600,000; from 50,000 to 580,000; from 50,000 to 560,000; from 50,000 to 540,000; from 50,000 to 520,000; from 50,000 to 500,000; from 50,000 to 480,000; from 50,000 to 460,000; from 50,000 to 440,000; from 50,000 to 420,000; from 50,000 to 400,000; from 50,000 to 380,000; from 50,000 to 360,000; from 50,000 to 340,000; from 50,000 to 320,000; from 50,000 to 300,000; from 50,000 to 280,000; from 50,000 to 260,000; from 50,000 to 240,000; from 50,000 to 220,000; from 50,000 to 200,000; from 50,000 to 180,000; from 50,000 to 160,000; from 50,000 to 140,000; from 50,000 to 120,000; from 50,000 to 100,000; from 50,000 to 80,000; from 50,000 to 60,000; from 100,000 to 980,000; from 100,000 to 960,000; from 100,000 to 940, 000; from 100,000 to 920,000; from 100,000 to 900,000; from 100,000 to 880,000; from 100,000 to 860,000; from 100,000 to 840,000; from 100,000 to 820,000; from 100,000 to 800,000; from 100,000 to 780,000; from 100,000 to 760,000; from 100,000 to 740,000; from 100,000 to 720, 000; from 100,000 to 700,000; from 100,000 to 680,000; from 100,000 to 660,000; from 100,000 to 640,000; from 100,000 to 620,000; from 100,000 to 600,000; from 100,000 to 580,000; from 100,000 to 560,000; from 100,000 to 540,000; from 100,000 to 520,000; from 100,000 to 500, 000; from 100,000 to 480,000; from 100,000 to 460,000; from 100,000 to 440,000; from 100,000 to 420,000; from 100,000 to 400,000; from 100,000 to 380,000; from 100,000 to 360,000; from 100,000 to 340,000; from 100,000 to 320,000; from 100,000 to 300,000; from 100,000 to 280, 000; from 100,000 to 260,000; from 100,000 to 240,000; from 100,000 to 220,000; from 100,000 to 200,000; from 100,000 to 180,000; from 100,000 to 160,000; from 100,000 to 140,000; from 100,000 to 120,000; from 150,000 to 980,000; from 150,000 to 960,000; from 150,000 to 940, 000; from 150,000 to 920,000; from 150,000 to 900,000; from 150,000 to 880,000; from 150,000 to 860,000; from 150,000 to 840,000; from 150,000 to 820,000; from 150,000 to 800,000; from 150,000 to 780,000; from 150,000 to 760,000; from 150,000 to 740,000; from 150,000 to 720, 000; from 150,000 to 700,000; from 150,000 to 680,000; from 150,000 to 660,000; from 150,000 to 640,000; from 150,000 to 620,000; from 150,000 to 600,000; from 150,000 to 580,000; from 150,000 to 560,000; from 150,000 to 540,000; from 150,000 to 520,000; from 150,000 to 500, 000; from 150,000 to 480,000; from 150,000 to 460,000; from 150,000 to 440,000; from 150,000 to 420,000; from 150,000 to 400,000; from 150,000 to 380,000; from 150,000 to 360,000; from 150,000 to 340,000; from 150,000 to 320,000; from 150,000 to 300,000; from 150,000 to 280, 000; from 150,000 to 260,000; from 150,000 to 240,000; from 150,000 to 220,000; from 150,000 to 200,000; from 150,000 to 180,000; from 150,000 to 160,000 Da). In some embodiments, the MHC multimer is between 1,000,000 Da and 3,000,000 Da, for example from 1,000,000 to 2,800,000 Da; from 1,000,000 to 2,600,000 Da; from 1,000,000 to 2,400,000 Da; from 1,000,000 to 2,200,000 Da; from 1,000, 000 to 2,000,000 Da; from 1,000,000 to 1,800,000 Da; from 1,000,000 to 1,600,000 Da; from 1,000,000 to 1,400,000 Da.

Above it was described how to design and produce the key components of the MEW multimers, i.e. the MHC-peptide complex. In the following it is described how to generate the MHC monomer or MHC multimer products disclosed herein.

Number of MEW Complexes Per Multimer

A non-exhaustive list of possible MEW mono- and multimers illustrates the possibilities 'n' indicates the number of MHC complexes comprised in the multimer disclosed herein:

a) n=1, Monomers b) n=2, Dimers, multimerization can for example be based on IgG scaffold, streptavidin with two MHC's, coiled-coil dimerization e.g. Fos.Jun dimerization c) n=3, Trimers, multimerization can for example be based on streptavidin as scaffold with three MHC's, TNFalpha-MHC hybrids, triplex DNA-MHC conjugates or other trimer structures d) n=4, Tetramers, multimerization can for example be based on streptavidin with all four binding sites occupied by MHC molecules or based on dimeric IgA e) n=5, Pentamers, multimerization for example can take place around a pentameric coil-coil structure f) n=6, Hexamers g) n=7, Heptamers h) n=8-12, Octa-dodecamers, multimerization can for example use Streptactin i) n=10, Decamers, multimerization can for example use IgM j) $1<n<100$, Dextramers, as multimerization domain polymers such as polypeptides, polysaccharides and Dextrans can for example be used.

k) $1<n<1000$, Multimerization can for example make use of dendritic cells (DC), antigen-presenting cells (APC), micelles, liposomes, beads, surfaces e.g. microtiterplate, tubes, microarray devices, micro-fluidic systems l) $1<n$, n in billions or trillions or higher, multimerization can for example take place on beads, and surfaces e.g. microtiterplate, tubes, microarray devices, micro-fluidic systems In some embodiments, the panel disclosed herein comprises MHC multimers $(a\text{-}b\text{-}P)_n$, wherein n>1, comprising two or more MHC proteins each in complex with an antigenic peptide P to form an MHC-peptide complex. In a preferred embodiment the MHC proteins are class I MHC proteins.

In some embodiments, the panel disclosed herein comprises MHC multimers $(a\text{-}b\text{-}P)_n$, wherein the value of n is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750, 800, 850, 900, 950 and 1000.

In some embodiments, the panel disclosed herein comprises MHC multimers $(a\text{-}b\text{-}P)_n$, wherein the value of n is $1<n\geq 1000$, such as between 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-35, 35-40, 40-45, 45-50, 50-55, 55-60, 60-65, 65-70, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-325, 325-350, 350-375, 375-400, 400-450, 450-500, 500-550, 550-600, 600-650, 650-700, 700-750, 750-800, 800-850, 850-900, 900-950, 950-1000.

In some embodiments, the panel disclosed herein comprises MHC multimers $(a\text{-}b\text{-}P)_n$, wherein the value of n is >1, such as 2, such as >2, such as ≥2, such as 3, such as >3, such as ≥3, such as 4, such as >4, such as ≥4, such as 5, such as >5, such as ≥5, such as 6, such as >6, such as ≥6, such as 7, such as >7, such as ≥7, such as 8, such as >8, such as ≥8, such as 9, such as >9, such as ≥9, such as 10, such as >10, such as ≥10.

MHC multimers thus include MHC-dimers, MHC-trimers, MHC-tetramers, MHC-pentamers, MHC-hexamers, and MHC n-mers, as well as organic molecules, cells, membranes, polymers and particles that comprise two or more MHC-peptide complexes. Example organic molecule-based multimers include functionalized cyclic structures such as benzene rings where e.g. a benzene ring is functionalized and covalently linked to e.g. three MHC complexes; example cell-based MHC multimers include dendritic cells and antigen presenting cells (APCs); example membrane-based MHC multimers include liposomes and micelles carrying MHC-peptide complexes in their membranes; example polymer-based MHC multimers include MHC-dextramers (dextran to which a number of MHC-peptide complexes are covalently or non-covalently attached) and example particles include beads or other solid supports with MHC complexes immobilized on the surface. Obviously, any kind of multimerization domain can be used, including any kind of cell, polymer, protein or other molecular structure, or particles and solid supports.

Any of the three components of a MHC complex can be of any of the below mentioned origins. The list is non-exhaustive. A complete list would encompass all Chordate species. By origin is meant that the sequence is identical or highly homologous to a naturally occurring sequence of the specific species.

List of origins: Human, Mouse, Primate (including Chimpansee, Gorilla, Orang Utan), Monkey (including Macaques), Porcine (Swine/Pig), Bovine (Cattle/Antilopes), Equine (Horse), Camelides (Camels), Ruminants (Deer), Canine (Dog), Feline (Cat), Bird (including Chicken, Turkey), Fish, Reptiles and Amphibians.

In some embodiments, the MHC disclosed herein is a MHC class I complex of HLA-type A. In some embodiments, the MHC is a MHC class I complex of HLA-type B. In some embodiments, the MHC is a MHC class I complex of HLA-type C.

Generation of MHC Multimers

Different approaches to the generation of various types of MHC multimers are described in, e.g., U.S. Pat. No. 5,635,363, WO02/072631 and WO99/42597, US20040209295, and is described elsewhere herein. In brief, MHC multimers can be generated by first expressing and purifying the individual protein components of the MHC protein, and then combining the MHC protein components and the peptide, to form the MHC-peptide complex. Then an appropriate number of MHC-peptide complexes are linked together by covalent or non-covalent bonds to a multimerization domain. This can be done by chemical reactions between reactive groups of the multimerization domain (e.g. vinyl sulfone functionalities on a dextran polymer) and reactive groups on the MHC protein (e.g. amino groups on the protein surface), or by non-covalent interaction between a part of the MHC protein (e.g. a biotinylated peptide component) and the multimerization domain (e.g. four binding sites for biotin on the streptavidin tetrameric protein). As an alternative, the MHC multimer can be formed by the non-covalent association of amino acid helices fused to one component of the MHC protein, to form a pentameric MHC multimer, held together by five helices in a coiled-coil structure making up the multimerization domain.

Appropriate chemical reactions for the covalent coupling of MHC and the multimerization domain include nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions.

Appropriate molecules, capable of providing non-covalent interactions between the multimerization domain and the MHC-peptide complex, involve the following molecule pairs and molecules: streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity.

Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. In particular, when the MHC complex is tagged, the binding entity can be an "anti-tag". By "anti-tag" is meant an antibody binding to the tag and any other molecule capable of binding to such tag.

Generation of Protein Chains of MHC

MHC class I heavy chain (HC) and β2-mircroglobulin (β2m) can be obtained from a variety of sources.

a) Natural sources by means of purification from eukaryotic cells naturally expressing the MHC class 1 or β2m molecules in question.
b) The molecules can be obtained by recombinant means e.g. using.
   a. in vitro translation of mRNA obtained from cells naturally expressing the MHC or β2m molecules in question
   b. by expression and purification of HC and/or β2m gene transfected cells of mammalian, yeast, bacterial or other origin. This last method will normally be the method of choice. The genetic material used for transfection/transformation can be:
      i. of natural origin isolated from cells, tissue or organisms
      ii. of synthetic origin i.e. synthetic genes identical to the natural DNA sequence or it could be modified to introduce molecular changes or to ease recombinant expression.

The genetic material can encode all or only a fragment of β2m, all or only a fragment of MHC class 1 heavy chain. Of special interest are MHC class 1 heavy chain fragments consisting of, the complete chain minus the intramembrane domain, a chain consisting of only the extracellular a1 and a2 class 1 heavy chain domains, or any of the mentioned β2m and heavy chain fragments containing modified or added designer domain(s) or sequence(s).

Modified MHC I Complexes

MHC I complexes modified in any way as described above, can bind TCR.

Modifications include mutations (substitutions, deletions or insertions of natural or non-natural amino acids, or any other organic molecule. The mutations are not limited to those that increase the stability of the MHC complex, and could be introduced anywhere in the MHC complex. One example of special interest is mutations introduced in the a3 subunit of MHC I heavy chain. The a3-subunit interacts with CD8 molecules on the surface of T cells. To minimize binding of MHC multimer to CD8 molecules on the surface of non-specific T cells, amino acids in a3 domain involved in the interaction with CD8 can be mutated. Such a mutation can result in altered or abrogated binding of MHC to CD8 molecules. Another example of special interest is mutations in areas of the p2-domain of MHC II molecules responsible for binding CD4 molecules.

Another embodiment is chemically modified MHC complexes where the chemical modification could be introduced anywhere in the complex, e.g. a MHC complex where the peptide in the peptide-binding cleft has a dinitrophenyl group attached.

Modified MHC complexes could also be MHC I or MHC II fusion proteins where the fusion protein is not necessarily more stable than the native protein. Of special interest is MHC complexes fused with genes encoding an amino acid sequence capable of being biotinylated with a Bir A enzyme (Schatz, P. J. (1993), Biotechnology 11 (10): 1138-1143). This biotinylation sequence could be fused with the COOH-terminal of p2m or the heavy chain of MHC I molecules or the COOH-terminal of either the a-chain or b-chain of MHC II. Similarly, other sequences capable of being enzymatically or chemically modified can be fused to the NH2 or COOH-terminal ends of the MHC complex.

Stabilization of Empty MHC Complexes and MHC-Peptide Complexes

Classical MHC complexes are in nature embedded in the membrane. Some embodiments include multimers comprising a soluble form of MHC where the transmembrane and cytosolic domains of the membrane-anchored MHC complexes are removed. The removal of the membrane-anchoring parts of the molecules can influence the stability of the MHC complexes. The stability of MHC complexes is an important parameter when generating and using MHC multimers.

MHC I complexes having a single membrane-anchored heavy chain that contains the complete peptide binding groove and is stable in the soluble form when complexed with p2m. The long-term stability is dependent on the binding of peptide in the peptide binding groove. Without a peptide in the peptide binding groove the heavy chain and p2m tend to dissociate. Similarly, peptides with high affinity for binding in the peptide binding groove will typically stabilize the soluble form of the MHC complex while peptides with low affinity for the peptide-binding groove will typically have a smaller stabilizing effect.

In nature MHC I molecules consist of a heavy chain combined with p2m, and a peptide of typically 8-11 amino acids. Herein, MHC I molecules also include molecules consisting of a heavy chain and p2m (empty MHC), or a heavy chain combined with a peptide or a truncated heavy chain comprising a1 and a2 subunits combined with a peptide, or a full-length or truncated heavy chain combined with a full-length or truncated p2m chain. These MHC I molecules can be produced in *E. coli* as recombinant proteins, purified and refolded in vitro (Garboczi et al., (1992), Proc. Natl. Acad. Sci. 89, 3429-33). Alternatively, insect cell systems or mammalian cell systems can be used. To produce stable MHC I complexes and thereby generate reliable MHC I multimers several strategies can be followed. Stabilization strategies for MHC I complexes are described in the following.

Stabilization Strategies for MHC I Complexes

Generation of Covalent Protein Fusions

MHC I molecules can be stabilized by introduction of one or more linkers between the individual components of the MHC I complex. This could be a complex consisting of a heavy chain fused with p2m through a linker and a soluble peptide, a heavy chain fused to p2m through a linker, a heavy chain/p2m dimer covalently linked to a peptide through a linker to either heavy chain or p2m, and where there can or cannot be a linker between the heavy chain and p2m, a heavy chain fused to a peptide through a linker, or the a1 and a2 subunits of the heavy chain fused to a peptide through a linker. In all of these example protein-fusions, each of the heavy chain, p2m and the peptide can be truncated.

The linker could be a flexible linker, e.g. made of glycine and serine and e.g. between 5-20 residues long. The linker could also be rigid with a defined structure, e.g. made of amino acids like glutamate, alanine, lysine, and leucine creating e.g. a more rigid structure.

In heavy chain-p2m fusion proteins the COOH terminus of p2m can be covalently linked to the NH2 terminus of the heavy chain, or the NH2 terminus of p2m can be linked to the COOH terminus of the heavy chain. The fusion-protein can also comprise a p2m domain, or a truncated p2m domain, inserted into the heavy chain, to form a fusion-protein of the form "heavy chain (first part)-p2m-heavy chain (last part)". Likewise, the fusion-protein can comprise a heavy chain domain, or a truncated heavy chain, inserted into the p2m chain, to form a fusion-protein of the form "P2m(first part)-heavy chain-p2m(last part)".

In peptide-p2m fusion proteins the COOH terminus of the peptide is preferable linked to the NH2 terminus of p2m but the peptide can also be linked to the COOH terminal of p2m via its NH2 terminus. In heavy chain-peptide fusion proteins it is preferred to fuse the NH2 terminus of the heavy chain to the COOH terminus of the peptide, but the fusion can also be between the COOH terminus of the heavy chain and the NH2 terminus of the peptide. In heavy chain-p2m-peptide fusion proteins the NH2 terminus of the heavy chain can be fused to the COOH terminus of p2m and the NH2 terminus of p2m can be fused to the COOH terminus of the peptide.

Non-Covalent Stabilization by Binding to an Unnatural Component

Non-covalent binding of unnatural components to the MHC I complexes can lead to increased stability. The unnatural component can bind to both the heavy chain and the p2m, and in this way promote the assemble of the complex, and/or stabilize the formed complex. Alternatively, the unnatural component can bind to either p2m or heavy chain, and in this way stabilize the polypeptide in its correct conformation, and in this way increase the affinity of the heavy chain for p2m and/or peptide, or increase the affinity of p2m for peptide.

Here, unnatural components mean antibodies, peptides, aptamers or any other molecule with the ability to bind peptides stretches of the MHC complex. Antibody is here to be understood as truncated or full-length antibodies (of isotype IgG, IgM, IgA, IgE), Fab, scFv or bi-Fab fragments or diabodies.

An example of special interest is an antibody binding the MHC I molecule by interaction with the heavy chain as well as p2m. The antibody can be a bispecific antibody that binds with one arm to the heavy chain and the other arm to the p2m of the MHC complex. Alternatively the antibody can be monospecific, and bind at the interface between heavy chain and p2m.

Another example of special interest is an antibody binding the heavy chain but only when the heavy chain is correct folded. Correct folded is here a conformation where the MHC complex is able to bind and present peptide in such a way that a restricted T cell can recognize the MHC-peptide complex and be activated. This type of antibody can be an antibody like the one produced by the clone W6/32 (M0736 from Dako, Denmark) that recognizes a conformational epitope on intact human and some monkey MHC complexes containing p2m, heavy chain and peptide.

Generation of Modified Proteins or Protein Components

One way to improve stability of a MHC I complex am to increase the affinity of the binding peptide for the MHC complex. This can be done by mutation/substitution of amino acids at relevant positions in the peptide, by chemical modifications of amino acids at relevant positions in the peptide or introduction by synthesis of non-natural amino acids at relevant positions in the peptide. Alternatively, mutations, chemical modifications, insertion of natural or non-natural amino acids or deletions could be introduced in the peptide binding cleft, i.e. in the binding pockets that accommodate peptide side chains responsible for anchoring the peptide to the peptide binding cleft. Moreover, reactive groups can be introduced into the antigenic peptide; before, during or upon binding of the peptide, the reactive groups can react with amino acid residues of the peptide binding cleft, thus covalently linking the peptide to the binding pocket.

Mutations/substitutions, chemical modifications, insertion of natural or non-natural amino acids or deletions could also be introduced in the heavy chain and/or p2m at positions outside the peptide-binding cleft. By example, it has been shown that substitution of XX with YY in position nn of human b2Gh enhance the biochemical stability of MHC Class I molecule complexes and thus may lead to more efficient antigen presentation of subdominant peptide epitopes.

Some embodiments include removal of “unwanted cysteine residues” in the heavy chain by mutation, chemical modification, amino acid exchange or deletion.

“Unwanted cysteine residues” is here to be understood as cysteines not involved in the correct folding of the final MHC I molecule. The presence of cysteine not directly involved in the formation of correctly folded MHC I molecules can lead to formation of intra molecular disulfide bridges resulting in a non-correct folded MHC complex during in vitro refolding. Another method for covalent stabilization of MHC I complex am to covalently attach a linker between two of the subunits of the MHC complex. This can be a linker between peptide and heavy chain or between heavy chain and beta2microglobulin.

Other Stabilization of MHC I Complexes

Stabilization with Soluble Additives

The stability of proteins in aqueous solution depends on the composition of the solution. Addition of salts, detergents organic solvent, polymers etc. can influence the stability. Salts, detergents, organic solvent, polymers and any other soluble additives can be added to increase the stability of MHC complexes. Of special interest are additives that increase surface tension of the MHC molecule without binding the molecule. Examples are sucrose, mannose, glycine, betaine, alanine, glutamine, glutamic acid and ammoniumsulfate. Glycerol, mannitol and sorbitol are also included in this group even though they are able to bind polar regions.

Another group of additives of special interest are able to increase surface tension of the MHC molecule and simultaneously interact with charged groups in the protein. Examples are MgSCL, NaCl, polyethylenglycol, 2-methyl-2,4-pentandiol and guanidiniumsulfate.

Correct formation of MHC complexes is dependent on binding of peptide in the peptide-binding cleft; the bound peptide appears to stabilize the complex in its correct conformation. Addition of molar excess of peptide will force the equilibrium towards correctly folded MHC-peptide complexes. Likewise is excess p2m also expected to drive the folding process in direction of correct folded MHC I complexes. Therefore peptide identical to the peptide bound in the peptide-binding cleft and/or p2m are included as stabilizing soluble additives.

Other additives of special interest for stabilization of MHC II molecules are BSA, fetal and bovine calf serum or individual protein components in serum with a protein stabilizing effect.

All of the above mentioned soluble additives can be added to any solution containing MHC complexes in order to increase the stability of the molecule. This can be during the refolding process, to the formed MHC complex, to the soluble MHC monomer, to a solution of MHC multimers comprising one or more MHC complexes or to solutions used during analysis of MHC specific T cells with MHC multimers.

Other additives of special interest for stabilization of MHC molecules are BSA, fetal and bovine calf serum or individual protein components in serum with a protein stabilizing effect.

Chemically Modified MHC I Complexes

There are a number of amino acids that are reactive towards chemical cross linkers. In the following, chemical reactions are described that are advantageous for the cross-linking or modification of MHC I complexes.

The amino group at the N-terminal of both chains and of the peptide, as well as amino groups of lysine side chains, are nucleophilic and can be used in a number of chemical reactions, including nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions. Example reagents that can be used in a reaction with the amino groups are activated carboxylic acids such as NETS-ester, tetra and pentafluoro phenolic esters, anhydrides, acid chlorides and fluorides, to form stable amide bonds. Likewise, sulphonyl chlorides can react with these amino groups to form stable sulphone-amides. Iso-Cyanates can also react with amino groups to form stable ureas, and isothiocyanates can be used to introduce thio urea linkages.

Aldehydes, such as formaldehyde and glutardialdehyde will react with amino groups to form shiffs bases, than can be further reduced to secondary amines.

The guanidino group on the side chain of arginine will undergo similar reactions with the same type of reagents. Another very useful amino acid is cysteine. The thiol on the side chain is readily alkylated by maleimides, vinyl sulphones and halides to form stable thioethers, and reaction with other thiols will give rise to disulphides.

Carboxylic acids at the C-terminal of both chains and peptide, as well as on the side chains of glutamic and aspartic acid, can also be used to introduce cross-links. They will require activation with reagents such as carbodiimides, and can then react with amino groups to give stable amides.

Thus, a large number of chemistries can be employed to form covalent cross-links. The crucial point is that the chemical reagents are bi-functional, being capable of reacting with two amino acid residues.

They can be either homo bi-functional, possessing two identical reactive moieties, such as glutardialdehyde or can be hetero bi-functional with two different reactive moieties, such as GMBS (MaleimidoButyryloxy-Succinimide ester).

Alternatively, two or more reagents can be used; i.e. GMBS can be used to introduce maleimides on the a-chain, and iminothiolane can be used to introduce thiols on the b-chain; the malemide and thiol can then form a thioether link between the two chains.

In some embodiments the methods and compositions disclosed herein, some types of cross-links are particularly useful. The folded MHC-complex can be reacted with dextrans possessing a large number (up to many hundreds) of vinyl sulphones. These can react with lysine residues on both the a and b chains as well as with lysine residues on the peptide protruding from the binding site, effectively cross linking the entire MHC-complex. Such cross linking is indeed a favored reaction because as the first lysine residue reacts with the dextran, the MHC-complex becomes anchored to the dextran favoring further reactions between the MHC complex and the dextran multimerization domain. Another great advantage of this dextran chemistry is that it can be combined with fluorochrome labelling; i.e. the dextran is reacted both with one or several MHC-complexes and one or more fluorescent protein such as APC.

Another valuable approach is to combine the molecular biological tools described above with chemical cross linkers. As an example, one or more lysine residues can be inserted into the a-chain, juxtaposed with glutamic acids in the b-chain, where after the introduced amino groups and carboxylic acids are reacted by addition of carbodiimide. Such reactions are usually not very effective in water, unless as in this case, the groups are well positioned towards reaction. This implies that one avoids excessive reactions that could otherwise end up denaturing or changing the conformation of the MHC-complex.

Likewise a dextran multimerization domain can be cross-linked with appropriately modified MHC-complexes; i.e. one or both chains of the MHC complex can be enriched with lysine residues, increasing reactivity towards the vinylsulphone dextran. The lysine's can be inserted at positions opposite the peptide binding cleft, orienting the MHC-complexes favorably for T-cell recognition.

Another valuable chemical tool is to use extended and flexible cross-linkers. An extended linker will allow the two chains to interact with little or no strain resulting from the linker that connects them, while keeping the chains in the vicinity of each other should the complex dissociate. An excess of peptide should further favour reformation of dissociated MHC-complex.

Multimerization Domain

A number of MHC complexes associate with a multimerization domain to form a MHC multimer. The size of the multimerization domain spans a wide range, from multimerization domains based on small organic molecule scaffolds to large multimers based on a cellular structure or solid support. The multimerization domain may thus be based on different types of carriers or scaffolds, and likewise, the attachment of MHC complexes to the multimerization domain may involve covalent or non-covalent linkers. Characteristics of different kinds of multimerization domains are described below.

Molecular Weight of Multimerization Domain

In some embodiments, the multimerization domain(s) is less than 1,000 Da (small molecule scaffold). Examples include short peptides (e.g. comprising 10 amino acids), and various small molecule scaffolds (e.g. aromatic ring structures).

In some embodiments, the multimerization domain(s) is between 1,000 Da and 10,000 Da (small molecule scaffold, small peptides, small polymers). Examples include polycyclic structures of both aliphatic and aromatic compounds, peptides comprising e.g. 10-100 amino acids, and other polymers such as dextran, polyethylenglycol, and polyureas. In some embodiments, the multimerization domain(s) is between 10,000 Da and 100,000 Da (Small molecule scaffold, polymers e.g. dextran, streptavidin, IgG, pentamer structure). Examples include proteins and large polypeptides, small molecule scaffolds such as steroids, dextran, dimeric streptavidin, and multi-subunit proteins such as used in Pentamers. In some embodiments, the multimerization domain(s) is between 100,000 Da and 1,000,000 Da (Small molecule scaffold, polymers e.g. dextran, streptavidin, IgG, pentamer structure). Typical examples include larger polymers such as dextran (used in e.g. Dextramers), and streptavidin tetramers. In some embodiments, the multimerization domain(s) is larger than 1,000,000 Da (Small molecule scaffold, polymers e.g. dextran, streptavidin, IgG, pentamer structure, cells, liposomes, artificial lipid bilayers, polystyrene beads and other beads. Most examples of this size involve cells or cell-based structures such as micelles and liposomes, as well as beads and other solid supports.

As disclosed herein, multimerization domains can comprise carrier molecules, scaffolds or combinations of the two.

Type of Multimerization Domain

In principle any kind of carrier or scaffold can be used as multimerization domain, including any kind of cell, polymer, protein or other molecular structure, or particles and solid supports. Below different types and specific examples of multimerization domains are listed.

Cell. Cells can be used as carriers. Cells can be either alive and mitotic active, alive and mitotic inactive as a result of irradiation or chemically treatment, or the cells may be dead. The MHC expression may be natural (i.e. not stimulated) or may be induced/stimulated by e.g. Inf-y. Of special interest are natural antigen presenting cells (APCs) such as dendritic cells, macrophages, Kupfer cells, Langerhans cells, B-cells and any MHC expressing cell either naturally expressing, being transfected or being a hybridoma. Cell-like structures. Cell-like carriers include membrane-based structures carrying MHC-peptide complexes in their membranes such as micelles, liposomes, and other structures of membranes, and phages such as filamentous phages.

Solid support. Solid support includes beads, particulate matters and other surfaces. Some embodiments include beads (magnetic or non-magnetic beads) that carry electrophilic groups e.g. divinyl sulfone activated polysaccharide, polystyrene beads that have been functionalized with tosyl-activated esters, magnetic polystyrene beads functionalized with tosyl-activated esters), and where MHC complexes may be covalently immobilized to these by reaction of nucleophiles comprised within the MHC complex with the electrophiles of the beads. Beads may be made of sepharose, sephacryl, polystyrene, agarose, polysaccharide, polycarbamate or any other kind of beads that can be suspended in aqueous buffer.

Some embodiments include surfaces, i.e. solid supports and particles carrying immobilized MHC complexes on the surface. Of special interest are wells of a microtiter plate or other plate formats, reagent tubes, glass slides or other supports for use in microarray analysis, tubings or channels of micro fluidic chambers or devices, Biacore chips and beads Molecule. Multimerization domains may also be molecules or complexes of molecules held together by non-covalent bonds. The molecules constituting the multimerization domain can be small organic molecules or large polymers, and may be flexible linear molecules or rigid, globular structures such as e.g. proteins. Different kinds of molecules used in multimerization domains are described below.

Small organic molecules. Small organic molecules here includes steroids, peptides, linear or cyclic structures, and aromatic or aliphatic structures, and many others. The prototypical small organic scaffold is a functionalized benzene ring, i.e. a benzene ring functionalized with a number of reactive groups such as amines, to which a number of MHC molecules may be covalently linked. However, the types of reactive groups constituting the linker connecting the MHC complex and the multimerization domain, as well as the type of scaffold structure, can be chosen from a long list of chemical structures. A non-comprehensive list of scaffold structures are listed below.

Typical scaffolds include aromatic structures, benzodiazepines, hydantoins, piperazines, indoles, furans, thiazoles, steroids, diketopiperazines, morpholines, tropanes, coumarines, qinolines, pyrroles, oxazoles, amino acid precursors, cyclic or aromatic ring structures, and many others. Typical carriers include linear and branched polymers such as peptides, polysaccharides, nucleic acids, and many others. Multimerization domains based on small organic or polymer molecules thus include a wealth of different structures, including small compact molecules, linear structures, polymers, polypeptides, polyureas, polycarbamates, cyclic structures, natural compound derivatives, alpha-, beta-, gamma-, and omega-peptides, mono-, di- and tri-substituted peptides, L- and D-form peptides, cyclohexane- and cyclopentane-backbone modified beta-peptides, vinylogous polypeptides, glycopolypeptides, polyamides, vinylogous sulfonamide peptide, Polysulfonamide-conjugated peptide (i.e., having prosthetic groups), Polyesters, Polysaccharides such as dextran and aminodextran, polycarbamates, polycarbonates, polyureas, poly-peptidylphosphonates, Azatides, peptoids (oligo N-substituted glycines), Polyethers, ethoxyformacetal oligomers, poly-thioethers, polyethylene, glycols (PEG), polyethylenes, polydisulfides, polyarylene sulfides, Polynucleotides, PNAs, LNAs, Morpholinos, oligo pyrrolinone, polyoximes, Polyimines, Polyethyleneimine, Polyacetates, Polystyrenes, Polyacetylene, Polyvinyl, Lipids, Phospholipids, Glycolipids, polycycles, (aliphatic), polycycles (aromatic), polyheterocycles, Proteoglycan, Polysiloxanes, Polyisocyanides, Polyisocyanates, polymethacrylates, Monofunctional, Difunctional, Trifunctional and Oligofunctional open-chain by drocarbons, Monofunctional, Difunctional, Trifunctional and Oligofunctional Nonaromat Carbocycles, Monocyclic, Bicyclic, Tricyclic and Polycyclic Hydrocarbons, Bridged Polycyclic Hydrocarbones, Monofunctional, Difunctional, Trifunctional and Oligofunctional Nonaromatic, Heterocycles, Monocyclic, Bicyclic, Tricyclic and Polycyclic Heterocycles, bridged Polycyclic Heterocycles, Monofunctional, Difunctional, Trifunctional and Oligofunctional Aromatic Carbo cycles, Monocyclic, Bicyclic, Tricyclic and Polycyclic Aromatic Carbocycles, Monofunctional, Difunctional, Trifunctional and Oligofunctional Aromatic Hetero cycles. Monocyclic, Bicyclic, Tricyclic and Polycyclic Heterocycles. Chelates, fullerenes, and any combination of the above and many others.

Biological polymers. Biological molecules here include peptides, proteins (including antibodies, coiled-coil helices, streptavidin and many others), nucleic acids such as DNA and RNA, and polysaccharides such as dextran. The biological polymers may be reacted with MHC complexes (e.g. a number of MHC complexes chemically coupled to e.g. the amino groups of a protein), or may be linked through e.g. DNA duplex formation between a carrier DNA molecule and a number of DNA oligonucleotides each coupled to a MHC complex. Another type of multimerization domain based on a biological polymer is the streptavidin-based tetramer, where a streptavidin binds up to four biotinylated MHC complexes, as described above.

Self-assembling multimeric structures. Several examples of commercial MHC multimers exist where the multimer is formed through self-assembling. Thus, the Pentamers are formed through formation of a coiled-coil structure that holds together 5 MHC complexes in an apparently planar structure. In a similar way, the Streptamers are based on the Streptactin protein which oligomerizes to form a MHC multimer comprising several MHC complexes.

In the following, alternative ways to make MHC multimers based on a molecule multimerization domain are described. They involve one or more of the above-mentioned types of multimerization domains.

MHC dextramers can be made by coupling MHC complexes to dextran via a streptavidin-biotin interaction. In principle, biotin-streptavidin can be replaced by any dimerization domain, where one half of the dimerization domain is coupled to the MHC-peptide complex and the other half is coupled to dextran. For example, an acidic helix (one half of a coiled-coil dimer) is coupled or fused to MHC, and a basic helix (other half of a coiled-coil dimmer) is coupled to dextran. Mixing the two results in MHC binding to dextran by forming the acid/base coiled-coil structure.

Antibodies can be used as scaffolds by using their capacity to bind to a carefully selected antigen found naturally or added as a tag to a part of the MHC molecule not involved in peptide binding. For example, IgG and IgE will be able to bind two MHC molecules, IgM having a pentameric structure will be able to bind 10 MHC molecules. The antibodies can be full-length or truncated; a standard antibody-fragment includes the Fab2 fragment.

Peptides involved in coiled-coil structures can act as scaffold by making stable dimeric, trimeric, tetrameric and pentameric interactions. Examples hereof are the Fos-Jun heterodimeric coiled coil, the *E. coli* homo-trimeric coiled-coil domain Lpp-56, the engineered Trp-zipper protein forming a discrete, stable, a-helical pentamer in water at physiological pH.

Further examples of suitable scaffolds, carriers and linkers are streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase), glutathione, Calmodulin-binding peptide (CBP), Strep-tag, Cellulose Binding Domain, Maltose Binding Protein, S-Peptide Tag, Chitin Binding Tag, Immunoreactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. Non limiting examples are streptavidin-biotin and jun-fos. In particular, when the MHC molecule is tagged, the binding entity may be an "anti-tag". By "anti-tag" is meant an antibody binding to the tag, or any other molecule capable of binding to such tag.

MHC complexes can be multimerized by other means than coupling or binding to a multimerization domain. Thus, the multimerization domain may be formed during the multimerization of MHCs. One such method is to extend the bound antigenic peptide with dimerization domains. One end of the antigenic peptide is extended with dimerization domain A (e.g. acidic helix, half of a coiled-coil dimer) and the other end is extended with dimerization domain B (e.g. basic helix, other half of a coiled-coil dimer). When MHC complexes are loaded/mixed with these extended peptides the following multimer structure will be formed: A-MHC-BA-MHC-BA-MHC-B etc. The antigenic peptides in the mixture can either be identical or a mixture of peptides with comparable extended dimerization domains. Alternatively both ends of a peptide are extended with the same dimerization domain A and another peptide (same amino acid sequence or a different amino acid sequence) is extended with dimerization domain B. When MHC and peptides are mixed the following structures are formed: A-MHC-AB-MHC-BA-MHC-AB-MHC-B etc. Multimerization of MHC complexes by extension of peptides are restricted to MHC II molecules since the peptide binding groove of MHC I molecules is typically closed in both ends thereby limiting the size of peptide that can be embedded in the groove, and therefore preventing the peptide from extending out of the groove.

Another multimerization approach applicable to MHC complexes is based on extension of the N- and/or C-terminal of the MHC complex. For example the N-terminus of the MHC complex is extended with dimerization domain A and the C-terminus is extended with dimerization domain B. When MHC complexes are incubated together they pair with each other and form multimers like: A-MHC-BA-MHC-BA-MHC-BA-MHC-B etc. Alternatively the N-terminus and the C-terminus of a MHC complex are both extended with dimerization domain A and the N-terminal and C-terminal of another preparation of MHC complex (either the same or a different MHC) are extended with dimerization domain B. When these two types of MHC complexes are incubated together multimers will be formed: A-MHC-AB-MHC-BA-MHC-AB-MHC-B etc.

In all the above-described examples the extension can be either chemically coupled to the peptide/MHC complex or introduced as extension by gene fusion.

Dimerization domain AB can be any molecule pair able to bind to each other, such as acid/base coiled-coil helices, antibody-antigen, DNA-DNA, PNA-PNA, DNA-PNA, DNA-RNA, LNA-DNA, leucine zipper e.g. Fos/Jun, streptavidin-biotin and other molecule pairs as described elsewhere herein.

Linker Molecules

A number of MHC complexes associate with a multimerization domain to form a MHC multimer. The attachment of MHC complexes to the multimerization domain may involve covalent or non-covalent linkers, and may involve small reactive groups as well as large protein-protein interactions.

The coupling of multimerization domains and MHC complexes involve the association of an entity X (attached to or part of the multimerization domain) and an entity Y (attached to or part of the MHC complex). Thus, the linker that connects the multimerization domain and the MHC complex comprises an XY portion.

Covalent linker. The XY linkage can be covalent, in which case X and Y are reactive groups. In this case, X can be a nucleophilic group (such as —$NH_2$, —OH, —SH, —NH—$NH_2$), and Y an electrophilic group (such as CHO, COOH, CO) that react to form a covalent bond XY; or Y can be a nucleophilic group and X an electrophilic group that react to form a covalent bond XY. Other possibilities exist, e.g either of the reactive groups can be a radical, capable of reacting with the other reactive group. A number of reactive groups X and Y, and the bonds that are formed upon reaction of X and Y, are shown in FIG. 5 of WO 2009/106073.

X and Y can be reactive groups naturally comprised within the multimerization domain and/or the MEW complex, or they can be artificially added reactive groups. Thus, linkers containing reactive groups can be linked to either of the multimerization domain and MHC complex; subsequently the introduced reactive group(s) can be used to covalently link the multimerization domain and MHC complex.

Example natural reactive groups of MEW complexes include amino acid side chains comprising —$NH_2$, —OH, —SH, and —NH—. Example natural reactive groups of multimerization domains include hydroxyls of polysaccharides such as dextrans, but also include amino acid side chains comprising —$NH_2$, —OH, —SH, and —NH— of polypeptides, when the polypeptide is used as a multimerization domain. In some MHC multimers, one of the polypeptides of the MHC complex (i.e. the b2M, heavy chain or the antigenic peptide) is linked by a protein fusion to the multimerization domain. Thus, during the translation of the fusion protein, an acyl group (reactive group X or Y) and an amino group (reactive group Y or X) react to form an amide bond. Example MHC multimers where the bond between the multimerization domain and the MHC complex is covalent and results from reaction between natural reactive groups, include MHC-pentamers (described in US20040209295) and MHC-dimers, where the linkage between multimerization domain and MEW complex is in both cases generated during the translation of the fusion protein.

Example artificial reactive groups include reactive groups that are attached to the multimerization domain or MEW complex, through association of a linker molecule comprising the reactive group. The activation of dextran by reaction of the dextran hydroxyls with divinyl sulfone, introduces a reactive vinyl group that can react with e.g. amines of the MHC complex, to form an amine that now links the multimerization domain (the dextran polymer) and the MEW complex. An alternative activation of the dextran multimerization domain involves a multistep reaction that results in the decoration of the dextran with maleimide groups, as described in U.S. Pat. No. 6,387,622. In this approach, the amino groups of MEW complexes are converted to —SH groups, capable of reacting with the maleimide groups of the activated dextran. Thus, in the latter example, both the reactive group of the multimerization domain (the maleimide) and the reactive group of the MEW complex (the thiol) are artificially introduced.

Sometimes activating reagents are used in order to make the reactive groups more reactive. For example, acids such as glutamate or aspartate can be converted to activated esters by addition of e.g. carbodiimid and NHS or nitrophenol, or by converting the acid moiety to a tosyl-activated ester. The activated ester reacts efficiently with a nucleophile such as —SH, —OH, etc.

In some embodiments, the multimerization domains (including small organic scaffold molecules, proteins, protein complexes, polymers, beads, liposomes, micelles, cells) that form a covalent bond with the MHC complexes can be divided into separate groups, depending on the nature of the reactive group that the multimerization domain contains. One group comprise multimerization domains that carry nucleophilic groups (e.g. $—NH_2$, —OH, —SH, —CN, $—NH—NH_2$), exemplified by polysaccharides, polypeptides containing e.g. lysine, serine, and cysteine; another group of multimerization domains carry electrophilic groups (e.g. —COOH, —CHO, —CO, NHS-ester, tosyl-activated ester, and other activated esters, acid-anhydrides), exemplified by polypeptides containing e.g. glutamate and aspartate, or vinyl sulfone activated dextran; yet another group of multimerization domains carry radicals or conjugated double bonds.

The multimerization domains appropriate for this disclosure thus include those that contain any of the reactive groups shown in FIG. 5 of WO 2009/106073 or that can react with other reactive groups to form the bonds shown in FIG. 5 of WO 2009/106073.

Likewise, MHC complexes can be divided into separate groups, depending on the nature of the reactive group comprised within the MHC complex. One group comprise MHCs that carry nucleophilic groups (e.g. $—NH_2$, —OH, —SH, —CN, $—NH— NH_2$), e.g. lysine, serine, and cysteine; another group of MHCs carry electrophilic groups (e.g. —COOH, —CHO, —CO, NETS-ester, tosyl-activated ester, and other activated esters, acid-anhydrides), exemplified by e.g. glutamate and aspartate; yet another group of MHCs carry radicals or conjugated double bonds.

The reactive groups of the MHC complex are either carried by the amino acids of the MHC-peptide complex (and may be comprised by any of the peptides of the MHC-peptide complex, including the antigenic peptide), or alternatively, the reactive group of the MHC complex has been introduced by covalent or non-covalent attachment of a molecule containing the appropriate reactive group.

Preferred reactive groups in this regard include —CSO2OH, phenylchloride, —SH, —SS, aldehydes, hydroxyls, isocyanate, thiols, amines, esters, thioesters, carboxylic acids, triple bonds, double bonds, ethers, acid chlorides, phosphates, imidazoles, halogenated aromatic rings, any precursors thereof, or any protected reactive groups, and many others. Example pairs of reactive groups, and the resulting bonds formed, are shown in FIG. 5 of WO 2009/106073.

Reactions that may be employed include acylation (formation of amide, pyrazolone, isoxazolone, pyrimidine, comarine, quinolinon, phthalhydrazide, diketopiperazine, benzodiazepinone, and hydantoin), alkylation, vinylation, disulfide formation, Wittig reaction, Horner-Wittig-Emmans reaction, arylation (formation of biaryl or vinylarene), condensation reactions, cycloadditions ((2+4), (3+2)), addition to carbon-carbon multiplebonds, cycloaddition to multiple bonds, addition to carbon-hetero multiple bonds, nucleophilic aromatic substitution, transition metal catalyzed reactions, and may involve formation of ethers, thioethers, secondary amines, tertiary amines, beta-hydroxy ethers, beta-hydroxy thioethers, beta-hydroxy amines, beta-amino ethers, amides, thioamides, oximes, sulfonamides, di- and tri functional compounds, substituted aromatic compounds, vinyl substituted aromatic compounds, alkyn substituted aromatic compounds, biaryl compounds, hydrazines, hydroxylamine ethers, substituted cycloalkenes, substituted cyclodienes, substituted 1, 2, 3 triazoles, substituted cycloalkenes, beta-hydroxy ketones, beta-hydroxy aldehydes, vinyl ketones, vinyl aldehydes, substituted alkenes, substituted alkenes, substituted amines, and many others.

MHC dextramers can be made by covalent coupling of MHC complexes to the dextran backbone, e.g. by chemical coupling of MHC complexes to dextran backbones. The MHC complexes can be coupled through either heavy chain or b2-microglobulin if the MHC complexes are MHC I or through a-chain or p-chain if the MHC complexes are MHC II. MHC complexes can be coupled as folded complexes comprising heavy chain/beta2microglobulin or a-chain/p-chain or either combination together with peptide in the peptide-binding cleft. Alternatively either of the protein chains can be coupled to dextran and then folded in vitro together with the other chain of the MHC complex not coupled to dextran and together with peptide. Direct coupling of MHC complexes to dextran multimerization domain can be via an amino group or via a sulphide group. Either group can be a natural component of the MHC complex or attached to the MHC complex chemically. Alternatively, a cysteine may be introduced into the genes of either chain of the MHC complex.

Another way to covalently link MHC complexes to dextran multimerization domains is to use the antigenic peptide as a linker between MHC and dextran. Linker containing antigenic peptide at one end is coupled to dextran. Antigenic peptide here means a peptide able to bind MHC complexes in the peptide-binding cleft. As an example, 10 or more antigenic peptides may be coupled to one dextran molecule. When MHC complexes are added to such peptide-dextran construct the MHC complexes will bind the antigenic peptides and thereby MHC-peptide complexes are displayed around the dextran multimerization domain. The antigenic peptides can be identical or different from each other. Similarly MHC complexes can be either identical or different from each other as long as they are capable of binding one or more of the peptides on the dextran multimerization domain.

Non-covalent linker. The linker that connects the multimerization domain and the MHC complex comprises an XY portion. Above different kinds of covalent linkages XY were described. However, the XY linkage can also be non-covalent.

Non-covalent XY linkages can comprise natural dimerization pairs such as antigen-antibody pairs, DNA-DNA interactions, or can include natural interactions between small molecules and proteins, e.g. between biotin and streptavidin. Artificial XY examples include XY pairs such as $HiS_6$ tag (X) interacting with Ni-NTA (Y) and PNA-PNA interactions.

Protein-protein interactions. The non-covalent linker may comprise a complex of two or more polypeptides or proteins, held together by non-covalent interactions. Example polypeptides and proteins belonging to this group include Fos/Jun, Acid/Base coiled coil structure, antibody/antigen (where the antigen is a peptide), and many others.

Some embodiments involve non-covalent interactions between polypeptides and/or proteins are represented by the Pentamer structure described in US 20040209295. Some embodiments involve the use of antibodies, with affinity for the surface of MHC opposite to the peptide-binding groove. Thus, an anti-MHC antibody, with its two binding site, will bind two MHC complexes and in this way generate a bivalent MHC multimer. In addition, the antibody can stabilize the MHC complex through the binding interactions. This is particularly relevant for MHC class II complexes, as these are less stable than class I MHC complexes.

Polynucleotide-polynucleotide interactions. The non-covalent linker may comprise nucleotides that interact non-covalently. Example interactions include PNA/PNA, DNA/DNA, RNA/RNA, LNA/DNA, and any other nucleic acid duplex structure, and any combination of such natural and unnatural polynucleotides such as DNA/PNA, RNA/DNA, and PNA/LNA.

Protein-small molecule interactions. The non-covalent linker may comprise a macromolecule (e.g. protein, polynucleotide) and a small molecule ligand of the macromolecule. The interaction may be natural (i.e., found in Nature, such as the Streptavidin/biotin interaction) or non-natural (e.g. His-tag peptide/Ni-NTA interaction). Example interactions include Streptavidin/biotin and anti-biotin antibody/biotin.

Combinations—non-covalent linker molecules. Other combinations of proteins, polynucleotides, small organic molecules, and other molecules, may be used to link the MHC to the multimerization domain. These other combinations include protein-DNA interactions (e.g. DNA binding protein such as the gene regulatory protein CRP interacting with its DNA recognition sequence), RNA aptamer-protein interactions (e.g. RNA aptamer specific for growth hormone interacting with growth hormone).

Synthetic molecule-synthetic molecule interaction. The non-covalent linker may comprise a complex of two or more organic molecules, held together by non-covalent interactions. Example interactions are two chelate molecules binding to the same metal ion (e.g. EDTA-$Ni^{++}$-NTA), or a short polyhistidine peptide (e.g. $His_6$) bound to NTA-$Ni^{++}$.

In another preferred embodiment the multimerization domain is a bead. The bead is covalently or non-covalently coated with MEW multimers or single MEW complexes, through non-cleavable or cleavable linkers. As an example, the bead can be coated with streptavidin monomers, which in turn are associated with biotinylated MEW complexes; or the bead can be coated with streptavidin tetramers, each of which are associated with 0, 1, 2, 3, or 4 biotinylated MHC complexes; or the bead can be coated with MHC-dextramers where e.g. the reactive groups of the MHC-dextramer (e.g. the divinyl sulfone-activated dextran backbone) has reacted with nucleophilic groups on the bead, to form a covalent linkage between the dextran of the dextramer and the beads.

Figure 6:
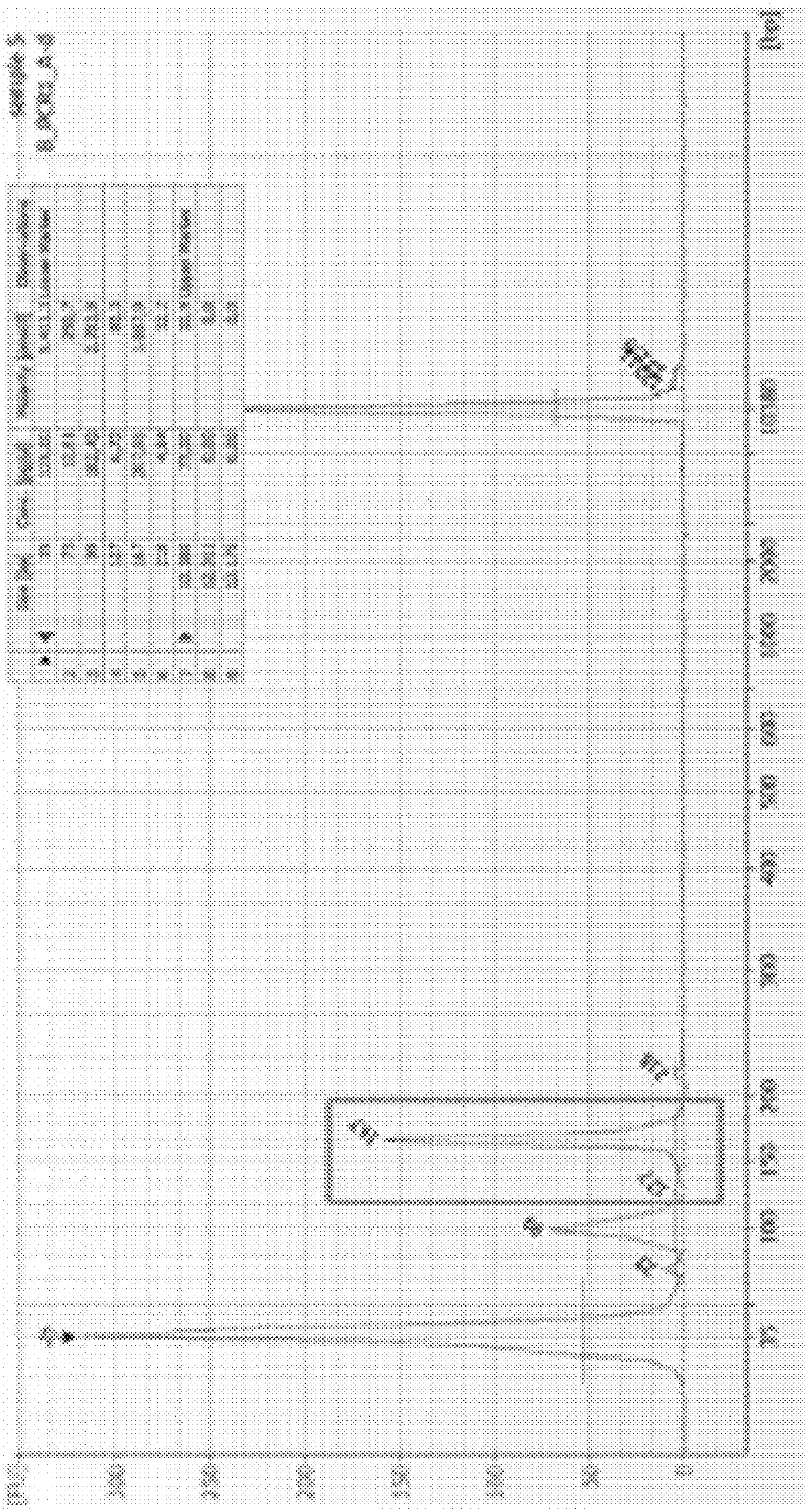
FIG. 6 depicts a non-limiting exemplary Bioanalyzer trace containing both the dCODE® and AbSeq™ library PCR amplicons (approximately 170 bp).

In some embodiments, the MEW multimers described above (e.g. where the multimerization domain is a bead) further contains a flexible or rigid, and water soluble, linker that allows for the immobilized MHC complexes to interact efficiently with cells, such as T-cells with affinity for the MHC complexes. In some embodiments, the linker is cleavable, allowing for release of the MHC complexes from the bead. If T-cells have been immobilized, by binding to the MHC complexes, the T-cells can very gently be released by cleavage of this cleavable linker. Non-limiting cleavable linkers are shown in FIG. 6 of WO 2009/106073. In some embodiments, the linker is advantageously cleaved at physiological conditions, allowing for the integrity of the isolated cells.

Further non-limiting examples of linker molecules include Calmodulin-binding peptide (CBP), 6×HIS, Protein A, Protein G, biotin, Avidin, Streptavidin, Strep-tag, Cellulose Binding Domain, Maltose Binding Protein, S-Peptide Tag, Chitin Binding Tag, Immuno-reactive Epitopes, Epitope Tags, GST tagged proteins, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope. The list of dimerization- and multimerization domains, described elsewhere in this document, define alternative non-covalent linkers between the multimerization domain and the MHC complex.

The abovementioned dimerization- and multimerization domains represent specific binding interactions. Another type of non-covalent interactions involves the non-specific adsorption of e.g. proteins onto surfaces. As an example, the non-covalent adsorption of proteins onto glass beads represents this class of XY interactions. Likewise, the interaction of MHC complexes (comprising full-length polypeptide chains, including the transmembrane portion) with the cell membrane of for example dendritic cells is an example of a non-covalent, primarily non-specific XY interaction.

In some of the abovementioned embodiments, several multimerization domains (e.g. streptavidin tetramers bound to biotinylated MHC complexes) are linked to another multimerization domain (e.g. the bead). For the purpose of this disclosure we shall call both the smaller and the bigger multimerization domain, as well as the combined multimerization domain, for multimerization domain.

Additional Features of MHC Multimer

Additional components may be coupled to carrier or added as individual components not coupled to carrier.

Attachment of Biologically Active Molecules to MHC Multimers

Engagement of MHC complex to the specific T cell receptor leads to a signaling cascade in the T cell. However, T-cells normally respond to a single signal stimulus by going into apoptosis. T cells needs a second signal in order to become activated and start development into a specific activation state e.g. become an active cytotoxic T cell, helper T cell or regulatory T cell.

It is to be understood that a MHC multimer disclosed herein may further comprise one or more additional substituents. The definition of the terms "one or more", "a plurality", "a", "an", and "the" also apply here. Such biologically active molecules may be attached to the construct in order to affect the characteristics of the constructs, e.g. with respect to binding properties, effects, MHC molecule specificities, solubility, stability, or detectability. For instance, spacing could be provided between the MHC complexes, one or both chromophores of a Fluorescence Resonance Energy Transfer (FRET) donor/acceptor pair could be inserted, functional groups could be attached, or groups having a biological activity could be attached.

MHC multimers can be covalently or non-covalently associated with various molecules: having adjuvant effects; being immune targets e.g. antigens; having biological activity e.g. enzymes, regulators of receptor activity, receptor ligands, immune potentiators, drugs, toxins, co-receptors, proteins and peptides in general; sugar moieties; lipid groups; nucleic acids including siRNA; nano particles; small molecules. In the following these molecules are collectively called biologically active molecules. Such molecules can be attached to the MHC multimer using the same principles as those described for attachment of MHC complexes to multimerization domains as described elsewhere herein. In brief, attachment can be done by chemical reactions between reactive groups on the biologically active molecule and reactive groups of the multimerization domain and/or between reactive groups on the biologically active molecule and reactive groups of the MHC-peptide complex. Alternatively, attachment is done by non-covalent interaction between part of the multimerization domain and part of the biological active molecule or between part of the MHC-peptide complex and part of the biological active molecule. In both covalent and non-covalent attachment of the biologically molecule to the multimerization domain a linker molecule can connect the two. The linker molecule can be covalent or non-covalent attached to both molecules. Examples of linker molecules are described elsewhere herein. Some of the HCmer structures better allows these kind of modifications than others.

Biological active molecules can be attached repetitively aiding to recognition by and stimulation of the innate immune system via Toll or other receptors.

In particular, the biologically active molecule may be selected from: (i) proteins such as MEW Class 1-like proteins like MIC A, MIC B, CD1d, HLA E, HLA F, HLA G, HLA H, ULBP-1, ULBP-2, and ULBP-3; (ii) co-stimulatory molecules such as CD2, CD3, CD4, CD5, CD8, CD9, CD27, CD28, CD30, CD69, CD134 (0X40), CD137 (4-1 BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells; (iii) cell modulating molecules such as CD16, NKp30, NKp44, NKp46, NKrdO, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin; (iv) accessory molecules such as LFA-1, CD11a/18, CD54 (ICAM-1), CD106 (VCAM), and CD49a,b,c,d,e,f/CD29 (VLA-4); (v) adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P; (vi) toxic molecules selected from toxins, enzymes, antibodies, radioisotopes, chemiluminescent substances, bioluminescent substances, polymers, metal particles, and haptens, such as cyclophosphamide, methrotrexate, Azathioprine, mizoribine, 15-deoxuspergualin, neomycin, staurosporine, genestein, herbimycin A, Pseudomonas exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin; and combinations of any of the foregoing, as well as antibodies (monoclonal, polyclonal, and recombinant) to the foregoing, where relevant. Antibody derivatives or fragments thereof may also be used.

Methods Involving Panels of MHC Multimers

Some embodiments relating to determining binding of MHC multimers provided in panels as defined herein with MHC-peptide recognizing cells in a sample, such as a sample suspected of comprising MHC-peptide recognizing cells.

As used everywhere herein, the term "MHC-peptide recognizing cells" are intended to mean cells which are able to recognize and bind to MHC multimers. The intended meaning of "MHC multimers" is given above. MHC-peptide recognizing cells may also be called MHC-peptide recognizing cell clones, target cells, target MHC-peptide recognizing cells, target MHC molecule recognizing cells, MHC molecule receptors, MHC receptors, MHC peptide specific receptors, or peptide-specific cells. The term "MHC-peptide recognizing cells" is intended to include all subsets of normal, abnormal and defect cells, which recognize and bind to the MHC molecule. Actually, it is the receptor on the MHC-peptide recognizing cell that binds to the MHC molecule.

In diseases and various conditions peptides are displayed by means of MHC multimers, which are recognized by the immune system, and cells targeting such MHC multimers are produced (MHC-peptide recognizing cells). Thus, the presence of such MHC protein recognizing cells is a direct indication of the presence of MHC multimers displaying the peptides recognized by the MHC protein recognizing cells. The peptides displayed are indicative and may be involved in various diseases and conditions.

The MHC multimers disclosed herein have numerous uses and are a valuable and powerful tools e.g. in the fields of therapy, diagnosis, prognosis, monitoring, stratification, and determining the status of diseases or conditions. Thus, the MHC multimers may be applied in the various methods involving the detection of MHC-peptide recognizing cells and in a number of applications, including analyzes such as flow cytometry, immunohistochemistry (IHC), and ELISA-like analyzes.

Detection Principles

Diagnostic procedures, immune monitoring and some therapeutic processes disclosed herein all involve identification and/or enumeration and/or isolation of antigen-specific T cells. Identification and enumeration of antigen-specific T cells may be done in a number of ways, and several assays are currently employed to provide this information.

In the following it is described how MHC multimers and/or antigenic peptides as described herein can be used to detect specific T cell receptors (TCRs) and thereby antigen-specific T cells in a variety of methods and assays. In some embodiments, detection includes detection of the presence of antigen-specific TCR/T cells in a sample, detection of and isolation of cells or entities with antigen-specific TCR from a sample and detection and enrichment of cells or entities with antigen-specific TCR in a sample.

The sample may be a biological sample including solid tissue, solid tissue section and fluid samples such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, synovial fluid, fluid from joints, vitreous fluid, vaginal or urethral secretions, semen, or the like. Herein, disaggregated cellular tissues such as, for example, hair, skin, synovial tissue, tissue biopsies and nail scrapings are also considered as biological samples.

Many of the assays and methods disclosed herein are particularly useful for assaying T-cells in blood samples.

Blood samples includes but is not limited to whole blood samples or blood processed to remove erythrocytes and platelets (e.g., by Ficoll density centrifugation or other such methods known to one of skill in the art) and the remaining PBMC sample, which includes the T-cells of interest, as well as B-cells, macrophages and dendritic cells, is used directly. Also included are blood samples processed in other ways e.g. isolating various subsets of blood cells by selecting or deselecting cells or entities in blood.

In order to be able to detect specific T cells by MHC multimers, labels can be used (e.g., a receptor-binding reagent specific oligonucleotide comprising a unique receptor identifier sequence).

Labelling Molecules

Labelling molecules are molecules that can be detected in a certain analysis, i.e. the labelling molecules provide a signal detectable by the used method. The amount of labelling molecules may In some embodiments, be quantified. In some embodiments, the one or more MHC multimers comprises one or more labels. In some embodiments, the one or more labels comprises the receptor-binding reagent specific oligonucleotide. In some embodiments, the one or more labels comprises the receptor-binding reagent specific oligonucleotide and one or more additional labels, optionally the one or more additional labels is selected from the group comprising a peptide label, a fluorophore label, heavy metal labels, isotope labels, radiolabels, radionuclide, stable isotopes, chains of isotopes and single atoms, a chemiluminescent label, a bioluminescent label, a radioactive label, an enzyme label, a DNA fluorescent stain, a lanthanide, a ionophore, a chelating chemical compound binding to specific ions, or any combination thereof.

The labelling molecule may be any labelling molecule suitable for direct or indirect detection. By the term "direct" is meant that the labelling molecule can be detected per se without the need for a secondary molecule, i.e. is a "primary" labelling molecule. By the term "indirect" is meant that the labelling molecule can be detected by using one or more "secondary" molecules, i.e. the detection is performed by the detection of the binding of the secondary molecule(s) to the primary molecule.

The labelling molecule can be attached to the multimerization domain. In some embodiments, the labelling molecule is attached to the MHC molecule.

The labelling molecule may further be attached via a suitable linker. Linkers suitable for attachment to labelling molecules would be readily known by the person skilled in the art and as described elsewhere herein for attachment of MHC molecules to multimerization domains.

Examples of such suitable labelling compounds are polymers, nucleic acids, oligonucleotides, peptides, fluorescent labels, phosphorescent labels, enzyme labels, chemiluminescent labels, bioluminescent labels, haptens, antibodies, dyes, nanoparticle labels, elements, metal particles, heavy metal labels, isotope labels, radioisotopes, stable isotopes, chains of isotopes and single atoms.

Labels may be organic or inorganic molecules or particles.

Organic molecules labels include ribonucleic acids (e.g. RNA, DNA or unnatural DNA, RNA, and XNA (e.g. PNA, LNA, GNA, TNA) and mononucleotides, peptides and other polyamides (e.g. peptides comprising b-amino acid residues), lipids, carbohydrates, amino acids, and many other molecules.

Inorganic molecule labels include the elements (e.g., Lanthanum, Cerium, Praseodymium, Neodymium, Promethium, Samarium, Europium, Gadolinium, Terbium, Dysprosium, and the rest of the elements known). The elements may be coupled to the linker by way of chelates that coordinate the ions (interact non-covalently with the ions), where the chelates are then linked to the linker (in cases such as Gadolinium where the element can exist on ionic form), or the element may be contained in micelles. For some applications, rare elements are favorable, and for some applications, heavy metals are particularly favorable.

A molecule label may have a molecular weight of between 1 Da and several million Da. In some instances a very low molecular weight can be advantageous, such as a molecular weight of 1-10 Da, 11-50 Da, 50-250 Da, or 251-500 Da. This may for example be the case when mass spectrometry is used to detect the identity of element labels (e.g. Gadolinium, Gd). In other cases a low molecular weight, e.g. 501-2000 Da, 2001-5000 Da, or 5001-10000 Da may be preferred. This may be the case when e.g. peptide labels are used, where the peptide label comprises around 10-40 amino acid residues. In yet other cases, a high molecular weight of the molecule label is practical, and the molecular weight of the molecule label may be 10001-50000 Da, 50001-200000 Da, or 200000-1000000 Da. This may be the case e.g. in cases where a ribonucleic acid label is used, where the coding region (also called the barcode region or barcode sequence) is of significant length (e.g. 10-20 nucleotides) and where it is practical to have flanking primer binding regions of each 10-20 nucleotides, plus other sequences of different practical use. The resulting oligonucleotide label may in these cases be 30-1000 nt long, corresponding to molecular weights of about 10000-600000 Da. Finally, multi molecule structures, such as in cases where a number of different fluorescent proteins are ordered in an array by binding to specific regions in a template DNA, where the total label thus comprises a long oligonucleotide to which is bound a number of proteins, and the total molecular weight of the label may thus be 50000-200000 Da, 200001-100000, or 1000001-10000000 Da.

In some embodiments, the labels are fluorophores and other molecules that emit or absorb radiation. The fluorophores and other molecules emitting or absorbing radiation may be of organic or inorganic nature, and can be e.g. small molecules as well as large proteins. In some embodiments, it is particularly favorable if all the fluorophores and other molecules that emit or absorb radiation are within the same narrow range of emission wavelength optimum, such as having wavelength optima in the range 1-10 nm, 11-30 nm, 31-100 nm, 101-200 nm, 201-300 nm, 301-400 nm, 401-500 nm, 501-600 nm, 601-700 nm, 701-800 nm, 800-900 nm, 901-1200 nm, 1201-1500 nm, or larger than 1500 nm. As an example, if the instrument has a narrow range of wavelengths that can be detected, it is advantageous that all labels fall within this range of detection. On the other hand, if the instrument used to detect the radiation emitted by the labels has a wide span of detectable wavelengths, it is desirable that the different labels used in an experiment fall in several of the above-mentioned ranges, as this will result in little overlap between emission of different labels, and therefore more accurate detection of relative abundance of the different labels of an experiment. Emitted radiation may be phosphorescence, luminescence, fluorescence and more.

The labelling compound may suitably be selected: from fluorescent labels such as 5-(and 6)-carboxyfluorescein, 5- or 6-carboxy-fluorescein, 6-(fluorescein)-5-(and 6)-carboxamido hexanoic acid, fluorescein isothio cyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+, from haptens such as DNP, biotin, and digoxiginin, from enzymatic labels such as horse radish peroxidase (HRP), alkaline phosphatase (AP), beta-galactosidase (GAL), glucose-6-phosphate dehydrogenase, beta-N-acetyl-glucosaminidase, b-glucuronidase, invertase, Xanthine Oxidase, firefly luciferase and glucose oxidase (GO), from luminescence labels such as luminol, isoluminol, acridinium esters, 1,2-dioxetanes and pyridopyridazines, from radioactivity labels such as incorporated isotopes of iodide, cobalt, selenium, tritium, and phosphor, and from single atoms such as zinc (Zn), iron (Fe), magnesium (Mg), any of the lanthanides (Ln) including La, Ce, Pr, Nd, Pm, Sm, Eu, Gd, Tb, Dy, Ho, Er, Tm, Yb and Lu; scandium (Sc) and yttrium (Y).

Radioactive labels may in particular be interesting in connection with labelling of the peptides harbored by the MHC multimers.

Different principles of labelling and detection exist, based on the specific property of the labelling molecule. Examples of different types of labelling are emission of radioactive radiation (radionuclide, isotopes), absorption of light (e.g. dyes, chromophores), emission of light after excitation (fluorescence from fluorochromes), NMR (nuclear magnetic resonance form paramagnetic molecules) and reflection of light (scatter from e.g. such as gold-, plastic- or glass-beads/particles of various sizes and shapes). Alternatively, the labelling molecules can have an enzymatic activity, by which they catalyze a reaction between chemicals in the near environment of the labelling molecules, producing a signal, which include production of light (chemi-luminescence), precipitation of chromophor dyes, or precipitates that can be detected by an additional layer of detection molecules. The enzymatic product can deposit at the location of the enzyme or, in a cell based analysis system, react with the membrane of the cell or diffuse into the cell to which it is attached. Examples of labelling molecules and associated detection principles are shown in Table 3.

TABLE 3

Examples of labelling molecules and associated detection principles

| Labelling substance | Effect | Assay-principle |
|---|---|---|
| Fluorochromes | emission of light having a specific spectra | “Photometry, Microscopy, spectroscopy PMT, photographic film, CCD’s (Color-Capture Device or Charge-coupled device). |
| Radionuclide | irradiation, α, β or gamma rays | Scintillation counting, GM-tube, photographic film, excitation of phosphor-imager screen |
| Enzyme; HRP, (horse reddish peroxidase), peroxidases in general | catalysis of $H_2O_2$ reduction using luminol as Oxygen acceptor, resulting in oxidized luminal + light catalysis of $H_2O_2$ reduction using a soluble dye, or molecule containing a hapten, such as a biotin residue as Oxygen acceptor, resulting in precipitation. The hapten can be recognized by a detection molecule. | “Photometry, Microscopy, spectroscopy PMT, photographic film, CCD’s (Color-Capture Device or Charge-coupled device), Secondary label linked antibody |
| Particles; gold, polystyrene beads, pollen and other particles | Change of scatter, reflection and transparency of the associated entity | Microscopy, cytometry, electron microscopy PMT’s, light detecting devices, flowcytometry scatter |
| AP (Alkaline Phosphatase) | Catalyze a chemical conversion of a non-detectable to a precipitated detectable molecule, such as a dye or a hapten | “Photometry, Microscopy, spectroscopy Secondary label linked antibody |
| Ionophores or chelating chemical compounds binding to specific ions, e.g. $Ca^{2+}$ | Change in absorption and emission spectrums when binding. Change in intensity | “Photometry, Cytometry, spectroscopy |
| Lanthanides | Fluorescence Phosphorescence Paramagnetic | “photometry, cytometry, spectroscopy NMR (Nuclear magnetic resonance) |
| DNA fluorescing stains | Propidium iodide Hoechst stain DAPI AMC DraQ5 ™ Acridine orange 7-AAD | “Photometry, cytometry, spectroscopy |
| Oligonucleotide tag/ identifier | Unique sequence | PCR amplification, sequencing |

Photometry is to be understood as any method that can be applied to detect the intensity, analyze the wavelength spectra, and or measure the accumulation of light derived form a source emitting light of one or multiple wavelength or spectra.

Labelling molecules can be used to label MHC multimers as well as other reagents used together with MHC multimers, e.g. antibodies, aptamers or other proteins or molecules able to bind specific structures in another protein, in sugars, in DNA or in other molecules. In the following molecules able to bind a specific structure in another molecule are named a marker. Labelling molecules can be attached to a given MHC multimer or any other protein marker by covalent linkage as described for attachment of MHC multimers to multimerization domains elsewhere herein. The attachment can be directly between reactive groups in the labelling molecule and reactive groups in the marker molecule or the attachment can be through a linker covalently attached to labelling molecule and marker, both as described elsewhere herein. When labelling MHC multimers the label can be attached either to the MHC complex (heavy chain, p2m or peptide) or to the multimerization domain.

In particular, one or more labelling molecules may be attached to the carrier molecule, or one or more labelling molecules may be attached to one or more of the scaffolds, or one or more labelling compounds may be attached to one or more of the MHC complexes, or one or more labelling compounds may be attached to the carrier molecule and/or one or more of the scaffolds and/or one or more of the MHC complexes, or one or more labelling compounds may be attached to the peptide harbored by the MHC molecule.

A single labelling molecule on a marker does not always generate sufficient signal intensity. The signal intensity can be improved by assembling single label molecules into large multi-labelling compounds, containing two or more label molecule residues. Generation of multi-label compounds can be achieved by covalent or non-covalent, association of labelling molecules with a major structural molecule. Examples of such structures are synthetic or natural polymers (e.g. dextramers), proteins (e.g. streptavidin), or polymers. The labelling molecules in a multi-labelling compound can all be of the same type or can be a mixture of different labelling molecules.

In some applications, it may be advantageous to apply different MHC complexes, either as a combination or in individual steps. Such different MHC multimers can be differently labelled (i.e. by labelling with different labelling compounds) enabling visualization of different target MHC-peptide recognizing cells. Thus, if several different MHC multimers with different labelling compounds are present, it is possible simultaneously to identify more than one specific receptor, if each of the MHC multimers presents a different peptide.

Detection principles can be applied to flow cytometry, stationary cytometry, and batch-based analysis. Most batch-based approaches can use any of the labelling substances depending on the purpose of the assay. Flow cytometry primarily employs fluorescence, whereas stationary cytometry primarily employs light absorption, e.g. dyes or chromophore deposit from enzymatic activity. In the following section, principles involving fluorescence detection will be exemplified for flow cytometry, and principles involving chromophore detection will be exemplified in the context of stationary cytometry. However, the labelling molecules can be applied to any of the analyzes described in this disclosure.

Labelling Molecules of Particular Utility in Flow Cytometry

In flow cytometry the typical label is detected by its fluorescence. Most often a positive detection is based on the presents of light from a single fluorochrome, but in other techniques the signal is detected by a shift in wavelength of emitted light; as in FRET based techniques, where the exited fluorochrome transfer its energy to an adjacent bound fluorochrome that emits light, or when using $Ca^{2+}$ chelating fluorescent props, which change the emission (and absorption) spectra upon binding to calcium.

Some non-limiting labelling molecules employed in flow cytometry are illustrated in Tables 4-5 and described in the following.

Fluorescent labels can be selected from one or more of the following: (i) Fluor dyes, Pacific Blue™, Pacific Orange™, Cascade Yellow™; (ii) AlexaFluor® (AF), e.g., AF405, AF488.AF500, AF514, AF532, AF546, AF555, AF568, AF594, AF610, AF633, AF635, AF647, AF680, AF700, AF710, AF750, AF800; (iii) Quantum Dot based dyes, QDot® Nanocrystals (Invitrogen, MolecularProbs), e.g., Qdot®525, Qdot®565, Qdot®585, Qdot®605, Qdot®655, Qdot®705, Qdot®800; (iv) DyLight™ Dyes (Pierce) (DL), e.g., DL549, DL649, DL680, DL800; (v) Fluorescein (Flu) or any derivate of that, ex. FITC; (vi) Cy-Dyes, e.g., Cy2, Cy3, Cy3.5, Cy5, Cy5.5, Cy7; (vii) fluorescent Proteins, e.g., RPE, PerCp, APC, green fluorescent proteins, GFP and GFP-derived mutant proteins; BFP.CFP, YFP, DsRed, T1, Dimer2, mRFP1, MBanana, mOrange, dTomato, tdTo ato, Tangerine, Strawberry, mCherry; (viii) Tandem dyes, e.g., RPE-Cy5, RPE-Cy5.5, RPE-Cy7, RPE-AlexaFluor® tandem conjugates, RPE-Alexa610, RPE-TxRed, APC-Aleca600, APC-Alexa610, APC-Alexa750, APC-Cy5, APC-Cy5.5; (ix) lonophors; ion chelating fluorescent props, e.g., Props that change wavelength when binding a specific ion, such as Calcium Props that change intensity when binding to a specific ion, such as Calcium; (x) Combinations of fluorochromes on the same marker. Thus, the marker is not identified by a single fluorochrome but by a code of identification being a specific combination of fluorochromes, as well as inter related ratio of intensities.

TABLE 4

Examples of preferred fluorochromes

| Fluorofor/Fluorochrome | Excitation nm | Emission nm |
|---|---|---|
| 2-(4'-maleimidylanilino)naphthalene-6-sulfonic acid, sodium salt | 322 | 417 |
| 5-((((2-iodoacetyl)amino)ethyl)amino)naphthalene-1-sulfonic acid | 336 | 490 |
| Pyrene-1-butanoic acid | 340 | 376 |
| AlexaFluor 350 (7-amino-6-sulfonic acid-4-methyl coumarin-3-acetic acid) | 346 | 442 |

TABLE 4-continued

| Examples of preferred fluorochromes | | |
|---|---|---|
| Fluorofor/Fluorochrome | Excitation nm | Emission nm |
| AMCA (7-amino-4-methyl coumarin-3-acetic acid) | 353 | 442 |
| 7-hydroxy-4-methyl coumarin-3-acetic acid | 360 | 455 |
| Marina Blue (6,8-difluoro-7-hydroxy-4-methyl coumarin-3-acetic acid) | 362 | 459 |
| 7-dimethylamino-coumarin-4-acetic acid | 370 | 459 |
| Fluorescamin-N-butyl amine adduct | 380 | 464 |
| 7-hydroxy-coumarine-3-carboxylic acid | 386 | 448 |
| CascadeBlue (pyrene-trisulphonic acid acetyl azide) | 396 | 410 |
| Cascade Yellow | 409 | 558 |
| Pacific Blue (6,8 difluoro-7-hydroxy coumarin-3-carboxylic acid) | 416 | 451 |
| 7-diethylamino-coumarin-3-carboxylic acid | 420 | 468 |
| N-(((4-azidobenzoyl)amino)ethyl)-4-amino-3,6-disulfo-1,8-naphthalimide, dipotassium salt | 426 | 534 |
| Alexa Fluor 430 | 434 | 539 |
| 3-perylenedodecanoic acid | 440 | 448 |
| 8-hydroxypyrene-1,3,6-trisulfonic acid, trisodium salt | 454 | 511 |
| 12-(N-(7-nitrobenz-2-oxa-1,3-diazol-4-yl)amino)dodecanoic acid | 467 | 536 |
| N,N'-dimethyl-N-(iodoacetyl)-N'-(7-nitrobenz-2-oxa-1,3-diazol-4-yl)ethylenediamine | 478 | 541 |
| Oregon Green 488 (difluoro carboxy fluorescein) | 488 | 518 |
| 5-iodoacetamidofluorescein | 492 | 515 |
| Propidium iodide-DNA adduct | 493 | 636 |
| Carboxy fluorescein | 495 | 519 |

Examples of preferred fluorochrome families are shown in Table 5.

TABLE 5

| Fluorochrome family Example fluorochrome | |
|---|---|
| Fluorochrome family | Example fluorochrome |
| AlexaFluor ® (AF) | AF ®350, AF405, AF430, AF488, AF500, AF514, AF532, AF546, AF555, AF568, AF594, AF610, AF633, AF635, AF647, AF680, AF700, AF710, AF750, AF800 |
| Quantum Dot (Qdot ®) based dyes | Qdot ®525, Qdot ®565, Qdot ®585, Qdot ®605, Qdot ®655, Qdot ® 705, Qdot ®800 |
| DyLight ™ Dyes (DL) | DL549, DL649, DL680, DL800 |
| Small fluorescing dyes | FITC, Pacific Blue ™, Pacific Orange ™, Cascade Yellow ™, Marina blue ™, DSred, DSred-2, 7-AAD, TO-Pro-3, |
| Cy-Dyes | Cy2, Cy3, Cy3.5, Cy5, Cy5.5, Cy7 |
| Phycobili Proteins: | R-Phycoerythrin (RPE), PerCP, Allophycocyanin (APC), B-Phycoerythrin, C-Phycocyanin |
| Fluorescent Proteins | (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine, mStrawberry, mCherry |
| Tandem dyes with RPE | RPE-Cy5, RPE-Cy5.5, RPE-Cy7, RPE-AlexaFluor ® tandem conjugates; RPE-Alexa610, RPE-TxRed |
| Tandem dyes with APC | APC-Alexa600, APC-Alexa610, APC-Alexa750, APC-Cy5, APC-Cy5.5 |
| Calcium dyes | Indo-1-Ca2+ Indo-2-Ca2+ |

Peptide Label

The label can be a peptide label comprising a stretch of consecutive amino acid residues. This is the 'coding region' the identity of which can be determined.

The peptide label can comprise or consist of a defined number of consecutive amino acids. It follows that the peptide label, in some embodiments, comprises 2 or more consecutive amino acids, such as 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-45, 45-50, 50-55, 55-60, 60-65, 65-70, 70-75, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-350, 350-400, 400-450, 450-500, 500-600, 600-700, 700-800, 800-900, 900-1000, 1000-1500, 1500-2000, or more than 2000, consecutive amino acids.

The peptide label can comprise a stretch of consecutive amino acid residues (coding region) and a protease cleavage site. The protease cleavage site can be preferably located proximal to the linker that connects the label to the MHC multimer.

When the MHC multimer is brought into proximity of a protease, the peptide label is cleaved and the coding region released from the MHC multimer. The sample cells may be precipitated and the supernatant can be analyzed by mass spectrometry to determine the identity and amount of the labels that was released.

Proteases capable of cleaving the peptide labels may be coated on the surface of sample cells, for example by adding antibody-protease conjugates where the antibody recognizes a particular cell surface structure.

The peptide label can comprise natural (or standard) amino acids, non-naturally occurring amino acids (non-proteinogenic or non-standard), or both. In some embodiments, the peptide label comprises standard and non-standard amino acids. A natural amino acid is a naturally occurring amino acid existing in nature and being naturally incorporated into polypeptides (proteinogenic). They consist of the 20 genetically encoded amino acids Ala, Arg, Asn, Asp, Cys, Gin, Glu, Gly, His, lie, Leu, Lys, Met, Phe, Pro, Ser, Tyr, Thr, Trp, Val, and 2 which are incorporated into proteins by unique synthetic mechanisms: Sec (selenocysteine, or U) and Pyl (pyrrolysine, 0). These are all L-stereoisomers. Aside from the 22 natural or standard amino acids, there are many other non-naturally occurring amino acids (non-proteinogenic or non-standard They are either not found in proteins, or are not produced directly and in isolation by standard cellular machinery. Non-standard amino acids are usually formed through modifications to standard amino acids, such as post-translational modifications. Any amino acids disclosed herein can be in the L- or D-configuration. The standard and/or non-standard amino acids can be linked by peptide bonds to form a linear peptide chain.

The term peptide also embraces post-translational modifications introduced by chemical or enzyme-catalyzed reactions, as are known in the art. Also, functional equivalents may comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) which do not normally occur in human proteins.

Protein post-translational modification (PTM) increases the functional diversity of the proteome by the covalent addition of functional groups or proteins, proteolytic cleavage of regulatory subunits or degradation of entire proteins. These modifications include phosphorylation, glycosylation, ubiquitination, nitrosylation, methylation, acetylation, lipidation (C-terminal glycosyl phosphatidylinositol (GPI) anchor, N-terminal myristoylation, S-myristoylation, S-prenylation), amidation, and proteolysis and influence almost all aspects of normal cell biology and pathogenesis.

Receptor-Binding Reagent Specific Oligonucleotides

A MHC monomer or MHC multimer as disclosed herein can comprise at least one nucleic acid label, such as a nucleotide label, for example an oligonucleotide label (e.g., receptor-binding reagent specific oligonucleotide). In some embodiments, the label is an oligonucleotide, such as a DNA oligonucleotide (DNA label). The terms nucleic acid label, nucleic acid molecule, nucleotide label, oligonucleotide label, DNA molecule, DNA label, DNA tag, receptor-binding reagent specific oligonucleotide, DNA oligonucleotides and nucleic acid component may be used interchangeably herein. In some embodiments, the nucleic acid label comprises one or more of the following components: barcode region, 5' first primer region (forward) 3' second primer region (reverse), random nucleotide region, connector molecule, stability-increasing components, short nucleotide linkers in between any of the above-mentioned components adaptors for sequencing, and/or annealing region.

The nucleic acid label can comprise at least a barcode region (e.g., barcode sequence, unique receptor identifier sequence). A barcode region comprises a sequence of consecutive nucleic acids. A nucleic acid label disclosed herein can comprise a number of consecutive nucleic acids. The nucleic acid can be any type of nucleic acid or modifications thereof, naturally occurring or synthetically made (artificial nucleic acids). The nucleic acid label can comprise or consists of DNA, and/or comprise or consist of RNA.

In some embodiments, the nucleic acid label comprises or consists of artificial nucleic acids or Xeno nucleic acid (XNA). Artificial nucleic acid analogs have been designed and synthesized by chemists, and include PNA, morpholino- and LNA, as well as GNA, TNA, HNA and CeNA. Each of these is distinguished from naturally occurring DNA or RNA by changes to the backbone of the molecule. In some embodiments, the nucleic acid label comprises or consists of one or more of XNA, PNA, LNA, TNA, GNA, HNA and CeNA, In some embodiments, the at least one nucleic acid molecule comprises or consists of DNA, RNA, and/or artificial nucleotides such as PLA or LNA. Preferably DNA, but other nucleotides may be included to, e.g., increase stability.

The oligonucleotide can be a natural oligonucleotide such as DNA or RNA, or it is PNA, LNA, or another type of unnatural oligonucleotide. The oligonucleotides can be modified on the base entity, the sugar entity, or in the linker connecting the individual nucleotides. The length of the nucleic acid molecule may also vary, for example have a length in the range 20-100 nucleotides, such as 30-100, 30-80 or 30-50 nucleotides. In some embodiments, the at least one nucleic acid molecule is an oligonucleotide of length 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides.

In some embodiments, the nucleic acid label comprises 1 to 1,000,000 nucleotides, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides; for example 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000, 1000-1500, 1500-2000, 2000-3000, 3000-4000, 4000-5000, 5000-7500, 7500-10,000, 10,000-100,000, 100,000-1,000,000 nucleotides.

A nucleic acid label can comprise a number of consecutive nucleic acids. The sequence of the nucleic acids serves as a code that can be identified, such as amplified and/or sequenced. In some embodiments, the nucleic acid label comprises a central stretch of nucleic acids (barcode region) designed to be amplified by for example PCR.

The identifiable consecutive nucleic acids, or the identifiable sequence, of the nucleic acid label are denoted a “barcode”, “barcode region”, “nucleic acid barcode”, “unique sequence”, “unique nucleotide sequence”, “unique receptor identifier sequence” and “coding sequence” herein (used interchangeably). The barcode region comprises of a number of consecutive nucleic acids making up a nucleic acid sequence.

In some embodiments, a nucleic acid barcode is a unique oligo-nucleotide sequence ranging for 10 to more than 50 nucleotides. In this embodiment, the barcode has shared amplification sequences in the 3' and 5' ends, and a unique sequence in the middle. This unique sequence can be revealed by sequencing and can serve as a specific barcode for a given MHC multimer. The unique sequence, the barcode, is composed of a series of nucleotides that together forms a sequence (series of nucleotides) that can be specifically identified based on its composition. This sequence composition enables barcode #1 to be distinguishable from barcode #2, #3, #4 etc., up to more than 100,000 barcodes, based solely on the unique sequence of each barcode. The complete nucleotide barcode may also be composed of a combination of series of unique nucleotide sequences linked to each other. The series of unique sequences will together assign the barcode.

In some embodiments, each unique nucleotide sequence (barcode) holds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides.

In some embodiments, the label is an oligonucleotide and/or the unique sequence has a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides. In some embodiments, the unique sequence is shorter than the total length of the label.

In some embodiments, the barcode region comprises or consists of 2-5, 5-10, 10-15, 15-20, 20-25, 25-30, 30-40, 40-45, 45-50, 50-60, 60-70, 70-80, 80-90, 90-100, 100-110, 110-120, 120-130, 130-140, 140-150, 150-175, 175-200, 200-250, 250-300, 300-400, 400-500 nucleotides.

The unique nucleotide sequence (barcode) is solely used as an identification tag for the molecular interaction between the MHC molecule and its target. The unique nucleotide sequences preferably are not identical to any natural occurring DNA sequence, although sequence similarities or identities may occur.

Each nucleic acid barcode should hold sufficient difference from the additional barcodes in a given experiment to allow specific identification of a given barcode, distinguishable from the others.

The nucleic acid component (e.g., DNA) has a special structure. Thus, in an embodiment the at least one nucleic acid molecule (label) is composed of at least a 5' first primer region, a central region (barcode region), and a 3' second primer region. In this way the central region (the barcode region) can be amplified by a primer set.

The coupling of the nucleic acid molecule to the multimerization domain may also vary. Thus, in some embodiments, the at least one nucleic acid molecule is linked to said multimerization domain via a streptavidin-biotin binding and/or streptavidin-avidin binding. Other coupling moieties may also be used.

In some embodiments, the nucleic acid label comprises a connector molecule, which connector molecule is able to interact with a component on multimerization domain or the MHC molecule. In some embodiments, the connector molecule is biotin or avidin. In some embodiments, the linker comprises streptavidin to which the label binds via its biotin or avidin connector molecule. In some embodiments, the nucleic acid label comprises a random nucleotide region. This random nt region is a potential tool for detecting label contaminants. A random nt region, in some embodiments, comprises from 3-20 nucleotides, such as 3, 4, 5, 6, 7, 8, 9, 10, 11, 12, 13, 14, 15, 16, 17, 18, 19 or 20 nt.

The different labels used in an experiment can possess the same amplification properties and share common primer regions: Common primer regions together with shared amplification properties will ensure that all labels that are present after cellular interaction and sorting are amplified equally whereby no sequences will be biased due to the sequencing reaction.

With identical primer regions on differing labels there is an inherent risk of contaminating one label with another—especially following amplification reactions. To be able to trace potential contaminants a short ‘random nucleotide region’ can be included in the nucleic acid label. Since the random nucleotide region is unique for each label, it will be possible to inspect the sequencing data and see whether numerous reads of a given label is present. I.e. the random nucleotide region is a clonality control region. In some embodiments, the random nucleotide region consist of 2-20 nucleic acids; such as 2, 3, 4, 5, 6, 7, 8, 9, 10, 11, 12, 13, 14, 15, 16, 17, 18, 19 or 20 nucleic acids. A random nucleotide region consisting of 6 nucleotides may be denoted ‘IM6’ herein, and so forth. In some embodiments, the nucleic acid label comprises one or more stability-increasing components (such as HEG or TEG).

The label is preferably stable when mixing with cells: as this may expose the label to nuclease digestion. A measure to minimize this may be to add modifications in the form of hexaethylene glycol (HEG) or TEG at one or both ends of the oligonucleotide label. Additionally stability can be accounted for in the buffers applied by adding constituents that exert a protective effect towards the oligo-nucleotides, e.g., herring DNA and EDTA.

In some embodiments, the nucleic acid label comprises a sample identifying sequence. To be able to analyze more than a single sample in each sequencing reaction the nucleic acid labels may be appointed an additional recognition feature, namely a sample identifying sequence. The sample identifying sequence is not a part of the initial design of the label, but will be appointed after cellular interaction and sorting via primers in a PCR—thus all cells originating from the same sample, will have the same sample identification sequence. In some embodiments, the sample identifying sequence is a short sequence, consisting of 2-20 nucleotides, such as 2, 3, 4, 5, 6, 7, 8, 9, 10, 11, 12, 13, 14, 15, 16, 17, 18, 19, 20, or a range between any two of these, nucleotides. The sample identifying sequence may be attached to a primer, such as the forward primer.

The nucleic acid label is, in some embodiments, a "1 oligo system" comprising a forward primer, a barcode region and a reverse primer. The nucleic acid label is, in some embodiments, a "2 oligo system" with two sequences, the first comprising a forward primer, a barcode region and a annealing region; and the second comprising an annealing region, a barcode region and a reverse primer.

Kits

Disclosed herein include kits, for example a kit comprising: a plurality of receptor detection constructs, wherein a receptor detection construct comprises two or more receptor-binding reagents, wherein a receptor-binding reagent is capable of specifically binding to a receptor, and wherein each of the receptor detection constructs comprises a receptor-binding reagent specific oligonucleotide comprising a unique receptor identifier sequence for the receptor-binding reagent. The kit can comprise: a plurality of cellular component-binding reagents, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to a cellular component target. In some embodiments, the receptor-binding reagent specific oligonucleotide comprises a second universal sequence, the cellular component-binding reagent specific oligonucleotide comprises a third universal sequence, and the second universal sequence and the third universal sequence are different. In some embodiments, the second universal sequence is less than about 85% (e.g., 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or a number or a range between any two of these values) identical to the third universal sequence.

The kit can comprise: a plurality of oligonucleotide barcodes, wherein each of the plurality of oligonucleotide barcodes comprises a first universal sequence, a molecular label and a target-binding region, and wherein at least 10 of the plurality of oligonucleotide barcodes comprise different molecular label sequences. The plurality of oligonucleotide barcodes can be associated with a solid support. The target-binding region can comprise a gene-specific sequence, an oligo(dT) sequence, a random multimer, or any combination thereof. The kit can comprise: a reverse transcriptase. The reverse transcriptase can comprise a viral reverse transcriptase (e.g., murine leukemia virus (MLV) reverse transcriptase or a Moloney murine leukemia virus (MMLV) reverse transcriptase). The kit can comprise: a DNA polymerase lacking at least one of 5' to 3' exonuclease activity and 3' to 5' exonuclease activity, (e.g., a Klenow Fragment). The kit can comprise: a buffer, a cartridge, or both. The kit can comprise: one or more reagents for a reverse transcription reaction and/or an amplification reaction. In some embodiments, the plurality of oligonucleotide barcodes each comprise a cell label. Each cell label of the plurality of oligonucleotide barcodes can comprise at least 6 nucleotides. In some embodiments, oligonucleotide barcodes of the plurality of oligonucleotide barcodes associated with the same solid support can comprise the same cell label. In some embodiments, oligonucleotide barcodes of the plurality of oligonucleotide barcodes associated with different solid supports can comprise different cell labels.

The solid support can comprise a synthetic particle, a planar surface, or a combination thereof. At least one oligonucleotide barcode of the plurality of oligonucleotide barcodes can be immobilized or partially immobilized on the synthetic particle, or at least one oligonucleotide barcode of the plurality of oligonucleotide barcodes can be enclosed or partially enclosed in the synthetic particle. The synthetic particle can be disruptable (e.g., a disruptable hydrogel particle). The synthetic particle can comprise a bead. The bead can be a sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. Each oligonucleotide barcode of the plurality of oligonucleotide barcodes can comprise a linker functional group. The synthetic particle can comprise a solid support functional group. The support functional group and the linker functional group can be associated with each other, and optionally the linker functional group and the support functional group can be individually selected from the group consisting of C6, biotin, streptavidin, primary amine(s), aldehyde(s), ketone(s), and any combination thereof.

The kit can comprise: one or more primers comprising the first universal sequence, first universal sequence, and/or third universal sequence. The second universal sequence can comprise a sequence at least about 80% (e.g., 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values) identical to SEQ ID NO: 1 (GGAGGGAGGTTAGCGAAGGT). The target-binding region can comprise a poly(dT) region and the cellular component-binding reagent specific oligonucleotide can comprise a poly(dA) region. The cellular component-binding reagent specific oligonucleotide can comprise an alignment sequence adjacent to the poly(dA) region. In some embodiments, (a) the alignment sequence comprises a guanine, a cytosine, a thymine, a uracil, or a combination thereof (b) the alignment sequence comprises a poly(dT) sequence, a poly(dG) sequence, a poly(dC) sequence, a poly(dU) sequence, or a combination thereof and/or (c) the alignment sequence is 5' to the poly(dA) region. The cellular component-binding reagent specific oligonucleotide can be associated with the cellular component-binding reagent through a linker. The cellular component-binding reagent specific oligonucleotide can be configured to be detachable from the cellular component-binding reagent. The linker can comprise a carbon chain. The carbon chain can comprise 2-30 carbons, and further optionally the carbon chain can comprise 12 carbons. The linker can comprise 5' amino modifier C12 (5AmMC12), or a derivative thereof.

The cellular component target can comprise a protein target. The cellular component-binding reagent can comprise an antibody or fragment thereof. The cellular component target can comprise a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. The cellular component-binding reagent can comprise an antibody or fragment thereof. The cellular component target can be on a cell surface. The receptor-binding reagent specific oligonucleotide can comprise a third molecular label and/or the cellular component-binding reagent specific oligonucleotide can comprise a second molecular label. The receptor-binding reagent specific oligonucleotide can be about 10 nucleotides to about 100 nucleotides in length. The receptor can comprise a cluster of differentiation (CD) molecule. The receptor can comprise an immune receptor (e.g., a T cell receptor (TCR)). The unique receptor identifier sequence can be about 3 nucleotides to about 100 nucleotides in length. The target-binding region can comprise a poly(dT) region and the receptor-binding reagent specific oligonucleotide can comprise a poly(dA) region. The receptor-binding reagent specific oligonucleotide can comprise an alignment sequence adjacent to the poly(dA) region. In some embodiments, (a) the alignment sequence comprises a guanine, a cytosine, a thymine, a uracil, or a combination thereof (b) the alignment sequence comprises a poly(dT) sequence, a poly(dG) sequence, a poly(dC) sequence, a poly(dU) sequence, or a combination thereof and/or (c) the alignment sequence is 5' to the poly(dA) region. The receptor-binding reagent specific oligonucleotide can be associated with the receptor-binding reagent through a linker. The receptor-binding reagent specific oligonucleotide can be configured to be detachable from the receptor-binding reagent. The linker can comprise a carbon chain. The carbon chain can comprise 2-30 carbons, and further optionally the carbon chain can comprise 12 carbons. The linker can comprise 5' amino modifier C12 (5AmMC12), or a derivative thereof. The plurality of receptor detection constructs can comprise one or more MHC multimers described herein. The two or more receptor-binding reagents comprise two or more MHC-peptide complexes described herein.

EXAMPLES

Some aspects of the embodiments discussed above are disclosed in further detail in the following examples, which are not in any way intended to limit the scope of the present disclosure.

Example 1 Protocols dCODE™ Dextramer® (BD-Rhapsody™) Staining Protocol

This protocol can be used for the profiling and quantitation of antigen-specific T cells in cell samples, using the BD Rhapsody™ Single-Cell Analysis System, together with targeted mRNA analysis.

The dCODE™ Dextramer® (BD-Rhapsody™ compatible) reagent can comprise a dextran polymer backbone carrying multiple MHC-peptide complexes, a corresponding unique DNA Barcode oligo and R-phycoerythrin (PE) for sorting of dCODE Dextramer positive cells, before loading the sample into the Rhapsody™ system.

Figure 9A:
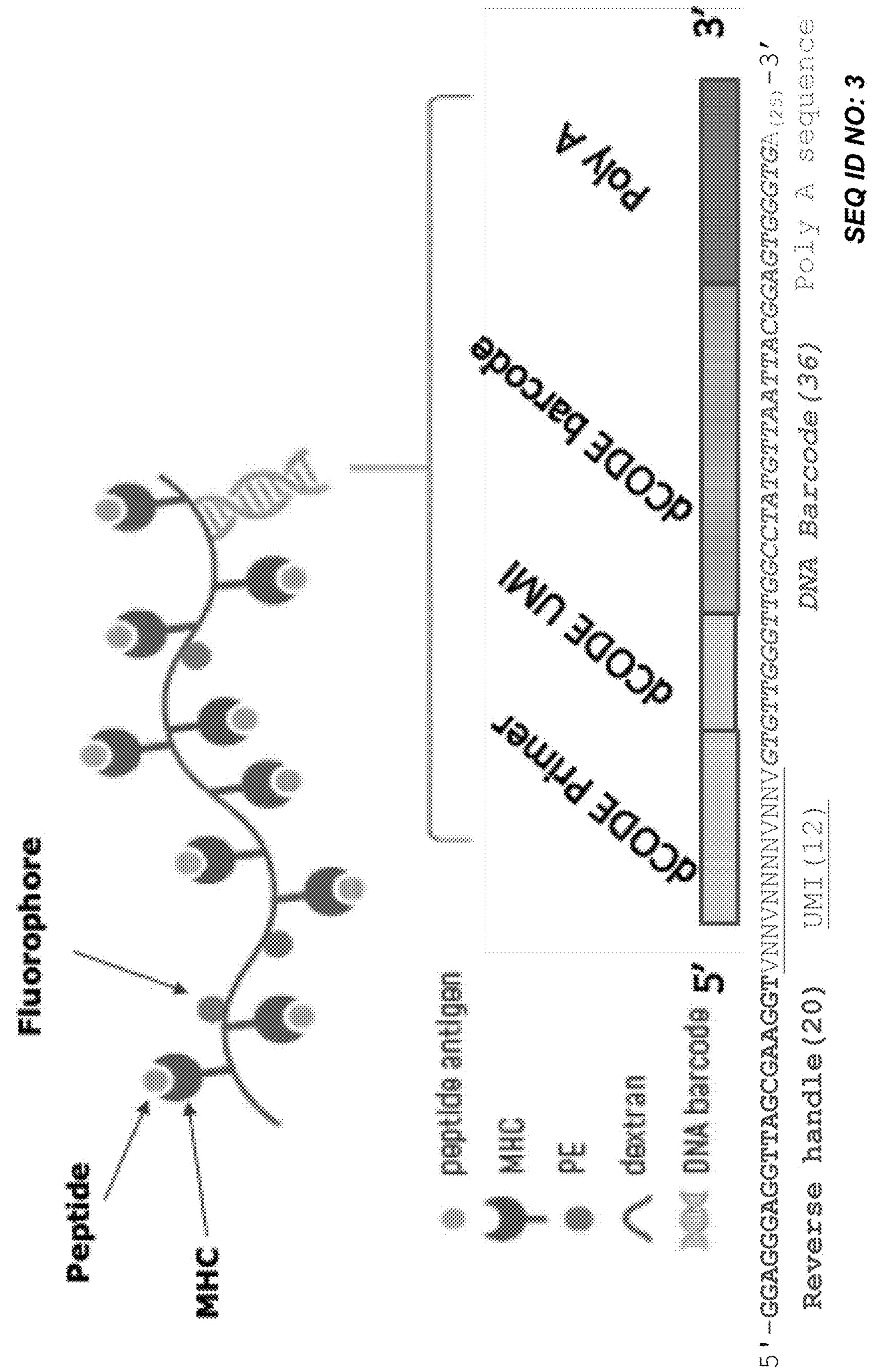
FIGS. 9A-9F depict non-limiting exemplary experimental workflows and molecular mechanisms of Immudex dCODE and BD Rhapsody System single cell sequencing.

The unique DNA Barcode oligo can comprise a BD-Rhapsody™ compatible PCR handle sequences for PCR amplification, a Unique Molecule Identifier (UMI) sequence, and a DNA Barcode sequence that specifies the MHC-peptide specificity (See, e.g., FIG. 9A; SEQ ID NO: 3).

The dCODE Dextramer (Rhapsody™) can provided at a concentration of 1.6×10-7 M in PBS buffer containing 1% bovine serum albumin (BSA) and 15 mM NaN3, pH 7.2.

2 μl (one test) can be used for staining of 1-3×$10^6$ PBMC.

Each dCODE Dextramer can be uniquely identified by its HLA-allele/Peptide/DNA Barcode.

dCODE Dextramer (Rhapsody™)—Gold: Single reagents of 25 tests (50 μl), 50 tests (100 μl) or 150 tests (300 μl) each.

dCODE Dextramer (Rhapsody™)—Explore: Panels of 16, 32, 48, 64, 80, or 96 dCODE Dextramer (Rhapsody™) reagents for 10 tests (20 μl), 25 tests (50 μl) or 50 tests (100 μl) each.

Reagents can be stored in the dark at 2-8° C.

Additional materials can include: Cell labeling buffer: PBS, pH 7.4 containing 1-5% serum and 0.1 g/l Herring sperm DNA (shirred) or BD™ Stain Buffer (FBS) (Cat. No. 554656), added 0.1 g/l Herring sperm DNA (shirred); Wash buffer: PBS, pH 7.4 containing 1-5% serum; 100 μMd-Biotin in PBS; antibodies identifying relevant cell surface markers for sorting (e.g., CD3, CD4, CD8); Fixable Viability Stain for sorting live cells; BD AbSeq Ab-Oligo; Calcein AM (Thermo Fisher Scientific Cat. No. C1430); and/or INCYTO™ disposable hemocytometer (INCYTO Cat. No. DHC-N01-5). *For FACSorting do not use fluorophores with light emission spectra similar to Calcein AM (FITC) and Drag7™ (Cy5, Cy5-tandems, or APC), which are used for viability assessment by the Rhapsody™ scanner.

dCODE Dextramer specific primers: dCODE PCR1 primer (5'-GGAGGGAGGTTAGCGAAGGT-3'; SEQ ID NO: 1) and dCODE PCR2 Primer (5'-CAGACGTGTGCTCTTCCGATCTGGAGGGAGGTTAGCGAAGGT-3'; SEQ ID NO: 2). Primers can be used at a 10 μM concentration.

BD Protocols: Doc ID: 210966: Single Cell Capture and cDNA Synthesis with the BD Rhapsody™; Doc ID: 214293: BD Rhapsody™ Targeted mRNA and AbSeq Amplification Kit.

Prepare Single Cell PBMC Sample

Note that incubation time should be increased for larger pools of dCODE Dextramer reagents. For more than 25 specificities, 20-30 min incubation can be used.

(Step 1) Resuspend 1-3×$10^6$ PBMC in 500 cell labeling buffer.

If FVS is used, resuspend cells in 10000 wash buffer (Azide free) and add recommended volume of FVS.

Incubate for 15 min at RT. (All incubations must be performed shielded from light). Add 2 ml Wash buffer, centrifuge 300-600 g 5 min, resuspend cells in 50 μl cell labeling buffer, and continue to step 2.

Prepare dCODE Dextramer Pool and Label Cells with dCODE Dextramer

*Cell labeling with dCODE Dextramer is performed before staining with antibodies.

(Step 2) Centrifuge dCODE Dextramer® (Rhapsody™) at 10,000×g for 1 min (Step 3) Add 0.2 μl 100 μM d-Biotin per dCODE Dextramer specificity into an empty flow tube (Falcon® tubes, 5 mL Round Bottom Polystyrene Test Tube (Corning Cat. No. 352054)).

(Step 4) Add 2 μl of each dCODE Dextramer specificity and mix (Latch Rack for 500 μL Tubes (Thermo Fisher Scientific Cat. No. 4890); 8-Channel Screw Cap Tube Capper (Thermo Fisher Scientific Cat. No. 4105MAT)).

(Step 5) Add the pool of dCODE Dextramer reagents to the cell sample and mix (Step 6) Incubate at room temperature for 10 min (All incubations must be performed shielded from light). (Pools of dCODE Dextramers should be used immediately, and cannot be stored). While incubating prepare 2× AbSeq master mix.

Preparing 2× BD AbSeq Ab-Oligo Labelling Master Mix

The protocol can comprise creating freshly pooled antibodies before each experiment. The protocol can comprise creating pools with 30% overage to ensure adequate volumes for labelling (the reagents are viscous and form bubbles easily). The protocol can comprise, for high-plex panels, using an 8-Channel Screw Cap Tube Capper (Thermo Fisher Scientific Cat. No. 4105MAT) and multichannel pipette to pipet BD AbSeq Ab-Oligos into 8-tube strips. This protocol is based on using HPBMC (peripheral blood mononuclear cells).

(Step 7) Place all BD AbSeq Ab-Oligos to be pooled into a Latch Rack for 500 Tubes. Arrange the tubes so that they can be easily uncapped and re-capped with an 8-Channel Screw Cap Tube Capper and aliquoted with a multi-channel pipette. (Latch Rack for 500 μL Tubes (Thermo Fisher Scientific Cat. No. 4890); 8-Channel Screw Cap Tube Capper (Thermo Fisher Scientific Cat. No. 4105MAT)).

(Step 8) Centrifuge BD AbSeq Ab-Oligos in the Latch Rack in a tabletop centrifuge with a plate adapter tubes at 400× g for 30 seconds and place on ice.

(Step 9) In pre-amplification workspace, pipet reagents into a new 1.5 mL LoBind Tube on ice as shown in Table 6.

TABLE 6

| Mixture | | |
|---|---|---|
| Component | (N = no. antibodies) 1 sample | 1 < N < 100 add 30% overhead |
| Per BD AbSeq Ab-Oligo | 2 μl | 2 × (1 + 0, 3) μl |
| BD Stain Buffer (FBS) (Cat. No. 554656) | 100 μl − (2 × N) | 100 μl − (2, 6 × N) |
| Total | 100 μl | 130 μl |

(Step 10) Pipet-mix the 2× AbSeq labeling master mix, and place back on ice.

AbSeg™ Labeling

*Cell labeling with dCODE Dextramer is performed before staining with antibodies.

(Step 11) Bring the volume of the dCODE labeling reaction up to 100 μl with the labeling buffer, used.

Volume of labeling buffer: 100 μl-Cell volume−2× "number of dCODE specificities", (if volume is >100 μl just continue to next step).

(Step 12) Add the AbSeq 2× pool to the sample, and pipet mix.

(Step 13) Add the sorting antibody conjugates. Use volume of antibody as recommend by the manufacture and pipette mix.

(Step 14) Incubate at 4° c. for 30-60 min.

Washing Labelled Cells (Step 15) If staining is performed in 4 ml Falcon tubes, add 2 ml wash buffer.

(Step 16) Centrifuge at 300-600× g for 5 min. and remove the supernatant. Repeat for a total of 3 times. If labeling in 96-well microtiter plates, make 6 sequential washes using 200 μl wash buffer per well. Centrifuge at 300-600× g for 5 min between each wash and remove supernatant.

(Step 17) Resuspend cells in adequate volume of wash buffer and store sample on ice until sorting is performed. If not performing cell sort, go directly to step 20.

(Step 18) FACSort Dextramer positive cells using the PE-fluorescence of the dCODE Dextramer following the guidelines and practices of your sorting facility. (Use sort "Yield" mode, as you will lose more positive cells if using "purity" sort mode).

(Step 19) Collect sorted cells directly into tube containing suitable volume of Serum. Keep the unsorted and sorted cells at 4° c. while performing the sort. (Use the maximum volume of 100% Serum (FBS) in the sort tube, still having room for the sorted cell volume; FCS in the sorting tube improve viability of the sorted cells).

(Step 20) Centrifuge the sorted cell sample 300-600 g, 5-10 min (depending on the sort volume), invert to decant supernatant into biohazardous waste. Keep the tube inverted and gently blot on a lint-free wiper to remove residual supernatant from tube rim. Proceed immediately to step 21.

Preparing Cells for Rhapsody™ Cell Counting Cartridge Loading, and cDNA Synthesis (Step 21) Follow the BD protocol from Start: "Single Cell Capture and cDNA Synthesis with the BD Rhapsody™ Single-Cell Analysis System" Doc ID: 210966.

Library Generation (Step 22) Proceed with the library generation using the protocol immediately below and the protocol of mRNA Targeted and BD™ AbSeq Library Preparation with the BD Rhapsody™ Targeted mRNA and AbSeq Amplification Kit (Doc ID: 214293).

Sequencing Requirements

For sequencing of the dCODE library follow the requirement and recommendations as for AbSeq in the "mRNA Targeted and BD™ AbSeq Library Preparation with the BD Rhapsody™ Targeted mRNA and AbSeq Amplification Kit, protocol. (Doc ID: 214293)

dCODE Dextramer® (Rhapsody™) Library Preparation

This protocol describes library preparation from cDNA capture beads.

This protocol provides instructions on creating dCODE Dextramer®, with or without AbSeg™ and mRNA single cell libraries with the BD Rhapsody™ Single-Cell Analysis system or the BD Rhapsody™ Express Single-Cell Analysis system for sequencing on Illumina sequencers.

To create the libraries, dCODE® Dextramer, BD AbSeq and BD Rhapsody mRNA targets are encoded on Cell Capture Beads and then amplified in PCR1.

After PCR1, the BD AbSeq and dCODE® PCR1 products are separated from the mRNA targeted PCR1 products by double-sided size selection with Agencourt® AMPure® XP magnetic beads. Size selection of library molecules is achieved by specific and successive use of volume ratios between DNA samples and AMPure beads.

Successful preparation of mRNA and AbSeq libraries can comprise the following: (1) the dCODE® and BD Rhapsody mRNA targeted PCR1 products undergo PCR2 amplification; (2) the dCODE, AbSeq and mRNA libraries undergo separate index PCR with library index primers; and/or (3) after index PCR, the dCODE®, BD Rhapsody mRNA and BD AbSeq libraries can be combined for sequencing.

FIG. 5 depicts a non-limiting exemplary schematic workflow of the compositions and methods provided herein. PCR1: universal oligo (black), dCODE® (Orange), ABSeq™ (purple), and mRNA target (Yellow) represent the primers used in PCR1 for amplification of the Capture bead bound cDNA. PCR2: Selective amplification of the mRNA targeted library, and the dCODE® library. PCR3: Using different index primers for each library (compatible with Illumina Sequencing systems), enables sequencing the libraries in a pool.

The protocol can include the following materials: Agencourt AMPure XP magnetic beads (Beckman Coulter Cat. No. A63880); Absolute ethyl alcohol, molecular biology grade; Nuclease-free water; Magnetic Separation Rack for 1.5 mL tubes; and/or Qubit™ dsDNA HS Assay Kit (Thermo Fisher Scientific Cat. No. Q32851). The protocol can include BD Rhapsody™ Targeted mRNA and AbSeq Amplification Kit (Cat. No. 633774).

dCODE Dextramer® (Rhapsody™) can be combined with the following BD Rhapsody™ workflow: mRNA Targeted and BD™ AbSeq Library Preparation with the BD Rhapsody™ Targeted mRNA and AbSeq Amplification Kit (Doc ID: 214293) (An outline of the workflow is shown in FIG. 5). dCODE Dextramer® can be used in combination with the BD™ AbSeq Library Preparation with or without AbSeq™ antibodies.

Performing PCR 1 Amplification of Captured dCODE®, AbSeq Oligoes and mRNA Targeted (Step 1) In pre-amplification workspace, pipet reagents into a new 1.5 mL LoBind Tube on ice using the reaction mixture shown in Table 7 (dCODE®, AbSeg™ and mRNA targeted) or Table 8 (dCODE® and mRNA targeted, only). (Use 20% excess if multiple samples is amplified).

TABLE 7

PCR1 reaction mix, for dCODE ®, ABSeq ™ and target mRNA

| A: Kit component name | 1 × (μL) | 2 × (+20%) |
|---|---|---|
| Nuclease-Free Water [a)] | 4, 0 | 9, 6 |
| PCR MasterMix [a)] | 100, 0 | 240, 0 |
| PCR1 primer panel (mRNA targeted primers) [b)] | 40, 0 | 96, 0 |
| AbSeq PCR1 Primer [a)] | 12, 0 | 28, 8 |
| dCODE primer 2 (10 μM) [c)] | 12, 0 | 28, 8 |
| Universal Oligo [a)] | 20, 0 | 48, 0 |
| Bead RT/PCR Enhancer [a)] | 12, 0 | 28, 8 |
| Total volume | 200 | 480 |

[a)] Reagents provided in "BD Rhapsody™ Targeted mRNA and AbSeq Amplification Kit (Cat. No. 633774)"
[b)] BD Biosciences primers
[c)] See primers at end of protocol

TABLE 8

PCR1 reaction mix, for dCODE ®, and target mRNA, only

| B: Kit component name | 1 × (μL) | 2 × (+20%) |
|---|---|---|
| Nuclease-Free Water [a)] | 16, 0 | 38, 4 |
| PCR MasterMix [a)] | 100, 0 | 240, 0 |
| PCR1 primer panel (mRNA targeted primers) [b)] | 40, 0 | 96, 0 |
| dCODE primer 2 (10 μM) [c)] | 12, 0 | 28, 8 |
| Universal Oligo [a)] | 20, 0 | 48, 0 |
| Bead RT/PCR Enhancer [a)] | 12, 0 | 28, 8 |
| Total volume | 200 | 480 |

[a)] Reagents provided in "BD Rhapsody™ Targeted mRNA and AbSeq Amplification Kit (Cat. No. 633774)"
[b)] BD Biosciences primers
[c)] See primers at end of protocol (Step 2) Gently vortex mix, briefly centrifuge, and place back on ice.

(Step 3) Proceed as follows: entire sample, skip to step 5; sub-sample, proceed to step 4.

(Step 4) Sub-sample the Exonuclease I-treated beads: (a) Based on the number of wells with viable cells and a bead detected by the BD™ Rhapsody Scanner or the number of cells targeted for capture in the cartridge, determine the volume of beads to subsample for targeted sequencing; (b) Pipet-mix to completely resuspend the beads, and pipet the calculated volume of bead suspension into a new 1.5 mL LoBind Tube. The remaining beads can be stored at 2° C. to 8° C. for ≤3 months.

(Step 5) Place tube of Exonuclease I-treated beads in Bead Resuspension Buffer (Cat. No. 650000066) on 1.5 mL magnet for <2 minutes. Remove supernatant.

(Step 6) Remove tube from magnet, and resuspend beads in 200 μL PCR1 reaction mix. Do not vortex.

(Step 7) Ensuring that the beads are fully resuspended, pipet 50 μL PCR1 reaction mix with beads into each of four 0.2 mL PCR tubes. Transfer any residual mix to one of the tubes.

(Step 8) Bring reaction mix to the post-amplification workspace.

(Step 9) Program the thermal cycler as shown in Table 9. Do not use fast cycling mode.

TABLE 9

PCR Program

| Step | Cycles | Temp | time |
|---|---|---|---|
| Hot start | 1 | 95° C.[a] | 3 min |
| Denaturation | 11-15[b] | 95° C. | 30 sec |
| Annealing | | 60° C. | 3 min |
| Extension | | 72° C. | 1 min |
| Final extension | 1 | 72° C. | 5 min |
| Hold | 1 | 4° C. | ∞ |

[a]To avoid beads settling due to prolonged incubation time on thermal cycler before the denaturation step, pause the instrument at 95° C. before loading the samples. Different thermal cyclers might have different pause time settings. In certain brands of thermal cyclers, however, BD Biosciences has observed a step-skipping error with the pause/unpause functions. To ensure that the full three-minute denaturation is not skipped, verify that the pause/unpause functions are working correctly on your thermal cycler. To avoid the step-skipping problem, a one-minute 95° C. pause step can be added immediately before the three-minute 95° C. denaturation step.
[b]Suggested PCR cycles might need to be optimized for different cell types, number of antibodies in BD ™ AbSeq panel, and cell number as shown in Table 10.

TABLE 10

PCR Cycles

| No. cells in PCR1 | Suggested PCR cycles for resting PBMCs |
|---|---|
| 500 | 15 |
| 1,000 | 14 |
| 2,500 | 13 |
| 5,000 | 12 |
| 10,000 | 11 |

(Step 10) Ramp heated lid and heat block of post-amplification thermal cycler to ≥95° C. by starting the thermal cycler program and then pausing it. Do not proceed to thermal cycling until each tube is gently mixed by pipette to ensure uniform bead suspension.

(Step 11) For each 0.2 mL PCR tube, gently pipet-mix, immediately place tube in thermal cycler and unpause the thermal cycler program. Stopping point: The PCR can run overnight but proceed with purification ≤24 hours after PCR.

(Step 12) After PCR, briefly centrifuge tubes.

(Step 13) Pipet-mix and combine the four reactions into a new 1.5 mL LoBind Tube. Retain the supernatant in the next step.

(Step 14) Place the 1.5 mL tube on magnet for 2 minutes, and carefully pipet the supernatant (mRNA targeted PCR1 products and BD AbSeq PCR1 products) into the new 1.5 mL LoBind Tube without disturbing the beads. Note: (Optional) Remove tube with the Cell Capture Beads from magnet, and pipet 200 μL cold Bead Resuspension Buffer (Cat. No. 650000066) into tube. Pipet-mix. Do not vortex. Store beads at 2° C. to 8° C. in post-amplification workspace.

Purifying PCR1 Products by Double-Sided Size Selection

Perform double-sided AMPure bead purification to separate the shorter BD AbSeq PCR1 products (~170 bp) from the longer mRNA targeted PCR1 products (350-800 bp). In the protocol, keep both the supernatant (dCODE® and BD AbSeq products) and the AMPure beads (mRNA targeted products) for purification. Perform the purification in the post-amplification workspace.

Separating BD AbSeq PCR1 Products from mRNA Targeted PCR1 Products (Step 1) In a new 5.0 mL LoBind tube, prepare 5 mL fresh 80% (v/v) ethyl alcohol by combining 4.0 mL absolute ethyl alcohol, molecular biology grade (major supplier) with 1.0 mL nuclease-free water (major supplier). Vortex tube for 10 seconds to mix. Make fresh 80% ethyl alcohol, and use it in ≤24 hours.

(Step 2) Bring Agencourt AMPure XP magnetic beads (Beckman Coulter Cat. No. A63880) to room temperature (15° C. to 25° C.). Vortex high speed for 1 minute until beads are fully resuspended.

(Step 3) Pipet 140 μL AMPure beads into the tube with 200 μL mRNA targeted PCR1 products and BD AbSeq PCR1 products (step 14 of Performing PCR1). Pipet-mix 10 times.

(Step 4) Incubate at room temperature (15° C. to 25° C.) for 5 minutes.

(Step 5) Place 1.5 mL LoBind Tube on magnet for 5 minutes.

(Step 6) Keeping tube on magnet, transfer the 340 μL supernatant (BD AbSeq PCR1 products) to a new 1.5 mL tube without disturbing beads (mRNA targeted PCR1 products).

(Step 7) Store the supernatant (step 6) at room temperature (15° C. to 25° C.) while purifying and eluting mRNA targeted PCR1 products in Purifying mRNA targeted PCR1 products. Purify the BD AbSeq PCR1 products in Purifying BD AbSeq PCR1 products.

Purifying mRNA Targeted PCR1 Products (Step 1) Keeping tube on magnet, gently add 500 μL fresh 80% ethyl alcohol to the tube of AMPure beads bound with mRNA targeted PCR1 products, and incubate 30 seconds. Remove supernatant.

(Step 2) Repeat step 1 once for two washes.

(Step 3) Keeping tube on magnet, use a small-volume pipette to remove residual supernatant from tube, and discard.

(Step 4) Air-dry beads at room temperature (15° C. to 25° C.) for 5 minutes.

(Step 5) Remove tube from magnet, and resuspend bead pellet in 30 μL of Elution Buffer (Cat. No. 91-1084). Vigorously pipet-mix until beads are uniformly dispersed. Small clumps do not affect performance.

(Step 6) Incubate at room temperature (15° C. to 25° C.) for 2 minutes, and briefly centrifuge.

(Step 7) Place tube on magnet until solution is clear, usually ≤30 seconds.

(Step 8) Pipet the eluate (~30 μL) into a new 1.5 mL LoBind Tube (purified mRNA targeted PCR1 products).

Stopping point: Store at 2° C. to 8° C. before proceeding in ≤24 hours or at −25° C. to −15° C. for ≤6 months.

Purifying BD AbSeq PCR1 Products (Step 1) Pipet 100 μL AMPure XP beads into the tube with 340 μL BD AbSeq PCR1 products from step 6 of Separating BD AbSeq PCR1 products from mRNA targeted PCR1 products. Pipet-mix 10 times.

(Step 2) Incubate at room temperature (15° C. to 25° C.) for 5 minutes.

(Step 3) Place on magnet for 5 minutes.

(Step 4) Keeping tube on magnet, remove supernatant, and discard.

(Step 5) Keeping tube on magnet, gently add 500 μL fresh 80% ethyl alcohol, and incubate 30 seconds. Remove supernatant.

(Step 6) Repeat step 5 once for two washes.

(Step 7) Keeping tube on magnet, use a small-volume pipette to remove residual supernatant from tube, and discard.

(Step 8) Air-dry beads at room temperature (15° C. to 25° C.) for 5 minutes.

(Step 9) Remove tube from magnet, and resuspend bead pellet in 30 μL Elution Buffer (Cat. No. 91-1084). Vigorously pipet-mix until beads are uniformly dispersed. Small clumps do not affect performance.

(Step 10) Incubate at room temperature (15° C. to 25° C.) for 2 minutes, and briefly centrifuge.

(Step 11) Place tube on magnet until solution is clear, usually ≤30 seconds.

(Step 12) Pipet the eluate (~30 μL) into a new 1.5 mL LoBind Tube (purified BD AbSeq PCR1 products).

Stopping point: Store at 2° C. to 8° C. before proceeding in ≤24 hours or at −25° C. to −15° C. for ≤6 months.

Note: The dCODE® library is copurified with the AbSeq library from PCR1.

Quantifying BD AbSeq PCR1 Products (Step 1) Measure the yield of the largest peak of the BD AbSeq PCR1 products (~170 bp) by using the Agilent Bioanalyzer with the High Sensitivity Kit (Agilent Cat. No. 5067-4626). Follow the manufacturer's instructions.

(Step 2) Dilute an aliquot of BD AbSeq products to 0.1-1.1 ng/μL with Elution Buffer (Cat. No. 91-1084) before index PCR of BD AbSeq PCR1 products.

FIG. 6 depicts a non-limiting exemplary Bioanalyzer trace containing both the dCODE® and AbSeq™ library PCR amplicons (approximately 170 bp).

Performing PCR2 on the mRNA Targeted PCR1 Products (Step 1) In pre-amplification workspace, pipet reagents into a new 1.5 mL LoBind Tube on ice to generate the reaction mixture shown in Table 11.

Before use of BD Rhapsody™ 10×PCR2 Custom primers and/or BD Rhapsody™ 10×PCR2 Supplement primers, dilute 1 part of the 10×PCR primer stock to 9 parts of IDTE buffer to prepare a 1× primer solution. BD Rhapsody™ targeted (predesigned) primer panels are provided at 1× concentration and should not be diluted.

TABLE 11

PCR2 reaction mix

| Component | For 1 library (μL) | For 1 library + 20% overage (μL) |
|---|---|---|
| PCR MasterMix (Cat. No. 91-1083) | 25.0 | 30.0 |
| Universal Oligo (Cat. No. 650000074) | 2.0 | 2.4 |

TABLE 11-continued

| PCR2 reaction mix | | |
|---|---|---|
| Component | For 1 library (µL) | For 1 library + 20% overage (µL) |
| PCR2 primer panel (BD Biosciences) | 10.0 | 12.0 |
| (Optional) PCR2 panel supplement | (2.5) | (3.0) |
| Nuclease-Free Water (Cat. No. 650000076) | Up to 8.0 | Up to 9.6 |
| Total | 45.0 | 54.0 |

(Step 2) Gently vortex mix, briefly centrifuge, and place back on ice.

(Step 3) Bring PCR2 mix into post-amplification work-space.

(Step 4) In a new 0.2 mL PCR tube, pipet 5.0 µL purified mRNA targeted PCR1 products into 45 µL PCR2 reaction mix.

(Step 5) Gently vortex, and briefly centrifuge.

(Step 6) Program the thermal cycler as shown in Table 12. Do not use fast cycling mode.

TABLE 12

| PCR Program | | | |
|---|---|---|---|
| Step | Cycles | Temp | time |
| Hot start | 1 | 95° C. | 3 min |
| Denaturation | 10[a] | 95° C. | 30 sec |
| Annealing | | 60° C. | 3 min |
| Extension | | 72° C. | 1 min |
| Final extension | 1 | 72° C. | 5 min |
| Hold | 1 | 4° C. | ∞ |

[a]Cycle number might require optimization according to cell number and type.

Stopping point: The PCR can run overnight.

Purifying mRNA Targeted PCR2 Products

Perform purification in the post-amplification workspace.

(Step 1) Bring AMPure XP beads to room temperature (15° C. to 25° C.), and vortex at high speed 1 minute until beads are fully resuspended.

(Step 2) Briefly centrifuge mRNA targeted PCR2 products.

(Step 3) Pipet 40 µL AMPure XP beads into tube with 50 µL the mRNA targeted PCR2 products. Pipet-mix 10 times.

(Step 4) Incubate at room temperature (15° C. to 25° C.) for 5 minutes.

(Step 5) Place tube on strip tube magnet for 3 minutes. Remove supernatant.

(Step 6) Keeping tube on magnet, gently add 200 µL fresh 80% ethyl alcohol into tube, and incubate 30 seconds. Remove supernatant.

(Step 7) Repeat step 6 once for two washes.

(Step 8) Keeping tube on magnet, use a small-volume pipette to remove residual supernatant from tube, and discard.

(Step 9) Air-dry beads at room temperature (15° C. to 25° C.) for 3 minutes.

(Step 10) Remove tube from magnet, and resuspend bead pellet in 30 µL Elution Buffer (Cat. No. 91-1084). Pipet-mix until beads are fully resuspended.

(Step 11) Incubate at room temperature (15° C. to 25° C.) for 2 minutes, and briefly centrifuge.

(Step 12) Place tube on magnet until solution is clear, usually ≤30 seconds.

(Step 13) Pipet entire eluate (~30 µL) into a new 1.5 mL LoBind Tube (purified mRNA targeted PCR2 products).

Stopping point: Store at 2° C. to 8° C. before proceeding on the same day or at −25° C. to −15° C. for ≤6 months.

(Step 14) Estimate the concentration by quantifying 2 µL of the mRNA targeted PCR2 products with a Qubit™ Fluorometer using the Qubit dsDNA HS Assay Kit. Follow the manufacturer's instructions.

(Step 15) Dilute an aliquot of mRNA targeted PCR2 products to 0.2-2.7 ng/µL with Elution Buffer (Cat. No. 91-1084).

Performing PCR 2 on the Purified PCR 1 Product

The dCODE and (optional) AbSeq purified PCR1 product is used for amplifying the dCODE® library using unique dCODE library primers (listed below).

(Step 1) In pre-amplification workspace, pipet reagents into a new 1.5 mL LoBind Tube on ice to generate the reaction mixture shown in Table 13. (If more than one sample make 20% overhead on the reaction mix).

TABLE 13

| dCODE SPECIFIC PCR 2 REACTION MIX | | |
|---|---|---|
| Kit component name[a)] | µl 1x | 2x + 20% |
| Nuclease-Free Water | 8 | 19, 2 |
| PCR MasterMix | 25 | 60, 0 |
| Universal Oligo | 2 | 4, 8 |
| dCODE specific primer 2 | 10 | 24, 0 |
| Total | 45 | 108 |
| PCR1 purified AbSeq library (UNDILUTED) | 5 | 5 µl/ sample |

[a)]Reagents for PCR2 amplification is included in the "BD Rhapsody ™ Targeted mRNA and AbSeq Amplification Kit (Cat. No. 633774)

(Step 2) Gently vortex mix, briefly centrifuge, and place back on ice.

(Step 3) Bring PCR2 mixes into post-amplification work-space.

(Step 4) In two separate, new 0.2 mL PCR tubes: (i) mRNA targeted PCR1 products: Pipet 5.0 µL products into 45.0 µL mRNA targeted PCR2 reaction mix; (ii) Sample Tag PCR1 products: Pipet 5.0 µL products into 45.0 µL Sample Tag PCR2 reaction mix.

(Step 5) Gently vortex, and briefly centrifuge.

(Step 6) For dCODE library PCR2, program the thermal cycler as shown in Table 14. (Do not use fast cycling mode)

TABLE 14

| dCODE LIBRARY PCR2 | | | |
|---|---|---|---|
| Step | Cycles | Temp | time |
| Hot start | 1 | 95° C. | 3 min |
| Denature | 10* | 95° C. | 30 sec |
| Annealing | | 66° C. | 30 sec |
| Extension | | 72° C. | 1 min |
| Final extension | 1 | 72° C. | 5 min |
| Hold | 1 | 4° C. | ∞ |

*Cycle number might require optimization according to expected cell number

Purifying the dCODE Library (Step 1) Bring AMPure XP beads to room temperature (15° C. to 25° C.), and vortex at high speed 1 minute until beads are fully resuspended (Step 2) Briefly centrifuge PCR2 products.

(Step 3) To 50.0 µL PCR2 products pipet 60 µL AMPure beads.

(Step 4) Pipet-mix 10 times, and incubate at room temperature (15° C. to 25° C.) for 5 minutes.

(Step 5) Place tube on strip tube magnet for 3 minutes. Remove supernatant.

(Step 6) Keeping tube on magnet, gently add 200 μL fresh 80% ethyl alcohol into tube, and incubate 30 seconds. Remove supernatant.

(Step 7) Repeat step 6 once for two washes.

(Step 8) Keeping tube on magnet, use a small-volume pipette to remove residual supernatant from tube and discard.

(Step 9) Air-dry beads at room temperature (15° C. to 25° C.) for 3 minutes.

(Step 10) Remove tubes from magnet and resuspend bead pellet in 30 Elution Buffer (Cat. No. 91-1084). Pipet-mix until beads are fully resuspended.

(Step 11) Incubate at room temperature (15° C. to 25° C.) for 2 minutes, and briefly centrifuge.

(Step 12) Place tubes on magnet until solution is clear, usually ≤30 seconds.

(Step 13) Pipet entire eluate (~30 μL) of the sample into a new 1.5 mL LoBind Tubes (purified dCODE PCR2 products).

(Step 14) Estimate the concentration of the sample by quantifying 2 μL of the PCR2 products with a Qubit™ Fluorometer using the Qubit dsDNA HS Assay Kit.

Stopping point: Store at 2° C. to 8° C. before proceeding on the same day or at −25° C. to −15° C. for ≤6 months.

Quantify the dCODE® Library

Measure the yield of the dCODE® PCR2 products (amplicon should be app. 190 bp) by using the Agilent Bioanalyzer with the High Sensitivity Kit (Agilent Cat. No. 5067-4626). Follow the manufacturer's instructions.

Figure 7:
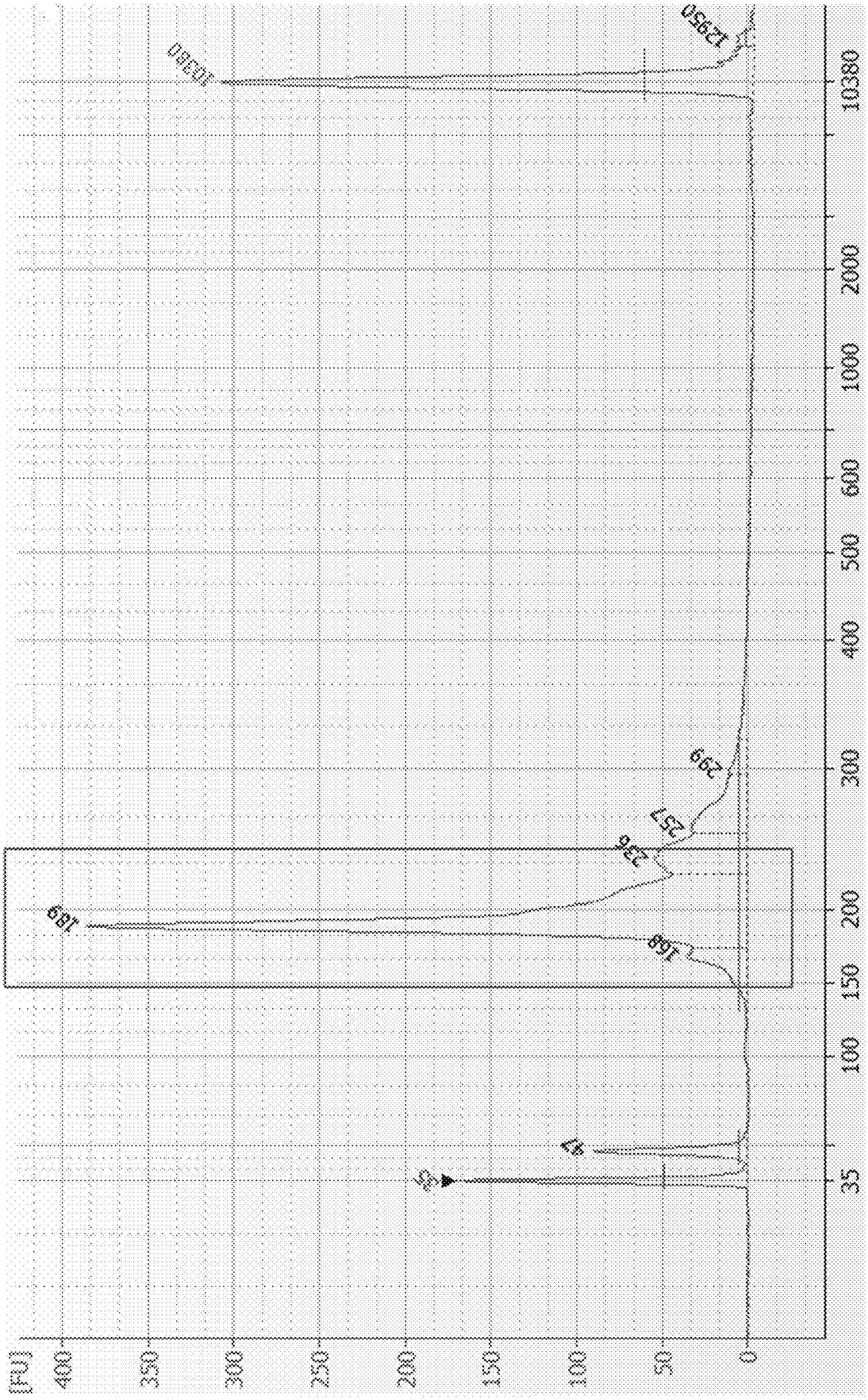
FIG. 7 depicts a non-limiting exemplary Bioanalyzer trace containing dCODE PCR2 product (approximately 190 bp).

FIG. 7 depicts a non-limiting exemplary Bioanalyzer trace containing dCODE PCR2 product (approximately 190 bp).

Performing Index PCR to Prepare Final Libraries

Index PCR3 is performed on each of the prepared purified PCR1 products (AbSeg™ library (optional) and PCR2 (dCODE and mRNA), using different reverse index primers (provided in the "BD Rhapsody™ Targeted mRNA and AbSeq Amplification Kit (Cat. No. 633774)).

(Step 1) In pre-amplification workspace, prepare the 1 library+20% overage of the final amplification mix (Table 15) for each of the products. Pipet reagents into a new 1.5 mL LoBind Tube on ice.

For a single cartridge or sample, consider using the same index for all libraries for that cartridge or sample. If libraries are to be indexed differently, make separate index PCR mixes containing different library reverse primers for each library type.

TABLE 15

INDEX PCR MIX

| Component | For 1 library (μL) | For 1 library + 20% overage (μL) |
|---|---|---|
| PCR Master Mix (Cat. No. 91-1083) | 25.0 | 30.0 |
| Library Forward Primer (Cat. No. 91-1085) | 2.0 | 2.4 |
| Library Reverse Primer 1-4 (Cat. No. 650000080, 650000091-93) | 2.0 | 2.4 |
| Nuclease-Free Water (Cat. No. 650000076) | 18.0 | 21.6 |
| Total | 47.0 | 56.4 |

(Step 2) Gently vortex mix, briefly centrifuge, and place back on ice.

(Step 3) Bring index PCR mixes to post-amplification workspace.

(Step 4) In two separate, new 0.2 mL PCR tubes: (a) mRNA targeted PCR2 products, Pipet 3.0 μL of 0.2-2.7 ng/μL products into 47.0 μL index PCR mix; (b) BD AbSeq PCR1 products: Pipet 3.0 μL of 0.1-1.1 ng/μL products into 47.0 μL index PCR mix. Index PCR3 on the dCODE® PCR2 purified product is also performed as described for the AbSeg™ library in step 4—using 3.0 μL of 0.1-1.1 ng/μL dCODE® PCR2 products into 47.0 μL index PCR3 mix.

(Step 5) Gently vortex, and briefly centrifuge.

(Step 6) Program the thermal cycler as shown in Table 16. Do not use fast cycling mode.

TABLE 16

PCR

| Step | Cycles | Temp | time |
|---|---|---|---|
| Hot start | 1 | 95° C. | 3 min |
| Denaturation | 6-8[a] | 95° C. | 30 sec |
| Annealing | | 60° C. | 30 sec |
| Extension | | 72° C. | 30 sec |
| Final extension | 1 | 72° C. | 1 min |
| Hold | 1 | 4° C. | ∞ |

[a]Suggested PCR cycles shown in Table 17.

TABLE 17

PCR CYCLE NUMBER

| Conc. index PCR input for mRNA targeted libraries (ng/μL) | Conc. index PCR input for BD AbSeq libraries (ng/μL) | Suggested PCR cycles |
|---|---|---|
| 1.2-2.7 | 0.5-1.1 | 6 |
| 0.6-1.2 | 0.25-0.5 | 7 |
| 0.2-0.6 | 0.1-0.25 | 8 |

Stopping point: The PCR can run overnight.

Quantification and Quality Control of the dCODE® Final Indexed Library

Figure 8:
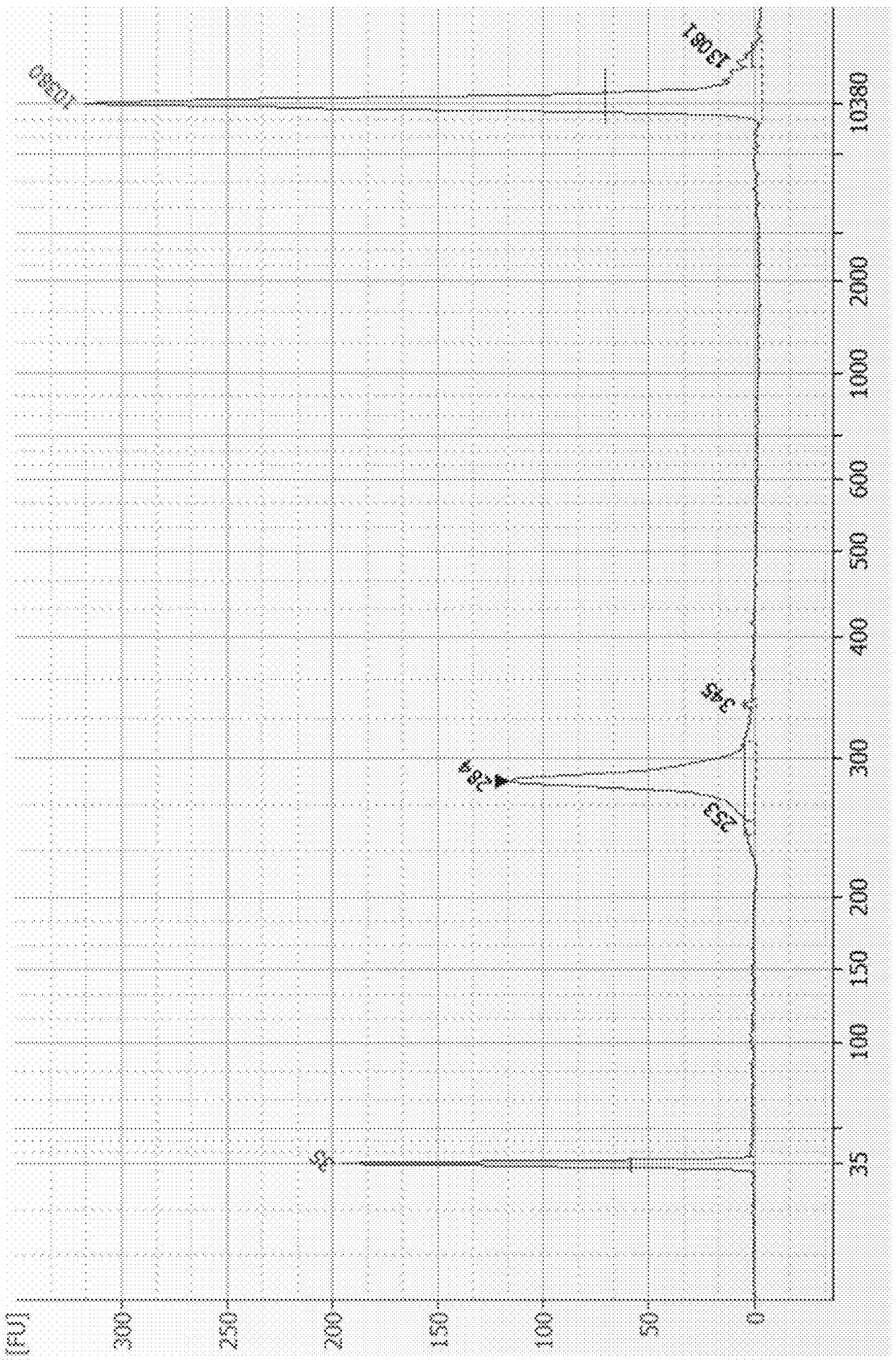
FIG. 8 depicts a non-limiting exemplary Bioanalyzer trace containing Index PCR3 dCODE library products (approximately 285 bp).

Measure the yield of the index PCR3 products (app. 290 bp) by using the Agilent Bioanalyzer with the High Sensitivity Kit (Agilent Cat. No. 5067-4626). Follow the manufacturer's instructions. FIG. 8 depicts a non-limiting exemplary Bioanalyzer trace containing Index PCR3 dCODE library products (approximately 285 bp).

Sequencing Requirements

For sequencing of the dCODE library follow the requirement and recommendations for AbSeg™ in the "mRNA Targeted and BD™ AbSeq Library Preparation with the BD Rhapsody™ Targeted mRNA and AbSeq Amplification Kit, protocol. (Doc ID: 214293).

BD Rhapsody™ Protocol mRNA Targeted and BD™ AbSeq Library Preparation with the BD Rhapsody™ Targeted mRNA and AbSeq Amplification Kit (Doc ID: 214293).

Amplification Primers for dCODE™ Dextramer® Specific Library Preparation

```
dCODE PCR1 primer
(5'-GGAGGGAGGTTAGCGAAGGT-3'; SEQ ID NO: 1)
and

dCODE PCR2 Primer
(5'-CAGACGTGTGCTCTTCCGATCTGGAGGGAGGTTAGCGAAGGT-3';
SEQ ID NO: 2).
```

Primers can be used at a 10 μM concentration.

Example 2

Multiomic Characterization of T Cell Populations at the Single Cell Level Utilizing Sensitive dCODE Dextramer and BD AbSeq Ab-Oligos on the BD Rhapsody Single-Cell Analysis System Adoptively transferred antigen-specific T cells have shown great efficacy in treatment of some virus-associated diseases and malignancies. A major driver of the development of adoptive T cell therapy has been the ability to successfully characterize the functional status and antigen specificity of T cells. However, this has been limited by inefficient detection of antigen-specific T cells, possibly due to their low frequency and low binding affinities to known MHC-peptide complexes. This example demonstrates the combination combine two powerful technologies, advanced dCODE™ Dextramer® from Immudex and single-cell multiomics analysis using the BD Rhapsody™ Single-Cell Analysis System, using the compositions and methods provided herein, to detect and characterize disease-specific CD8+ T cells within thousands of PBMCs. The disclosed compositions and methods can identify over 350 mRNAs alongside a panel of over 20 BD® AbSeq Cell Surface Protein Markers which can be associated with T cell activation states. These data can be used to define T cell phenotypes alongside antigen specificity of enriched CD8+ Dextramer+ cells from a PBMC population. This example outlines the utility of the disclosed compositions and methods for high-resolution T cell profiling that has broader implications and utility in immuno-oncology, infectious diseases and autoimmunity. Protocols similar to those provided in Example 1 were employed.

Approach

Figure 9B:
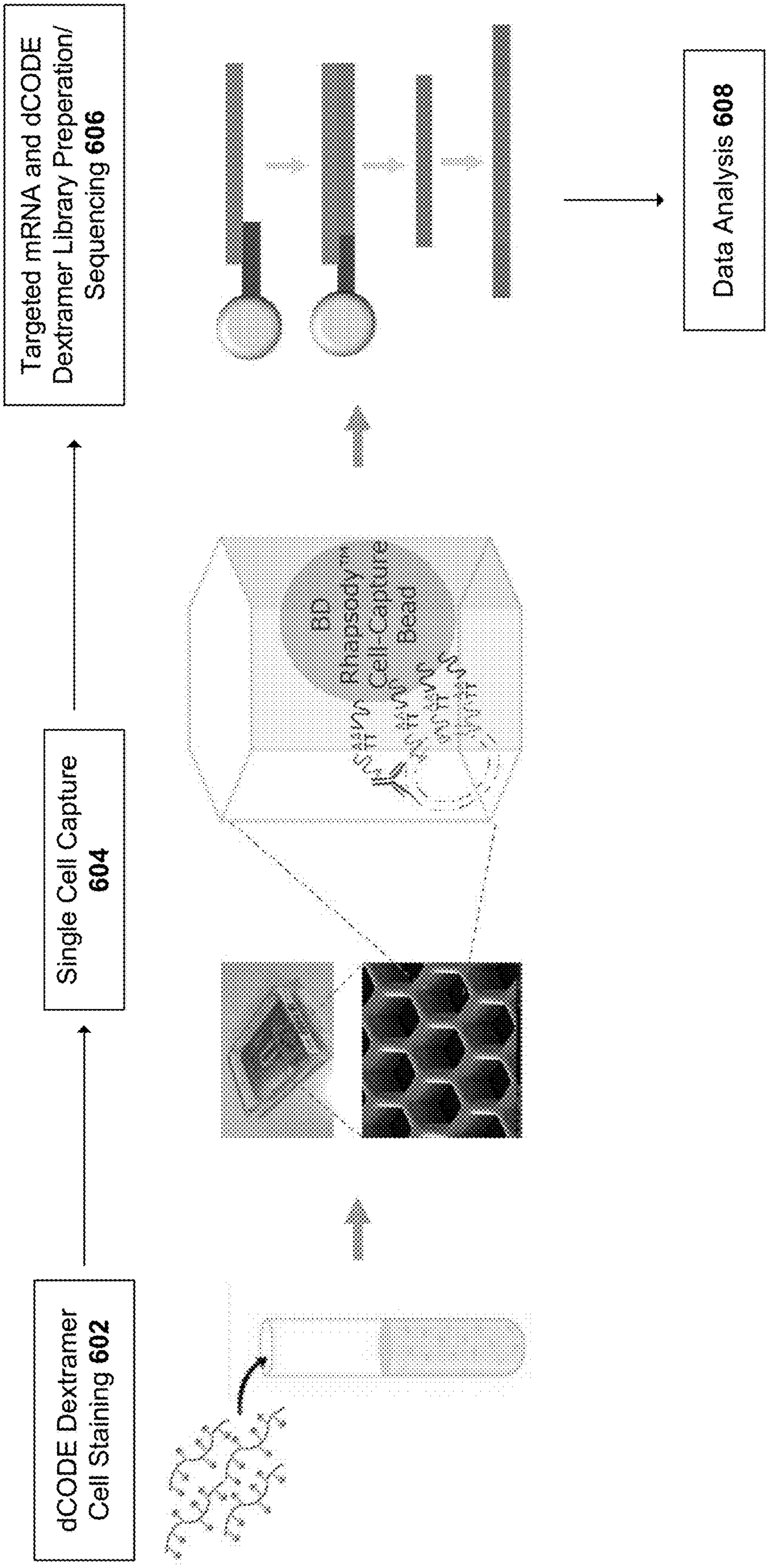
Figure 9C:
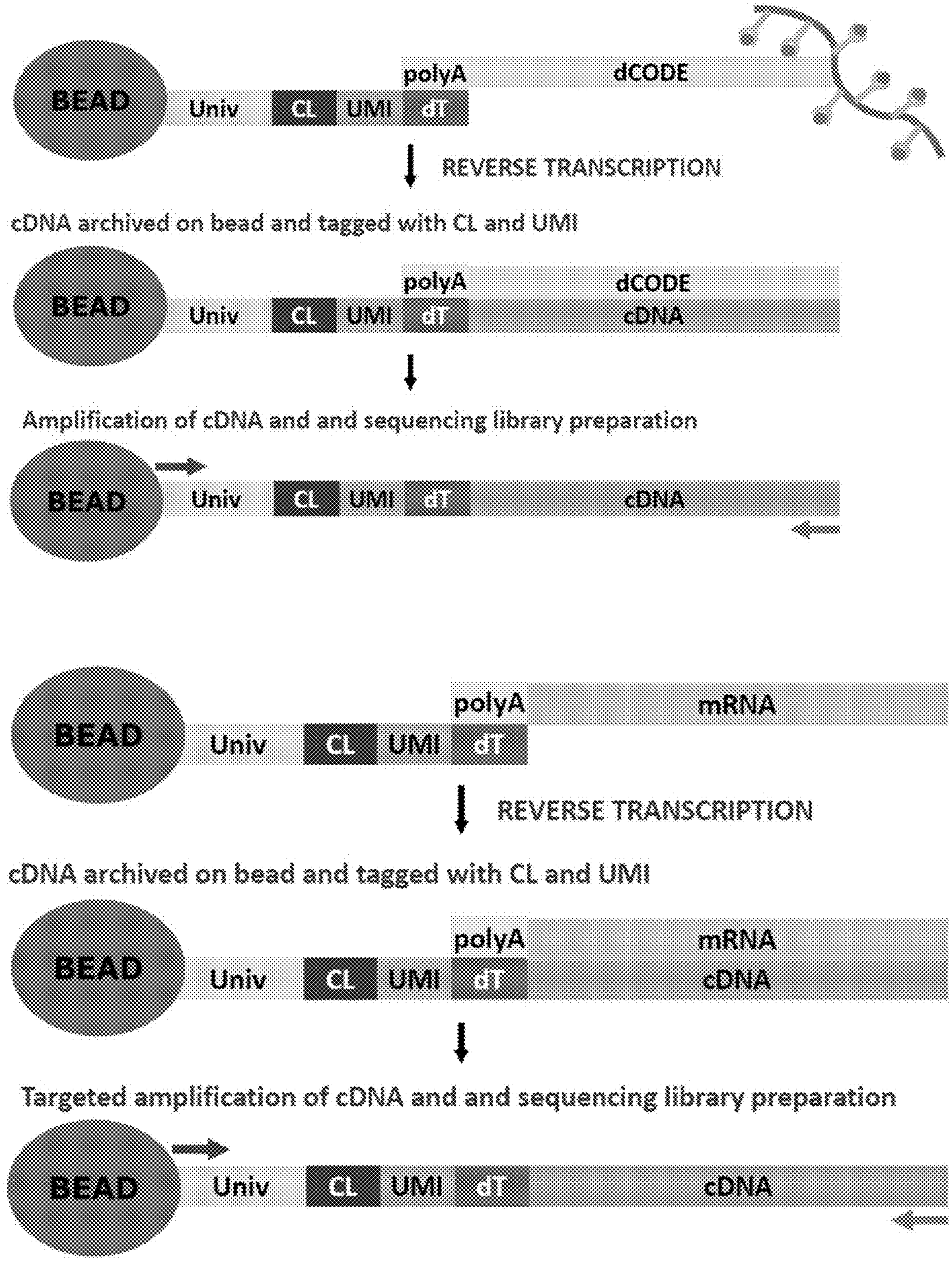
Figure 9D:
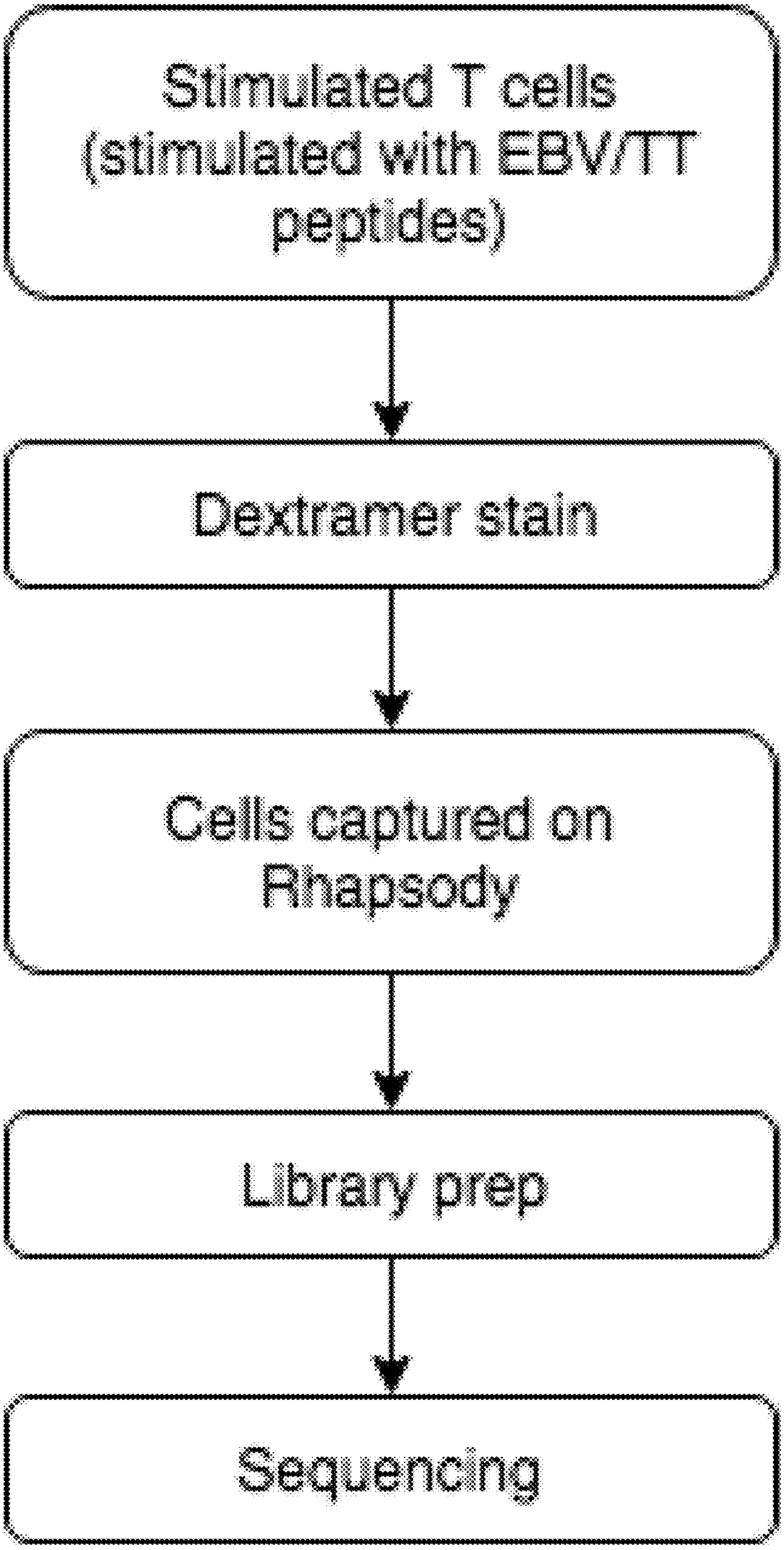
Figure 9E:
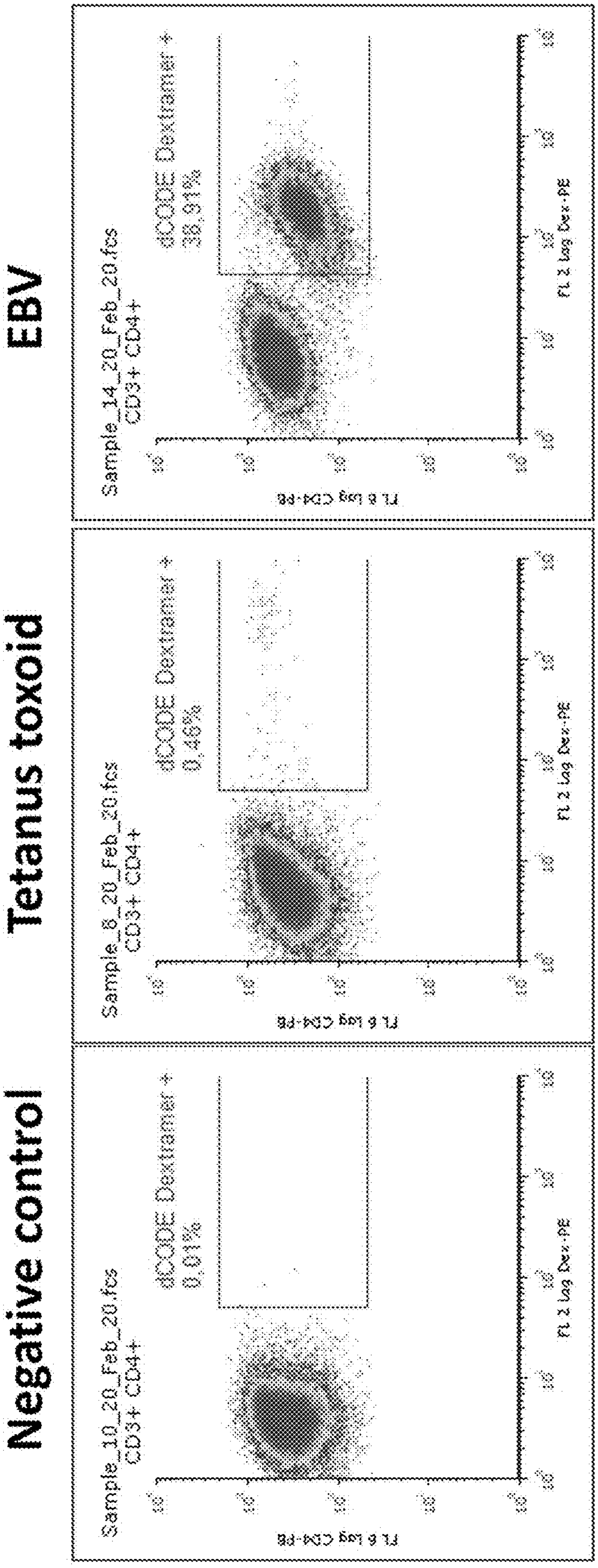
Figure 9F:
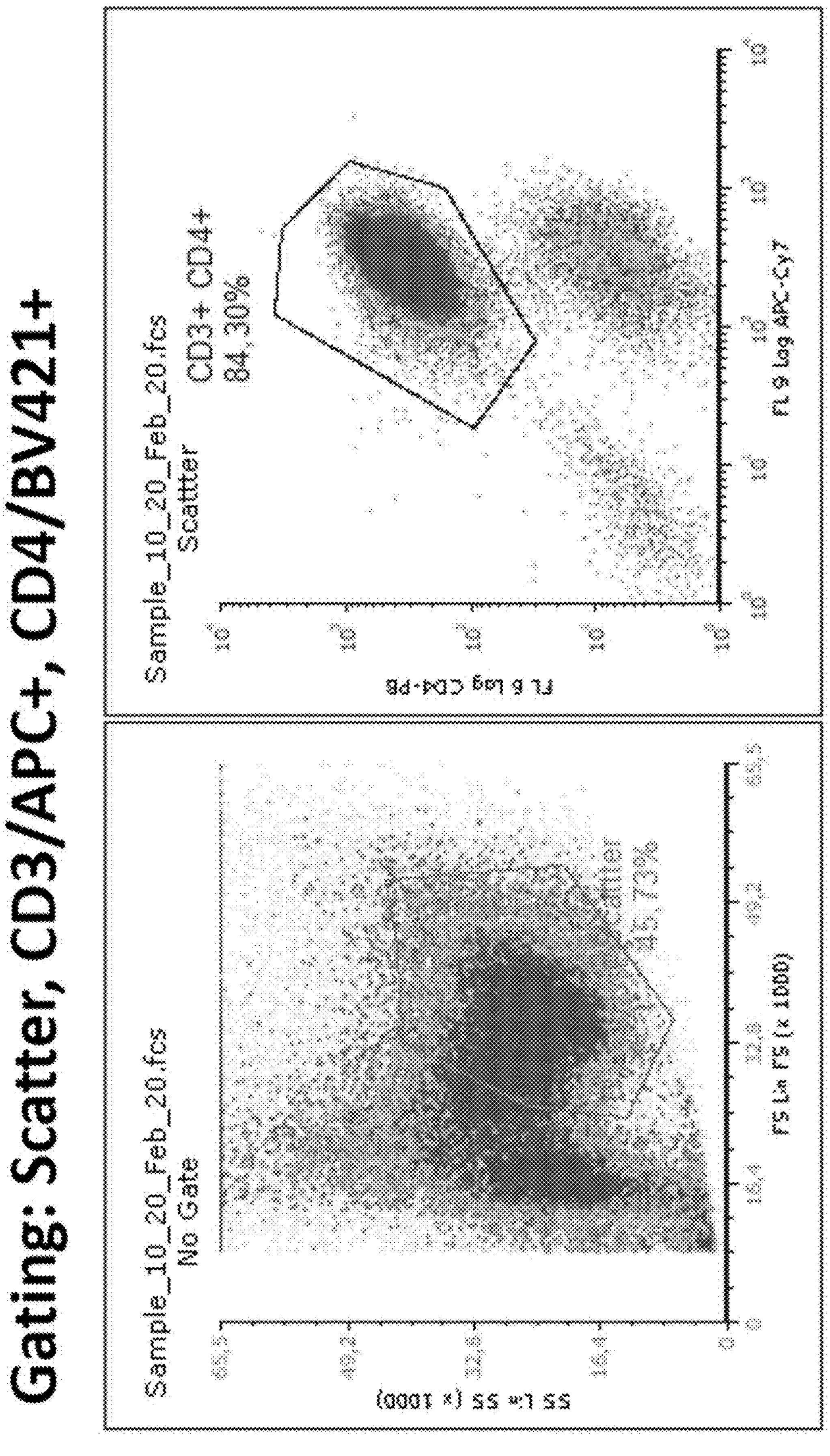

FIGS. 9A-9F depict non-limiting exemplary experimental workflows and molecular mechanisms of Immudex dCODE and BD Rhapsody System single cell sequencing. FIG. 9A depicts a non-limiting exemplary Immudex dCODE Dextramer design compatible with BD Rhapsody System. They contain a dCODE-specific barcode that is associated with a specific antigen epitope that can be amplified and sequence simultaneously along with targeted mRNA. FIG. 9B depicts a non-limiting exemplary BD Rhapsody System targeted workflow with dCODE Dextramer. FIG. 9C depicts non-limiting exemplary beads with hybridized mRNA and dCODE retrieved from cartridge. Cells are first stained with a panel of dCODE Dextramers followed by single cell capture on the BD Rhapsody System that uses microwells to isolate individual cells prior to cell lysis. Upon lysis poly-adenylated sequences from mRNA and dCODE Dextramers (as shown in FIG. 9C) are captured on the beads. cDNA and library preparations for sequencing are completed followed by data analysis using SeqGeq™ Software. FIGS. 9D-9F depict a non-limiting exemplary experimental design: Human PBMCs stained with 3 Dextramers. In this study, hPBMCs were stimulated with two peptide antigens, EBV and Tetanus toxoid (TT). Following stimulation the cells were stained simultaneously stained with dCODE EBV- and TT-specific dextramers as well as a negative control dextramer before capture on the BD Rhapsody System. Dextramer-specific populations were examined using the BD Rhapsody System as well as by conventional FACS, where the cells were labeled individually with the same dCODE Dextramer reagents. dCODE Dextramer® specificities were DRB1*0101, with the following antigen peptides: EBV/TSLYNLRRGTALA (SEQ ID NO: 4), TT/KIYSYFPSVISKV (SEQ ID NO: 5), Negative Control Clip/PVSKMRMATPLLMQA (SEQ ID NO: 6). Gating antibodies, CD3/APC and CD4/BV421 were used to define the MHC Class II antigen specific T cells, as CD3+, CD4+ and dCODE (PE) positive.

Results

Figure 10A:
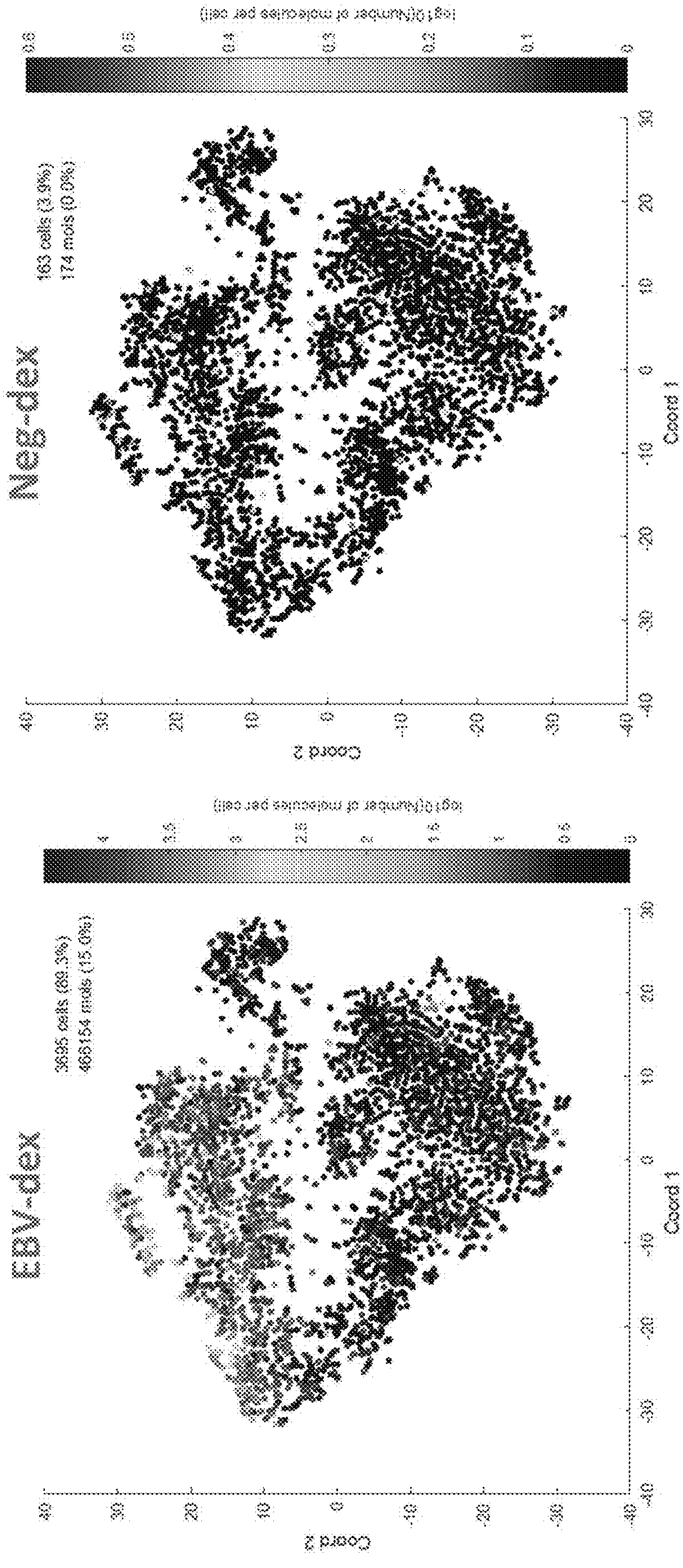
FIGS. 10A-10B show non-limiting exemplary data related to the detection of dextramers on specific cell populations distinct from negative control.
Figure 10A:
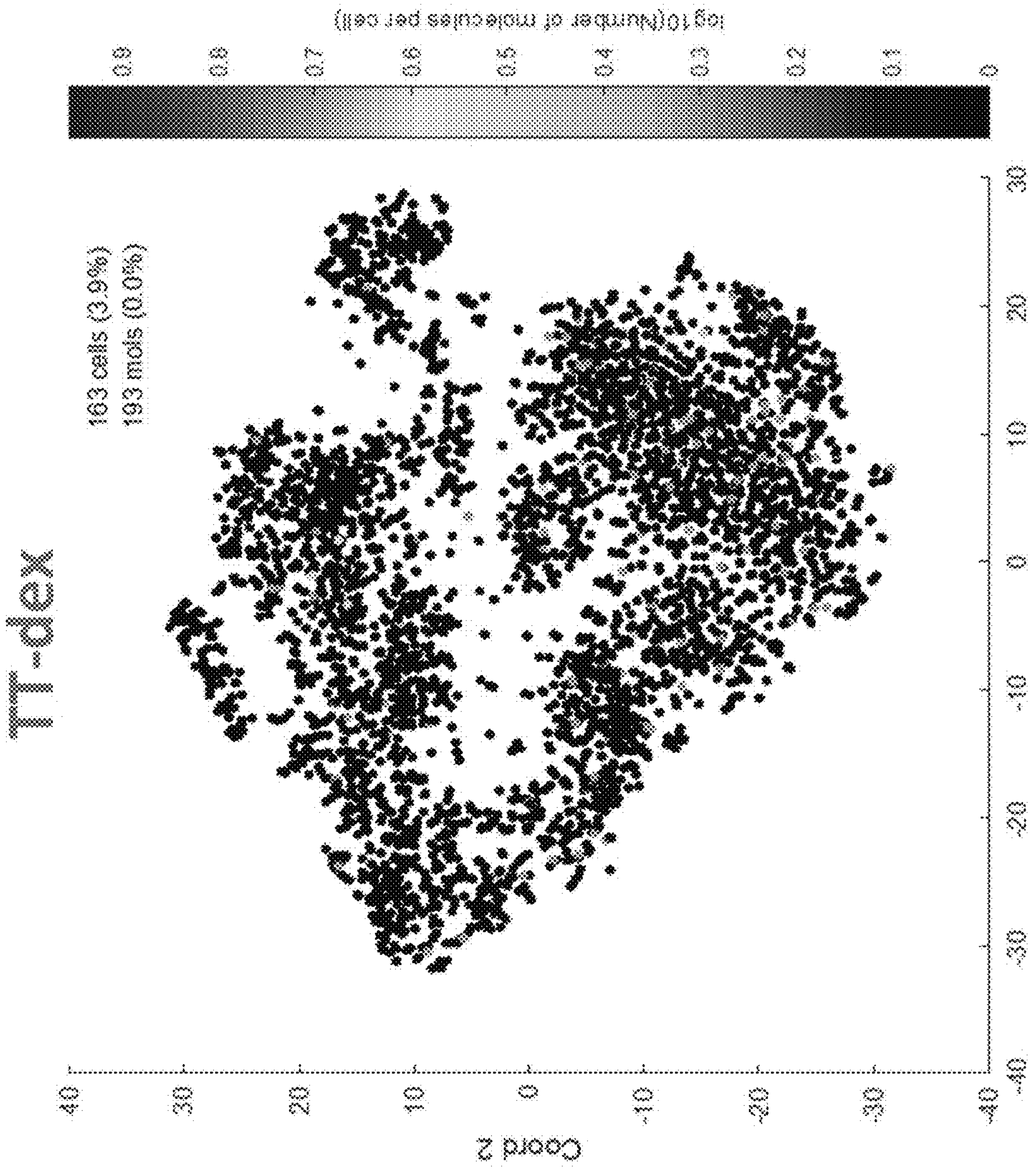
Figure 10A:
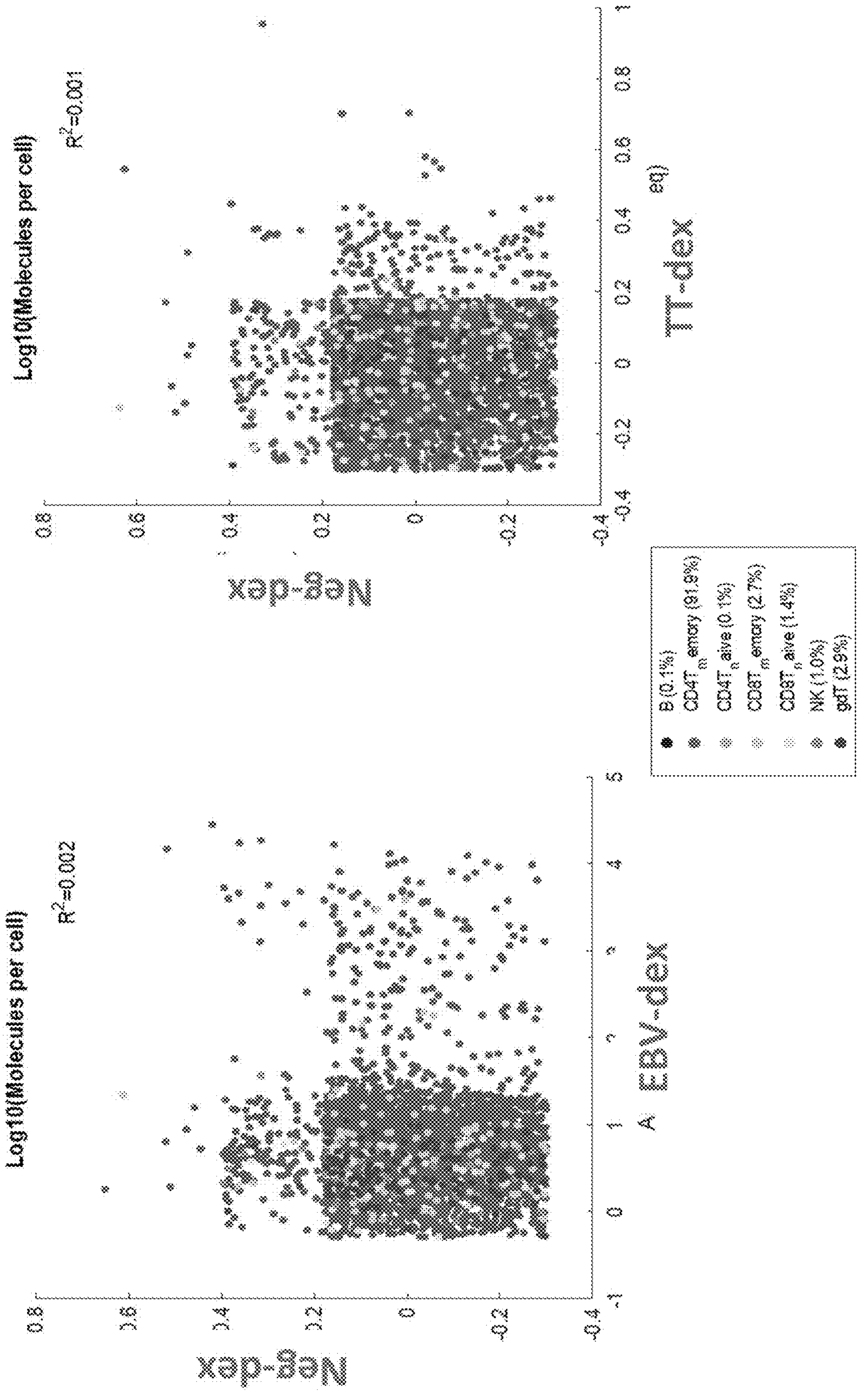
Figure 10B:
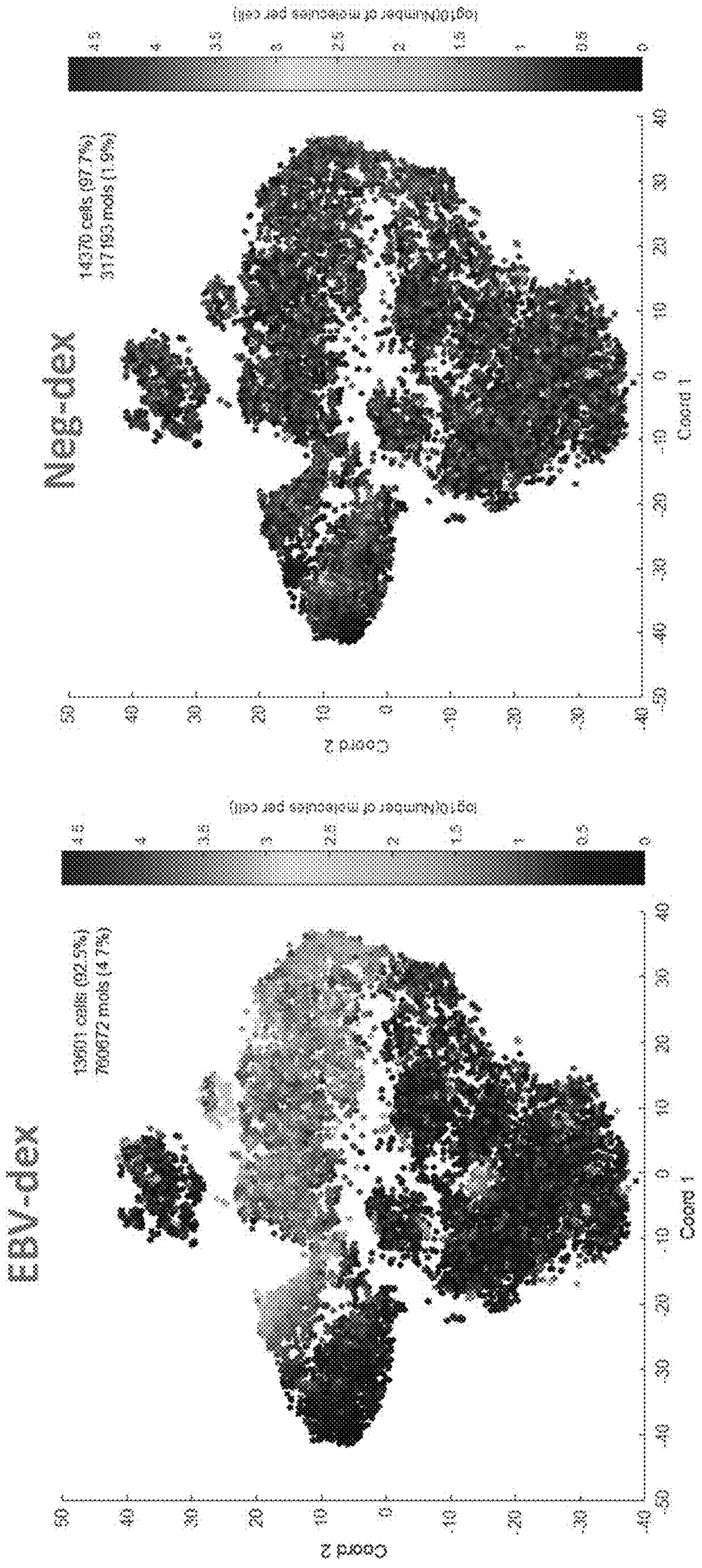
Figure 10B:
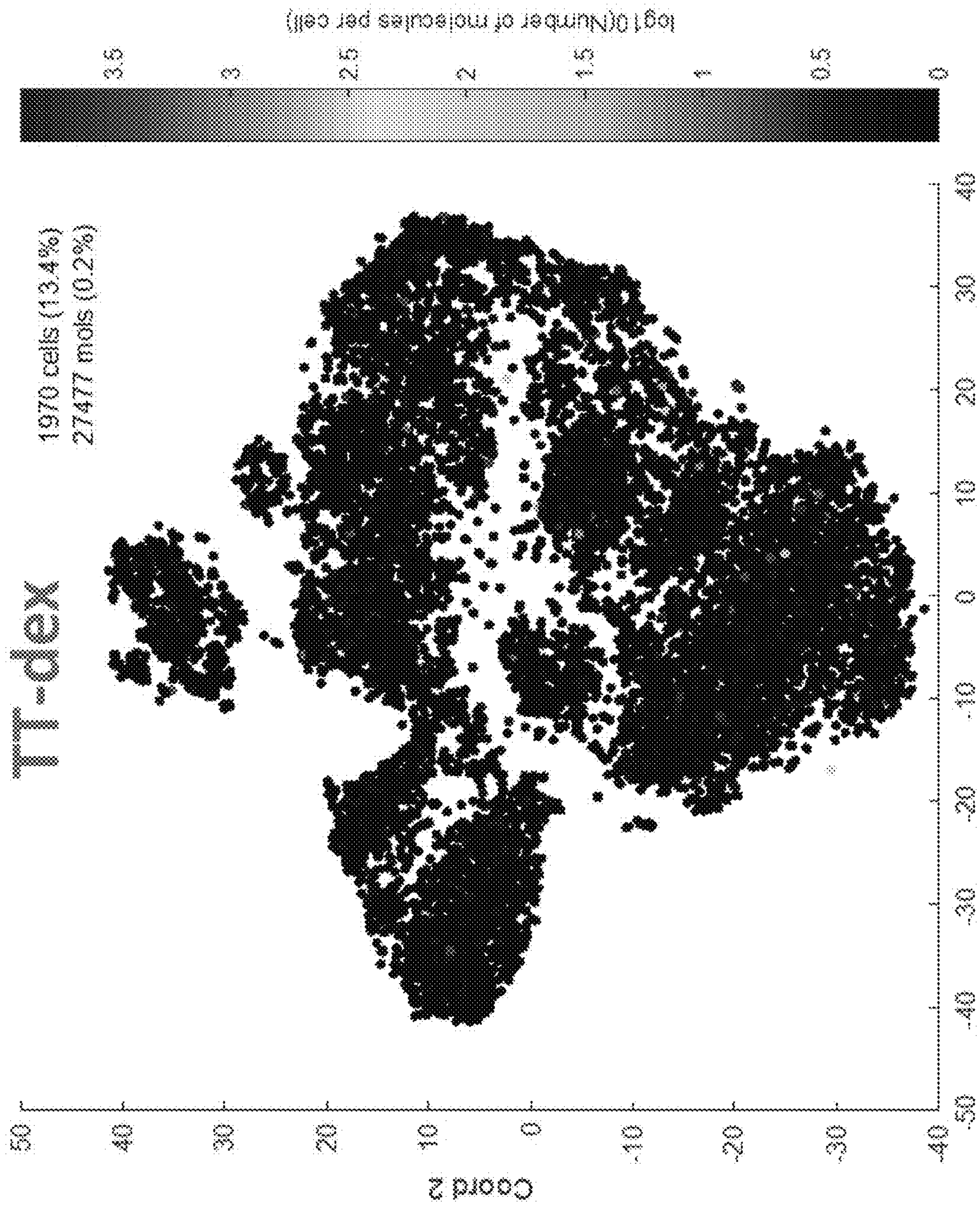
Figure 10B:
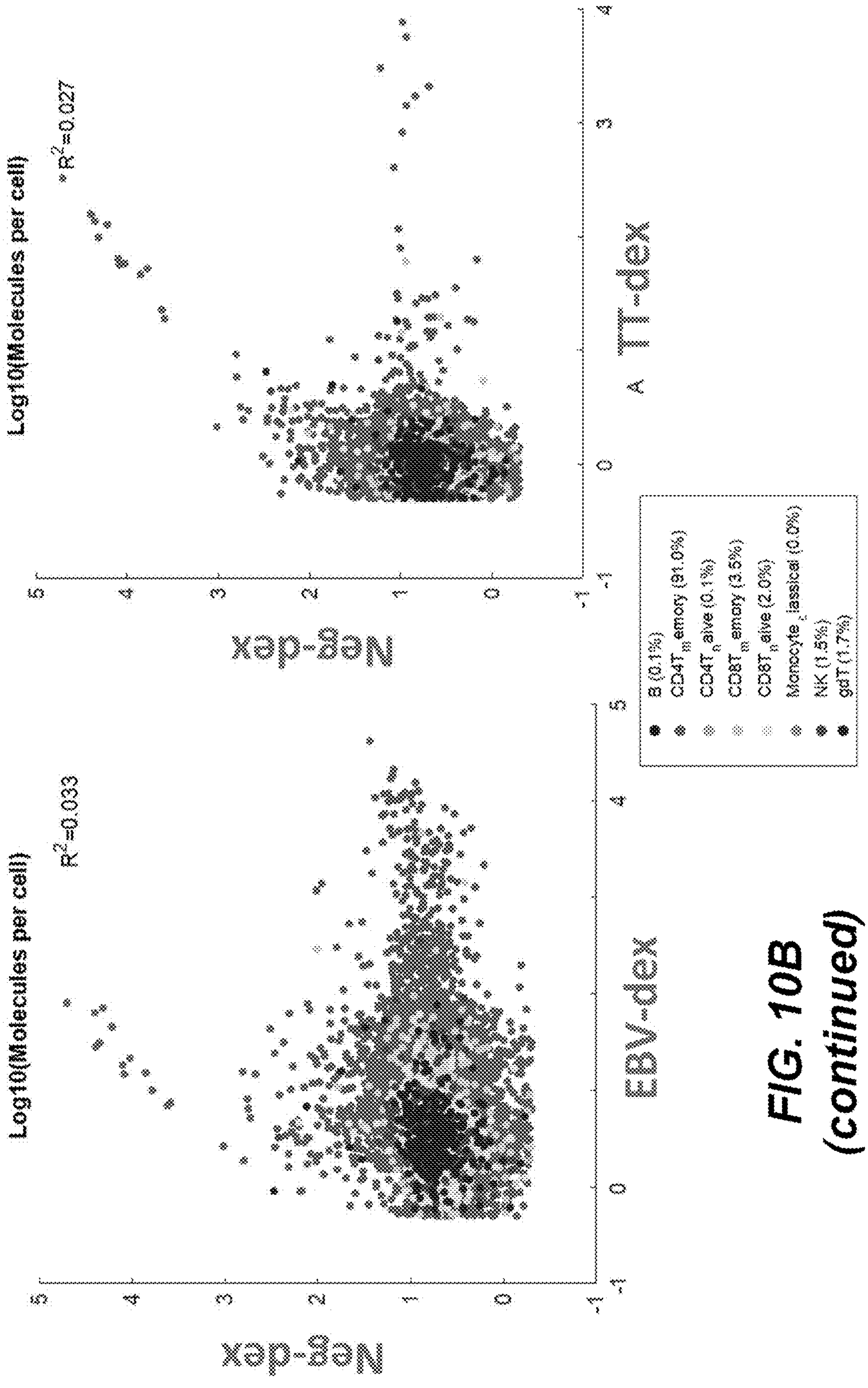

Dextramers can be Detected on Specific Cell Populations Distinct from Negative Control FIGS. 10A-10B show non-limiting exemplary data related to the detection of dextramers on specific cell populations distinct from negative control. Antigen specific T cells in hPBMC samples were identified using dCODE Dextramers®. Detection of EBV and TT dCODE Dextamers® shown in tSNE plots from two independent experiments using 6,000 cells (FIG. 10A) and 30,000 cells (FIG. 10B). Neg-dex represent non-specific binding from a negative control that can be distinguished from both EBV and TT dCODE Dextramers®.

Figure 11A:
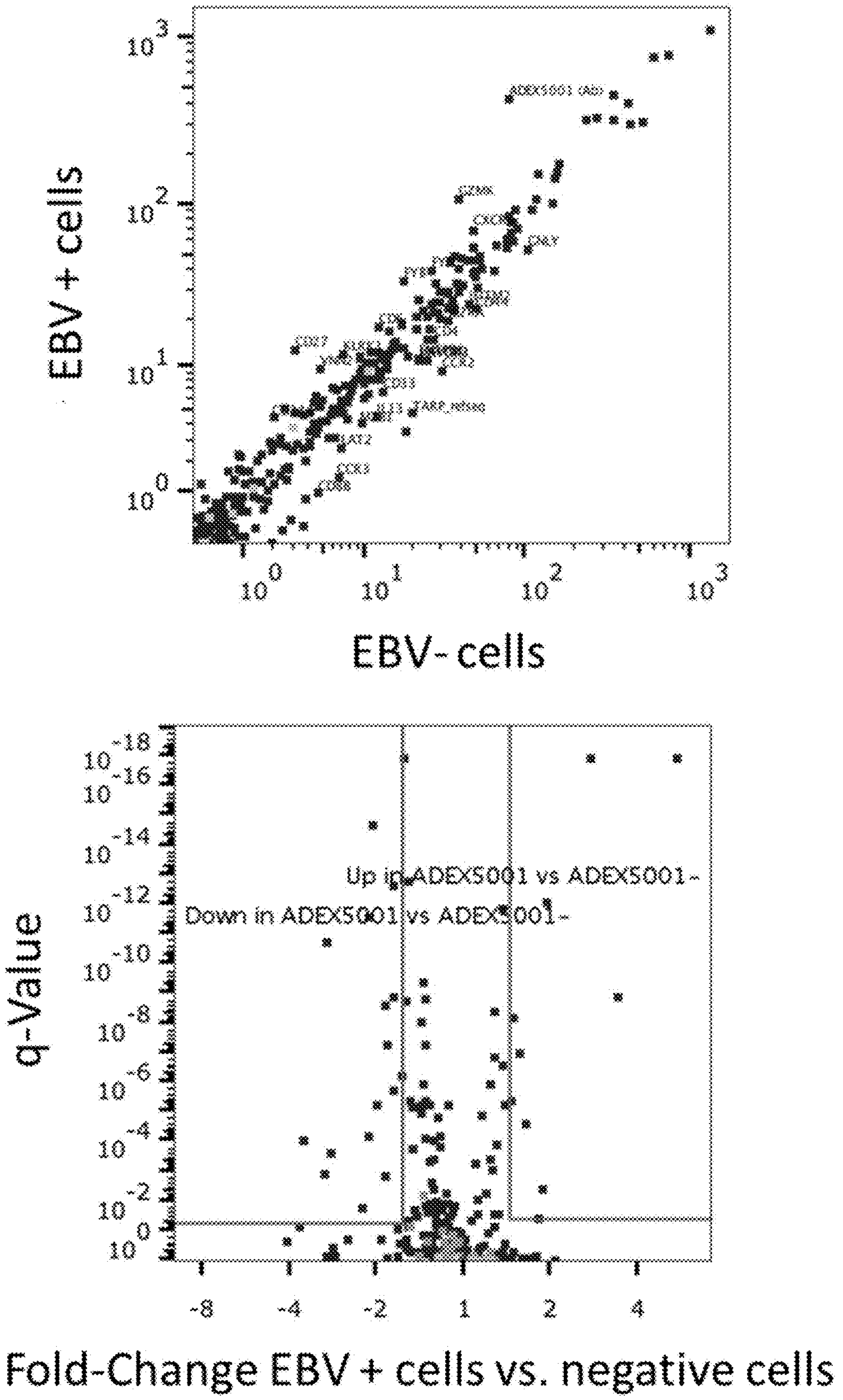
FIGS. 11A-11B show non-limiting exemplary data related to gene expression analysis in EBV+ antigen specific T cells.
Figure 11B:
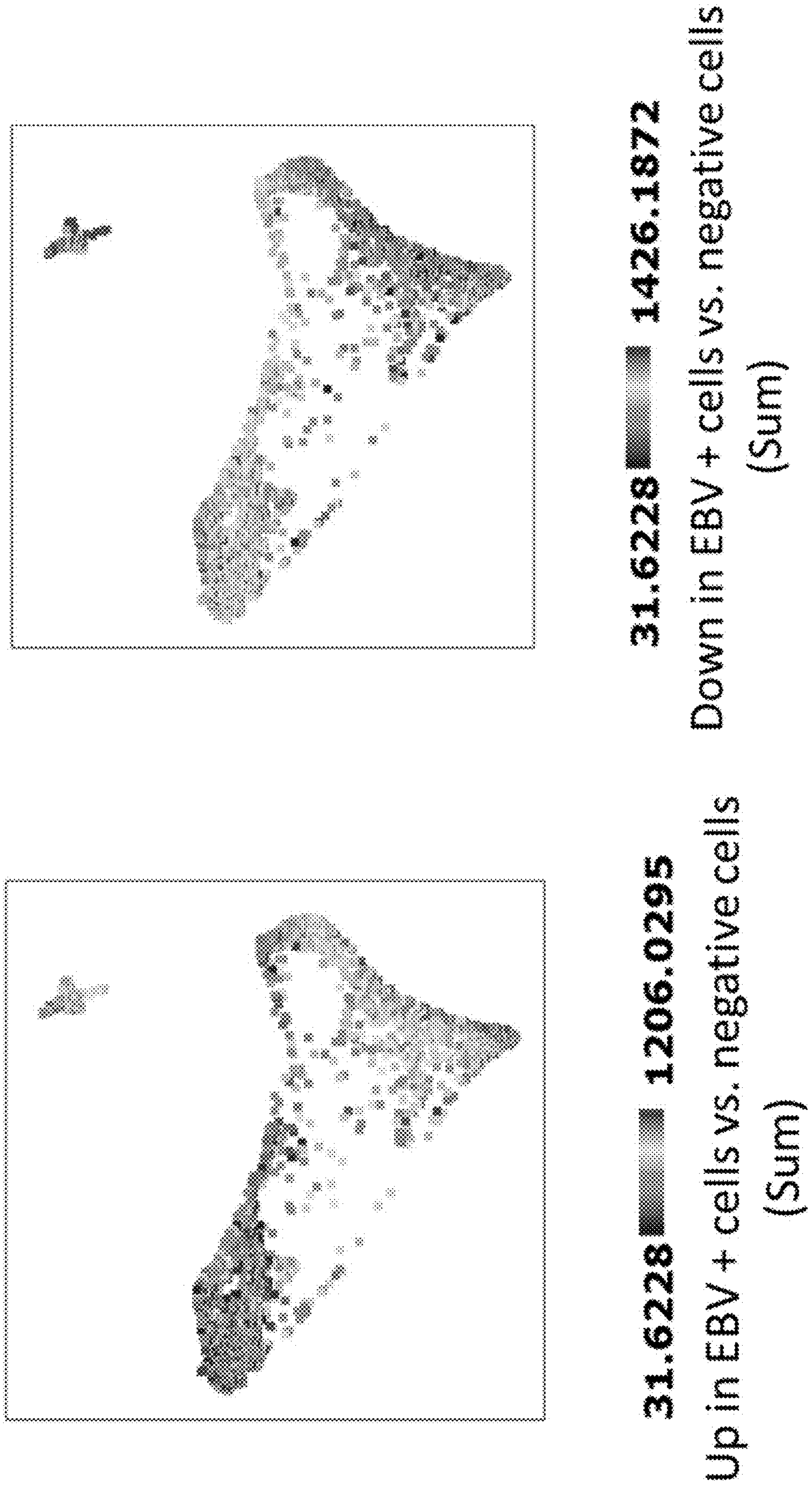

Differential Gene Expression Analysis Shows a Distinct Transcriptional Profile in dCODE Dextramer® Positive T Cells FIGS. 11A-11B show non-limiting exemplary data related to gene expression analysis in EBV+ antigen specific T cells. Differential gene expression between Dextramer EBV+ population vs. EBV-Negative can be identified. The sum of molecules from the upregulated and downregulated genes can be found in opposite coordinates in the TriMap space respectively showing that these cells have distinct transcriptional profiles (Tables 18-19).

TABLE 18

| UP-REGULATED GENES | | | | |
|---|---|---|---|---|
| Feature | FC | q-Val | Mean Test | Mean Ctrl |
| ADEX5001 (Ab) | 5.46 | 1.00E−17 | 435.06 | 78.88 |
| CD27 | 3.43 | 1.24E−09 | 13.24 | 3.16 |
| GZMK | 2.76 | 1.00E−17 | 109.78 | 39.08 |
| FYB | 1.93 | 7.81E−13 | 34.83 | 17.57 |
| VNN2 | 1.87 | 3.72E−03 | 9.96 | 4.86 |
| CD244 | 1.83 | 3.82E−02 | 4.59 | 2.05 |
| KLRK1 | 1.64 | 2.26E−05 | 12.24 | 7.09 |
| FYN | 1.56 | 1.00E−07 | 41.43 | 26.24 |
| CXCR4 | 1.49 | 6.19E−09 | 72.09 | 48.18 |
| CD6 | 1.46 | 4.27E−06 | 18.44 | 12.28 |

TABLE 19

| DOWN-REGULATED GENES | | | | |
|---|---|---|---|---|
| Feature | FC | q-Val | Mean Test | Mean Ctrl |
| TARP refseq | 0.28 | 8.56E−05 | 4.91 | 19.98 |
| CCR3 | 0.33 | 1.20E−03 | 1.48 | 6.49 |
| CCR2 | 0.34 | 1.64E−11 | 9.66 | 30.56 |
| CD8B | 0.35 | 2.25E−04 | 0.99 | 4.71 |

TABLE 19-continued

| DOWN-REGULATED GENES | | | | |
|---|---|---|---|---|
| Feature | FC | q-Val | Mean Test | Mean Ctrl |
| IL13 | 0.45 | 1.67E−02 | 4.70 | 11.79 |
| IFITM3 | 0.47 | 2.31E−12 | 11.12 | 24.76 |
| LAT2 | 0.47 | 6.03E−05 | 2.67 | 6.75 |
| CD44 | 0.49 | 1.78E−15 | 23.67 | 49.48 |
| MZB1 | 0.50 | 5.44E−06 | 4.12 | 9.28 |
| GNLY | 0.53 | 1.29E−03 | 54.51 | 103.01 |
| HAVCR2 | 0.54 | 2.36E−09 | 11.21 | 21.76 |
| ENTPD1 | 0.55 | 4.72E−08 | 11.62 | 21.98 |
| CD33 | 0.57 | 1.84E−06 | 6.97 | 12.96 |
| CD4 | 0.57 | 1.25E−09 | 15.18 | 27.29 |
| IFITM2 | 0.58 | 2.09E−13 | 25.20 | 44.44 |
| IL2RA | 0.62 | 5.75E−07 | 20.00 | 33.08 |

Conclusions dCODE Dextramer® reagents along with BD AbSeq Antibodies can be used to detect multiple antigen specific T cell populations in donor samples using the BD Rhapsody System. BD Targeted mRNA and AbSeq Antibody Panels can enable deep characterization of disease specific T cells in these donor samples. dCODE Dextramer® reagents can also be used together with the BD Rhapsody CDR3 VDJ Single Cell Protocol to provide the sequences of the variable regions of the detected disease-specific T cell receptors.

dCODE Dextramers are compatible with the BD Rhapsody System and can be used alongside targeted mRNA panels to identify antigen-specific cells. All dCODE Dextramers used to stain cells were detected in sequencing experiments and further verified by conventional FACS. Thus, the compositions and methods provided herein can identify distinct cell populations that have expression of positive but not negative dextramers even with low frequencies of antigen-specific T cells.

Example 3 dCODE Dextramer and BD AbSeq Ab-Oligo Library Preparations

Figure 12A:
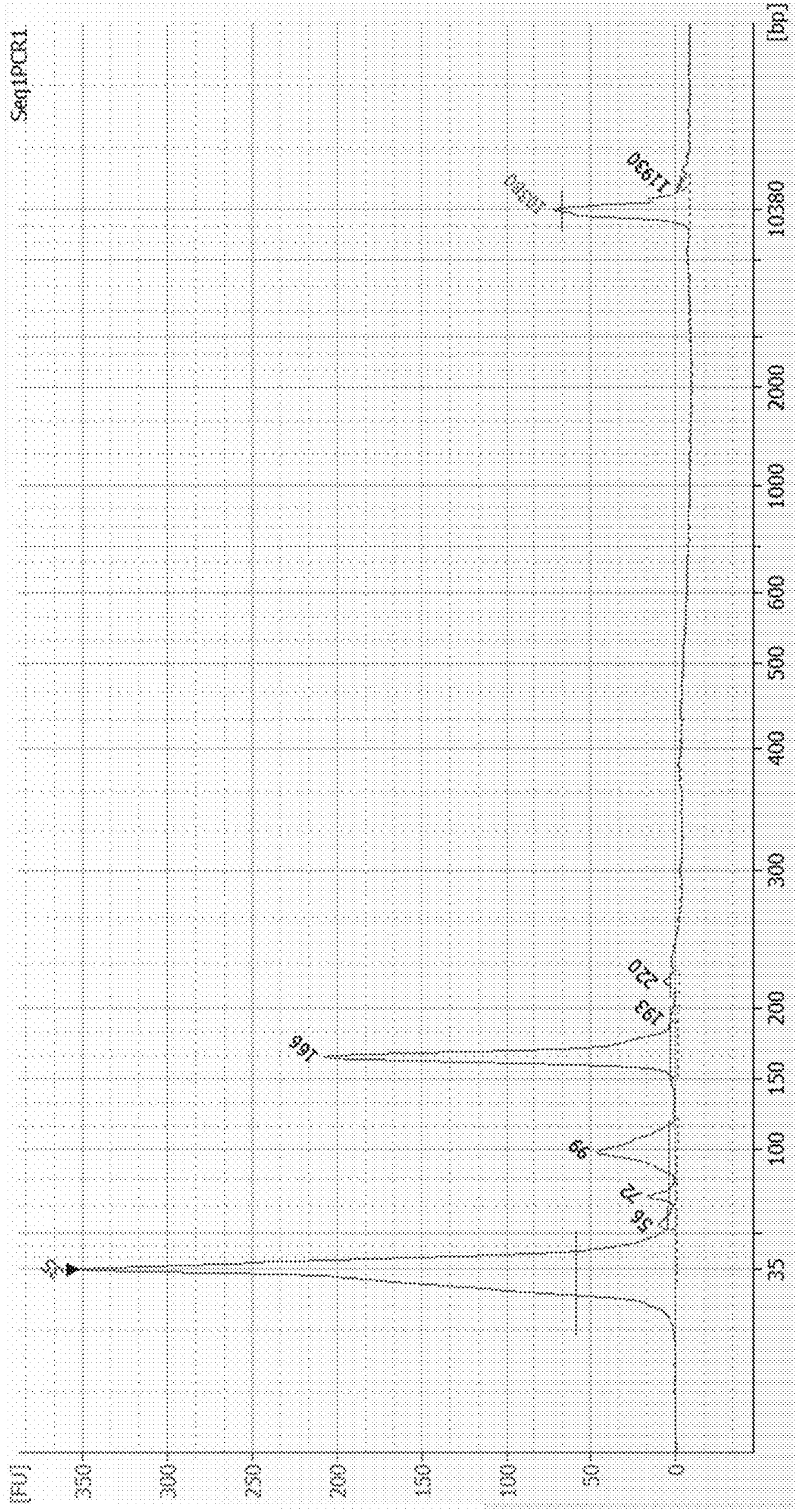
FIGS. 12A-12D depict non-limiting exemplary Bioanalyzer traces.
Figure 12B:
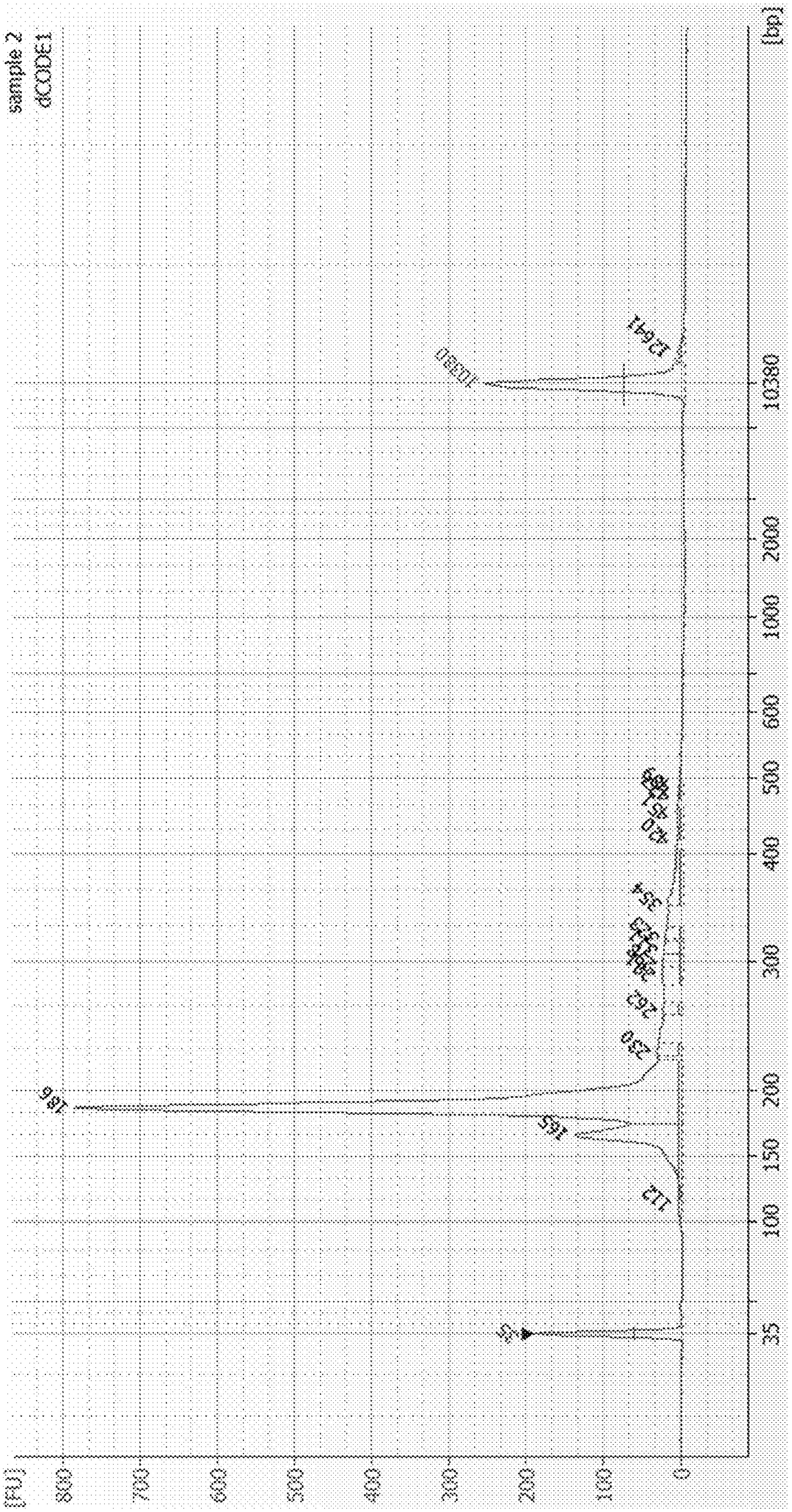
Figure 12C:
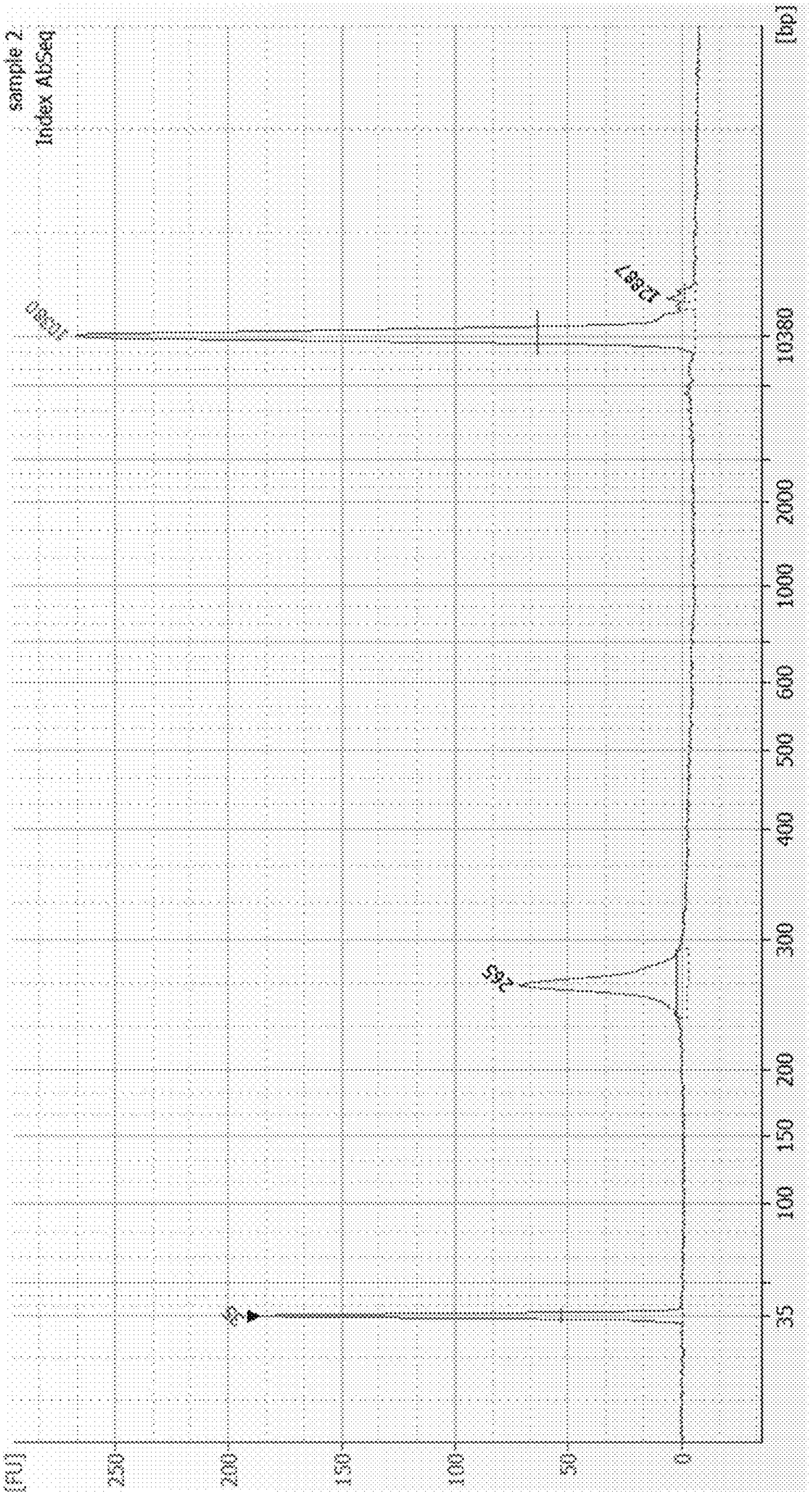
Figure 12D:
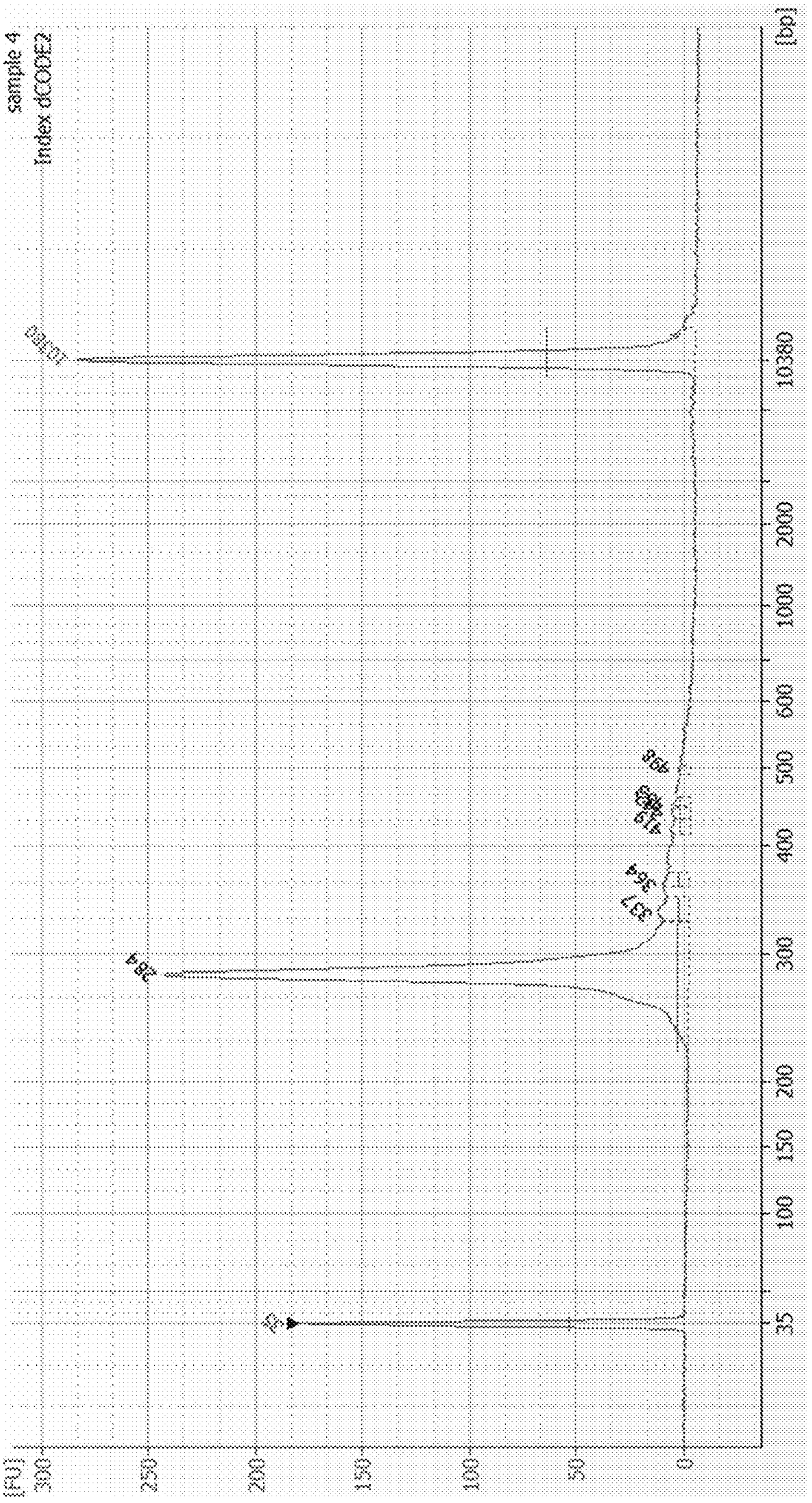

This example outlines the utility of the disclosed compositions and methods for high-resolution T cell profiling. Protocols similar to those provided in Example 1 were employed. FIGS. 12A-12D depict non-limiting exemplary Bioanalyzer traces. FIG. 12A depicts a Bioanalyzer trace of both the RiO dCODE® and AbSeg™ library PCR1 amplicons (peak 166 bp). After PCR1 the library was split. FIG. 12B depicts a Bioanalyzer trace the RiO dCODE® library PCR2 amplicons (peak approximately 190 bp) and demonstrates the separate amplification of only the RiO dCODE dextramer after a second PCR (PCR2) using primers specific for dCODE. Visualization of the separate dCODE library can serve as a QC metric before sequencing. FIGS. 12C-12D depict Bioanalyzer traces of the final library (indexing PCR) preps for Abseq (FIG. 12C; peak 265 bp) and RiO dCODE dextramers (FIG. 12D; peak approximately 290 bp). As they are now independently amplified, this allows a user to sequence these libraries per their recommended sequencing depth as described herein.

Figure 13A:
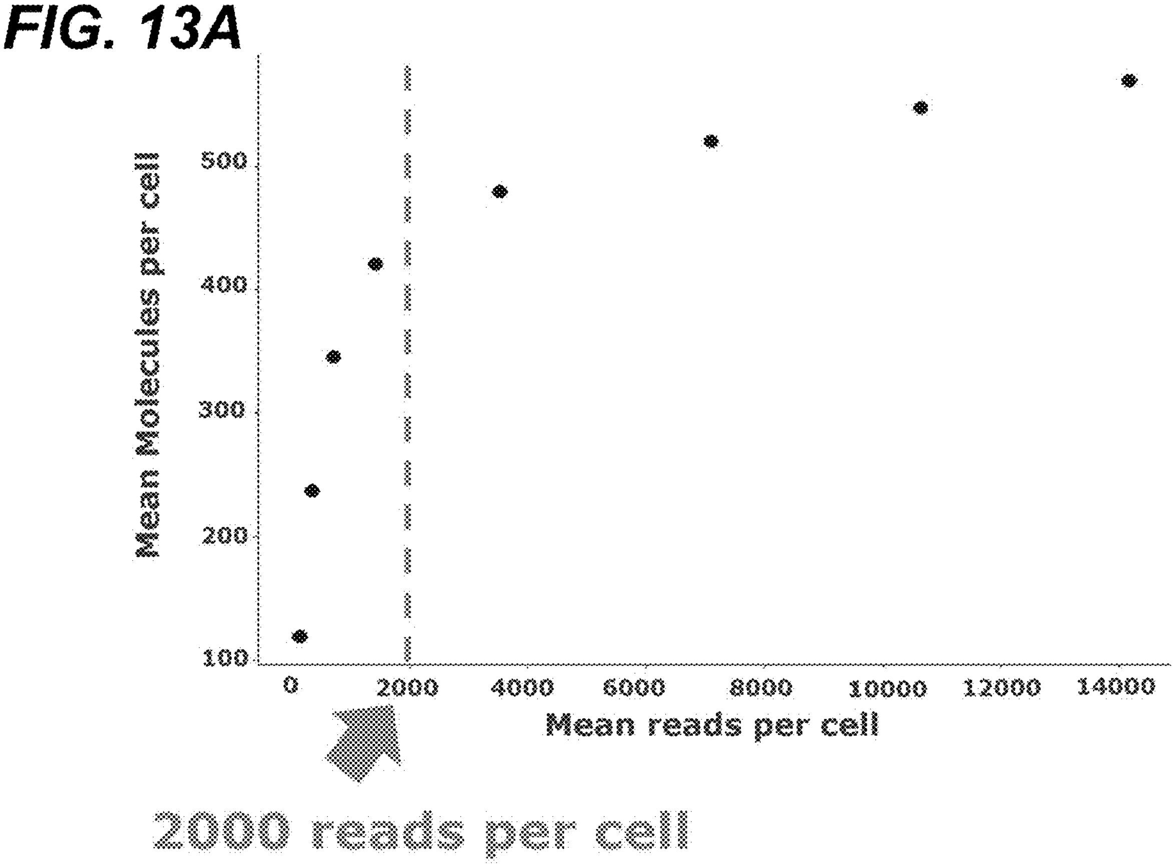
FIGS. 13A-13B depict non-limiting exemplary saturation curves for dCODE Dextramer® (FIG. 13A) and for BD® AbSeq (FIG. 13B; 4-plex, high expressor).
Figure 13B:
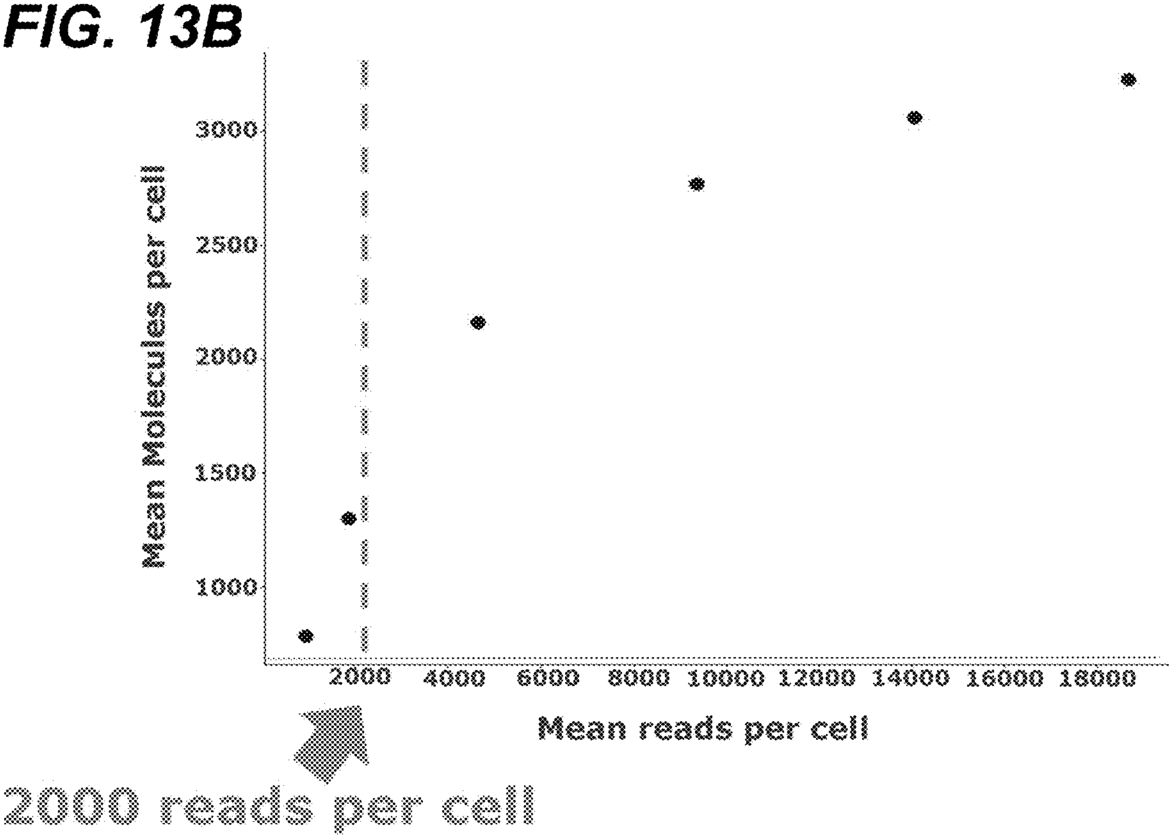

A combined dCODE and AbSeq library could require deep sequencing to detect dCODE molecules. FIGS. 13A-13B depict non-limiting exemplary saturation curves for dCODE Dextramer® (FIG. 13A) and for BD® AbSeq (FIG. 13B; 4-plex, high expressor). Saturation curves can depend on the type of AbSeq and dCODE panels used. As seen in FIGS. 13A-13B, at a sequencing depth of 2000 reads per cell, for dCode about 400 molecules per cell is expected to be detected, but for AbSeq about 2200 molecules per cell is expected to be detected. Accordingly, if these libraries had not been separated and they had to be sequenced together, a user would have to sequence the libraries extremely deeply to be able to detect dCODE molecules. Accordingly, separating the libraries as described herein can be an optimal solution to this problem.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method, comprising:

contacting a plurality of receptor detection constructs with a plurality of cells to form a first plurality of cells associated with the receptor detection constructs, wherein the plurality of cells comprise a plurality of cellular component targets and copies of a nucleic acid target, wherein one or more cells of the plurality of cells comprise a receptor that a receptor-binding reagent is capable of specifically binding to, and wherein each of the plurality of receptor detection constructs comprises two or more receptor-binding reagents and a receptor-binding reagent specific oligonucleotide comprising a unique receptor identifier sequence for the receptor-binding reagent;

contacting a plurality of cellular component-binding reagents with the first plurality of cells associated with the receptor detection constructs to form a second plurality of cells, wherein each of the plurality of cellular component-binding reagents comprises a cellular component-binding reagent specific oligonucleotide comprising a unique identifier sequence for the cellular component-binding reagent, and wherein the cellular component-binding reagent is capable of specifically binding to at least one of the plurality of cellular component targets;

barcoding the cellular component-binding reagent specific oligonucleotides with a plurality of oligonucleotide barcodes to generate a plurality of barcoded cellular component-binding reagent specific oligonucleotides each comprising a sequence complementary to at least a portion of the unique identifier sequence;

barcoding the receptor-binding reagent specific oligonucleotides with the plurality of oligonucleotide barcodes to generate a plurality of barcoded receptor-binding reagent specific oligonucleotides each comprising a sequence complementary to at least a portion of the unique receptor identifier sequence;

barcoding copies of the nucleic acid target of the plurality of cells with the plurality of oligonucleotide barcodes to generate a plurality of barcoded nucleic acid molecules each comprising a sequence complementary to at least a portion of the nucleic acid target;

generating a sequencing library comprising a plurality of nucleic acid target library members, a plurality of cellular component target library members, and a plurality of receptor library members, wherein generating the sequencing library comprises:

attaching sequencing adaptors to the plurality of barcoded nucleic acid molecules, or products thereof, to generate the plurality of nucleic acid target library members; and attaching sequencing adaptors to the plurality of barcoded cellular component-binding reagent specific oligonucleotides, or products thereof, to generate the plurality of cellular component target library members;

attaching sequencing adaptors to the plurality of barcoded receptor-binding reagent specific oligonucleotides, or products thereof, to generate the plurality of receptor library members; and generating a sequencing mixture comprising (i) nucleic acid target library members, (ii) cellular component target library members, and (iii) receptor library members, wherein generating a sequencing mixture comprises mixing (i) nucleic acid target library members, (ii) cellular component target library members, and (iii) receptor library members at a predetermined ratio, and wherein the (i) nucleic acid target library members, (ii) cellular component target library members, and (iii) receptor library members are physically separate from one another prior to generating the sequencing mixture; and obtaining sequencing data comprising a plurality of sequencing reads of nucleic acid target library members, a plurality of sequencing reads of cellular component target library members, and a plurality of sequencing reads of receptor library members.

2. The method of claim 1, wherein barcoding copies of the nucleic acid target of the plurality of cells with the plurality of oligonucleotide barcodes comprises:

contacting copies of the nucleic acid target of the plurality of cells with the plurality of oligonucleotide barcodes, wherein each oligonucleotide barcode of the plurality of oligonucleotide barcodes comprises a first universal sequence, a first molecular label, and a target-binding region capable of hybridizing to the nucleic acid target; and extending the plurality of oligonucleotide barcodes hybridized to the copies of the nucleic acid target to generate a plurality of barcoded nucleic acid molecules each comprising a sequence complementary to the at least a portion of the nucleic acid target.

3. The method of claim 1, wherein the cellular component-binding reagent specific oligonucleotide comprises a third universal sequence, and wherein barcoding the cellular component-binding reagent specific oligonucleotides with the plurality of oligonucleotide barcodes comprises:

contacting the cellular component-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the cellular component-binding reagent specific oligonucleotides; and extending the plurality of oligonucleotide barcodes hybridized to the cellular component-binding reagent specific oligonucleotides to generate a plurality of barcoded cellular component-binding reagent specific oligonucleotides each comprising a sequence complementary to at least a portion of the unique identifier sequence.

4. The method of claim 1, wherein the receptor-binding reagent specific oligonucleotide comprises a second universal sequence, and wherein barcoding the receptor-binding reagent specific oligonucleotides with the plurality of oligonucleotide barcodes comprises:

contacting receptor-binding reagent specific oligonucleotides with the plurality of oligonucleotide barcodes, wherein each oligonucleotide barcode of the plurality of oligonucleotide barcodes comprises a first universal sequence, a first molecular label, and a target-binding region capable of hybridizing to the receptor-binding reagent specific oligonucleotide; and extending the plurality of oligonucleotide barcodes hybridized to the receptor-binding reagent specific oligonucleotides to generate a plurality of barcoded receptor-binding reagent specific oligonucleotides each comprising a sequence complementary to at least a portion of the unique receptor identifier sequence.

5. The method of claim 1, wherein the second plurality of cells comprises one or more single cells, comprising, prior to (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes:

partitioning the second plurality of cells to a plurality of partitions, wherein a partition of the plurality of partitions comprises a single cell from the second plurality of cells; and in the partition comprising the single cell, (i) contacting copies of the nucleic acid target of the plurality of cells with the plurality of oligonucleotide barcodes, (ii) contacting the cellular component-binding reagent specific oligonucleotides with the plurality of oligonucleotide barcodes, and/or (iii) contacting the receptor-binding reagent specific oligonucleotides with the plurality of oligonucleotide barcodes, wherein the partition is a well or a droplet.

6. The method of claim 1, wherein each of the plurality of sequencing reads of the plurality of barcoded nucleic acid molecules, or products thereof, comprise (1) a molecular label sequence, and/or (2) a subsequence of the nucleic acid target, and wherein the method further comprises:

determining the copy number of the nucleic acid target in each of the one or more single cells based on the plurality of sequencing reads of nucleic acid target library members, wherein determining the copy number of the nucleic acid target in each of the one or more single cells comprises determining the copy number of the nucleic acid target in each of the one or more single cells based on the number of first molecular labels with distinct sequences, complements thereof, or a combination thereof, associated with the one or more nucleic acid target library members, or products thereof.

7. The method of claim 1, wherein each of the plurality of sequencing reads of receptor library members, comprise (1) a molecular label sequence, (2) at least a portion of the unique receptor identifier sequence, or (3) a cell label sequence, and wherein each unique cell label sequence indicates a single cell of the second plurality of cells, and wherein the method further comprises:

(i) determining the number of copies of the receptor in the one or more single cells based on the plurality of sequencing reads of receptor library members;

(ii) determining the identity of the receptor-binding reagent bound to the one or more single cells based on the plurality of sequencing reads of receptor library members; and/or iii) determining the identity of the receptor in the one or more single cells based on the plurality of sequencing reads of receptor library members.

8. The method of claim 1, wherein the plurality of receptor detection constructs comprises one or more MHC multimers, wherein the two or more receptor-binding reagents comprise two or more MHC-peptide complexes; wherein an MHC multimer comprises $(a\text{-}b\text{-}P)_n$, wherein n>1, wherein polypeptides a and b together form a functional MHC protein capable of binding peptide P, and (a-b-P) is a MHC-peptide complex formed when peptide P binds to the functional MHC protein; and wherein MHC-peptide complex of a MHC multimer is associated with one or more multimerization domains.

9. The method of claim 8, further comprising: (i) associating a T cell receptor (TCR) receptor in the one or more single cells with the peptide P based on the plurality of sequencing reads of receptor library members; and/or (ii) measuring the presence, frequency, number, activity and/or state of T cells specific for a peptide P, thereby detecting an antigen-specific T cell response.

10. The method of claim 1, wherein the sequencing mixture comprises a predetermined ratio of (i) nucleic acid target library members, (ii) cellular component target library members, and/or (iii) receptor library members, wherein the predetermined ratio of cellular component target library members to receptor library members is about 1:1 to 10000:1, and wherein the predetermined ratio of cellular component target library members to receptor library members is configured to achieve a ratio of sequencing reads of cellular component target library members to sequencing reads of receptor library members that is about 1:1 to 10000:1.

11. The method of claim 1, wherein the ratio of sequencing reads of cellular component target library members to sequencing reads of receptor library members is about 1:1 to 10000:1.

12. The method of claim 1, wherein the ratio of sequencing reads of cellular component target library members to sequencing reads of receptor library members is at least about 2-fold lower as compared to a method wherein: (i) the plurality of barcoded receptor-binding reagent specific oligonucleotides and the plurality barcoded cellular component-binding reagent specific oligonucleotides are amplified together; (ii) the second universal sequence and third universal sequence are the same; and/or (iii) the sequencing mixture does not comprise a predetermined ratio of cellular component target library members to receptor library members.

13. The method of claim 4, wherein the second universal sequence and the third universal sequence are different, and wherein the second universal sequence is less than about 85% identical to the third universal sequence.

14. The method of claim 4, wherein the second universal sequence comprises a sequence at least about 85% identical to SEQ ID NO: 1 (GGAGGGAGGTTAGCGAAGGT).

* * * * *